United States Patent
Yamabe et al.

(10) Patent No.: US 7,166,617 B2
(45) Date of Patent: Jan. 23, 2007

(54) CYCLIC AMIDE DERIVATIVES

(75) Inventors: Haruko Yamabe, Tokyo (JP); Masahiro Okuyama, Tokyo (JP); Akira Nakao, Tokyo (JP); Mitsuru Ooizumi, Tokyo (JP); Ken-ichi Saito, Tokyo (JP)

(73) Assignee: Mitsubishi Pharma Corporation, Osaki (JP)

( * ) Notice: Subject to any disclaimer, the term of this patent is extended or adjusted under 35 U.S.C. 154(b) by 80 days.

(21) Appl. No.: 10/220,359

(22) PCT Filed: Feb. 26, 2001

(86) PCT No.: PCT/JP01/01413

§ 371 (c)(1),
(2), (4) Date: Dec. 30, 2002

(87) PCT Pub. No.: WO01/64670

PCT Pub. Date: Sep. 7, 2001

(65) Prior Publication Data

US 2003/0212094 A1 Nov. 13, 2003

(30) Foreign Application Priority Data

Feb. 29, 2000 (JP) .............................. 2000-054674

(51) Int. Cl.
*A61K 31/445* (2006.01)
*C07D 401/06* (2006.01)

(52) U.S. Cl. ...................... 514/323; 514/326; 546/140; 546/141; 546/148; 546/157; 546/158; 546/165; 546/187; 546/198; 546/200; 546/201

(58) Field of Classification Search ................ 546/200, 546/198, 201, 140, 141, 157, 158, 165, 187, 546/148; 514/323, 321, 312, 314, 316, 307, 514/308, 309, 326
See application file for complete search history.

(56) References Cited

U.S. PATENT DOCUMENTS

| | | | | |
|---|---|---|---|---|
| 3,742,951 A | 7/1973 | Zaffaroni | ................ | 128/268 |
| 3,797,494 A | 3/1974 | Zaffaroni | ................ | 128/268 |
| 3,921,636 A | 11/1975 | Zaffaroni | ................ | 128/260 |
| 3,947,578 A | 3/1976 | Derible et al. | .......... | 424/267 |
| 3,996,934 A | 12/1976 | Zaffaroni | ................ | 128/268 |
| 4,000,287 A | 12/1976 | Werner | ................ | 424/267 |
| 4,031,894 A | 6/1977 | Urquhart et al. | ........ | 128/268 |
| 4,062,953 A | 12/1977 | Wade et al. | ............ | 424/232 |
| 4,168,315 A | 9/1979 | Rynbrandt et al. | ....... | 424/270 |
| 4,495,194 A | 1/1985 | Dolak et al. | ............ | 514/323 |
| 4,762,842 A | 8/1988 | Cohen et al. | ............ | 514/288 |

(Continued)

FOREIGN PATENT DOCUMENTS

HU     P8705398     9/1987

(Continued)

OTHER PUBLICATIONS

Yamabe et al., "Preparation of cyclic amide . . . " CA 135:226879 (2001).*

(Continued)

*Primary Examiner*—Celia Chang
(74) *Attorney, Agent, or Firm*—Edwards Angell Palmer & Dodge LLP; David G. Conlin; Dwight D. Kim

(57) ABSTRACT

Novel compounds represented by the following formula (I) that act as a ligand to sigma receptor/binding cite and a medicament comprising the same as an active ingredient:

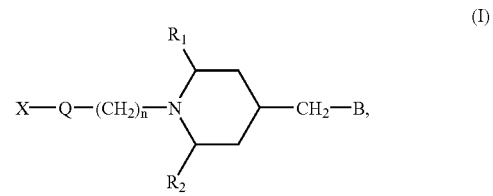

(I)

wherein X represents an alkyl group, an aryl group, a heterocyclic group or the like; Q represents a group represented by —CH$_2$—, —CO—, —O—, —CH(OR$_7$)— or the like wherein R$_7$ represents a hydrogen atom, an alkyl group or the like; n represents an integer of from 0 to 5; R$_1$ and R$_2$ each represent a hydrogen atom, an alkyl group or the like; B represents either of the following groups:

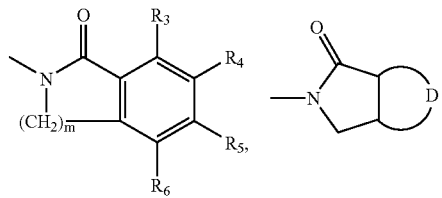

wherein R$_3$, R$_4$, R$_5$, and R$_6$ each represent a hydrogen atom, a halogen atom, an alkoxyl group or the like; m represents 1 or 2; and the ring of:

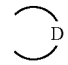

represents an aromatic heterocyclic ring.

15 Claims, No Drawings

U.S. PATENT DOCUMENTS

| | | | |
|---|---|---|---|
| 4,783,471 A | 11/1988 | Carr et al. | 514/317 |
| 4,812,461 A | 3/1989 | Antoku et al. | 514/278 |
| 4,877,798 A | 10/1989 | Sorensen | 514/317 |
| 4,908,369 A | 3/1990 | Schechter et al. | 514/277 |
| 4,908,372 A | 3/1990 | Carr et al. | 514/322 |
| 4,912,117 A | 3/1990 | Carr et al. | 514/317 |
| 4,948,799 A | 8/1990 | Antoku et al. | 514/278 |
| 4,988,711 A | 1/1991 | Angerbauer et al. | 514/326 |
| 5,001,134 A | 3/1991 | Ferrand et al. | 514/321 |
| 5,021,428 A | 6/1991 | Carr et al. | 514/317 |
| 5,093,341 A | 3/1992 | Carr et al. | 514/321 |
| 5,106,855 A | 4/1992 | McLees | 514/317 |
| 5,134,149 A | 7/1992 | Carr et al. | 514/317 |
| 5,141,930 A | 8/1992 | Nakao et al. | 514/211 |
| 5,166,211 A | 11/1992 | Carr et al. | 514/330 |
| 5,169,096 A | 12/1992 | Carr et al. | 246/232 |
| 5,182,399 A | 1/1993 | Kane | 546/199 |
| 5,231,099 A | 7/1993 | Cook | 514/279 |
| 5,286,866 A | 2/1994 | Carr et al. | 546/241 |
| 5,292,752 A | 3/1994 | Carr et al. | 514/317 |
| 5,356,906 A | 10/1994 | Ciganek et al. | 514/323 |
| 5,371,093 A | 12/1994 | Carr et al. | 514/321 |
| 5,380,731 A | 1/1995 | Carr et al. | 514/322 |
| 5,480,892 A | 1/1996 | Ciganek et al. | 514/323 |

FOREIGN PATENT DOCUMENTS

| | | |
|---|---|---|
| WO | WO 91/06297 | 5/1991 |
| WO | WO 92/18127 | 10/1992 |
| WO | WO 93/22310 | 11/1993 |
| WO | WO 98 31800 | 7/1998 |
| WO | WO 00 48203 | 8/2000 |
| WO | WO 00 55332 | 9/2000 |

OTHER PUBLICATIONS

Database EMBL 'Online!, Jun. 28, 1999, T. Arakawa, et al., AV169321 XP002199699.

Database EMBL 'Online!, Feb. 20, 1997, M. Marra, et al., "The WahU-HHMI mouse EST project", AA222797 XP002199700.

A. Bosserhoff, et al., "Mouse CD-RAP/MIA gene Structure, chromosomal localization, and expression in cartilage and chondrosarcoma.", Developmental Dynamics, vol 208, No. 4, 1997, pp. 516-525, XP001080394 ISSN: 1058-8388.

U.H. Dietz, et al., "Cloning of a retinoic acid-sensitive mRNA expressed in cartilage and during chondrogenesis.", Journal of Biological Chemistry, vol. 271, No. 6, 1996, pp. 3311-3316, XP001079161 ISSN: 0021-9258.

PCT/US 93/02771 International Search Report.

Frank, et al., "A Systematic Evaluation of the Properties of Self-Stimulation Train-Duration Response Functions", 1987, vol. 101, No. 4, 546-559.

Carbo, et al., "Differential inhibitory effects of a $5\text{-}HT_3$ antagonist on drug-induced stimulation of dopamine release", European Journal of Pharmacology, 164 (1989) 515-519.

Bozarth, et al., "Involvement of the Ventral Tegmental Dopamine System in Opioid and Psychomotor Stimulant Reinforcement", NIDA Res Monogr 67: 190-6, 1986.

Golino, et al., "Divergent Effects of Serotonin on Coronary-Artery Dimensions and Blood Flow in Patients with Coronary Atherosclerosis and Control Patients", The New England Journal of Medicine, Mar. 7, 1991, vol. 324, No. 641-648.

Peroutka, et al., "Multiple Serotonin Receptors: Differential Binding of $[^3H]$5-Hydroxythyptamine, $[^3H]$ Lysergic Acid Diethylamide and $[^3H]$ Spiroperidol", Molecular Pharmacology, 16, 687-699.

Di Chiara, et al., "Opposite Effects of Mu and Kappa Opiate Agonists on Dopamine Release in the Nucleus Accumbens and in the Dorsal Caudate of Freely Moving Rats[1]", The Journal of Pharmacology and Expermintal Therapeutics, vol. 244, No. 3, 1067-1080.

Schmidt, et al., "$5\text{-}HT_2$ Antagonists Stereoselectively Prevent the Neurotoxicity of 3,4-Methylenedioxymethamphetamine by Blocking the Acute Stimulation of Dopamine Synthesis: Reversal by L Dopa", The Journal of Pharmacology and Experimental Therapeutics, (1991), vol. 256, No. 1, 230-235.

Stewart, et al., "Role of Unconditioned and Conditioned Drug Effects in the Self-Administration of Opiates and Stimulants", Psychological Review, 1984, vol. 91, No. 2, 251-268.

Fibiger, et al., "Mesocorticolimbic Dopamine Systems and Reward", Ann NY Acad Sci 537:206-15, 1988.

Chemical Abstracts, The American Chemical Society, vol. 105, No. 5, Aug. 4, 1986.

Bush, et al., "The Role of the Endothelium in Arterial Thrombosis and the Influence of Antithrombotic Therapy", Drug Development Research 7:319-340 (1986).

* cited by examiner

CYCLIC AMIDE DERIVATIVES

This application is a U.S. national phase application, filed pursuant to 35 U.S.C. §371, of PCT international application No. PCT/JP01/01413, field Feb. 26, 2001, and which claims priority to Japanese Application 54674/2000,filed Feb. 29, 2000.

TECHNICAL FIELD

The present invention relates to novel compounds that act as a ligand for the sigma receptor/binding site and medicaments comprising said compounds as an active ingredient.

BACKGROUND ART

The recently identified sigma receptor/binding site of the brain is an important target for the development of antipsychotic drugs that are free from the side affects of currently available antipsychotic drugs having antagonistic activity on the dopamine D2 receptor (J. M. Walker and W. D. Bowen, F. O. Walker and R. R. Matsumoto, B. de Costa and K. C. Rice, Pharmacological Reviews, 42, pp. 355–402, 1990; G. Debonnel, J. Psychiatr. Neurosci., 18, 4, pp. 157–172, 1993; G.Debonnel and C. de Montigny, Life Sciences, 58, 9, pp. 721–734, 1996). Further, some data have been reported that suggest the regulation of signal transmission by a sigma ligand (also referred to as "sigma receptor ligand" in the specification) and its receptor through control of a calcium level in synaptosomes (P. J. Brent, H. Saunders and P. R. Dunkley, Neurosci. Lett., 211, pp. 138–142, 1996).

The term "receptor" used herein means a membrane binding type receptor and other binding sites. Existence of at least two sorts of sigma receptor subtypes, i.e., sigma 1 and sigma 2, has been revealed, and classification of sigma binding sites has been proposed (R. Quirion, W. D. Bowen, Y. Itzhak, J. L. Junien, J. M. Musacchio, R. B. Rothman, T. P. Su, W. Tam and D. P. Taylor, TiPS, 13, pp. 85–86, 1992). The sigma 1 binding site is characterized to have high affinity for haloperidol, di-o-tolylguanidine (DTG) and (+)-benzomorphane such as (+)-pentazocine, whilst the sigma 2 binding site is characterized to have high affinity for haloperidol and DTG, but have low affinity for (+)-benzomorphane.

The sigma 1 ligand has an action on the gastrointestinal tract, and it seems that the sigma 1 site may mediate suppression to muscarine-like acetylcholine receptor/phosphoinositide response by the sigma ligands. The sigma 1 binding site is present not only in brains, but on spleen cells (Y. Lin, B. B. Whitlock, J. A. Pultz and S. A. Wolfe Jr, J. Neuroimmunol., 58, pp. 143–154, 1995), and such sigma ligands may suppress the immune system (H. H. Garza, S. Mayo, W. D. Bowen, B. R. DeCosta and D. J. J. Carr, J. of Immunology, 151, 9, pp. 4672–4680, 1993).

The sigma 2 binding site is abundant in livers (A. E. Bruce, S. B. Hellewell and W. D. Bowen, Neurosci. Abstr., 16, 370, 1990; A. S. Basile, I. A. Paul and B. DeCosta, Eur. J. Pharmacol. Mol. Pharm. Sect., 227, pp. 95–98, 1992; C. Torrence-Campbell and W. D. Bowen, Eur. J. Pharmacol., 304, pp. 201–210, 1996), kidneys (W. D. Bowen, G. Feinstein and J. S. Orringer, Soc. Neurosci. Abstr., 18, 456, abstract 195.8, 1992), and hearts (M. Dumont and S. Lemaire, Eur. J. Pharmacol., 209, pp. 245–248, 1991).

The sigma 2 binding site in brains exists in hypothalamus, cerebellum, pons medulla and medulla oblongata. In hippocampus, frontal lobe and occipital lobe in rat brains, it exists more abundantly than the sigma 1 binding site (D. J. McCann, A. D. Weissmann and T. P. Su, Soc. Neurosci. abstr. 18, 22, abstract 16.5, 1992). In hippocampus synaptosomes of guinea pig, there are also the sigma 2 binding site that is selectively labeled with [$^3$H] BIMU (D. W. Bonhaus, D. N. Loury, L. B. Jakeman, Z. To, A. DeSouza, R. M. Eglen and E. H. F. Wong J. Pharmacol. Exp. Ther., 267, 2, pp. 961–970, 1993). The relationship between the sigma 2 binding site and cortex as well as limbic system supports the usefulness of compounds used for treatment of mental diseases (D. C. Mash and C. P. Zabetian, Synapse, 12, pp. 195–205, 1992).

It has been believed that the sigma 2 binding site is involved in motility functions, especially dystonia (R. R. Matsumoto, M. K. Hemstreet, N. L. Lai and A. Thurkauf, B. R. DeCosta, K. C. Rice, S. B. Hellewell, W. D. Bowen and J. M. Walker, Pharmacol. Biochem. Behav., 36, pp. 151–155, 1990). However, no evidence demonstrating such an action has been found in primate models of functional disorders of extrapyramidal tract (L. T. Meltzer, C. L. Christoffersen, K. A. Serpa, T. A. Pugsley, A. Razmpour and T. G. Heffner, Neuropharmacology, 31, 9, pp. 961–967, 1992).

Haloperidol, which is a clinically effective dopaminergic antipsychotic agent, shows high affinity for these two sigma subtypes. However, a reduced metabolite of haloperidol that acts on the central nervous system has more excellent affinity and selectivity for the sigma 2 receptor than dopamine D2 as compared to haloperidol (J. C. Jaen., B. W. Caprathe, T. A. Pugsley, L. D. Wise and H. Akunne, J. Med. Chem., 36, pp. 3929–3936, 1993). Since a selective agent has not been available, pharmacological significance, distribution and functions of the sigma 2 binding site have not yet been elucidated. On the other hand, recent studies revealed that the sigma 2 site played a role for controlling functions of ileum (G. G. Kinney, E. W. Haris, R. Ray and T. J. Hudzik, Europ. J. Pharmacol., 294, pp. 547–553, 1995). These data suggest that the selective sigma 2 ligand is useful for the treatment of irritable bowel syndrome.

Such sigma ligands are disclosed in Japanese Patent Application Laid-Open No. 9-302607, Japanese National Phase PCT Laid-Open Publication No. 10-508826 and the like. However, no cyclic amide derivative, such as isoindoline-1-on as a typical example, has been described yet.

As compounds which have a similar structure to those of general formula (I) of the present invention, Japanese National Phase PCT Laid-Open Publication No. 7-506107 discloses 4-imidomethyl-1-[2'-phenyl-2'-oxoethyl]piperidines such as:

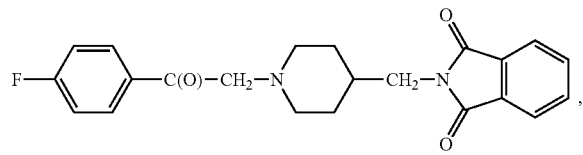

and hydrochlorides thereof and the like. However, these compounds are described as serotonine 2 antagonists, and whether or not they can act as sigma ligands has not yet been known. Moreover, these compounds having a phthalimide group may probably have a problem of insufficient safety.

DISCLOSURE OF THE INVENTION

An object of the present invention is to provide a novel compound that has excellent affinity for the sigma binding site. Another object of present invention is to provide a medicament comprising a compound having the aforementioned characteristics as an active ingredient which is useful for diseases that can be therapeutically and/or preventively treated by nerve control effect of the sigma ligand.

The inventors of the present invention earnestly studied to achieve the aforementioned objects. As a result, they found that compounds represented by the formula (I) below had high affinity for the sigma ligand binding site and low inhibition constant Ki for sigma 1 and/or sigma 2. They also found that these compound had a selective binding profile completely different from those of conventional known compounds, and were useful for treatment of diseases that can be therapeutically and/or preventively treated by the nerve control function of the sigma ligands. The present invention was achieved on the basis of these findings.

The present invention thus provides compounds represented by the following formula (I) or salts thereof, or hydrates thereof or solvates thereof:

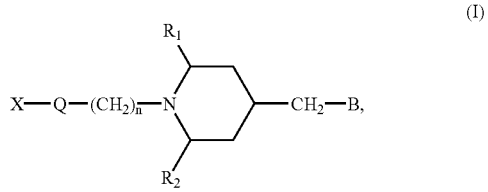

(I)

wherein:

X represents an alkyl group, a cycloalkyl-substituted alkyl group, an aryl-substituted alkyl group, an aryl-substituted alkenyl group, an aryl-substituted alkynyl group, a monocyclic or polycyclic cycloalkyl group which may be substituted with an alkyl group, an aryl group, a heterocyclic group, or a substituted or unsubstituted amino group;

Q represents a group represented by —$CH_2$—, —CO—, —O—, —S—, —CH($OR_7$)—, —C(=$CH_2$)— or —C(=$NR_8$)— (wherein $R_7$ represents a hydrogen atom, an alkyl group, a hydroxyalkyl group, or an acyl group, and $R_8$ represents a hydroxyl group, an alkoxyl group, an aralkyloxy group, an acyloxy group, an acylamino group, or an alkoxycarbonyl amino group);

n represents an integer of from 0 to 5;

$R_1$ and $R_2$ each independently represent a hydrogen atom or an alkyl group, or $R_1$ and $R_2$ combine to form an alkylene group;

B represents either of the following groups:

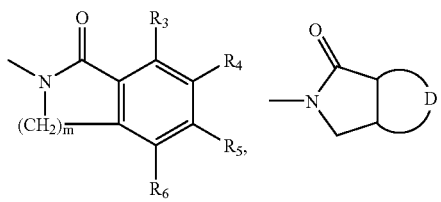

(wherein $R_3$, $R_4$, $R_5$ and $R_6$ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group);

m represents 1 or 2; and the ring of:

represents a 5- or 6-membered aromatic heterocyclic ring containing one or two heteroatoms which may be substituted.

According to another aspect of the present invention, provided are medicaments which comprises a substance selected from the group consisting of the aforementioned compounds and salts thereof, and hydrates thereof and solvates thereof as an active ingredient. As a preferred embodiment thereof, provided are the aforementioned medicaments which are used for diseases that can be therapeutically and/or preventively treated by nerve controlling function of a sigma ligand (for example, central nervous system diseases, gastroenteric diseases, heart defective diseases and the like). The present invention also provides a sigma ligand which comprises a substance selected from the group consisting of the aforementioned compounds and salts thereof, and hydrates thereof and solvates thereof.

According to further aspects of the present invention, provided are a use of a substance selected from the group consisting of the aforementioned compounds and salts thereof, and hydrates thereof and solvates thereof for the manufacture of the aforementioned medicaments, preferably in the form of a pharmaceutical composition, and methods for therapeutically and/or preventively treating diseases by the nerve controlling function of sigma ligands, which comprise the step of administering to a mammal including a human an effective amount of a substance selected from the group consisting of the aforementioned compounds and salts thereof, and hydrates thereof and solvates thereof.

BEST MODE FOR CARRYING OUT THE INVENTION

In the above-described formula (I), X represents an alkyl group, a cycloalkyl-substituted alkyl group, an aryl-substituted alkyl group, an aryl-substituted alkenyl group, an aryl-substituted alkynyl group, a monocyclic or polycyclic cycloalkyl group which may be substituted with an alkyl group, an aryl group, a heterocyclic group, or a substituted or unsubstituted amino group.

The term "alkyl group" and the term "alkyl" for a group containing an alkyl group as a moiety used herein encompass, for example, linear or branched alkyl groups having 1 to 6 carbon atoms, preferably 1 to 4 carbon atoms. More specifically, as the alkyl group, methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group and the like may be used.

In the specification, when "alkyl group" is referred to, the term encompasses those having one or more substituents, unless otherwise indicated. Examples of the substituent include a halogen atom, a nitro group, a cycloalkyl group, an aryl group, an aryloxy group, a heteroaryl group, a hydroxyl group, an alkoxyl group, a halogenated alkoxyl group, a carboxyl group, an alkoxycarbonyl group, a substituted or unsubstituted amino group, an acyl group or a cyano group. As these substituents, those described below may preferably be used.

The term "cycloalkyl group" and the term "cycloalkyl" for a group containing a cycloalkyl group as a moiety used herein encompass, for example, a 3- to 8-membered cycloalkyl group, preferably an approximately 3- to 6-membered cycloalkyl group (a monocyclic cycloalkyl group unless otherwise specifically mentioned). These cycloalkyl groups may have one or two alkyl groups on their rings. More specifically, for example, cyclopropyl group, methylcyclopropyl group, cyclobutyl group, cyclopentyl group, cyclohexyl group, methylcyclohexyl group, dimethylcyclohexyl group and the like may be used as the cycloalkyl group. As the polycyclic cycloalkyl group, a 5- to 12-membered polycycloalkyl group such as norbornyl group or adamantyl group may be used, and adamantyl group may preferably be used.

Examples of the cycloalkyl-substituted alkyl group include, for example, cyclopropylmethyl group, methylcyclopropylmethyl group, cyclopropylethyl group, cyclopropylpropyl group, cyclobutylmethyl group, cyclobutylethyl group, cyclopentylmethyl group, cyclohexylmethyl group, dimethylcyclohexylmethyl group and the like.

The term "aryl group" and the term "aryl" for a group containing an aryl group as a moiety used herein encompass, for example, a monocyclic, bicyclic or tricyclic aryl group containing about from 6 to 14 atoms. For example, phenyl group, 1-naphthyl group, and 2-naphthyl group, as well as phenanthryl group, anthracenyl group and the like may be used. Further, "aryl group" encompasses bicyclic or tricyclic aryl groups whose ring or rings are partially hydrogenated, including 5,6,7,8-tetrahydronaphthyl group.

The term "alkenyl group" used herein encompass linear or branched alkenyl groups having 2 to 6 carbon atoms, preferably 3 to 6 carbon atoms, and containing one or more double bonds, preferably one double bond. For example, 1-propenyl group, allyl group, isopropenyl group, 1-butenyl group, 3-butenyl group, 1-pentenyl group, 2-pentenyl group, 3-pentenyl group, 4-pentenyl group, 1-hexenyl group, 2-hexenyl group and the like may be used as the alkenyl group. The double bond contained in the alkenyl group may be either in cis- or trans-configuration.

The term "alkynyl group" encompasses a linear or branched alkynyl group having from 2 to 6 carbon atoms, preferably from 3 to 6 carbon atoms, for example, 2-propynyl group, 3-butynyl group, 4-pentynyl group, 5-hexynyl group and the like.

As the heterocyclic group, a 5- to 10-membered monocyclic to tricyclic heterocyclic group containing 1 to 4 hetero atoms which are selected from oxygen atom, sulfur atom and nitrogen atom as ring-constituting atoms. For example, applicable groups include furyl group (furan ring), benzofuranyl group (benzofuran ring), isobenzofuranyl group (isobenzofuran ring), thienyl group (thiophene ring), benzothiophenyl group (benzothiophene ring), pyrrolyl group (pyrrole ring), imidazolyl group (imidazole ring), pyrazolyl group (pyrazole ring), thiazolyl group (thiazole ring), benzothiazolyl group (benzothiazole ring), isothiazolyl group (isothiazole ring), benzisothiazolyl group (benzisothiazole ring), triazolyl group (triazole ring), tetrazolyl group (tetrazole ring), pyridyl group (pyridine ring), pyrazinyl group (pyrazine ring), pyrimidinyl group (pyrimidine ring), pyridazinyl group (pyridazine ring), indolyl group (indole ring), isoindolyl group (isoindole ring), benzimidazolyl group (benzimidazole ring), purinyl group (purine ring), quinolyl group (quinoline ring), isoquinolyl group (isoquinoline ring), dihydroisoquinolyl group (dihydroquinoline ring), phthalazinyl group (phthalazine ring), naphthylidinyl group (naphthylidine ring), quinoxalinyl group (quinoxaline ring), cinnolinyl group (cinnoline ring), pteridinyl group (pteridine ring), oxazolyl group (oxazole ring), isoxazolyl group (isoxazole ring), benzoxazolyl group (benzoxazole ring), benzisoxazolyl group (benzisoxazole ring), furazanyl group (furazan ring), oxazinyl group (oxazine ring) and the like may be used. Additionally, those heterocyclic groups whose ring or rings are partially hydrogenated may also be used, including pyrrolidinyl group (pyrrolidine ring), imidazolidinyl group (imidazolidine ring), piperidinyl group (piperidine ring), piperazinyl group (piperazine ring), morpholinyl group (morpholine ring) and the like. Among them, a 5- to 7-membered monocylic heterocyclic group containing 1 or 2 heteroatoms, or a 8- to 10-membered bicyclic heteroaryl group containing 1 or 2 heteroatoms may preferably be used as the heterocyclic group according to the present invention.

In the specification, when "cycloalkyl group", "aryl group", "heterocyclic group" or "heteroaryl group" is referred to, the term encompasses a cycloalkyl group, an aryl group, a heterocyclic group, or a heteroaryl group having one or more substituents on the ring, unless otherwise indicated. Examples of the substituent include a halogen atom, a nitro group, an alkyl group, a cycloalkyl group, an alkenyl group, an alkynyl group, a halogenated alkyl group, a hydroxyl group, an alkoxyl group, a halogenated alkoxyl group, a carboxyl group, an alkoxycarbonyl group, a phenyl group, a phenoxy group, a substituted or unsubstituted amino group, an acyl group, a cyano group and the like. As these substituents, those explained above or those described below may preferably be used.

Examples of the substituted or unsubstituted amino group include, for example, an amino group, an alkyl amino group such as a monoalkylamino group and a dialkylamino group, an acylamino group such as an alkanoylamino group and an arylcarbonylamino group, an aralkylamino group, an alkylsulfonylamino group and the like. More specifically, examples include an alkylamino group such as monomethylamino group, dimethylamino group, ethylamino group, diethylamino group, methylethylamino group, propylamino group, dipropylamino group, butylamino group, pentylamino group, and hexyl amino group; an acylamino group such as acetylamino groups, trifluoroacetylamino group, propionylamino group, benzoylamino group, and p-methoxybenzoylamino group; an aralkylamino group such as benzylamino group and p-methoxybenzylamino group; and an alkylsulfonylamino group such as methylsulfonylamino group, ethylsulfonylamino group, n-propylsulfonylamino group, and n-hexylsulfonylamino group.

When the term "halogen atom" or "halogenated" is referred to in the specification, any of fluorine atom, chlorine atom, bromine atom, and iodine atom may be used as the halogen atom. The term "halogenated alkyl group" used in the specification encompasses, for example, monofluoromethyl group, difluoromethyl group, trifluoromethyl group, trifluoroethyl group, pentafluoroethyl group, monochloromethyl group, dichloromethyl group, trichloromethyl group and the like, and preferred examples thereof include trifluoromethyl group.

The term "alkoxyl group" and the term "alkoxy" for a group containing an alkoxyl group as a moiety used herein encompass, for example, linear or branched alkoxyl groups having 1 to 6 carbon atoms, preferably 1 to 4 carbon atoms. More specifically, methoxy group, ethoxy group, n-propoxy group, isopropoxy group, n-butoxy group, isobutoxy group, tert-butoxy group, n-pentyloxy group, n-hexyloxy group and the like may be used as the alkoxy group. For example, trifluoromethoxy group, trifluoroethoxy group, monochloromethoxy group, trichloromethoxy group and the like may be used as the halogenated alkoxy group.

As the alkoxycarbonyl group, for example, alkoxycarbonyl groups formed by the aforementioned alkoxyl groups may be used, and more specifically, methoxycarbonyl group, ethoxycarbonyl group, n-propoxycarbonyl group, isopropoxycarbonyl group and the like may be used.

Examples of the acyl group include an alkanoyl group (e.g., an alkylcarbonyl group, a halogenated alkylcarbonyl group and the like), an arylcarbonyl groups, a heteroarylcarbonyl group and the like. More specifically, formyl group, acetyl group, propionyl group, trifluoromethylcarbonyl group, pentafluoroethylcarbonyl group, benzoyl group, p-methoxybenzoyl group, 3-pyridylcarbonyl group and the like may be used.

As X, an alkyl group, an aryl-substituted alkyl group, an aryl-substituted alkenyl group, an aryl-substituted alkynyl group, an aryl group, a monocyclic cycloalkyl group, a monocyclic heterocyclic group, a 8- to 10-membered bicyclic heteroaryl group containing 1 or 2 heteroatoms, or an amino group which is substituted with an alkyl or aryl group may preferably be used in the present invention. More preferably, a substituted or unsubstituted phenyl group (examples of the substituent include one or more substituents selected from the group consisting of, for example, a halogen atom, an alkyl group, a halogenated alkyl group, an alkoxyl group, a halogenated alkoxyl group, an aralkyl group, an aralkyloxy group, a phenyl group, a phenoxy group, a furyl group, an acyl group, an amino group, an alkyl amino group, an acyl amino group, a nitro group and a cyano group), a 5- or 6-membered monocyclic heterocyclic group, or a 8- to 10-membered bicyclic heteroaryl group containing one or two heteroatoms may be used.

More preferable examples of X in the present invention include, a substituted or unsubstituted phenyl group (the substituent is preferably one or more substituents selected from the group consisting of a halogen atom, an alkyl group, a halogenated alkyl group, an alkoxyl group, a halogenated alkoxyl group, and a cyano group, and more preferably one or more substituents selected from the group consisting of a halogen atom and an alkoxyl group). p-Fluorophenyl group is most preferred.

In the above-described formula (I), Q represents a group represented by —$CH_2$—, —CO—, —O—, —S—, —CH($OR_7$)—, —C(=$CH_2$)— or —C(=$NR_8$)—. $R_7$ represents a hydrogen atom, an alkyl group, a hydroxyalkyl group, or an acyl group, more preferably a hydrogen atom, a lower alkyl group, or an acetyl group, and most preferably an hydrogen atom or an acetyl group. $R_8$ represents a hydroxyl group, an alkoxyl group, an aralkyloxy group, an acyloxy group, an acylamino group, or an alkoxycarbonyl amino group, and more preferably a hydroxyl group, an alkoxyl group, or an acylamino group. $R_8$ is most preferably a hydroxy group or an acetylamino group.

As Q, a group represented by —$CH_2$—, —CO—, —O—, —C(=NOH)—, or —CH(=$NR_7$)— may be preferred in the present invention, and a group represented by —$CH_2$—, —CO—, —O— or —CH(OH)— is more preferred. Most preferred is —CO—.

In the above-described formula (I), n represents an integer of from 0 to 5, preferably from 0 to 4, more preferably from 1 to 3, and most preferably 1.

In the above-described formula (I), $R_1$ and $R_2$ each independently represent a hydrogen atom or an alkyl group, or $R_1$ and $R_2$ combine to form an alkylene group. Among them, $R_1$ and $R_2$ preferably represent independently a hydrogen atom or an alkyl group, and most preferably both of $R_1$ and $R_2$ are hydrogen atoms.

In B of the above-described formula (I), $R_3$, $R_4$, $R_5$ and $R_6$ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group. Among them, preferably, $R_3$, $R_4$, $R_5$, and $R_6$ each independently represent a substituent selected from the group consisting of a hydrogen atom, a halogen atom, a nitro group, an alkyl group, a hydroxyl group, an alkoxyl group and a cyano group. More preferably, three of $R_3$, $R_4$, $R_5$, and $R_6$ are hydrogen atoms and the remaining one represents a substituent selected from the group consisting of a hydrogen atom, a halogen atom, a nitro group, an alkyl group, a hydroxyl group, an alkoxyl group, and a cyano group. More preferably, three of $R_3$, $R_4$, $R_5$, and $R_6$ are hydrogen atoms and the remaining one represents a substituent selected from the group consisting of a hydrogen atom, a halogen atom, an alkoxyl group, and a cyano group. Most preferably, three of $R_3$, $R_4$, $R_5$, and $R_6$ are hydrogen atoms and the remaining one represents a hydrogen atom, a flourine atom, chlorine atom, bromine atom, methoxy group, or cyano group. m represents an integer of 1 or 2, and preferably 1.

In a group represented by B, the ring of:

represents a 5- or 6-membered aromatic heterocyclic ring containing one or two heteroatoms which may be substituted. Among them, an aromatic heterocyclic ring selected from the group consisting of furan ring, thiophene ring, and pyridine ring is preferred, and an unsubstituted thiophene ring or furan ring is more preferred.

Examples of preferred classes of compounds falling within the aforementioned formula (I) includes:

(1) those wherein X represents an alkyl group, an aryl-substituted alkyl group, an aryl-substituted alkenyl group, an aryl-substituted alkynyl group, an aryl group, a monocyclic cycloalkyl group, a monoclyclic heterocyclic group, a 8- to 10-membered bicyclic heteroaryl group containing 1 or 2 heteroatoms, or a substituted or unsubstituted amino group; Q represents a group represented by —$CH_2$—, —CO—, —O—, —S—, —CH($OR_7$)—, or —C(=$NR_8$)— (wherein $R_7$ represents a hydrogen atom, an alkyl group, or an acyl group, and $R_8$ represents a hydroxyl group, an alkoxyl group, or an acylamino group); n represents an integer of from 0 to 4; $R_1$ and $R_2$ each independently represent a hydrogen atom or an alkyl group; $R_3$, $R_4$, $R_5$, and $R_6$ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group; m represents 1 or 2; and the ring of:

is a heterocyclic ring selected from the group consisting of a furan ring, a thiophene ring, and a pyridine ring which may be substituted.

Examples of more preferred classes of compounds include:

(2) the compounds according to (1) wherein X represents an alkyl group, an aryl-substituted alkyl group, an aryl-substituted alkenyl group, an aryl-substituted alkynyl group, an aryl group, a monocyclic cycloalkyl group, a monoclyclic heterocyclic group, a 8- to 10-membered bicyclic heteroaryl group containing 1 or 2 heteroatoms, or an amino group which is substituted with an alkyl or aryl group, both $R_1$ and $R_2$ are hydrogen atoms, $R_3$, $R_4$, $R_5$, and $R_6$ each independently represent a substituent selected from the group consisting of a hydrogen atom, a halogen atom, a nitro group, an alkyl group, a hydroxyl group, an alkoxyl group, and a cyano group, m represents 1 or 2, and the ring of:

is a furan ring, a thiophene ring, or a pyridine ring which may be substituted;

(3) compounds according to (1) wherein X represents a substituted or unsubstituted phenyl group (the substituent is one or more substituents selected from the group consisting of a halogen atom, an alkyl group, a halogenated alkyl group, an alkoxyl group, a halogenated alkoxyl group, and a cyano group), a 5- or 6-membered monocyclic heterocyclic group, or a 8- to 10-membered bicyclic heteroaryl group containing one or two heteroatoms, both $R_1$ and $R_2$ are hydrogen atoms, three of $R_3$, $R_4$, $R_5$, and $R_6$ are hydrogen atoms and the remaining one represents a substituent selected from the group consisting of hydrogen atom, a halogen atom, a nitro group, an alkyl group, a halogenated alkyl group, a hydroxyl group, an alkoxyl group, a halogenated alkoxyl group, and a cyano group, m represents 1 or 2, and the ring of:

is a heterocyclic ring selected from the group consisting of a furan ring, a thiophene ring, and a pyridine ring each of which may be substituted;

(4) the compounds according to (2) or (3) above wherein Q represents —CH$_2$—, —CO—, —O—. —C(=NOH)—, or —CH(OR$_7$)— (wherein R$_7$ represents a hydrogen atom, an alkyl group, or an acyl group), B is represented by the following formula:

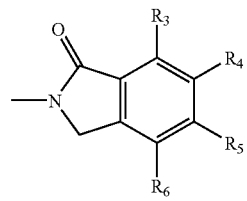

(wherein three of $R_3$, $R_4$, $R_5$, and $R_6$ are hydrogen atoms and the remaining one represents a substituent selected from the group consisting of a hydrogen atom, a halogen atom, a nitro group, an alkyl group, a hydroxyl group, an alkoxyl group, and a cyano group), and n is 1; and (5) compounds wherein X represents a substituted or unsubstituted phenyl group (the substituent is one or more substituents selected from the group consisting of a halogen atom and an alkoxyl group), Q represents —CH$_2$—, —CO—, —O—, or —CH(OH)—, n represents an integer of from 1 to 3, both $R_1$ and $R_2$ are hydrogen atoms, three of $R_3$, $R_4$, $R_5$, and $R_6$ are hydrogen atoms and the remaining one represents a hydrogen atom, a halogen atom or an alkoxyl group, m represents 1 or 2, and the following ring of:

is a thiophene or furan ring.

Examples of particularly preferred classes of compounds include:

(6) the compounds wherein X represents a substituted or unsubstituted phenyl group, naphthyl group, tert-butyl group, cyclohexyl group, a substituted or unsubstituted pyrrolyl group, piperidinyl group, benzisoxazolyl group, benzodioxolyl group, tetrahydroquinolyl group, indolinyl group, or a substituted or unsubstituted phenylamino group, Q represents —CH$_2$—, —CO—, —O—, —S—, —CH(OH)—, or —C(=NHO)—, n represents an integer of 1 or 2, each of $R_1$ and $R_2$ is a hydrogen atom, three of $R_3$, $R_4$, $R_5$, and $R_6$ are hydrogen atoms and the remaining one represents a substituent selected from the group consisting of a hydrogen atom, a fluorine atom, a chlorine atom, a bromine atom, and a methoxy group, m represents 1 or 2, and the ring of:

is a furan or thiophene ring;

(7) the compounds wherein X represents p-fluorophenyl group, Q represents —CH$_2$—, —CO—, —O—, or —CH(OH)—, n represents 1, both $R_1$ and $R_2$ are hydrogen atoms, three of $R_3$, $R_4$, $R_5$, and $R_6$ are hydrogen atoms and the remaining one represents a hydrogen atom, a halogen atom, or a methoxy group, and m represents 1;
(8) the compounds according to (7) wherein Q represents —CO—;
(9) the compounds according to (8) wherein all of $R_3$, $R_4$, $R_5$, and $R_6$ are hydrogen atoms;
(10) the compounds according to (8) wherein three of $R_3$, $R_4$, $R_5$, and $R_6$ are hydrogen atoms and the remaining one represents a halogen atom; and
(11) the compounds according to (6) wherein X represents p-fluorophenyl group, Q represents —CO—, n represents 1, and the ring of:

represents a furan or thiophene ring.

Specific examples of particularly preferred compounds of the present invention are listed in the following tables. However, the compounds of present invention are not limited to these examples. In the compounds mentioned below, both of $R_1$ and $R_2$ are hydrogen atoms. In the tables, for example, the description of "p-F-Ph" for X means that X is p-fluorophenyl group. Other descriptions are indicated in similar manners. Further, "Bu" represents a butyl or butylene group, "Pr" represents a propyl or propylene group, "Et" represents an ethyl or ethylene group, "Ac" represents an acetyl group, and """ represents the same group as the group shown in an upper line.

Table 1 shows the compounds wherein B is a group represented by the following formula:

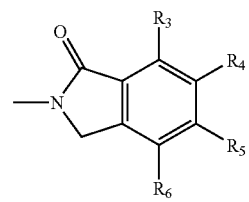

and Table 2 shows those wherein B is a group represented by the following formula.

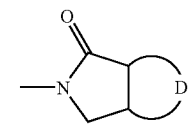

The compounds specifically disclosed in the examples of the specification are also preferred according to the present invention, as well as those described below.

TABLE 1

| No. | X | Q | n | $R_3$ | $R_4$ | $R_5$ | $R_6$ | m |
|---|---|---|---|---|---|---|---|---|
| 1 | p-F—Ph | C=O | 1 | H | H | H | H | 1 |
| 2 | " | " | " | Br | " | " | " | " |
| 3 | " | " | " | H | Br | " | " | " |
| 4 | " | " | " | " | H | Br | " | " |
| 5 | " | " | " | " | " | H | Br | " |
| 6 | " | " | " | " | Br | " | " | " |
| 7 | " | " | " | F | H | " | H | " |
| 8 | " | " | " | H | F | " | " | " |
| 9 | " | " | " | " | H | F | " | " |
| 10 | " | " | " | " | " | H | F | " |
| 11 | " | " | " | Cl | " | " | H | " |
| 12 | " | " | " | H | Cl | " | " | " |
| 13 | " | " | " | " | H | Cl | " | " |
| 14 | " | " | " | " | " | H | Cl | " |
| 15 | " | " | " | $OCH_3$ | " | " | H | " |
| 16 | " | " | " | H | $OCH_3$ | " | " | " |
| 17 | " | " | " | " | H | $OCH_3$ | " | " |
| 18 | " | " | " | " | " | H | $OCH_3$ | " |
| 19 | " | " | " | CN | " | " | H | " |
| 20 | " | " | " | H | CN | " | " | " |
| 21 | " | " | " | " | H | CN | " | " |
| 22 | " | " | " | " | " | H | CN | " |
| 23 | " | " | " | " | $NO_2$ | " | H | " |
| 24 | " | " | " | " | H | $NO_2$ | " | " |
| 25 | " | " | " | " | " | H | $NO_2$ | " |
| 26 | Ph | " | " | " | " | " | H | " |
| 27 | " | " | " | Br | " | " | " | " |
| 28 | " | " | " | H | Br | " | " | " |
| 29 | " | " | " | " | H | Br | " | " |
| 30 | " | " | " | " | " | H | Br | " |
| 31 | " | " | " | Br | " | " | " | " |
| 32 | " | " | " | F | H | " | H | " |
| 33 | " | " | " | H | F | " | " | " |
| 34 | " | " | " | " | H | F | " | " |
| 35 | " | " | " | " | " | H | F | " |
| 36 | Ph | C=O | 1 | Cl | H | H | H | 1 |
| 37 | " | " | " | H | Cl | H | " | " |
| 38 | " | " | " | " | H | Cl | " | " |
| 39 | " | " | " | " | " | H | Cl | " |

TABLE 1-continued

| No. | X | Q | n | R₃ | R₄ | R₅ | R₆ | m |
|---|---|---|---|---|---|---|---|---|
| 40 | " | " | " | OCH₃ | " | " | H | " |
| 41 | " | " | " | H | OCH₃ | " | " | " |
| 42 | " | " | " | " | H | OCH₃ | " | " |
| 43 | " | " | " | " | " | H | OCH₃ | " |
| 44 | " | " | " | CN | " | " | H | " |
| 45 | " | " | " | H | CN | " | " | " |
| 46 | " | " | " | " | H | CN | " | " |
| 47 | " | " | " | " | " | H | CN | " |
| 48 | " | " | " | " | NO₂ | " | H | " |
| 49 | " | " | " | " | H | NO₂ | " | " |
| 50 | " | " | " | " | " | H | NO₂ | " |
| 51 | p-Cl—Ph | " | " | " | " | " | H | " |
| 52 | " | " | " | " | Br | " | " | " |
| 53 | " | " | " | " | H | Br | " | " |
| 54 | " | " | " | " | " | H | Br | " |
| 55 | " | " | " | " | Br | " | " | " |
| 56 | " | " | " | " | F | " | H | " |
| 57 | " | " | " | " | H | " | F | " |
| 58 | " | " | " | " | " | Cl | H | " |
| 59 | " | " | " | " | Cl | H | " | " |
| 60 | " | " | " | " | H | OCH₃ | " | " |
| 61 | " | " | " | " | " | CN | " | " |
| 62 | " | " | " | " | NO₂ | H | " | " |
| 63 | " | " | " | " | H | " | NO₂ | " |
| 64 | p-H₃CO—Ph | " | " | " | " | " | H | " |
| 65 | " | " | " | " | Br | " | " | " |
| 66 | " | " | " | " | H | Br | " | " |
| 67 | " | " | " | " | " | H | Br | " |
| 68 | " | " | " | " | Br | " | " | " |
| 69 | " | " | " | " | F | " | H | " |
| 70 | " | " | " | " | H | " | F | " |
| 71 | p-H₃CO—Ph | C=O | 1 | H | H | Cl | H | 1 |
| 72 | " | " | " | " | Cl | H | " | " |
| 73 | " | " | " | " | H | OCH₃ | " | " |
| 74 | " | " | " | " | " | CN | " | " |
| 75 | " | " | " | " | NO₂ | H | " | " |
| 76 | " | " | " | " | H | " | NO₂ | " |
| 77 | p-F—Ph | CHOH | " | " | " | " | H | " |
| 78 | " | " | " | " | Br | " | " | " |
| 79 | " | " | " | " | H | Br | " | " |
| 80 | " | " | " | " | " | H | Br | " |
| 81 | p-F—Ph | CHOH | 1 | H | Br | H | Br | 1 |
| 82 | " | " | " | " | F | " | H | " |
| 83 | " | " | " | " | H | " | F | " |
| 84 | " | " | " | " | " | Cl | H | " |
| 85 | " | " | " | " | Cl | H | " | " |
| 86 | " | " | " | " | H | OCH₃ | " | " |
| 87 | " | " | " | " | " | CN | " | " |
| 88 | " | " | " | " | NO₂ | H | " | " |
| 89 | " | " | " | " | H | " | NO₂ | " |
| 90 | " | C=NOH | " | " | " | " | H | " |
| 91 | " | " | " | " | Br | " | " | " |
| 92 | " | " | " | " | H | Br | " | " |
| 93 | " | " | " | " | " | H | Br | " |
| 94 | " | " | " | " | Br | " | " | " |
| 95 | " | " | " | H | F | " | H | " |
| 96 | " | " | " | " | H | " | F | " |
| 97 | " | " | " | " | " | Cl | H | " |
| 98 | " | " | " | " | Cl | H | " | " |
| 99 | " | " | " | " | H | OCH₃ | " | " |
| 100 | " | " | " | " | " | CN | " | " |
| 101 | " | " | " | " | NO₂ | H | " | " |
| 102 | " | " | " | " | H | " | NO₂ | " |
| 103 | p-F—Ph | CHOAc | " | " | " | " | H | " |
| 104 | " | " | " | " | Br | " | " | " |
| 105 | " | " | " | " | H | Br | " | " |
| 106 | p-F—Ph | CHOAc | 1 | H | H | H | Br | 1 |
| 107 | " | " | " | " | Br | " | " | " |
| 108 | " | " | " | " | F | " | H | " |
| 109 | " | " | " | " | H | " | F | " |
| 110 | " | " | " | " | " | Cl | H | " |
| 111 | " | " | " | " | Cl | H | " | " |
| 112 | " | " | " | " | H | OCH₃ | " | " |
| 113 | " | " | " | " | " | CN | " | " |
| 114 | " | " | " | " | NO₂ | H | " | " |
| 115 | " | " | " | " | H | " | NO₂ | " |
| 116 | o,p-diF—Ph | C=NOH | " | " | " | " | H | " |

TABLE 1-continued

| No. | X | Q | n | R₃ | R₄ | R₅ | R₆ | m |
|---|---|---|---|---|---|---|---|---|
| 117 | " | " | " | " | Br | " | " | " |
| 118 | " | " | " | " | H | Br | " | " |
| 119 | " | " | " | " | " | H | Br | " |
| 120 | " | " | " | " | Br | " | " | " |
| 121 | o,p-diF—Ph | C=NOH | 1 | H | F | H | H | 1 |
| 122 | " | " | " | " | H | " | F | " |
| 123 | " | " | " | " | " | Cl | H | " |
| 124 | " | " | " | " | " | OCH₃ | " | " |
| 125 | " | " | " | " | " | CN | " | " |
| 126 | t-Bu | C=O | " | " | " | H | " | " |
| 127 | " | " | " | " | Br | " | " | " |
| 128 | " | " | " | " | H | Br | " | " |
| 129 | " | " | " | " | " | H | Br | " |
| 130 | " | " | " | " | Br | " | " | " |
| 131 | " | " | " | " | F | " | H | " |
| 132 | " | " | " | " | H | " | F | " |
| 133 | " | " | " | " | " | Cl | H | " |
| 134 | " | " | " | " | " | OCH₃ | " | " |
| 135 | " | " | " | " | " | CN | " | " |
| 136 | o-H₃CO—Ph | CH₂ | 0 | " | " | H | " | " |
| 137 | " | " | " | " | Br | " | " | " |
| 138 | " | " | " | " | H | Br | " | " |
| 139 | " | " | " | " | " | H | Br | " |
| 140 | " | " | " | " | Br | " | " | " |
| 141 | o-H₃CO—Ph | CH₂ | 0 | H | F | H | H | 1 |
| 142 | " | " | " | " | H | " | F | " |
| 143 | " | " | " | " | " | Cl | H | " |
| 144 | " | " | " | " | " | OCH₃ | " | " |
| 145 | " | " | " | " | " | CN | " | " |
| 146 | " | " | 1 | " | " | H | " | " |
| 147 | " | " | " | " | Br | " | " | " |
| 148 | " | " | " | " | H | Br | " | " |
| 149 | " | " | " | " | " | H | Br | " |
| 150 | " | " | " | " | Br | " | " | " |
| 151 | " | " | " | " | F | " | H | " |
| 152 | " | " | " | " | H | " | F | " |
| 153 | " | " | " | " | " | Cl | H | " |
| 154 | " | " | " | " | " | OCH₃ | " | " |
| 155 | " | " | " | " | " | CN | " | " |
| 156 | Ph | C=O | 2 | " | " | H | " | " |
| 157 | " | " | " | " | Br | " | " | " |
| 158 | " | " | " | " | H | Br | " | " |
| 159 | " | " | " | " | " | H | Br | " |
| 160 | " | " | " | " | Br | " | " | " |
| 161 | Ph | C=O | 2 | H | F | H | H | 1 |
| 162 | " | " | " | " | H | " | F | " |
| 163 | " | " | " | " | " | Cl | H | " |
| 164 | " | " | " | " | " | OCH₃ | " | " |
| 165 | " | " | " | " | " | CN | " | " |
| 166 | p-F—Ph | " | 3 | " | " | H | " | " |
| 167 | " | " | " | " | Br | " | " | " |
| 168 | " | " | " | " | H | Br | " | " |
| 169 | " | " | " | " | " | H | Br | " |
| 170 | " | " | " | " | Br | " | " | " |
| 171 | " | " | " | " | F | " | H | " |
| 172 | " | " | " | " | H | " | F | " |
| 173 | " | " | " | " | " | Cl | H | " |
| 174 | " | " | " | " | " | OCH₃ | " | " |
| 175 | " | " | " | " | " | CN | " | " |
| 176 | Ph | CH₂ | 0 | H | H | H | H | 1 |
| 177 | " | " | " | " | Br | " | " | " |
| 178 | " | " | " | " | H | Br | " | " |
| 179 | " | " | " | " | " | H | Br | " |
| 180 | " | " | " | " | Br | " | " | " |
| 181 | " | " | " | " | F | " | H | " |
| 182 | " | " | " | " | H | " | F | " |
| 183 | " | " | " | " | " | Cl | H | " |
| 184 | " | " | " | " | " | OCH₃ | " | " |
| 185 | " | " | " | " | " | CN | " | " |
| 186 | p-F—Ph | " | " | " | " | H | " | " |
| 187 | " | " | " | " | Br | " | " | " |
| 188 | " | " | " | " | H | Br | " | " |
| 189 | " | " | " | " | " | H | Br | " |
| 190 | " | " | " | " | Br | " | " | " |
| 191 | " | " | " | " | F | " | H | " |
| 192 | " | " | " | " | H | " | F | " |
| 193 | " | " | " | " | " | Cl | H | " |

TABLE 1-continued

| No. | X | Q | n | R₃ | R₄ | R₅ | R₆ | m |
|---|---|---|---|---|---|---|---|---|
| 194 | " | " | " | " | " | OCH₃ | " | " |
| 195 | " | " | " | " | " | CN | " | " |
| 196 | " | " | " | 1 | " | H | " | " |
| 197 | " | " | " | " | " | Br | " | " |
| 198 | " | " | " | " | " | H | Br | " |
| 199 | " | " | " | " | " | H | " | Br |
| 200 | " | " | " | " | " | Br | " | " |
| 201 | p-F—Ph | " | " | 1 | H | F | H | H |
| 202 | " | " | " | " | " | H | " | F |
| 203 | " | " | " | " | " | " | Cl | H |
| 204 | " | " | " | " | " | " | OCH₃ | " |
| 205 | " | " | " | " | " | " | CN | " |
| 206 | p-F—Ph | O | 2 | " | " | H | " | " |
| 207 | " | " | " | " | " | Br | " | " |
| 208 | " | " | " | " | " | H | Br | " |
| 209 | " | " | " | " | " | " | H | Br |
| 210 | " | " | " | " | " | Br | " | " |
| 211 | p-F—Ph | O | 2 | H | F | H | H | 1 |
| 212 | " | " | " | " | H | " | F | " |
| 213 | " | " | " | " | " | " | Cl | H |
| 214 | " | " | " | " | " | " | OCH₃ | " |
| 215 | " | " | " | " | " | " | CN | " |
| 216 | " | " | 3 | " | " | H | " | " |
| 217 | " | " | " | " | " | Br | " | " |
| 218 | " | " | " | " | " | H | Br | " |
| 219 | " | " | " | " | " | H | " | Br |
| 220 | " | " | " | " | " | Br | " | " |
| 221 | " | " | " | " | " | F | " | H |
| 222 | " | " | " | " | " | H | " | F |
| 223 | " | " | " | " | " | " | Cl | H |
| 224 | " | " | " | " | " | " | OCH₃ | " |
| 225 | " | " | " | " | " | " | CN | " |
| 226 | " | " | 4 | " | " | H | " | " |
| 227 | " | " | " | " | " | Br | " | " |
| 228 | " | " | " | " | " | H | Br | " |
| 229 | " | " | " | " | " | H | Br | " |
| 230 | " | " | " | " | " | Br | " | " |
| 231 | " | " | " | " | " | F | " | H |
| 232 | " | " | " | " | " | H | " | F |
| 233 | " | " | " | " | " | " | Cl | H |
| 234 | " | " | " | " | " | " | OCH₃ | " |
| 235 | " | " | " | " | " | " | CN | " |
| 236 | 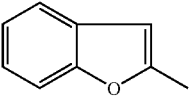 | CH₂ | 0 | " | " | H | " | " |
| 237 | " | " | " | " | " | Br | " | " |
| 238 | " | " | " | " | " | H | F | " |
| 239 | " | " | " | " | " | OCH₃ | H | " |
| 240 | " | " | " | " | " | CN | " | " |
| 241 | 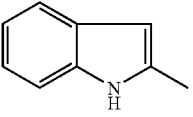 | " | 1 | H | H | H | H | 1 |
| 242 | " | " | " | " | " | Br | " | " |
| 243 | " | " | " | " | " | H | F | " |
| 244 | " | " | " | " | " | OCH₃ | H | " |
| 245 | " | " | " | " | " | CN | " | " |
| 246 | 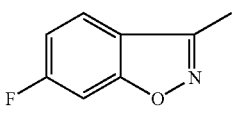 | CH₂ | 0 | H | H | H | H | 1 |
| 247 | " | " | " | " | " | Br | " | " |
| 248 | " | " | " | " | " | H | F | " |
| 249 | " | " | " | " | " | OCH₃ | H | " |
| 250 | " | " | " | " | " | CN | " | " |

TABLE 1-continued

| No. | X | Q | n | R₃ | R₄ | R₅ | R₆ | m |
|---|---|---|---|---|---|---|---|---|
| 251 | 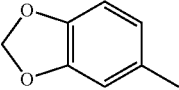 | C=O | 1 | " | " | H | " | " |
| 252 | " | " | " | " | " | Br | " | " |
| 253 | " | " | " | " | " | H | F | " |
| 254 | " | " | " | " | " | OCH₃ | H | " |
| 255 | " | " | " | " | " | CN | " | " |
| 256 | 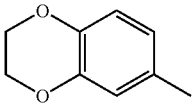 | " | " | " | " | H | " | " |
| 257 | " | " | " | " | " | Br | " | " |
| 258 | " | " | " | " | " | H | F | " |
| 259 | " | " | " | " | " | OCH₃ | H | " |
| 260 | " | " | " | " | " | CN | " | " |
| 261 | 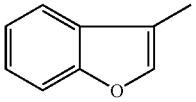 | CH₂ | 0 | " | " | H | " | " |
| 262 | " | " | " | " | " | Br | " | " |
| 263 | " | " | " | " | " | H | F | " |
| 264 | " | " | " | " | " | OCH₃ | H | " |
| 265 | " | " | " | " | " | CN | " | " |
| 266 | 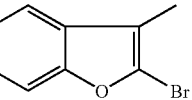 | " | " | " | " | H | " | " |
| 267 | " | " | " | " | " | Br | " | " |
| 268 | " | " | " | " | " | H | F | " |
| 269 | " | " | " | " | " | OCH₃ | H | " |
| 270 | " | " | " | " | " | CN | " | " |
| 271 | p-F—Ph—NH | C=O | 1 | H | H | H | H | 1 |
| 272 | " | " | " | H | H | Br | H | " |
| 273 | " | " | " | H | H | OCH₃ | H | " |
| 274 | " | " | 2 | H | H | H | H | " |
| 275 | " | CH₂ | 1 | H | H | H | H | " |
| 276 | " | CHOH | " | H | H | H | H | " |
| 277 | " | C=O | " | H | H | H | F | " |
| 278 | (Ph)₂N | " | " | H | H | H | H | " |
| 279 | " | " | " | H | H | Br | H | " |
| 280 | " | " | " | H | H | OCH₃ | H | " |
| 281 | " | " | 2 | H | H | H | H | " |
| 282 | " | CHOH | 1 | H | H | H | H | " |
| 283 | " | C=O | " | H | H | H | F | " |
| 284 | Ph—N(CH₃) | " | " | H | H | H | H | " |
| 285 | " | " | " | H | H | Br | H | " |
| 286 | " | " | " | H | H | OCH₃ | H | " |
| 287 | " | " | 2 | H | H | H | H | " |
| 288 | " | CHOH | 1 | H | H | H | H | " |
| 289 | " | C=O | " | H | H | H | F | " |
| 290 | p-F—PhN(CH₃) | " | " | H | H | H | H | " |
| 291 | " | " | " | H | H | Br | H | " |
| 292 | " | " | " | H | H | OCH₃ | H | " |
| 293 | " | CHOH | " | H | H | H | H | " |
| 294 | " | C=O | " | H | H | H | F | " |
| 295 | " | CH₂ | " | H | H | H | H | " |
| 296 | 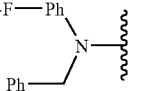 | C=O | " | H | H | H | H | " |
| 297 | " | " | " | H | H | Br | H | " |
| 298 | " | " | " | H | H | OCH₃ | H | " |
| 299 | " | CHOH | " | H | H | H | H | " |

TABLE 1-continued

| No. | X | Q | n | R₃ | R₄ | R₅ | R₆ | m |
|---|---|---|---|---|---|---|---|---|
| 300 | " | C=O | " | H | H | H | F | " |
| 301 | " | CH₂ | " | H | H | H | H | " |
| 302 | (p-CH₃O—Ph)NH | C=O | " | H | H | H | H | " |
| 303 | " | " | " | H | H | Br | H | " |
| 304 | " | " | " | H | H | OCH₃ | H | " |
| 305 | " | CHOH | " | H | H | H | H | " |
| 306 | " | C=O | " | H | H | H | F | " |
| 307 | " | CH₂ | " | H | H | H | H | " |
| 308 | (m-CH₃O—Ph)NH | C=O | " | H | H | H | H | " |
| 309 | " | " | " | H | H | Br | H | " |
| 310 | " | " | " | H | H | OCH₃ | H | " |
| 311 | (m-CH₃O—Ph)NH | CHOH | 1 | H | H | H | H | 1 |
| 312 | " | C=O | " | H | H | H | F | " |
| 313 | " | CH₂ | " | H | H | H | H | " |
| 314 | (o-CH₃O—Ph)NH | C=O | " | H | H | H | H | " |
| 315 | " | " | " | H | H | Br | H | " |
| 316 | " | " | " | H | H | OCH₃ | H | " |
| 317 | " | CHOH | " | H | H | H | H | " |
| 318 | " | C=O | " | H | H | H | F | " |
| 319 | " | CH₂ | " | H | H | H | H | " |
| 320 | 1,2,3,4-tetrahydroquinolin-1-yl | C=O | 1 | H | H | H | H | " |
| 321 | " | " | " | H | H | Br | H | " |
| 322 | " | " | " | H | H | H | F | " |
| 323 | " | " | " | H | H | OCH₃ | H | " |
| 324 | " | C=O | 2 | H | H | H | H | 1 |
| 325 | " | CH₂ | 1 | H | H | H | H | " |
| 326 | " | CHOH | " | H | H | H | H | " |
| 327 | " | C=O | " | H | H | H | F | " |
| 328 | piperidin-1-yl | " | 1 | H | H | H | H | " |
| 329 | " | " | " | H | H | Br | H | " |
| 330 | " | " | " | H | H | OCH₃ | H | " |
| 331 | " | CHOH | " | H | H | H | H | " |
| 332 | " | C=O | " | H | H | H | F | " |
| 333 | 2,3-dihydro-1H-indol-1-yl | " | " | H | H | H | H | " |
| 334 | " | " | " | H | H | Br | H | " |
| 335 | " | " | " | H | H | OCH₃ | H | " |
| 336 | " | " | " | H | H | H | F | " |
| 337 | " | CHOH | " | H | H | H | H | " |
| 338 | " | CH₂ | " | H | H | H | H | " |
| 339 | 1,2,3,4-tetrahydroisoquinolin-2-yl | C=O | " | H | H | H | H | " |
| 340 | " | " | " | H | H | Br | H | " |
| 341 | " | " | " | H | H | OCH₃ | H | " |
| 342 | " | " | " | H | H | H | F | " |
| 343 | " | CHOH | " | H | H | H | H | " |
| 344 | Ph—(CH₂)₂— | C=O | 1 | H | H | H | H | 1 |
| 345 | " | " | " | H | H | Br | H | " |
| 346 | " | " | " | H | H | OCH₃ | H | " |
| 347 | " | " | " | H | H | H | F | " |
| 348 | " | CHOH | " | H | H | H | H | " |

TABLE 1-continued

| No. | X | Q | n | R$_3$ | R$_4$ | R$_5$ | R$_6$ | m |
|---|---|---|---|---|---|---|---|---|
| 349 | Ph—CH$_2$— | C=O | " | H | H | H | H | " |
| 350 | " | " | " | H | H | Br | H | " |
| 351 | " | " | " | H | H | H | F | " |
| 352 | " | " | " | H | H | OCH$_3$ | H | " |
| 353 | " | " | " | H | H | CN | H | " |
| 354 | " | " | 2 | H | H | H | H | " |
| 355 | " | " | " | H | H | Br | H | " |
| 356 | " | " | 1 | H | H | H | F | " |
| 357 | " | CHOH | " | H | H | H | H | " |
| 358 | p-F—PhC(=CH$_2$)— | CH$_2$ | 0 | H | H | H | H | " |
| 359 | " | C=O | 1 | H | H | H | H | " |
| 360 | " | " | " | H | H | Br | H | " |
| 361 | " | " | " | H | H | OCH$_3$ | H | " |
| 362 | " | " | " | H | H | H | F | " |
| 363 | " | CHOH | " | H | H | H | H | " |
| 364 | Ph—CH=CH— | CH$_2$ | 0 | H | H | H | H | " |
| 365 | " | C=O | 1 | H | H | H | H | " |
| 366 | " | " | " | H | H | Br | H | " |
| 367 | " | " | " | H | H | OCH$_3$ | H | " |
| 368 | " | " | " | H | H | H | F | " |
| 369 | " | CHOH | " | H | H | H | H | " |
| 370 | Ph—C≡C— | CH$_2$ | 0 | H | H | H | H | " |
| 371 | " | C=O | 1 | H | H | H | H | " |
| 372 | " | " | " | H | H | Br | H | " |
| 373 | " | " | " | H | H | OCH$_3$ | H | " |
| 374 | " | " | " | H | H | H | F | " |
| 375 | " | CHOH | " | H | H | H | H | " |
| 376 | o-H$_3$CO—Ph | C=O | " | H | H | H | H | 1 |
| 377 | " | " | " | H | H | Br | H | " |
| 378 | " | " | " | H | H | OCH$_3$ | H | " |
| 379 | " | " | " | H | H | H | F | " |
| 380 | " | CHOH | " | H | H | H | H | " |
| 381 | m-H$_3$CO—Ph | C=O | 1 | H | H | H | H | 1 |
| 382 | " | " | " | H | H | Br | H | " |
| 383 | " | " | " | H | H | OCH$_3$ | H | " |
| 384 | " | " | " | H | H | H | F | " |
| 385 | " | CHOH | " | H | H | H | H | " |
| 386 | o-CH$_3$—Ph | C=O | " | H | H | H | H | " |
| 387 | " | " | " | H | H | Br | H | " |
| 388 | " | " | " | H | H | OCH$_3$ | H | " |
| 389 | " | " | " | H | H | H | F | " |
| 390 | " | CHOH | " | H | H | H | H | " |
| 391 | m-CH$_3$—Ph | C=O | " | H | H | H | H | " |
| 392 | " | " | " | H | H | Br | H | " |
| 393 | " | " | " | H | H | OCH$_3$ | H | " |
| 394 | " | " | " | H | H | H | F | " |
| 395 | " | CHOH | " | H | H | H | H | " |
| 396 | p-CH$_3$—Ph | C=O | " | H | H | H | H | " |
| 397 | " | " | " | H | H | Br | H | " |
| 398 | " | " | " | H | H | OCH$_3$ | H | " |
| 399 | " | " | " | H | H | H | F | " |
| 400 | " | CHOH | " | H | H | H | H | " |
| 401 | o,m-diF—Ph | C=O | " | H | H | H | H | " |
| 402 | " | " | " | H | H | Br | H | " |
| 403 | " | " | " | H | H | OCH$_3$ | H | " |
| 404 | " | " | " | H | H | H | F | " |
| 405 | " | CHOH | " | H | H | H | H | " |
| 406 | m-Cl—Ph | C=O | " | H | H | H | H | " |
| 407 | " | " | " | H | H | Br | H | " |
| 408 | " | " | " | H | H | OCH$_3$ | H | " |
| 409 | " | " | " | H | H | H | F | " |
| 410 | " | CHOH | " | H | H | H | H | " |
| 411 | 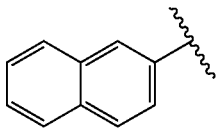 | C=O | " | H | H | H | H | " |
| 412 | " | " | " | H | H | Br | H | " |
| 413 | " | " | " | H | H | OCH$_3$ | H | " |
| 414 | " | " | " | H | H | H | F | " |
| 415 | " | CHOH | " | H | H | H | H | " |

TABLE 1-continued

| No. | X | Q | n | R₃ | R₄ | R₅ | R₆ | m |
|---|---|---|---|---|---|---|---|---|
| 416 | furan-2-yl | C=O | 1 | H | H | H | H | 1 |
| 417 | " | " | " | H | H | Br | H | " |
| 418 | " | " | " | H | H | OCH₃ | H | " |
| 419 | " | " | " | H | H | H | F | " |
| 420 | " | CHOH | " | H | H | H | H | " |
| 421 | thiophen-2-yl | C=O | " | H | H | H | H | " |
| 422 | " | " | " | H | H | Br | H | " |
| 423 | " | " | " | H | H | OCH₃ | H | " |
| 424 | " | " | " | H | H | H | F | " |
| 425 | " | CHOH | " | H | H | H | H | " |
| 426 | 5-bromothiophen-2-yl | C=O | " | H | H | H | H | " |
| 427 | " | " | " | H | H | Br | H | " |
| 428 | " | " | " | H | H | OCH₃ | H | " |
| 429 | " | " | " | H | H | H | F | " |
| 430 | " | CHOH | " | H | H | H | H | " |
| 431 | 1-benzylpyrrol-2-yl | C=O | " | H | H | H | H | " |
| 432 | " | " | " | H | H | Br | H | " |
| 433 | " | " | " | H | H | OCH₃ | H | " |
| 434 | " | " | " | H | H | H | F | " |
| 435 | " | CHOH | " | H | H | H | H | " |
| 436 | 1-n-butylpyrrol-2-yl | C=O | " | H | H | H | H | " |
| 437 | " | " | " | H | H | Br | H | " |
| 438 | " | " | " | H | H | OCH₃ | H | " |
| 439 | " | " | " | H | H | H | F | " |
| 440 | " | CHOH | " | H | H | H | H | " |
| 441 | 1-phenylpyrrol-2-yl | C=O | 1 | H | H | H | H | " |
| 442 | " | " | " | H | H | Br | H | " |
| 443 | " | " | " | H | H | OCH₃ | H | " |
| 444 | " | " | " | H | H | H | F | " |
| 445 | " | CHOH | " | H | H | H | H | " |
| 446 | cyclohexyl | C=O | 1 | H | H | H | H | 1 |

TABLE 1-continued

| No. | X | Q | n | R₃ | R₄ | R₅ | R₆ | m |
|---|---|---|---|---|---|---|---|---|
| 447 | " | " | " | H | H | Br | H | " |
| 448 | " | " | " | H | H | H | F | " |
| 449 | " | " | " | H | H | OCH₃ | H | " |
| 450 | " | " | " | H | H | CN | H | " |
| 451 | " | CHOH | 1 | H | H | H | H | " |
| 452 | " | " | " | H | H | Br | H | " |
| 453 | " | " | " | H | H | OCH₃ | H | " |
| 454 | " | C(=NOH) | " | H | H | H | H | " |
| 455 | " | " | " | H | H | Br | H | " |
| 456 | 2-Ph—Ph | CH₂ | 0 | H | H | H | H | " |
| 457 | " | " | " | H | H | Br | H | " |
| 458 | " | " | " | H | H | H | F | " |
| 459 | " | " | " | H | H | OCH₃ | H | " |
| 460 | " | " | " | H | H | CN | H | " |
| 461 | [2-(furan-2-yl)phenyl] | CH₂ | 0 | H | H | H | H | 1 |
| 462 | " | " | " | H | H | Br | H | " |
| 463 | " | " | " | H | H | H | F | " |
| 464 | " | " | " | H | H | OCH₃ | H | " |
| 465 | " | " | " | H | H | CN | H | " |
| 466 | (2-Ph—CO)Ph | " | " | H | H | H | H | " |
| 467 | " | " | " | H | H | Br | H | " |
| 468 | " | " | " | H | H | H | F | " |
| 469 | " | " | " | H | H | OCH₃ | H | " |
| 470 | " | " | " | H | H | CN | H | " |
| 471 | [5-(p-Cl-Ph)furan-2-yl] | CH₂ | 0 | H | H | H | H | " |
| 472 | " | " | " | H | H | Br | H | " |
| 473 | " | " | " | H | H | H | F | " |
| 474 | " | " | " | H | H | OCH₃ | H | " |
| 475 | " | " | " | H | H | CN | H | " |
| 476 | [1-phenylpyrrol-2-yl] | CH₂ | 0 | H | H | H | H | " |
| 477 | " | " | " | H | H | Br | H | " |
| 478 | " | " | " | " | H | H | F | " |
| 479 | " | " | " | H | H | OCH₃ | H | " |
| 480 | " | " | " | H | H | CN | H | " |
| 481 | [1-phenylpyrrol-3-yl] | " | " | H | H | H | H | " |
| 482 | " | " | " | H | H | Br | H | " |
| 483 | " | " | " | H | H | H | F | " |
| 484 | " | " | " | H | H | OCH₃ | H | " |
| 485 | " | " | " | H | H | CN | H | " |

TABLE 1-continued

| No. | X | Q | n | R₃ | R₄ | R₅ | R₆ | m |
|---|---|---|---|---|---|---|---|---|
| 486 | *2-(N-benzyl-pyrrol-2-yl)* | " | " | H | H | H | H | " |
| 487 | " | " | " | H | H | Br | H | " |
| 488 | " | " | " | H | H | H | F | " |
| 489 | " | " | " | H | H | OCH₃ | H | " |
| 490 | " | " | " | H | H | CN | H | " |
| 491 | *2-(N-n-Bu-pyrrol-2-yl)* | " | " | H | H | H | H | " |
| 492 | " | " | " | H | H | Br | H | " |
| 493 | " | " | " | H | H | H | F | " |
| 494 | " | " | " | H | H | OCH₃ | H | " |
| 495 | " | " | " | H | H | CN | H | " |
| 496 | *pyrrol-2-yl* | " | " | H | H | H | H | " |
| 497 | " | " | " | H | H | Br | H | " |
| 498 | " | " | " | H | H | H | F | " |
| 499 | " | " | " | H | H | OCH₃ | H | " |
| 500 | " | " | " | H | H | CN | H | " |
| 501 | 2-(n-Pr)O—Ph | " | 1 | H | H | H | H | " |
| 502 | " | " | " | H | H | Br | H | " |
| 503 | " | " | " | H | H | H | F | " |
| 504 | " | " | " | H | H | OCH₃ | H | " |
| 505 | " | " | " | H | H | CN | H | " |
| 506 | 2-Ph—CH₂O—Ph | CH₂ | 1 | H | H | H | H | 1 |
| 507 | " | " | " | H | H | Br | H | " |
| 508 | " | " | " | H | H | H | F | " |
| 509 | " | " | " | H | H | OCH₃ | H | " |
| 510 | " | " | " | H | H | CN | H | " |
| 511 | 2-Ph—Ph | " | " | H | H | H | H | " |
| 512 | " | " | " | H | H | Br | H | " |
| 513 | " | " | " | H | H | H | F | " |
| 514 | " | " | " | H | H | OCH₃ | H | " |
| 515 | " | " | " | H | H | CN | H | " |
| 516 | 2-Ph—EtO—Ph | " | " | H | H | H | H | " |
| 517 | " | " | " | H | H | Br | H | " |
| 518 | " | " | " | H | H | H | F | " |
| 519 | " | " | " | H | H | OCH₃ | H | " |
| 520 | " | " | " | H | H | CN | H | " |
| 521 | o-CF₃—Ph | CH₂ | 1 | H | H | H | H | 1 |
| 522 | " | " | " | H | H | Br | H | " |
| 523 | " | " | " | H | H | H | H | " |
| 524 | " | " | " | H | H | OCH₃ | H | " |
| 525 | " | " | " | H | H | CN | H | " |
| 526 | *naphth-1-yl* | CH₂ | 1 | H | H | H | H | 1 |
| 527 | " | " | " | H | H | Br | H | " |
| 528 | " | " | " | H | H | H | F | " |
| 529 | " | " | " | H | H | OCH₃ | H | " |
| 530 | " | " | " | H | H | CN | H | " |

TABLE 1-continued

| No. | X | Q | n | R₃ | R₄ | R₅ | R₆ | m |
|---|---|---|---|---|---|---|---|---|
| 531 | (2-naphthyl) | " | " | H | H | H | H | " |
| 532 | " | " | " | H | H | Br | H | " |
| 533 | " | " | " | H | H | H | F | " |
| 534 | " | " | " | H | H | OCH₃ | H | " |
| 535 | " | " | " | H | H | CN | H | " |
| 536 | m-CH₃—Ph | CH₂ | 1 | H | H | H | H | 1 |
| 537 | " | " | " | H | H | Br | H | " |
| 538 | " | " | " | H | H | H | F | " |
| 539 | " | " | " | H | H | OCH₃ | H | " |
| 540 | " | " | " | H | H | CN | H | " |
| 541 | m-F—Ph | CH₂ | 1 | H | H | H | H | 1 |
| 542 | " | " | " | H | H | Br | H | " |
| 543 | " | " | " | H | H | H | F | " |
| 544 | " | " | " | H | H | OCH₃ | H | " |
| 545 | " | " | " | H | H | CN | H | " |
| 546 | p-CH₃O—Ph | " | " | H | H | H | H | " |
| 547 | " | " | " | H | H | Br | H | " |
| 548 | " | " | " | H | H | H | F | " |
| 549 | " | " | " | H | H | OCH₃ | H | " |
| 550 | " | " | " | H | H | CN | H | " |
| 551 | m-CH₃O—Ph | " | " | H | H | H | H | " |
| 552 | " | " | " | H | H | Br | H | " |
| 553 | " | " | " | H | H | H | F | " |
| 554 | " | " | " | H | H | OCH₃ | H | " |
| 555 | " | " | " | H | H | CN | H | " |
| 556 | o-NO₂—Ph | " | " | H | H | H | H | " |
| 557 | " | " | " | H | H | Br | H | " |
| 558 | " | " | " | H | H | H | F | " |
| 559 | " | " | " | H | H | OCH₃ | H | " |
| 560 | " | " | " | H | H | CN | H | " |
| 561 | o-NH₂—Ph | CH₂ | 1 | H | H | H | H | 1 |
| 562 | " | " | " | H | H | Br | H | " |
| 563 | " | " | " | H | H | H | F | " |
| 564 | " | " | " | H | H | OCH₃ | H | " |
| 565 | " | " | " | H | H | CN | H | " |
| 566 | o-CH₃CONH—Ph | " | " | H | H | H | H | " |
| 567 | " | " | " | H | H | Br | H | " |
| 568 | " | " | " | H | H | H | F | " |
| 569 | " | " | " | H | H | OCH₃ | H | " |
| 570 | " | " | " | H | H | CN | H | " |
| 571 | o-CH₃NH—Ph | " | " | H | H | H | H | " |
| 572 | " | " | " | H | H | Br | H | " |
| 573 | " | " | " | H | H | H | F | " |
| 574 | " | " | " | H | H | OCH₃ | H | " |
| 575 | " | " | " | H | H | CN | H | " |
| 576 | (isoindolin-1-one-2-yl) | CH₂ | 1 | H | H | H | H | " |
| 577 | " | " | " | H | H | Br | H | " |
| 578 | " | " | " | H | H | H | F | " |
| 579 | " | " | " | H | H | OCH₃ | H | " |
| 580 | " | " | " | H | H | CN | H | " |
| 581 | " | " | 2 | H | H | H | H | " |
| 582 | " | " | " | H | H | Br | H | " |
| 583 | " | " | " | H | H | H | F | " |
| 584 | " | " | " | H | H | OCH₃ | H | " |
| 585 | " | " | " | H | H | CN | H | " |
| 586 | " | " | 3 | H | H | H | H | " |
| 587 | " | " | " | H | H | Br | H | " |
| 588 | " | " | " | H | H | H | F | " |
| 589 | " | " | " | H | H | OCH₃ | H | " |
| 590 | " | " | " | H | H | CN | H | " |

TABLE 1-continued

| No. | X | Q | n | R₃ | R₄ | R₅ | R₆ | m |
|---|---|---|---|---|---|---|---|---|
| 591 | 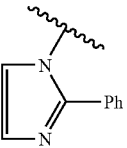 | CH₂ | 1 | H | H | H | H | 1 |
| 592 | " | " | " | H | H | Br | H | " |
| 593 | " | " | " | H | H | H | F | " |
| 594 | " | " | " | H | H | OCH₃ | H | " |
| 595 | " | " | " | H | H | CN | H | " |
| 596 | 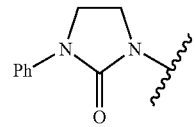 | " | 1 | H | H | H | H | " |
| 597 | " | " | " | H | H | Br | H | " |
| 598 | " | " | " | H | H | H | F | " |
| 599 | " | " | " | H | H | OCH₃ | H | " |
| 600 | " | " | " | H | H | CN | H | " |
| 601 | 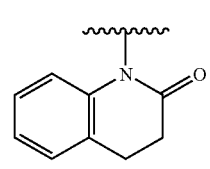 | CH₂ | 2 | H | H | H | H | 1 |
| 602 | " | " | " | H | H | Br | H | " |
| 603 | " | " | " | H | H | H | F | " |
| 604 | " | " | " | H | H | OCH₃ | H | " |
| 605 | " | " | " | H | H | CN | H | " |
| 606 | 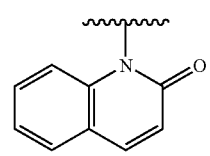 | " | " | H | H | H | H | " |
| 607 | " | " | " | H | H | Br | H | " |
| 608 | " | " | " | H | H | H | F | " |
| 609 | " | " | " | H | H | OCH₃ | H | " |
| 610 | " | " | " | H | H | CN | H | " |
| 611 | Ph | O | 2 | H | H | H | H | " |
| 612 | " | " | " | H | H | Br | H | " |
| 613 | " | " | " | H | H | H | F | " |
| 614 | " | " | " | H | H | OCH₃ | H | " |
| 615 | " | " | " | H | H | CN | H | " |
| 616 | o-F—Ph | " | " | H | H | H | H | " |
| 617 | " | " | " | H | H | Br | H | " |
| 618 | " | " | " | H | H | H | F | " |
| 619 | " | " | " | H | H | OCH₃ | H | " |
| 620 | " | " | " | H | H | CN | H | " |
| 621 | m-F—Ph | " | " | H | H | H | H | " |
| 622 | " | " | " | H | H | Br | H | " |
| 623 | " | " | " | H | H | H | F | " |
| 624 | " | " | " | H | H | OCH₃ | H | " |
| 625 | " | " | " | H | H | CN | H | " |
| 626 | p-Cl—Ph | " | " | H | H | H | H | " |
| 627 | " | " | " | H | H | Br | H | " |
| 628 | " | " | " | H | H | H | F | " |
| 629 | " | " | " | H | H | OCH₃ | H | " |
| 630 | " | " | " | H | H | CN | H | " |
| 631 | o-CH₃O—Ph | " | " | H | H | H | H | " |
| 632 | " | " | " | H | H | Br | H | " |
| 633 | " | " | " | H | H | H | F | " |
| 634 | " | " | " | H | H | OCH₃ | H | " |
| 635 | " | " | " | H | H | CN | H | " |
| 636 | m-CH₃O—Ph | " | " | H | H | H | H | " |
| 637 | " | " | " | H | H | Br | H | " |
| 638 | " | " | " | H | H | H | F | " |

TABLE 1-continued

| No. | X | Q | n | R₃ | R₄ | R₅ | R₆ | m |
|---|---|---|---|---|---|---|---|---|
| 639 | " | " | " | H | H | OCH₃ | H | " |
| 640 | " | " | " | H | H | CN | H | " |
| 641 | p-CH₃O—Ph | O | 2 | H | H | H | H | 1 |
| 642 | " | " | " | H | H | Br | H | " |
| 643 | " | " | " | H | H | H | F | " |
| 644 | " | " | " | H | H | OCH₃ | H | " |
| 645 | " | " | " | H | H | CN | H | " |
| 646 | o-CH₃—Ph | O | 2 | H | H | H | H | 1 |
| 647 | " | " | " | H | H | Br | H | " |
| 648 | " | " | " | H | H | H | F | " |
| 649 | " | " | " | H | H | OCH₃ | H | " |
| 650 | " | " | " | H | H | CN | H | " |
| 651 | m-CH₃—Ph | " | " | H | H | H | H | " |
| 652 | " | " | " | H | H | Br | H | " |
| 653 | " | " | " | H | H | H | F | " |
| 654 | " | " | " | H | H | OCH₃ | H | " |
| 655 | " | " | " | H | H | CN | H | " |
| 656 | p-CH₃—Ph | " | " | H | H | H | H | " |
| 657 | " | " | " | H | H | Br | H | " |
| 658 | " | " | " | H | H | H | F | " |
| 659 | " | " | " | H | H | OCH₃ | H | " |
| 660 | " | " | " | H | H | CN | H | " |
| 661 | p-CF₃—Ph | " | " | H | H | H | H | " |
| 662 | " | " | " | H | H | Br | H | " |
| 663 | " | " | " | H | H | H | F | " |
| 664 | " | " | " | H | H | OCH₃ | H | " |
| 665 | " | " | " | H | H | CN | H | " |
| 666 | p-CF₃O—Ph | " | " | H | H | H | H | " |
| 667 | " | " | " | H | H | Br | H | " |
| 668 | " | " | " | H | H | H | F | " |
| 669 | " | " | " | H | H | OCH₃ | H | " |
| 670 | " | " | " | H | H | CN | H | " |
| 671 | 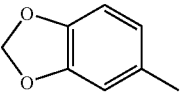 | " | " | H | H | H | H | " |
| 672 | " | " | " | H | H | Br | H | " |
| 673 | " | " | " | H | H | H | F | " |
| 674 | " | " | " | H | H | OCH₃ | H | " |
| 675 | " | " | " | H | H | CN | H | " |
| 676 | 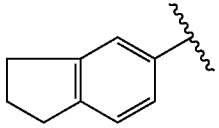 | O | 2 | H | H | H | H | 1 |
| 677 | " | " | " | H | H | Br | H | " |
| 678 | " | " | " | H | H | H | F | " |
| 679 | " | " | " | H | H | OCH₃ | H | " |
| 680 | " | " | " | H | H | CN | H | " |
| 681 | 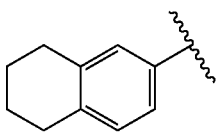 | O | 2 | H | H | H | H | 1 |
| 682 | " | " | " | H | H | Br | H | " |
| 683 | " | " | " | H | H | H | F | " |
| 684 | " | " | " | H | H | OCH₃ | H | " |
| 685 | " | " | " | H | H | CN | H | " |
| 686 | 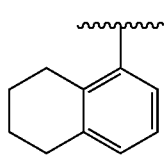 | " | " | H | H | H | H | " |
| 687 | " | " | " | H | H | Br | H | " |

TABLE 1-continued

| No. | X | Q | n | R₃ | R₄ | R₅ | R₆ | m |
|---|---|---|---|---|---|---|---|---|
| 688 | " | " | " | H | H | H | F | " |
| 689 | " | " | " | H | H | OCH₃ | H | " |
| 690 | " | " | " | H | H | CN | H | " |
| 691 | (2-PhCH₂CH₂)Ph | " | 3 | H | H | H | H | " |
| 692 | " | " | " | H | H | Br | H | " |
| 693 | " | " | " | H | H | H | F | " |
| 694 | " | " | " | H | H | OCH₃ | H | " |
| 695 | " | " | " | H | H | CN | H | " |
| 696 | 2-PhCH₂—Ph | " | " | H | H | H | H | " |
| 697 | " | " | " | H | H | Br | H | " |
| 698 | " | " | " | H | H | H | F | " |
| 699 | " | " | " | H | H | OCH₃ | H | " |
| 700 | " | " | " | H | H | CN | H | " |
| 701 | 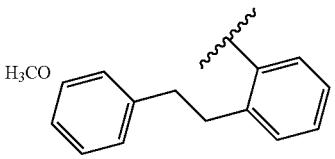 | " | " | H | H | H | H | " |
| 702 | " | " | " | H | H | Br | H | " |
| 703 | " | " | " | H | H | H | F | " |
| 704 | " | " | " | H | H | OCH₃ | H | " |
| 705 | " | " | " | H | H | CN | H | " |
| 706 | p-F—Ph | S | 2 | H | H | H | H | " |
| 707 | " | " | " | H | H | Br | H | " |
| 708 | " | " | " | H | H | H | F | " |
| 709 | " | " | " | H | H | OCH₃ | H | " |
| 710 | " | " | " | H | H | CN | H | " |
| 711 | " | " | 3 | H | H | H | H | " |
| 712 | " | " | " | H | H | Br | H | " |
| 713 | " | " | " | H | H | H | F | " |
| 714 | " | " | " | H | H | OCH₃ | H | " |
| 715 | " | " | " | H | H | CN | H | " |
| 716 | o-F—Ph | " | 2 | H | H | H | H | " |
| 717 | " | " | " | H | H | Br | H | " |
| 718 | " | " | " | H | H | H | F | " |
| 719 | " | " | " | H | H | OCH₃ | H | " |
| 720 | " | " | " | H | H | CN | H | " |
| 721 | m-F—Ph | " | " | H | H | H | H | " |
| 722 | " | " | " | H | H | Br | H | " |
| 723 | " | " | " | H | H | H | F | " |
| 724 | " | " | " | H | H | OCH₃ | H | " |
| 725 | " | " | " | H | H | CN | H | " |
| 726 | Ph | " | " | H | H | H | H | " |
| 727 | " | " | " | H | H | Br | H | " |
| 728 | " | " | " | H | H | H | F | " |
| 729 | " | " | " | H | H | OCH₃ | H | " |
| 730 | " | " | " | H | H | CN | H | " |
| 731 | o-CH₃O—Ph | S | 2 | H | H | H | H | 1 |
| 732 | " | " | " | H | H | Br | H | " |
| 733 | " | " | " | H | H | H | F | " |
| 734 | " | " | " | H | H | OCH₃ | H | " |
| 735 | " | " | " | H | H | CN | H | " |
| 736 | m-CH₃O—Ph | " | " | H | H | H | H | " |
| 737 | " | " | " | H | H | Br | H | " |
| 738 | " | " | " | H | H | H | F | " |
| 739 | " | " | " | H | H | OCH₃ | H | " |
| 740 | " | " | " | H | H | CN | H | " |
| 741 | 4-F—Ph | C=NOCH₃ | 1 | H | H | H | H | 1 |
| 742 | " | " | " | H | H | Br | H | " |
| 743 | " | " | " | H | H | H | F | " |
| 744 | " | " | " | H | H | OCH₃ | H | " |
| 745 | " | " | " | H | H | CN | H | " |
| 746 | 4-F—Ph | C=NNH(COOCH₃) | 1 | H | H | H | H | 1 |
| 747 | " | " | " | H | H | Br | H | " |
| 748 | " | " | " | H | H | H | F | " |
| 749 | " | " | " | H | H | OCH₃ | H | " |
| 750 | " | " | " | H | H | CN | H | " |
| 751 | " | C=NNH(COCH₃) | " | H | H | H | H | 1 |
| 752 | " | " | " | H | H | Br | H | " |
| 753 | " | " | " | H | H | H | F | " |
| 754 | " | " | " | H | H | OCH₃ | H | " |
| 755 | " | " | " | H | H | CN | H | " |

TABLE 1-continued

| No. | X | Q | n | R3 | R4 | R5 | R6 | m |
|---|---|---|---|---|---|---|---|---|
| 756 | " | C=NOCH2Ph | " | H | H | H | H | " |
| 757 | " | " | " | H | H | Br | H | " |
| 758 | " | " | " | H | H | H | F | " |
| 759 | " | " | " | H | H | OCH3 | H | " |
| 760 | " | " | " | H | H | CN | H | " |
| 761 | " | C=O | " | H | H | H | H | 2 |
| 762 | " | " | " | Br | H | H | H | " |
| 763 | " | " | " | H | Br | H | H | " |
| 764 | " | " | " | H | H | Br | H | " |
| 765 | " | " | " | H | H | H | Br | " |
| 766 | " | " | " | H | Br | H | Br | " |
| 767 | " | " | " | H | F | H | H | " |
| 768 | " | " | " | H | H | F | H | " |
| 769 | " | " | " | H | H | H | F | " |
| 770 | " | " | " | H | H | Cl | H | " |
| 771 | " | " | " | H | Cl | H | H | " |
| 772 | " | " | " | H | H | OCH3 | H | " |
| 773 | " | " | " | H | H | CN | H | " |
| 774 | " | " | " | H | NO2 | H | H | " |
| 775 | " | " | " | H | H | H | NO2 | " |

TABLE 2

| No. | X | Q | n | B |
|---|---|---|---|---|
| 776 | p-F—Ph | C=O | 1 | 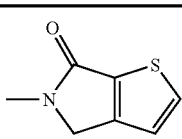 |
| 777 | " | " | 2 | " |
| 778 | " | " | 3 | " |
| 779 | " | " | 4 | " |
| 780 | " | CHOH | 1 | " |
| 781 | " | C=NOH | " | " |
| 782 | " | CHOAc | " | " |
| 783 | " | CH2 | " | " |
| 784 | Ph | C=O | " | " |
| 785 | " | CHOH | " | " |
| 786 | " | C=NOH | " | " |
| 787 | " | CHOAc | " | " |
| 788 | " | CH2 | " | " |
| 789 | p-Cl—Ph | C=O | " | " |
| 790 | " | CHOH | " | " |
| 791 | " | C=NOH | " | " |
| 792 | p-OCH3—Ph | C=O | " | " |
| 793 | " | CHOH | " | " |
| 794 | " | C=NOH | " | " |
| 795 | t-Bu | C=O | " | " |
| 796 | p-F—Ph | C=O | 1 | 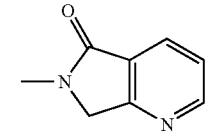 |
| 797 | " | " | 2 | " |
| 798 | " | " | 3 | " |
| 799 | " | " | 4 | " |
| 800 | " | CHOH | 1 | " |
| 801 | " | C=NOH | " | " |
| 802 | " | CHOAc | " | " |
| 803 | " | CH2 | " | " |
| 804 | Ph | C=O | " | " |
| 805 | " | CHOH | " | " |
| 806 | " | C=NOH | " | " |
| 807 | " | CHOAc | " | " |
| 808 | " | CH2 | " | " |
| 809 | p-Cl—Ph | C=O | " | " |
| 810 | " | CHOH | " | " |
| 811 | p-Cl—Ph | C=NOH | 1 | 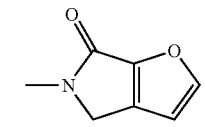 |
| 812 | p-OCH3—Ph | C=O | " | " |
| 813 | " | CHOH | " | " |
| 814 | " | C=NOH | " | " |
| 815 | t-Bu | C=O | " | " |
| 816 | p-F—Ph | C=O | 0 | 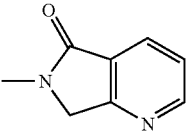 |
| 817 | " | " | 1 | " |
| 818 | " | " | 2 | " |
| 819 | " | " | 3 | " |
| 820 | " | CHOH | 1 | " |
| 821 | " | C=NOH | " | " |
| 822 | " | CHOAc | " | " |
| 823 | " | CH2 | " | " |
| 824 | Ph | C=O | " | " |
| 825 | " | CHOH | " | " |
| 826 | " | C=NOH | " | " |
| 827 | " | CHOAc | " | " |
| 828 | " | CH2 | " | " |
| 829 | p-Cl—Ph | C=O | " | " |
| 830 | " | CHOH | " | " |
| 831 | " | C=NOH | " | " |
| 832 | p-OCH3—Ph | C=O | " | " |
| 833 | " | CHOH | " | " |
| 834 | " | C=NOH | " | " |
| 835 | t-Bu | C=O | " | " |

Methods for preparing the compounds of present invention represented by formula (I) are not particularly limited. For example, the compounds can be prepared by any one of the methods described below. The preparations of preferred compounds falling within the compounds of present invention will be more specifically explained in the examples of the specification. Accordingly, those skilled in the art can prepare any of the compounds of present invention falling within the formula (I) by referring to the general explanations which follows and specific explanations of the examples, and suitably modifying or altering starting materials, reaction conditions, reagents and the like, if necessary.

Method for Preparation

Scheme A:

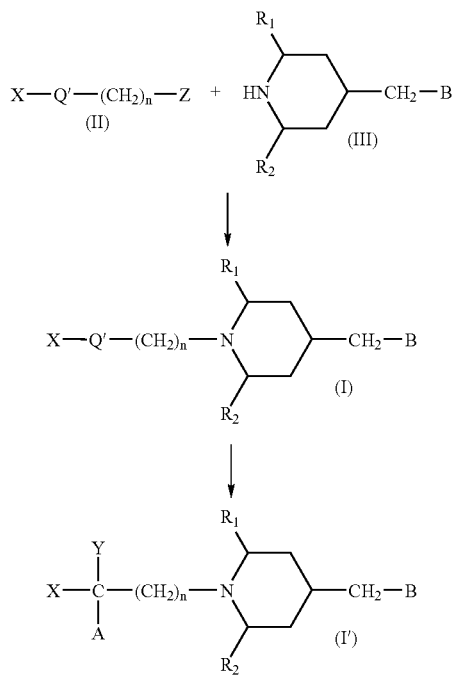

A compound of the formula (II) (in the formula, Z represents a halogen atom such as chlorine atom, bromine atom, or iodine atom, or tosylate or mesylate or the like, Q' represents —$CH_2$—, —CO—, —O— or —S—, and X is as described above) can be reacted with a nucleophilic amino derivative represented by the formula (III) ($R_1$, $R_2$, and B have the same meanings as those defined above) to obtain a corresponding compound of the formula (I). This reaction may usually be performed in a polar solvent such as dimethylformamide, N-methylpyrrolidone, ethanol, or acetonitrile in the presence of a base such as triethylamine, sodium hydrogencarbonate, or potassium carbonate.

When Q' is —CO—, the amino-keto derivative of the formula (I) can be reduced to obtain a hydroxy derivative of the formula (I') wherein A is hydroxyl group and Y is hydrogen atom. In general, the reduction can be performed at room temperature in an organic solvent such as ethanol, methanol, or tetrahydrofuran using sodium borohydride. The amino-keto derivative of the formula (I) can also be reacted with an organic metal reagent such as Y—MgBr to obtain a compound of the formula (I') wherein A is hydroxyl group.

The acyloxy and alkoxyl compounds can be prepared by usual methods starting from a free hydroxy derivative. An O-alkyl derivative can be prepared by solvolysis of a sulfonyl ester intermediate [Advanced Organic Chemistry, J. March., John Wiley & Sons, New York, pp. 264–317, 1985]. A chiral ether can also be obtained by solvolysis of a chiral sulfonyl ester derivative such as camphorsulfonate. An oxime of the keto derivative of the formula (I) wherein Q' is —CO— can be prepared by an oxime preparation such as those described in Organic Functional Group Preparation Vol. III, S. R. Sandler and W. Karo, Academic Press, London, pp. 430–481, 1989.

As the compound of formula (II) shown in scheme A wherein Q' is —$CH_2$— or —CO—, commercially available compounds may be used, or the compounds can be obtained by halogenation using a compound substituted with an alkyl group or an alkylketone group as a starting material or by any similar method. Where Q' is —O— or —S—, commercially available compounds may be used, or the compounds can be obtained by reacting a compound substituted with hydroxyl group or thiol group as a starting material with Z($CH_2$)nZ' (wherein Z and Z' represent a halogen atom, tosylate, mesylate or the like) or by any similar method.

As the syntheses of benzisoxazolidine derivative and benzisothioxazoline derivative, examples includes the methods described in known references [H. Uno, M. Kurokawa, K. Natsuka, Y. Yamato and H. Nishimura, Chem. Pharm. Bull., 24 (4), pp. 632–643, 1976; H. Uno and M. Kurokawa, Chem. Pharm. Bull., 26 (12), pp. 3888–3891, 1978].

Scheme B:

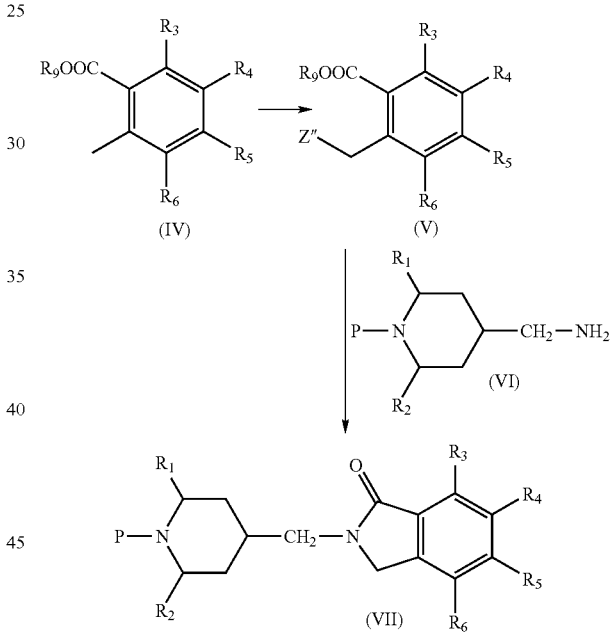

A compound of the formula (III) as the starting material in the scheme A above wherein m represent 1 can be produced as shown in the above-described scheme B according to the method of P. D. Leeson et al., (J. Med. Chem., 35, 1954–1968, 1992). A compound of formula (IV) (wherein $R_9$ represents an alkyl group, and $R_3$, $R_4$, $R_5$, and $R_6$ are as defined above) is halogenated in a solvent such as carbon tetrachloride by using, for example, N-bromosuccinimide to obtain a compound of formula (V) (wherein Z' represents a halogen atom) which is then allowed to react with a compound of formula (VI).

The substituent P of the compounds shown in the scheme represents a protective group for amino group such as those described in Protective Groups in Organic Synthesis [T. W. Greene and P. G. M. Wuts, John Wiley & Sons, New York, 1991], and the protective group is readily removed to give a piperidine compound of the formula (III).

Alternatively, compounds of formula (VII) may also be synthesized according to the methods described in literature (I. Takahashi, T. Kawakami, E. Hirano, H. Yokota and H. Kitajima, Synlett, 4, 353–355, 1996; S. M. Allin, C. C. Hodkinson and N. Taj, Synlett. 8, 781–782, 1996).

Compounds used as starting materials in the aforementioned methods may be a racemate or a desired optically active substance, and a corresponding racemate or an optical, active compound can be produced. It is also possible to produce a desired optically active substance by optical resolution according to known conventional methods. Basic compounds of the formula (I) can form acid addition salts, preferably pharmacologically acceptable salts, with various inorganic and organic acids. These salts can be easily prepared by treating a basic compound of the formula (I) with a mineral acid or an organic acid in a suitable organic solvent such as methanol, ethanol, isopropanol, or ethyl acetate.

The compounds of the present invention represented by the aforementioned general formula (I) may have one or more asymmetric carbons, and therefore the compounds may exist as optical isomers. Any of racemates, optical isomers in an optically pure form, and any mixtures of optical isomers fall within the scope of the present invention. Racemates can be resolved into optically pure enantiomers by a method well known to those skilled in the art. Furthermore, diastereomers based on two or more asymmetric carbons, and any mixtures thereof also fall within the scope of the present invention. Acid addition salts, preferably pharmaceutically acceptable acid addition salts, hydrates and any solvates of the compounds of the present invention represented by the aforementioned general formula (I) also fall within the scope of the present invention.

Examples of salts that can be formed with the compounds of the present invention include, for example, inorganic acid salts such as hydrochlorides, hydrobromides, hydroiodides, sulfates, nitrates, and phosphates, organic acid salts such as succinates, acetates, glycolates, methanesulfonates, and toluenesulfonates, alkali metal salts such as sodium salts and potassium salts, alkaline earth metal salts such as magnesium salts and calcium salts, ammonium salts such as ammonium salts and alkylammonium salts and the like. Examples of solvents possessed by the solvates that can be formed with the compounds of present invention include methanol, ethanol, isopropanol, acetone, ethyl acetate and the like. However, forms of the salts and solvates are not limited to those exemplified above.

The compounds of the present invention have high affinity for the sigma binding site (when a certain compound is referred to as a "sigma ligand" in the specification, it means that the compound has the aforementioned feature). Therefore, the compounds of the present invention are useful as medicaments for various diseases and symptoms which can be therapeutically and/or preventively treated by the nerve controlling function of the sigma ligands in mammals including human, preferably in human. Such diseases include, for example, diseases of central nervous system, gastrointestinal tract, and cardiovascular system.

The diseases of central nervous system include, for example, anxiety, depression or emotional abnormality, schizophrenia, narcotic intoxication or narcotic addiction, sharp pain, dyskinesia, cerebrovascular disease, epilepsy, dementia including Alzheimer's disease, Parkinson's syndrome, brain tumor, attention deficit disorder and the like. The gastrointestinal diseases include, for example, irritable bowel syndrome, irritable colon, spastic colon, colitis mucosus, enterocolitis, diverticulitis, dysentery. The diseases of cardiovascular system include, for example, hypertension, arrhythmia, angina pectoris. However, diseases treated by the medicaments of the present invention are not limited to these specific diseases and/or symptoms, and the medicaments can be used for therapeutic and/or preventive treatment of variety of diseases and/or symptoms in which sigma ligands in vivo are involved.

The compounds according to the present invention have excellent anti-methamphetamine activity and are useful as medicaments particularly for therapeutically and/or preventively treating schizophrenia, narcotic intoxication or narcotic addiction among the above-exemplified diseases and symptoms.

As the active ingredient of the medicaments of the present invention, one or more substances selected from the group consisting of the aforementioned compounds and salts thereof, and hydrates thereof and solvates thereof can be used. The administration route of the medicaments of the present invention is not particularly limited, and they can be administered orally or parenterally. As the medicament of the present invention, the aforementioned substances, per se, may be administered to patients. Preferably, the medicaments should be administered as preparations in the form of pharmaceutical compositions containing the active ingredient and one ore more pharmacologically and pharmaceutically acceptable additives. Examples of the pharmacologically and pharmaceutically acceptable additives include, for example, excipients, disintegrators, or disintegrating aids, binders, lubricants, coating agents, colorants, diluents, base materials, dissolving agents or dissolving aids, isotonic agents, pH modifiers, stabilizers, propellants, adhesives and the like. Examples of pharmaceutical preparations suitable for oral administration include, for example, tablets, capsules, powders, subtilized granules, granules, liquids, syrups and the like. Examples of pharmaceutical preparations suitable for parenteral administration include, for example, injections, drip infusions, ointments, creams, transmucosal preparations, eye drops, ear drops, inhalants, suppositories and the like. However, the forms of the preparations are not limited to these examples.

For the preparations suitable for oral administration, for example, excipients such as glucose, lactose, D-mannitol, starch, and crystalline cellulose; disintegrating agents or disintegrating aids such as carboxymethylcellulose, starch, and calcium carboxymethylcellulose; binders such as hydroxypropylcellulose, hydroxypropylmethylcellulose, polyvinylpyrrolidone, and gelatin; lubricants such as magnesium stearate and talc; coating agents such as hydroxypropylmethylcellulose, sucrose, polyethylene glycol, and titanium oxide; and base materials such as Vaseline, liquid paraffin, polyethylene glycol, gelatin, kaolin, glycerin, purified water, and hard fat may be used as additives. For the preparations suitable for injection or drip infusion, for example, dissolving agents or dissolving aids that can constitute aqueous injections or injections that are dissolved upon use such as distilled water for injections, physiological saline, and propylene glycol; isotonic agents such as glucose, sodium chloride, D-mannitol, and glycerin; pH modifiers such as inorganic acids, organic acids, inorganic bases and organic bases and the like may be used as additives for pharmaceutical preparations.

The doses of the medicament of the present invention should be suitably determined depending on a type of a disease to be treated, purpose of preventive or therapeutic treatment, the age, body weight and conditions of a patient and the like. A dose for adult patient per day may generally be within the range of about from 0.05 to 500 mg for oral administration. In general, the aforementioned dose may be administered once or two or more divided portions in a day, or may be administered every few days.

EXAMPLES

The present invention will be explained more specifically with reference to the following examples. However, the scope of the present invention is not limited by these examples.

In physicochemical properties, NMR means nuclear magnetic resonance spectrum, and the values are show as δ values which are generally used to indicate chemical shifts and the unit is ppm. TMS (tetramethylsilane) was used as internal standard. In the parentheses following the δ values, s indicates a single line, d indicates a double line, t indicates a triple line, q indicates a quadruple line, m indicates a multiple line, br indicates a broad absorption peak, and numbers following those letters represent the number of hydrogen atom.

Example 1

2-[[1-[2-(4-Fluorophenyl)-2-oxoethyl]piperidin-4-yl] methyl]isoindolin-1-one hydrochloride (Compound 1 in Table 1)

a) tert-Butyl 4-aminomethylpiperidine-1-carboxylate hydrochloride

By using 4-aminomethylpiperidine 5.71 g as a starting material, tert-butyl 4-aminomethylpiperidine-1-carboxylate was prepared according to the method described in Synthetic Commun., 22(16), 2357–2360 (1992). The resulting compound was dissolved in 80 ml of ethyl acetate, and the solution was added with 4N hydrogen chloride-ethyl acetate and stirred. The precipitated solids were collected by filtration to obtain the title compound (10.27 g, yield: 82%).

Melting point: 236–240° C. $^1$H-NMR(DMSO-$d_6$): 8.00 (3H,s), 3.92(2H, br d, J=12.6), 2.68(4H, m), 1.77–1.65(3H, m), 1.39(9H, s), 1.02(2H, m)

b) 2-Bromomethylbenzoic acid ethyl ester

2-Methylbenzoic acid ethyl ester (2.00 g, 11.9 mmol) was dissolved in carbon tetrachloride (60 ml), and the solution was added with N-bromosuccinimide (2.56 g, 14.4 mmol) and a catalytic amount of benzoylperoxide and then heated under reflux. After one hour, the reaction mixture was cooled to room temperature and added with hexane (40 ml) to remove insoluble solids by filtration. The filtrate was evaporated under reduced pressure to obtain the title compound 3.16 g as yellow oil. the product was used in the next reaction without purification.

c) tert-Butyl 4-(1-oxoisoindolin-2-yl-methyl)piperidine-1-carboxylate

The compound obtained in Example 1b (3.15 g), and the compound obtained in Example 1a (3.00 g, 12.0 mmol) were added in dimethylformamide (30 ml). The mixture was added with triethylamine (3.5 ml, 25 mmol) with stirring at room temperature, and then stirring was continued for 17 hours at the same temperature. Water was added to the reaction mixture and extracted with a mixed solvent of ethyl acetate-hexane. The organic layer was washed with 10% aqueous citric acid solution, water, aqueous sodium bicarbonate solution, and then with saturated brine and the dried over magnesium sulfate. Insoluble solids were removed by filtration, and the filtrate was evaporated under reduced pressure. The resulting oil was purified by silica gel column chromatography (ethyl acetate-hexane) to obtain the title compound as yellow oil (yield: 41%)

$^1$H-NMR(CDCl$_3$): 7.85(1H,d,J=7.5), 7.4–7.6(3H,m), 4.41 (2H,s), 4.0–4.2(2H,m), 3.4–3.6(2H,m), 2.6–2.8(2H,m), 1.8–2.0(1H,m), 1.5–1.7(4H,m), 1.45(9H,s)

d) 2-(Piperidin-4-yl-methyl)isoindolin-1-one hydrochloride

The compound obtained in Example 1c (1.61 g, 4.87 mmol) was dissolved in a mixed solvent of methylene chloride (5 ml) and ethanol (1 ml) and the solution was added with 4N hydrochloric acid in ethyl acetate (5 ml, 20 mmol) at room temperature. The mixture was stirred at the same temperature for 1 hour, and the precipitated solids were collected by filtration. The resulting solids were washed with ethyl acetate and then dried under reduced pressure to obtain the title compound as colorless solid (726 mg, yield: 56%).

$^1$H-NMR(DMSO-$d_6$): 8.83(1H,brs), 8.53(1H,brs), 7.4–7.7(4H,m), 4.50(2H,s), 3.44(2H,d,J=7.2), 3.2–3.3(2H, m), 2.7–2.9(2H,m), 1.9–2.1(1H,m), 1.6–1.8(2H,m), 1.3–1.5 (2H,m)

e) 2-[[1-[2-(4-Fluorophenyl)-2-oxoethyl]piperidin-4-yl]methyl]isoindolin-1-one The compound obtained in Example 1d (518 mg, 1.94 mmol) and 2-chloro-4'-fluoroacetophenone (358 mg, 2.07 mmol) was added to dimethylformamide (12 ml), and the solution was added with triethylamine (575 μl, 4.13 mmol) with stirring at room temperature. Stirring was continued at the same temperature for 4 hours, and then the reaction mixture was added with water and extracted with ethyl acetate. The organic layer was washed with water and then with saturated brine, and then dried over sodium sulfate. Insoluble solids were removed by filtration and the filtrate was evaporated under reduced pressure to obtain orange oil (0.70 g). The resulting oil was solidified by adding hexane, and the solids were collected by filtration and dried under reduced pressure to obtain the title compound as pale yellow solid (551 mg, yield: 77%).

$^1$H-NMR(CDCl$_3$): 8.0–8.1(2H,m), 7.85(1H,d=7.2), 7.4–7.55(3H,m), 7.12(2H,t), 4.41(2H,s), 3.73(2H,s), 3.51 (2H,d,J=7.5), 2.9–3.0(2H,m), 2.1–2.2(2H,m), 1.4–1.9(5H, m)

f) 2-[[1-[2-(4-Fluorophenyl)-2-oxoethyl]piperidin-4-yl]methyl]isoindolin-1-one hydrochloride The compound obtained in Example 1e (550 mg, 1.50 mmol) was dissolved in ethanol (2 ml), and the solution was added with 4N hydrochloric acid in ethyl acetate (2 ml, 8 mmol) at room temperature, and stirring was continued at the same temperature for 15 minutes. The reaction mixture was added with ethyl acetate (10 ml) and the precipitated solids were collected by filtration. The resulting solids were washed with ethyl acetate and then dried under reduced pressure to obtain white powder (364 mg). The product was recrystallized from ethanol-ethyl acetate to obtain the title compound as colorless solid (246 mg, yield: 41%)

Melting point: 182–188° C. $^1$H-NMR(DMSO-$d_6$): 9.93 (1H,brs), 8.0–8.2(2H,m), 7.4–7.7(6H,m), 4.9–5.1(2H,m), 4.53(2H,s), 2.9–3.6(6H,m), 1.6–2.2(5H, m)

Example 2

4-Bromo-2-[[1-[2-(4-fluorophenyl)-2-oxoethyl]piperidin-4-yl]methyl]isoindolin-1-one hydrochloride (Compound 5 in Table 1)

a) 3-Bromo-2-methylbenzoic acid ethyl ester

2-Methylbenzoic acid ethyl ester (18.3 mmol) was added dropwise to aluminium trichloride (45.7 mmol) and then $Br_2$ (22.0 mmol) was added dropwise. Stirring was continued at room temperature for 1 hour, and then the reaction mixture was added with ice and ethyl acetate to separate the organic layer. The organic layer was washed with water, an aqueous sodium bicarbonate solution, and then with saturated brine, and dried over sodium sulfate. The drying agent was removed by filtration, the layer was concentrated and three products was separated by silica gel column chromatography (hexane-ether), i.e., 3-bromo-2-methylbenzoic acid ethyl ester (yield: 14%), 5-bromo-2-methylbenzoic acid ethyl ester (yield: 13%), 3,5-dibromo-2-methylbenzoic acid ethyl ester (yield: 10%).

3-bromo-2-methylbenzoic acid ethyl ester:

$^1$H-NMR (CDCl$_3$): δ 7.71 (dd, J=7.9, 1.0 Hz, 1H), 7.69 (dd, J=7.9, 1.0 Hz, 1H), 7.10 (t, J=7.9 Hz, 1H), 4.37 (q, J=7.0 Hz, 2H), 2.63 (s, 3H), 1.40 (t, J=7.0 Hz, 3H).

5-bromo-2-methylbenzoic acid ethyl ester:

$^1$H-NMR (CDCl$_3$): δ 8.03 (d, J=2.1 Hz, 1H), 7.50 (dd, J=8.4, 2.1 Hz, 1H), 7.12(d, J=8.4 Hz, 1H), 4.36 (q, J=6.9 Hz, 2H), 2.54 (s, 3H), 1.40 (t, J=6.9 Hz, 3H).

3,5-dibromo-2-methylbenzoic acid ethyl ester:

$^1$H-NMR (CDCl$_3$): δ 7.85 (d, J=2 Hz, 1H), 7.84 (d, J=2 Hz, 1H), 4.37 (q, J=7.0 Hz, 2H), 2.57 (s, 3H), 1.40 (t, J=7.0 Hz, 3H).

b) tert-Butyl 4-(4-bromo-1-oxoisoindolin-2-ylmethyl)piperidine-1-carboxylate

By using 3-bromo-2-methylbenzoic acid ethyl ester obtained in Example 2a, the title compound was obtained by similar procedures to those of Examples 1b and 1c.

$^1$H-NMR (CDCl$_3$): δ 7.80 (d, J=9 Hz, 1H), 7.66 (d, J=6 Hz, 1H), 7.37 (dd, J=9, 6 Hz, 1H), 4.33 (s, 2H), 4.12 (m, 2H), 3.54 (br d, J=7 Hz, 2H), 2.70 (br t, J=12 Hz, 2H), 1.95 (m, 1H), 1.66 (br d, J=12 Hz, 2H), 1.45 (s, 9H), 1.24 (dq, J=12, 4 Hz, 2H).

c) 4-Bromo-2-(piperidin-4-ylmethyl)isoindolin-1-one hydrochloride

By using the compound obtained in Example 2b, the title compound was obtained in the same manner as Example 1d (yield: 62%).

$^1$H-NMR (DMSO-d$_6$): δ 8.92 (br s, 1H), 8.64 (br s, 1H), 7.83 (d, J=9 Hz, 1H), 7.71 (d, J=6 Hz, 1H), 7.48 (dd, J=9, 6 Hz, 1H), 4.45 (s, 2H), 3.45 (d, J=12 Hz, 2H), 3.24 (br d, J=12 Hz, 2H), 2.79 (br q, J=12 Hz, 2H), 2.06 (m, 1H), 1.74 (br d, J=12 Hz, 2H), 1.37 (br q, J=12 Hz, 2H).

d) 4-Bromo-2-[[1-[2-(4-fluorophenyl)-2-oxoethyl] piperidin-4-yl]methyl]isoindolin-1-one By using the compound obtained in Example 2c, the title compound was obtained by similar procedures to those of Example 1e (yield: 57%).

$^1$H-NMR (CDCl$_3$): δ 8.07 (m, 2H), 7.79 (d, J=7.8 Hz, 1H), 7.65 (d, J=7.8 Hz, 1H), 7.37 (t, J=7.8 Hz, 1H), 7.11 (t, J=8.6 Hz, 2H), 4.32 (s, 2H), 3.72 (s, 2H), 3.53 (d, J=7.2 Hz, 2H), 2.96 (br d, J=11.4 Hz, 2H), 2.16 (dt, J=11.4, 2.7 Hz, 2H), 1.84 (m, 1H), 1.69 (br d, J=12 Hz, 2H), 1.48 (dq, J=12, 4 Hz, 2H).

e) 4-Bromo-2-[[1-[2-(4-fluorophenyl)-2-oxoethyl] piperidin-4-yl]methyl]isoindolin-1-one hydrochloride By using the compound obtained in Example 2d, the title compound was obtained by similar procedure to those of Example 1f (yield: 66%).

Melting point: 152–154° C. $^1$H-NMR (DMSO-d$_6$): δ 9.98 (br s, 1H), 8.06–8.16 (m, 2H), 7.84 (d, J=8.1 Hz, 1H), 7.72 (d, J=7.5 Hz, 1H), 7.45–7.48 (m, 3H), 5.04–5.10 (m, 2H), 4.48 (s, 2H), 3.00–3.56 (m, 6H), 2.09 (m, 1H), 1.58–1.83 (m, 4H).

Example 3

5-Bromo-2-[[1-[2-(4-fluorophenyl)-2-oxoethyl]piperidin-4-yl]methyl]isoindolin-1-one hydrochloride (Compound 4 in Table 1)

a) 4-Bromo-2-methylbenzoic acid methyl ester

4-Bromo-2-methylbenzoic acid (4.06 g, 18.5 mmol) was dissolved in methanol (60 ml). The solution was added with concentrated sulfuric acid (1 ml), and then heated under reflux for 9 hours. The solvent was evaporated under reduced pressure, and the residue was diluted with ethyl ether (100 ml). The resulting dilution was washed with water, an aqueous sodium bicarbonate solution, and then with saturated brine, and dried over magnesium sulfate. Insoluble solids were removed by filtration, and the filtrate was concentrated under reduced pressure to obtain the tile compound as yellow oil (3.87 g, yield: 91%).

$^1$H-NMR(CDCl$_3$): 7.78(1H,d,J=8.3), 7.42(1H,d,J=1.9), 7.38(1H,dd,J=1.9,8.3), 3.88(3H,s), 2.58(3H,s)

b) 4-Bromo-2-bromomethylbenzoic acid methyl ester

By using the compound obtained in Example 3a (3.83 g, 16.7 mmol), the title compound (5.70 g) was obtained by similar procedures to those of Example 1b. The product was used in the next reaction without any treatment.

c) tert-Butyl 4-(5-bromo-1-oxoisoindolin-2-ylmethyl)piperidine-1-carboxylate

By using the compound obtained in Example 3b (5.70 g), the title compound was obtained as white solid by similar procedures to those of Example 1c (3.04 g, yield: 44%).

$^1$H-NMR(CDCl$_3$): 7.69–7.73(1H,m), 7.59–7.62(2H,m), 4.39(2H,s), 4.0–4.2(2H,m), 3.4–3.6(2H,m), 2.5–2.7(2H,m), 1.8–2.0(1H,m), 1.5–1.7(2H,m), 1.45(9H,s), 1.1–1.3(2H,m)

d) 5-Bromo-2-(piperidin-4-ylmethyl)isoindolin-1-one hydrochloride

By using the compound obtained in Example 3c (3.03 g, 7.40 mmol), the title compound was obtained as white solid by similar procedures to those of Example 1d 1.86 g (yield: 73%).

$^1$H-NMR(DMSO-d$_6$): 8.96(1H,brs), 8.68(1H,brs), 7.89 (1H,s), 7.69(1H,d,J=8.2), 7.61(1H,d,J=8.2), 4.50(2H,s), 3.42(2H,d,J=7.2), 3.1–3.3(2H,m), 2.6–2.9(2H,m), 1.9–2.1 (1H,m), 1.6–1.8(2H,m), 1.2–1.4(2H,m)

e) 5-Bromo-2-[[1-[2-(4-fluorophenyl)-2-oxoethyl]piperidin-4-yl]methyl]isoindolin-1-one By using the compound obtained in Example 3d (834 mg, 2.41 mmol), the title compound was obtained as pale yellow solid by similar procedures to those of Example 1e (727mg, yield: 68%).

$^1$H-NMR(CDCl$_3$): 8.0–8.1(2H,m), 7.68–7.72(1H,m), 7.58–7.62(2H,m), 7.08–7.15(2H,m), 4.38(2H,s), 3.73(2H,s), 3.49(2H,d,J=7.2), 2.8–3.0(2H,m), 2.0–2.2(2H,m), 1.6–1.9 (3H,m), 1.35–1.5(2H,m)

f) 5-Bromo-2-[[1-[2-(4-fluorophenyl)-2-oxoethyl]piperidin-4-yl]methyl]isoindolin-1-one hydrochloride By using the compound obtained in Example 3e (727 mg, 1.63 mmol), the title compound was obtained as colorless solid by similar procedures to those of Example 1f 704 mg (yield: 89%).

Melting point: 205–222° C. $^1$H-NMR(DMSO-d$_6$): 9.91 (1H,brs), 8.0–8.2(2H,m), 7.90(1H,s), 7.70(1H,d,J=8.2), 7.62 (1H,d,J=8.2), 7.4–7.5(2H,m), 5.0–5.2(2H,m), 4.53(2H,s), 3.3–3.6(4H,m), 2.9–3.1(2H,m), 2.0–2.2(1H,m), 1.5–1.9(4H, m)

Example 4

6-Bromo-2-[[1-[2-(4-fluorophenyl)-2-oxoethyl]piperidin-4-yl]methyl]isoindolin-1-one hydrochloride (Compound 3 in Table 1)

a) tert-Butyl 4-(6-bromo-1-oxoisoindolin-2-ylmethyl)piperidine-1-carboxylate By using 5-bromo-2-methylbenzoic acid ethyl ester obtained in Example 2a, the title compound was obtained by similar procedures to those of Examples 1b and 1c (yield: 52%).

$^1$H-NMR (CDCl$_3$): δ 7.98 (d, J=1.8 Hz, 1H), 7.65 (dd, J=8.0, 1.8 Hz, 1H), 7.32 (d, J=8.0 Hz, 1H), 4.36 (s, 2H), 4.10 (m, 2H), 3.48 (m, 2H), 2.69 (br t, J=12 Hz, 2H), 1.93 (m, 1H), 1.64 (br d, J=12 Hz, 2H), 1.45 (s, 9H), 1.24 (dq, J=12.3, 4.4 Hz, 2H).

b) 6-Bromo-2-(piperidin-4-ylmethyl)isoindolin-1-one hydrochloride

By using the compound obtained in Example 4a, the title compound was obtained by similar procedures to those of Example 1d (yield: 96%).

$^1$H-NMR (DMSO-d$_6$): δ 8.90 (br s, 1H), 8.61 (br s, 1H), 7.78–7.81 (m, 2H), 7.60 (d, J=8.8 Hz, 1H), 4.48 (s, 2H), 3.43 (d, J=7.4 Hz, 2H), 3.24 (br d, J=12 Hz, 2H), 2.80 (br q, J=12 Hz, 2H), 2.01 (m, 1H), 1.73 (br d, J=12 Hz, 2H), 1.37 (br q, J=12 Hz, 2H).

c) 6-Bromo-2-[[1-[2-(4-fluorophenyl)-2-oxoethyl]piperidin-4-yl]methyl]isoindolin-1-one By using the compound obtained in Example 4b, the title compound was obtained by similar procedures to those of Example 1e (yield: 93%).

$^1$H-NMR (CDCl$_3$): δ 8.07 (m, 2H), 7.97 (d, J=1.8 Hz, 1H), 7.65 (dd, J=8.1, 1.8 Hz, 1H), 7.32 (d, J=8.1 Hz, 1H), 7.12 (t, J=8.7 Hz, 2H), 4.36 (s, 2H), 3.72 (s, 2H), 3.50 (d, J=6.9 Hz, 2H), 2.96 (br d, J=12 Hz, 2H), 2.14 (dt, J=11.6, 2.4 Hz, 2H), 1.82 (m, 1H), 1.67 (br d, J=12 Hz, 2H), 1.46 (dq, J=11.7, 3.6 Hz, 2H).

d) 6-Bromo-2-[[1-[2-(4-fluorophenyl)-2-oxoethyl]piperidin-4-yl]methyl]isoindolin-1-one hydrochloride By using the compound obtained in Example 4c, the title compound was obtained by similar procedures to those of Example 1f (yield: 72%).

Melting point: 187–193° C. $^1$H-NMR (DMSO-d$_6$): δ 9.99 (br s, 1H), 8.05–8.16 (m, 2H), 7.62–7.78 (m, 2H), 7.60 (d, J=8.6 Hz, 1H), 7.47 (t, J=8.6 Hz, 2H), 5.03–5.09 (m, 2H), 4.51 (s, 2H), 3.01–3.55 (m, 6H), 2.03 (m, 1H), 1.62–1.86 (m, 4H).

Example 5

4,6-Dibromo-2-[[1-[2-(4-fluorophenyl)-2-oxoethyl]piperidin-4-yl]methyl]isoindolin-1-one hydrochloride (Compound 6 in Table 1)

a) tert-Butyl 4-(4,6-dibromo-1-oxoisoindolin-2-ylmethyl)piperidine-1-carboxylate By using 3,5-dibromo-2-methylbenzoic acid ethyl ester obtained in Example 2a, the title compound was obtained by similar procedures to those of Examples 1b and 1c (yield: 64%).

$^1$H-NMR (CDCl$_3$): δ 7.93 (d, J=1.5 Hz, 1H), 7.82 (d, J=1.5 Hz, 1H), 4.27 (s, 2H), 4.12 (m, 2H), 3.51 (d, J=6.7 Hz, 2H), 2.70 (br t, J=12 Hz, 2H), 1.94 (m, 1H), 1.64 (br d, J=12 Hz, 2H), 1.45 (s, 9H), 1.25 (dq, J=12, 4 Hz, 2H).

b) 4,6-Dibromo-2-(piperidin-4-ylmethyl)isoindolin-1-one hydrochloride

By using the compound obtained in Example 5a, the title compound was obtained by similar procedures to those of Example 1d (yield: 100%).

$^1$H-NMR (DMSO-d$_6$): δ 8.87 (br s, 1H), 8.60 (br s, 1H), 4.43 (s, 2H), 3.44 (d, J=7.5 Hz, 2H), 3.24 (br d, J=12 Hz, 2H), 2.79 (br q, J=12 Hz, 2H), 2.06 (m, 1H), 1.74 (br d, J=12 Hz, 2H), 1.36 (br q, J=12 Hz, 2H).

c) 4,6-Dibromo-2-[[1-[2-(4-fluorophenyl)-2-oxoethyl]piperidin-4-yl]methyl]isoindolin-1-one By using the compound obtained in Example 5b, the title compound was obtained by similar procedures to those of Example 1e (yield: 83%).

$^1$H-NMR (CDCl$_3$): δ 8.07 (m, 2H), 7.92 (d, J=1.4 Hz, 1H), 7.81 (d, J=1.4 Hz, 1H), 7.60 (t, J=8.6 Hz, 2H), 4.28 (s,

2H), 3.73 (s, 2H), 3.51 (d, J=7.3 Hz, 2H), 2.97 (br, d, J=12 Hz, 2H), 2.16 (br t, J=12 Hz, 2H), 1.83 (m, 1H), 1.68 (br d, J=12 Hz, 2H), 1.47 (dq, J=12, 3 Hz, 2H).

d) 4,6-Dibromo-2-[[1-[2-(4-fluorophenyl)-2-oxoethyl]piperidin-4-yl]methyl]isoindolin-1-one hydrochloride By using the compound obtained in Example 5c, the title compound was obtained by similar procedures to those of Example 1f (yield: 77%).

Melting point: 186–190° C. $^1$H-NMR (DMSO-$d_6$): δ 10.03 (br s, 1H), 8.06–8.16 (m, 3H), 7.86 (s, 1H), 7.47 (t, J=8.7 Hz, 2H), 5.04–5.10 (m, 2H), 4.46 (s, 2H), 3.30–3.56 (m, 6H), 2.08 (m, 1H), 1.58–1.91 (m, 4H).

Example 6

4-Fluoro-2-[[1-[2-(4-fluorophenyl)-2-oxoethyl]piperidin-4-yl]methyl]isoindolin-1-one hydrochloride
(Compound 10 in Table 1)

a) 3-Fluoro-2-methylbenzoic acid ethyl ester

By using 3-fluoro-2-methylbenzoic acid (2.0 g, 12.98 mmol), the title compound was obtained as colorless oil by similar procedures to those of Example 3a(1.31 g). The product was used in the next reaction without purification.

b) 2-Bromomethyl-3-fluorobenzoic acid ethyl ester

By using the compound obtained in Example 6a (1.31 g), the title compound was obtained as pale yellow oil by similar procedures to those of Example 1b (2.01 g). The product was used in the next reaction without purification.

c) tert-Butyl 4-[(4-fluoroisoindolin-1-one)-2-ylmethyl]piperidine-1-carboxylate By using the compound obtained in Example 6b (1.57 g), the title compound was obtained as colorless solid by similar procedures to those of Example 1c (1.68 g, yield: 63%).

$^1$H-NMR(CDCl$_3$): δ 7.65(d, 1H,J=7.5 Hz), 7.49–7.43 (ddd,1H,J=7.8,7.8,4.8 Hz), 7.22(dd,1H,J=8.6,8.5 Hz), 4.45 (s,2H), 4.11(br d,2H,J=11.7 Hz), 3.50(br d,2H,J=6.3 Hz), 2.70(br dd,2H,J=12.6,6.3 Hz), 1.98–1.91(m,1H), 1.67–1.62 (m,2H), 1.45(s, 9H), 1.35–1.19(m,2H).

d) 4-Fluoro-2-(piperidin-4-ylmethyl)isoindolin-1-one hydrochloride

By using the compound obtained in Example 6c (1.68 g, 4.82 mmol), the title compound was obtained as colorless solid by similar procedures to those of Example 1d (1.27 g, yield: 93%).

$^1$H-NMR(DMSO-$d_6$): δ 8.91(br s,1H), 8.65(br s,1H), 7.60–7.42(m,3H), 4.60(s,2H), 3.44(d,2H,J=7.5 Hz), 3.24(br d, 2H, J=12.6 Hz), 2.79(br dd,2H,J=23.3,12.2 Hz), 2.08–1.99(m,1H), 1.74(br d,2H,J=12.3 Hz), 1.45–1.31(m, 2H).

e) 4-Fluoro-2-[[1-[2-(4-fluorophenyl)-2-oxoethyl]piperidin-4-yl]methyl]isoindolin-1-one By using the compound obtained in Example 6d (1.27 g, 4.46 mmol), the title compound was obtained as pale brown solid by similar procedures to those of Example 1e (1.52 g, yield: 89%).

$^1$H-NMR(CDCl$_3$): δ 8.10–8.05(m,2H), 7.65(d,1H,J=7.3 Hz), 7.46–7.44(m,1H), 7.21(dd,2H,J=8.8,8.8 Hz), 7.11(dd, 2H,J=7.6,7.6 Hz), 4.45(s,2H), 3.71(s, 2H),3.52(d,2H,J=7.2 Hz), 2.96(br d,2H,J=11.6 Hz), 2.19–2.08(m, 2H), 1.71–1.67 (m,2H), 1.54–1.46(m,2H).

f) 4-Fluoro-2-[[1-[2-(4-fluorophenyl)-2-oxoethyl]piperidin-4-yl]methyl]isoindolin-1-one hydrochloride By using the compound obtained in Example 6e (500 mg, 1.30 mmol), the title compound was obtained as colorless solid by similar procedures to those of Example 1f (484 mg, yield: 89%).

Melting point: 177–196° C. $^1$H-NMR(DMSO-$d_6$): δ 9.92 (br s,1H), 8.16–8.06(m,2H), 7.59–7.44(m,5H), 5.04–5.01 (m, 2H), 4.63(s, 2H), 3.56–3.46(m,4H), 3.02(br d,2H,J=10.8 Hz), 2.09–2.06(m,1H), 1.91–1.62(m,4H).

Example 7

6-Fluoro-2-[[1-[2-(4-fluorophenyl)-2-oxoethyl]piperidin-4-yl]methyl]isoindolin-1-one hydrochloride
(Compound 8 in Table 1)

a) 5-Fluoro-2-methylbenzoic acid methyl ester

By using 5-fluoro-2-methylbenzoic acid (900 mg, 5.78 mmol), the title compound was obtained as colorless oil by similar procedures to those of Example 3a (1.01 g). The product was used in the next reaction without purification.

b) 2-Bromomethyl-5-fluorobenzoic acid methyl ester

By using the compound obtained in Example 7a (957 mg), the title compound was obtained by similar procedures to those of Example 1b (1.57 g). The product was used in the next reaction without purification.

c) tert-Butyl 4-(6-fluoro-1-oxoisoindolin-2-ylmethyl)piperidine-1-carboxylate By using the compound obtained in Example 7b (1.57 g), the title compound was obtained as colorless solid by similar procedures to those of Example 1c (1.13 g, yield: 57%).

$^1$H-NMR(CDCl$_3$): 7.50–7.54(1H,m), 7.38–7.43(1H,m), 7.20–7.28(1H,m), 4.38(2H,s), 4.0–4.2(2H,m), 3.4–3.6(2H, m), 2.6–2.8(2H,m), 1.8–2.0(1H,m), 1.5–1.7(2H,m), 1.45 (9H,s), 1.1–1.3(2H,m)

d) 6-Fluoro-2-(piperidin-4-ylmethyl)isoindolin-1-one hydrochloride

By using the compound obtained in Example 7c (1.09 g, 3.13 mmol), the title compound was obtained as colorless solid by similar procedures to those of Example 1d (722 mg, yield: 81%).

$^1$H-NMR(DMSO-d$_6$): 8.73(1H,brs), 8.46(1H,brs), 7.63–7.69(1H,m), 7.43–7.49(2H,m), 4.48(2H,s), 3.44(2H,d, J=7.3), 3.1–3.3(2H,m), 2.7–2.9(2H,m), 1.9–2.1(1H,m), 1.6–1.8(2H,m), 1.2–1.4(2H,m)

e) 6-Fluoro-2-[[1-[2-(4-fluorophenyl)-2-oxoethyl]piperidin-4-yl]methyl]isoindolin-1-one By using the compound obtained in Example 7d (721 mg, 2.53 mmol), the title compound was obtained as pale yellow solid by similar procedures to those of Example 1e (762 mg, yield: 78%).

$^1$H-NMR(CDCl$_3$): 8.04–8.10(2H,m), 7.49–7.53(1H,m), 7.37–7.41(1H,m), 7.22–7.26(1H,m), 7.08–7.15(2H,m), 4.38 (2H,s), 3.73(2H,s), 3.50(2H,d,J=7.3), 2.9–3.0(2H,m), 2.0–2.2(2H,m), 1.7–1.9(1H,m), 1.5–1.7(2H,m), 1.3–1.5(2H,m)

f) 6-Fluoro-2-[[1-[2-(4-fluorophenyl)-2-oxoethyl]piperidin-4-yl]methyl]isoindolin-1-one hydrochloride By using the compound obtained in Example 7e (762 mg, 1.98 mmol), the title compound was obtained as colorless solid by similar procedures to those of Example 1f (762 mg, yield: 91%).

Melting point: 193–205° C. $^1$H-NMR(DMSO-d$_6$): 9.96 (1H,brs), 8.0–8.2(2H,m), 7.64–7.70(1H,m), 7.3–7.5(4H,m), 5.0–5.2(2H,m), 4.52(2H,s), 3.4–3.6(4H,m), 3.9–4.1(2H,m), 1.9–2.1(1H,m), 1.5–1.9(4H,m)

Example 8

5-Chloro-2-[[1-[2-(4-fluorophenyl)-2-oxoethyl]piperidin-4-yl]methyl]isoindolin-1-one hydrochloride (Compound 13 in Table 1)

a) Ethyl 4-chloro-2-methylbenzoate

By using 4-chloro-2-methylbenzoic acid (300 mg, 1.76 mmol), the title compound was obtained as colorless solid by similar procedures to those of Example 3a (347 mg). The product was used in the next reaction without purification.

b) Ethyl 2-bromomethyl-4-chlorobenzoate

By using the compound obtained in Example 8a (347 mg), the title compound was obtained as pale brown oil by similar procedures to those of Example 1b (494 mg). The product was used in the next reaction without purification.

c) tert-Butyl 4-[(5-chloroisoindolin-1-one)-2-ylmethyl]piperidine-1-carboxylate By using the compound obtained in Example 8b (490 mg), the title compound was obtained as pale brown solid by similar procedures to those of Example 1c (375 mg, yield: 58%).

$^1$H-NMR(CDCl$_3$): δ 7.77(d, 1H,J=8.7 Hz), 7.48–7.44(m, 2H), 4.39(s,2H), 4.11(br s,2H), 3.49(br s,2H), 2.69(br dd,2H,J=12.2,12.2 Hz), 1.97–1.89(m,1H), 1.66–1.62(m, 2H), 1.45(s, 9H), 1.31–1.18(m,2H).

d) 5-Chloro-2-(piperidin-4-ylmethyl)isoindolin-1-one hydrochloride

By using the compound obtained in Example 8c (370 mg, 1.01 mmol), the title compound was obtained as colorless solid by similar procedures to those of Example 1d(211mg, yield: quantitative).

$^1$H-NMR(DMSO-d$_6$): δ 9.08(br s,1H), 8.81(br s,1H), 7.80 (s,1H),7.74(d,1H,J=8.0 Hz), 7.60(dd,1H,J=8.1,1.6 Hz), 4.56 (s,2H), 3.48(d,2H,J=7.4 Hz), 3.29(br d,2H,J=12.6 Hz), 2.85 (br dd,2H,J=23.0,12.0 Hz), 2.10–2.02(m,1H), 1.78(br d,2H, J=12.8 Hz), 1.51–1.37(m,2H).

e) 5-Chloro-2-[[1-[2-(4-fluorophenyl)-2-oxoethyl]piperidin-4-yl]methyl]isoindolin-1-one By using the compound obtained in Example 8d (205 mg, 0.68 mmol), the title compound was obtained as white solid by similar procedures to those of Example 1e (213 mg, yield: 78%).

$^1$H-NMR(CDCl$_3$): δ 8.07(dd,2H,J=8.9,5.6 Hz), 7.76(d, 1H,J=9.0 Hz), 7.44(d,2H,J=8.1 Hz), 7.12(dd,2H,J=8.7,8.7 Hz), 4.39 (s,2H), 3.73(s, 2H), 3.49(d,2H,J=7.2 Hz), 2.96(br d,2H,J=11.4 Hz), 2.19–2.11(m, 2H), 1.84–1.77(m,1H), 1.68 (br d,2H,J=12.6 Hz), 1.54–1.45(m,2H).

f) 5-Chloro-2-[[1-[2-(4-fluorophenyl)-2-oxoethyl]piperidin-4-yl]methyl]isoindolin-1-one hydrochloride By using the compound obtained in Example 8e (213 mg, 0.53 mmol), the title compound was obtained as colorless solid by similar procedures to those of Example 1f (155 mg, yield: 48%).

Melting point: 209–221° C. $^1$H-NMR(DMSO-d$_6$): δ 9.94 (br s,1H), 8.19–8.06(m,2H), 7.76(s,1H), 7.69(d,1H,J=8.1 Hz), 7.65(d, 1H,J=9.3 Hz), 7.48(dd,2H,J=8.7,8.7 Hz), 5.10–5.03(m, 2H), 4.54(s, 2H), 3.55–3.40(m,4H), 3.08–3.00 (m,2H), 2.09–1.99(m,1H), 1.86–1.61(m,4H).

Example 9

5-Methyloxy-2-[[1-[2-(4-fluorophenyl)-2-oxoethyl]piperidin-4-yl]methyl]isoindolin-1-one hydrochloride (Compound 17 in Table 1)

a) 4-Methyloxy-2-methylbenzoic acid methyl ester

Methyl 4-bromo-2-methylbenzoate (19.0 mmol) was dissolved in dimethylformamide (2.7 mL) and methanol (1.1 mL), and the solution was heated at 80° C. and then added with CuBr (1.09 mmol). After stirring was continued for 2 hours under heating, the mixture was cooled to room temperature. The mixture was added with diethyl ether (25 mL) and filtered. The filtrate was washed four times with water, an aqueous sodium bicarbonate solution, and then with saturated brine, and dried over sodium sulfated. The drying agent was removed by filtration and the filtrate was concentrated to give the title compound.

$^1$H-NMR (CDCl$_3$): δ 7.93 (d, J=9.3 Hz, 1H), 6.72–6.76 (m, 2H), 3.86 (s, 3H), 3.84 (s, 3H), 2.60 (s, 3H).

b) tert-Butyl 4-(5-methyloxy-1-oxoisoindolin-2-ylmethyl)piperidine-1-carboxylate By using the compound obtained in Example 9a, the title compound was obtained by similar procedures to those of Examples 1b and 1c (yield: 40%).

$^1$H-NMR (CDCl$_3$): δ 7.75 (d, J=8.4 Hz, 1H), 6.99 (dd, J=8.4, 2.1 Hz, 1H), 6.93 (d, J=2.1 Hz, 1H), 4.35 (s, 2H), 4.11 (m, 2H), 3.87 (s, 3H), 3.47 (m, 2H), 2.69 (br t, J=12 Hz, 2H), 1.93 (m, 1H), 1.65 (br d, J=12 Hz, 2H), 1.45 (s, 9H), 1.24 (dq, J=12, 4 Hz, 2H).

c) 5-Methyloxy-2-(piperidin-4-ylmethyl)isoindolin-1-one hydrochloride

By using the compound obtained in Example 9b, the title compound was obtained by similar procedures to those of Example 1d (yield: 100%).

$^1$H-NMR (DMSO-d$_6$): δ 9.13 (br s, 1H), 8.86 (br s, 1H), 7.57 (d, J=8.4 Hz, 1H), 7.15 (d, J=2.2 Hz, 1H), 7.02 (dd, J=8.6, 2.2 Hz, 1H), 4.43 (s, 2H), 3.83 (s, 3H), 3.39 (d, J=7.4 Hz, 2H), 3.22 (br d, J=12 Hz, 2H), 2.78 (br q, J=12 Hz, 2H), 1.98 (m, 1H), 1.71 (br d, J=12 Hz, 2H), 1.43 (br q, J=12 Hz, 2H).

d) 5-Methyloxy-2-[[1-[2-(4-fluorophenyl)-2-oxoethyl]piperidin-4-yl]methyl]isoindolin-1-one By using the compound obtained in Example 9c, the title compound was obtained by similar procedures to those of Example 1e (yield: 84%).

$^1$H-NMR (CDCl$_3$): δ 8.08 (m, 2H), 7.75 (d, J=7.8 Hz, 1H), 7.11 (t, J=8.4 Hz, 2H), 6.98 (dd, J=8.4, 2.4 Hz, 1H), 6.77 (d, J=2.4 Hz, 1H), 4.34 (s, 2H), 3.87 (s, 3H), 3.71 (s, 2H), 3.47 (d, J=7.2 Hz, 2H), 2.95 (br d, J=12 Hz, 2H), 2.15 (dt, J=11.7, 2.4 Hz, 2H), 1.80 (m, 1H), 1.67 (br d, J=12 Hz, 2H), 1.46 (dq, J=12, 4 Hz, 2H).

e) 5-Methyloxy-2-[[1-[2-(4-fluorophenyl)-2-oxoethyl]piperidin-4-yl]methyl]isoindolin-1-one hydrochloride By using the compound obtained in Example 9d, the title compound was obtained by similar procedures to those of Example 1f (yield: 65%).

Melting point: 205–214° C. $^1$H-NMR (DMSO-d$_6$): δ 10.07 (br s, 1H), 8.06–8.16 (m, 2H), 7.59 (d, J=8.4 Hz, 1H), 7.47 (t, J=8.4 Hz, 2H), 7.17 (s, 1H), 7.03 (d, J=8.4 Hz, 1H), 5.06–5.12 (m, 2H), 4.47 (s, 2H), 3.84 (s, 3H), 3.02–3.52 (m, 6H), 2.01 (m, 1H), 1.63–1.84 (m, 4H).

Example 10

5-Cyano-2-[[1-[2-(4-fluorophenyl)-2-oxoethyl]piperidin-4-yl]methyl]isoindolin-1-one hydrochloride (Compound 21 in Table 1)

a) 4-Cyano-2-methylbenzoic acid methyl ester

4-Bromo-2-benzoic acid (17.5 mmol) was dissolved in N-methyl-2-pyrrolidone (24 mL), and the solution was added with CuCN (21.0 mmol) and heated at 180° C. After 5 hours, the reaction mixture was cooled to room temperature and added with 40 mL of water and filtered. The solids remaining on the filter were extracted with acetone, and the extract was concentrated to give the title compound (yield: 45%).

$^1$H-NMR (CDCl$_3$): δ 7.97 (d, J=8.6 Hz, 1H), 7.55 (s, 1H), 7.54 (d, J=8.6 Hz, 1H), 3.93 (s, 3H), 2.62 (s, 3H).

b) tert-Butyl 4-(5-cyano-1-oxoisoindolin-2-ylmethyl)piperidine-1-carboxylate

By using the compound obtained in Example 10a, the title compound was obtained by similar procedures to those of Examples 1b and 1c (yield: 40%).

$^1$H-NMR (CDCl$_3$): δ 7.96 (d, J=7.5 Hz, 1H), 7.78 (d, J=7.5 Hz, 1H), 7.76 (s, 1H), 4.48 (s, 2H), 4.11 (m, 2H), 3.53 (m, 2H), 2.69 (br t, J=12 Hz, 2H), 1.95 (m, 1H), 1.64 (br d, J=12 Hz, 2H), 1.45 (s, 9H), 1.26 (dq, J=12, 4 Hz, 2H).

c) 5-Cyano-2-(piperidin-4-ylmethyl)isoindolin-1-one hydrochloride

By using the compound obtained in Example 10b, the title compound was obtained by similar procedures to those of Example 1d (yield: 100%).

$^1$H-NMR (DMSO-d$_6$): δ 9.06 (br s, 1H), 8.80 (br s, 1H), 8.16 (s, 1H), 7.95 (d, J=7.4 Hz, 1H), 7.84 (d, J=7.4 Hz, 1H), 4.57 (s, 2H), 3.45 (d, J=7.3 Hz, 2H), 3.22 (br d, J=12 Hz, 2H), 2.78 (br q, J=12 Hz, 2H), 2.02 (m, 1H), 1.73 (br d, J=12 Hz, 2H), 1.39 (br q, J=12 Hz, 2H).

d) 5-Cyano-2-[[1-[2-(4-fluorophenyl)-2-oxoethyl]piperidin-4-yl]methyl]isoindolin-1-one By using the compound obtained in Example 10c, the title compound was obtained by similar procedures to those of Example 1e (yield: 79%).

$^1$H-NMR (CDCl$_3$): δ 8.07 (m, 2H), 7.95 (d, J=7.8 Hz, 1H), 7.77 (d, J=7.8 Hz, 1H), 7.76 (s, 1H), 7.12 (t, J=8.4 Hz, 2H), 4.48 (s, 2H), 3.74 (s, 2H), 3.54 (d, J=7.2 Hz, 2H), 2.97 (br d, J=12 Hz, 2H), 2.15 (dt, J=11.4, 2.1 Hz, 2H), 1.84 (m, 1H), 1.66 (br d, J=12 Hz, 2H), 1.48 (dq, J=12, 4 Hz, (2H).

e) 5-Cyano-2-[[1-[2-(4-fluorophenyl)-2-oxoethyl]piperidin-4-yl]methyl]isoindolin-1-one hydrochloride By using the compound obtained in Example 10d, the title compound was obtained by similar procedures to those of Example 1f (yield: 85%).

Melting point: 212–217° C. $^1$H-NMR (DMSO-$_6$): δ 10.00 (br s, 1H), 8.18 (s, 1H), 8.06–8.14 (m, 2H), 7.97 (d, J=8 Hz, 1H), 7.86 (d, J=8 Hz, 1H), 7.48 (t, J=8.8 Hz, 2H), 5.06–5.12 (m, 2H), 4.61 (s, 2H), 3.01–3.61 (m, 6H), (m, 1H), 1.59–1.87 (m, 4H).

Example 11

4-Nitro-2-[[1-[2-(4-fluorophenyl)-2-oxoethyl]piperidin-4-yl]methyl]isiondolin-1-one hydrochloride (Compound 25 in Table 1)

a) 2-Methyl-3-nitrobenzoic acid methyl ester

By using 2-methyl-3-nitrobenzoic acid (3.0 g, 16.56 mmol), the title compound was obtained as colorless solid by similar procedures to those of Example 3a (1.74 g). The product was used in the next reaction without purification.

b) 2-Bromomethyl-3-nitrobenzoic acid methyl ester

By using the compound obtained in Example 11a (1.00 g), the title compound was obtained as pale yellow oil by similar procedures to those of Example 1b(1.43 g). The product was used in the next reaction without purification.

c) tert-Butyl 4-[(4-nitroisoindolin-1-one)-2-ylmethyl]piperidine-1-carboxylate By using the compound obtained in Example 11b (783 mg), the title compound was obtained as pale brown solid by similar method to those of Example 1c (590 mg, yield: 56%).

$^1$H-NMR(CDCl$_3$): δ 8.40(dd, 1H,J=8.2,0.9 Hz), 8.19(d, 1H,J=7.6 Hz), 7.71(dd,1H,J=7.9,7.9 Hz), 4.88(s,2H), 4.11(br s,2H), 3.57(br d,2H,J=7.2 Hz), 2.71(br dd,2H,J=12.9, 12.9 Hz), 2.04–1.96(m,1H), 1.69–1.58(m,2H), 1.45(s, 9H), 1.35–1.21(m,2H).

d) 4-Nitro-2(piperidin-4-ylmethyl)isoindolin-1-one hydrochloride

By using the compound obtained in Example 11c (590 mg, 1.57 mmol), the title compound was obtained as colorless solid by similar procedures to those of Example 1d (454 mg, yield: 93%).

$^1$H-NMR(DMSO-d$_6$): δ 8.96(br s,1H), 8.71(br s,1H), 8.45 (d,1H,J=8.4 Hz), 8.13(d,1H,J=7.5 Hz), 7.82(dd,1H,J=7.8, 7.8 Hz), 4.94(s,2H), 3.50(d,2H,J=7.5 Hz), 3.25(br d,2H, J=12.3 Hz), 2.77(br dd,2H,J=23.1,11.7 Hz), 2.13–2.06(m, 1H), 1.76(br d,2H,J=12.6 Hz), 1.47–1.33(m,2H).

e) 4-Nitro-2-[[1-[2-(4-fluorophenyl)-2-oxoethyl]piperidin-4-yl]methyl]isoindolin-1-one By using the compound obtained in Example 11d (454 mg, 1.46 mmol), the title compound was obtained as pale yellow solid by similar procedures to those of Example 1e (344 mg, yield: 57%).

$^1$H-NMR(CDCl$_3$): δ 8.40(d,1H,J=8.2 Hz), 8.18(d,1H, J=7.4 Hz), 8.10–8.05(m,2H), 7.70(dd,1H,J=7.8,7.8 Hz), 7.09(dd,2H,J=8.6,8.6 Hz), 4.88(s,2H), 3.72(s, 2H),3.57(d, 2H,J=7.2 Hz), 2.97(br d,2H,J=11.5 Hz), 2.21–2.12(m, 2H), 1.88–1.83(m,1H), 1.71(br s,2H), 1.56–1.47(m,2H).

f) 2-[[1-[2-(4-Fluorophenyl)-2-oxoethyl]piperidin-4-yl]methyl]-4-nitroisoindolin-1-one hydrochloride By using the compound obtained in Example 11e (320 mg, 0.78 mmol), the title compound was obtained as colorless solid by similar procedures to those of Example 1f (262 mg, yield: 75%).

Melting point: 177–181° C. $^1$H-NMR(DMSO-d$_6$): δ 9.90 (br s,1H), 8.46(d,1H,J=8.4 Hz), 8.16–8.09(m,3H), 7.83(dd, 1H,J=7.8,7.8 Hz), 7.48(dd, 2H,J=8.7,8.7 Hz), 4.97(s, 4H), 3.53(br s,4H), 3.02(br s,2H), 2.12(br s,1H), 1.83–1.61(m, 4H).

Example 12

6-Nitro-2-[[1-[2-(4-fluorophenyl)-2-oxoethyl]piperidin-4-yl]methyl]isoindolin-1-one fumarate (Compound 23 in Table 1)

a) 2-Methyl-5-nitrobenzoic acid methyl ester

By using 2-methyl-5-nitrobenzoic acid (2.0 g, 11.04 mmol), the title compound was obtained as colorless solid by similar procedures to those of Example 3a (2.14 g). The product was used in the next reaction without purification.

b) 2-Bromomethyl-5-nitrobenzoic acid methyl ester

By using the compound obtained in Example 12a (2.14 g), the title compound was obtained as pale brown oil by similar method to those of Example 1b (3.22 g). The product was used in the next reaction without purification.

c) tert-Butyl 4-[(6-nitroisoindolin-1-one)-2-ylmethyl]piperidine-1-carboxylate By using the compound obtained in Example 12b (3.22 g), the title compound was obtained as pale brown solid by similar procedures to those of Example 1c (864 mg, yield: 21%).

$^1$H-NMR(CDCl$_3$): δ 8.68(d, 1H,J=2.1 Hz), 8.43(dd,1H, J=8.4,1.8 Hz), 7.62(d,1H,J=8.1 Hz), 4.53(s,2H), 4.11(br s,2H), 3.53(br s,2H), 2.70(br dd,2H,J=12.0,12.0 Hz), 2.00–1.92(m,1H), 1.68–1.64(m,2H), 1.45(s, 9H), 1.33–1.20 (m,2H).

d) 6-Nitro-2-(piperidin-4-ylmethyl)isoindolin-1-one hydrochloride

By using the compound obtained in Example 12c (860 mg, 2.29 mmol), the title compound was used as colorless solid by similar procedures to those of Example 1d (732 mg, yield: quantitative).

$^1$H-NMR(DMSO-d$_6$): δ 8.93(br s,1H), 8.67(br s,1H), 8.47 (dd,1H,J=8.3,2.3 Hz), 8.35(d,1H,J=2.1 Hz), 7.92(d,1H, J=8.4 Hz), 4.67(s,2H), 3.46(br s,2H), 3.25(br d,2H,J=12.3 Hz), 2.80(br dd,2H,J=23.1,12.0 Hz), 2.07–2.00(m,1H), 1.75 (br d,2H,J=12.3 Hz), 1.46–1.34(m,2H).

e) 6-Nitro-2-[[1-[2-(4-fluorophenyl)-2-oxoethyl]piperidin-4-yl]methyl]isoindolin-1-one By using the compound obtained in Example 12d (725 mg, 2.33 mmol), the title compound was obtained as pale yellow solid by similar procedures to those of Example 1e (637 mg, yield: 67%).

$^1$H-NMR(CDCl$_3$): δ 8.68(d,1H,J=2.1 Hz), 8.43(dd,1H, J=8.4,2.1 Hz), 8.09–8.02(m,2H), 7.63(d,1H,J=8.4 Hz), 7.16–7.08(m,2H), 4.54(s,2H), 3.74(s, 2H), 3.55(d,2H,J=7.2 Hz), 2.98(br d,2H,J=9.9 Hz), 2.20–2.19(m, 2H), 1.87–1.81 (m,1H), 1.70(br d,2H,J=12.9 Hz), 1.56–1.47(m,2H).

f) 6-Nitro-2-[[1-[2-(4-fluorophenyl)-2-oxoethyl]piperidin-4-yl]methyl]isoindolin-1-one fumarate The compound obtained in Example 12e (287 mg, 0.70 mmol) was dissolved in dichloromethane (3 ml) and acetone (3 ml), and the solution was added with fumaric acid (41 mg, 0.35 mmol) at room temperature and stirred for 3 hours. The precipitated solids were collected by filtration to obtain the title compound as colorless solid (148 mg, yield: 40%).

Melting point: 195–206° C. $^1$H-NMR(DMSO-d$_6$): δ 8.46 (dd,1H,J=8.3,2.3 Hz), 8.34(d,1H,J=2.4 Hz), 8.11–8.07(m, 2H), 7.88(d,1H,J=8.4 Hz), 7.38–7.32(m, 2H), 6.61(s, 2H), 4.66(s, 2H), 3.86(s,2H), 3.44(d,2H,J=7.5 Hz), 2.90(br d,2H, J=11.4 Hz), 2.16(br t,2H,J=10.8 Hz), 1.79–1.74(m, 1H), 1.59(br d,2H,J=11.7 Hz), 1.30–1.19(m, 2H).

Example 13

2-[[1-(2-Phenyl-2-oxoethyl)piperidin-4-yl]methyl]isoindolin-1-one hydrochloride (Compound 26 in Table 1)

a) 2-[[1-(2-Phenyl-2-oxoethyl)piperidin-4-yl]methyl]isoindolin-1-one

A solution of the compound obtained in Example 1d (400 mg, 1.50 mmol), 2-bromoacetophenone (299 mg, 1.50 mmol), and triethylamine(0.46 ml, 3.30 mmol) in dimethylformamide (3 ml) was stirred at room temperature for 3 hours. The reaction mixture was added with water (10 ml) and stirred at room temperature, and then precipitated crystals were collected by filtration and washed with water to obtain the title compound (319 mg, yield: 61%).

$^1$H-NMR(CDCl$_3$): 8.01(d,2H), 7.84(d,1H), 7.56–7.42(m, 6H), 4.41(s,2H), 3.79(s,1H), 3.51(d,2H), 3.00(br d,2H), 2.16 (dt,2H), 1.82(m,1H), 1.70(m,2H), 1.52(dt,2H).

b) 2-[[1-(2-Phenyl-2-oxoethyl)piperidin-4-yl]methyl]isoindolin-1-one hydrochloride The compound obtained in Example 13a (319 mg) was dissolved in ethanol-ethyl acetate, and the solution was added with 4N hydrochloric acid in ethyl acetate. The precipitated crystals were collected by filtration to obtain the title compound as white solid (299 mg, yield: 85%).

Melting point: 190–197° C. $^1$H-NMR(DMSO-d$_6$): 9.91 (br s,1H), 8.03(m,2H), 7.77(m,1H), 7.65(m,1H), 7.49(m, 1H), 5.06(m,2H), 4.54(s,2H), 3.48(m,2H), 3.03(m,2H), 2.04 (m,1H), 1.99–1.61(m,4H).

Example 14

2-[[1-[2-(4-Chlorophenyl)-2-oxoethyl]piperidin-4-yl]methyl]isoindoline-1-one hydrochloride (Compound 51 in Table 1)

a) 2-[[1-[2-(4-Chlorophenyl)-2-oxoethyl]piperidin-4-yl]methyl]isoindolin-1-one A solution of the compound obtained in Example 1d (400 mg, 1.50 mmol), 2-bromo-4'-chloroacetophenone (350 mg, 1.50 mmol), and triethylamine(0.46 ml, 3.30 mmol) in dimethylformamide(3 ml) was stirred at room temperature for 3 hours. The reaction mixture was added with water and extracted with ethyl acetate. The extract was washed four times with water and dried over sodium sulfate. The solvent was evaporated and the residue was crystallized from ethyl acetate-hexane to obtain the title compound (318 mg, yield: 55%).

$^1$H-NMR(CDCl$_3$): 7.99(d,2H), 7.84(d,2H), 7.56–7.40(m, 5H), 4.41(s,2H), 3.73(s,2H), 3.51(d,1H), 2.95(br d,2H), 2.15 (dt,2H), 1.82(m,1H), 1.70(m,2H), 1.50(dt,2H).

b) 2-[[1-[2-(4-Chlorophenyl)-2-oxoethyl]piperidin-4-yl]methyl]isoindolin-1-one hydrochloride The compound obtained in Example 14a (318 mg) was dissolved in ethanol-ethyl acetate, and the solution was added with 4N hydrogen chloride in ethyl acetate. The crystals precipitated were collected by filtration to obtain the title compound as white solid (268 mg, yield: 77%).

Melting point: 188–196° C. $^1$H-NMR(DMSO-d$_6$): 9.97 (br s,1H), 8.00(m,2H), 7.68(m,3H), 7.57(m,2H), 7.47(m, 1H), 5.03(m,2H), 4.51(s,2H), 3.54–2.95(m,6H), 1.97(m, 1H), 1.80–1.60(m,4H).

Example 15

2-[[1-[2-(4-Methoxyphenyl)-2-oxoethyl]piperidin-4-yl]methyl]isoindoline-1-one hydrochloride (Compound 64 in Table 1)

a) 2-[[1-[2-(4-Methoxyphenyl)-2-oxoethyl]piperidin-4-yl]methyl]isoindolin-1-one A solution of the compound obtained in Example 1d (400 mg, 1.50 mmol), 2-bromo-4'-methoxyacetophenone (344 mg, 1.50 mmol), and triethylamine (0.46 ml, 3.30 mmol) in dimethylformamide (3 ml) was stirred at room temperature for 3 hours. The reaction mixture was added with water (10 ml) and stirred at room temperature. Then the crystals precipitated were collected by filtration and washed with water to obtain the title compound (537 mg, yield: 95%).

$^1$H-NMR(CDCl$_3$): 8.02(d,2H), 7.85(d,1H), 7.53–7.42(m, 3H), 6.91(d,2H), 4.41(s,2H), 3.87(s,3H), 3.73(s,2H), 3.51(d, 2H), 2.98(br d,2H), 2.15(dt,2H), 1.81(m,1H), 1.70(m,2H), 1.51(dt,2H).

b) 2-[[1-[2-(4-Methoxyphenyl)-2-oxoethyl]piperidin-4-yl]methyl]isoindolin-1-one hydrochloride The compound obtained in Example 15a (537 mg) was dissolved in ethanol-ethyl acetate and added with 4N hydrogen chloride in ethyl acetate. The crystals precipitated were collected by filtration to obtain the title compound as white solid (444 mg, yield: 75%).

Melting point: 163–168° C. $^1$H-NMR(DMSO-d$_6$): 9.85 (br s,1H), 7.95(m,2H), 7.67(d,1H), 7.59(d,2H), 7.47(m,1H), 7.12(d,2H), 4.95(m,2H), 4.51(s,2H), 3.86(s,3H), 3.45(m, 4H), 2.99(m,2H), 2.01(m,1H), 1.65(m,4H).

Example 16

(R,S)-2-[[1-[2-(4-Fluorophenyl)-2-hydroxyethyl]piperidin-4-yl]methyl]isoindolin-1-one hydrochloride (Compound 77 in Table 1)

a) (R,S)-2-[[1-[2-(4-Fluorophenyl)-2-hydroxyethyl]piperidin-4-yl]methyl]isoindolin-1-one The compound obtained in Example 1f (403 mg, 1.0 mmol) was treated with methylene chloride and 1N sodium hydroxide solution. The methylene chloride layer was dried over sodium sulfate and then the solvent was evaporated. The resulting residue was dissolved to give ethanol solution (15 ml), and the solution was added with sodium borohydride (30 mg, 0.79 mmol) and stirred at room temperature for 2 hours. The solvent was evaporated and the residue was added with water to form a suspension. The resulting crystals were collected by filtration to obtain the title compound as white solid (331 mg, yield: 90%).

$^1$H-NMR(CDCl$_3$): 7.86(d,1H), 7.55–7.43(m,3H), 7.32(m, 2H), 7.02(m,2H), 4.69(m,1H), 4.42(s,2H), 3.53(d,2H), 3.15 (m,1H), 2.82(m,1H), 2.49–2.00(m,4H), 1.84(m,1H), 1.70 (m,2H), 1.40(m,2H).

b) (R,S)-2-[[1-[2-(4-Fluorophenyl)-2-hydroxyethyl]piperidin-4-yl]methyl]isoindoline-1-one hydrochloride The compound obtained in Example 16a(331 mg) was dissolved in ethanol-ethyl acetate, and added with 4N hydrogen chloride in ethyl acetate. The crystals precipitated were collected by filtration to obtain the title compound as white solid (347 mg, yield: 95%).

Melting point: 223–228° C. $^1$H-NMR(DMSO-d$_6$): 9.82 (br s,1H), 7.68(d,1H), 7.61(d,2H), 7.48(m,3H), 7.22(m,2H), 6.26(m,1H), 5.15(m,1H), 4.52(s,2H), 3.63(m,2H), 3.45(d, 2H), 3.18(m,2H), 2.95(m,2H), 1.99(m,1H), 1.86–1.57(m, 4H).

Example 17

(R,S)-5-Bromo-2-[[1-[2-(4-fluorophenyl)-2-hydroxyethyl]piperidin-4-yl]methyl]isoindolin-1-one hydrochloride (Compound 79 in Table 1)

a) (R,S)-5-Bromo-2-[[1-[2-(4-fluorophenyl)-2-hydroxyethyl]piperidin-4-yl]methyl]isoindolin-1-one By using the compound obtained in Example 3e (678 mg, 1.52 mmol), the title compound was obtained as colorless solid by similar procedures to those of Example 16a (677 mg, yield: 99%).

$^1$H-NMR(CDCl$_3$): 7.70–7.74(1H,m), 7.60–7.63(2H,m), 7.31–7.36(2H,m), 6.99–7.06(2H,m), 4.69(1H,dd,J=3.6, 10.2), 4.40(2H,s), 3.51(2H,d,J=6.9), 3.1–3.2(1H,m), 2.7–2.8 (1H,m), 2.30–2.51(2H,m), 2.2–2.3(1H,m), 2.0–2.1(1H,m), 1.3–1.9(5H,m)

b) (R,S)-5-Bromo-2-[[1-[2-(4-fluorophenyl)-2-hydroxyethyl]piperidin-4-yl]methyl]isoindolin-1-one hydrochloride By using the compound obtained in Example 17a (313 mg, 0.700 mmol), the title compound was obtained as colorless solid by similar procedures to those of Example 1f (317 mg, yield: 94%).

Melting point: 230–240° C. $^1$H-NMR(DMSO-d$_6$): 9.81 (1H,brs), 7.90(1H,d,J=0.9), 7.70(1H,dd,J=0.9,8.0), 7.62(1H, d,J=8.0), 7.43–7.53(2H,m), 7.20–7.26(2H,m), 6.29–6.31(1H,m), 5.0–5.2(1H,m), 4.52(2H,s), 3.5–3.7(2H, m), 2.8–3.5(4H,m), 1.5–2.2(5H,m)

Example 18

2-[[1-[2-(4-Fluorophenyl)-2-(Z)-hydroxyiminoethyl]piperidin-4-yl]methyl]isoindolin-1-one fumarate (Z-isomer of Compound 90 in Table 1)

a) 2-[[1-[2-(4-Fluorophenyl)-2-(E,Z)-hydroxyiminoethyl]piperidin-4-yl]methyl]isoindolin-1-one The compound obtained in Example 1e (496 mg, 1.35 mmol) was dissolved in a mixed solvent of ethanol (10 ml) and pyridine (10 ml). The solution was added with hydroxylamine hydrochloride (255 mg, 3.67 mmol) at room temperature, and stirring was continued at the same temperature for 5 days. The reaction mixture was diluted with ethyl acetate and washed with an aqueous sodium bicarbonate solution and then with saturated brine, and dried over sodium sulfate. Insoluble solids were removed by filtration, and the solvent was evaporated under reduced pressure. The resulting solids were purified by silica gel column chromatography (methanol-dichloromethane) to obtain the title compound (295 mg, yield: 57%) and E-isomer (216 mg, yield: 42%) as colorless solids.

(Z-isomer)
$^1$H-NMR(CDCl$_3$): 7.85(1H,d,J=7.4), 7.42–7.64(5H,m), 7.01–7.07(2H,m), 4.41(2H,s), 3.74(2H,s), 3.52(2H,d,J=7.4), 3.0–3.1(2H,m), 2.13–2.22(2H,m), 1.8–2.0(1H,m), 1.7–1.8 (2H,m), 1.3–1.5(2H,m)

(E-isomer)
$^1$H-NMR(CDCl$_3$): 7.84(1H,d,J=6.9), 7.61–7.67(2H,m), 7.41–7.54(3H,m), 7.05–7.12(2H,m), 4.38(2H,s), 3.48(2H,d, J=7.2), 3.31(2H,s), 2.8–3.0(2H,m), 1.9–2.05(2H,m), 1.5–1.8 (3H,m), 1.3–1.4(2H,m)

b) 2-[[1-[2-(4-Fluorophenyl)-2-(Z)-hydroxyiminoethyl]piperidin-4-yl]methyl]isoindoline-1-one fumarate By using the Z-isomer compound obtained in Example 18a (289 mg, 0.756 mmol), the title compound was obtained as colorless solid by similar procedures to those of Example 36c (320 mg, yield: 85%).

Melting point: 178–180° C. $^1$H-NMR(DMSO-d$_6$): 7.76–7.81(2H,m), 7.4–7.7(4H,m), 7.16–7.23(2H,m), 6.62 (2H,s,fumaric acid), 4.45(2H,s), 3.61(2H,s), 3.2–3.4(2H,m), 2.7–2.8(2H,m), 1.9–2.1(2H,m), 1.6–1.8(1H,m), 1.4–1.6(2H, m), 1.0–1.2(2H,m)

Example 19

2-[[1-[2-(4-Fluorophenyl)-2-(E)-hydroxyiminoethyl]piperidin-4-yl]methyl]isoindolin-1-one fumarate (E-isomer of Compound 90 in Table 1)

By using the E-isomer compound obtained in Example 18a (214 mg, 0.560 mmol), the title compound was obtained as colorless solid by similar procedures to those of Example 36c (225 mg, yield: 81%).

Melting point: 186–188° C. $^1$H-NMR(DMSO-d$_6$): 11.03 (1H,brs,OH), 7.4–7.7(6H,m), 7.19–7.25(2H,m), 6.62(2H,s, fumaric acid), 4.46(2H,s), 3.2–3.4(2H,m), 2.8–2.9(2H,m), 1.9–2.05(2H,m), 1.6–1.8(1H,m), 1.4–1.6(2H,m), 1.0–1.2(2H,m)

Example 20

2-[[1-[2-(2,4-Difluorophenyl)-2-hydroxyiminoethyl]piperidin-4-yl]methyl]isoindolin-1-one hydrochloride (Compound 116 in Table 1)

a) 2-Chloro-2',4'-difluoroacetophenone oxime

2-Chloro-2',4'-difluoroacetophenone (3.09 g, 16.2 mmol) was dissolved in ethanol (30 ml). The solution was added under ice-cooling successively with hydroxylamine hydrochloride (1.23 g, 17.7 mmol) and sodium acetate (1.45 g, 17.7 mmol), and the mixture was allowed to warm to room temperature and stirred for 20 hours. The reaction solvent was evaporated under reduced pressure, and the residue was diluted with ethyl acetate and washed with an aqueous sodium bicarbonate solution and then with saturated brine, and dried over magnesium sulfate. Insoluble solids were removed by filtration, and the solvent was evaporated under reduced pressure. The residue was suspended in hexane and dried to obtain the title compound as colorless solid (2.29 g, yield: 69%).

$^1$H-NMR(CDCl$_3$): 8.74(1H,s), 7.48–7.56(1H,m), 6.85–6.99(2H,m), 4.63(2H,s)

b)

2-[[1-[2-(2,4-Difluorophenyl)-2-hydroxyiminoethyl]piperidin-4-yl]methyl]isoindoline-1-one By using the compound obtained in Example 20a (710 mg, 3.45 mmol) and the compound obtained in Example 1d (880 mg, 3.30 mmol), the title compound was obtained as colorless solid by similar procedures to those of Example 1e (1.38 g, yield: 100%).

$^1$H-NMR(CDCl$_3$): 8.3(1H,brs), 7.84(1H,d,J=7.5), 7.41–7.53(3H,m), 7.25–7.31(1H,m), 6.81–6.92(2H,m), 4.38 (2H,s), 3.46(2H,d,J=7.2), 3.33(2H,s), 2.87–2.91(2H,m), 1.96–2.05(2H,m), 1.5–1.9(3H,m), 1.2–1.4(2H,m)

c) 2-[[1-[2-(2,4-Difluorophenyl)-2-hydroxyiminoethyl]piperidin-4-yl]methyl]isoindolin-1-one hydrochloride By using the compound obtained in Example 20b (213 mg, 0.533 mmol), the title compound was obtained as colorless solid by similar procedures to those of Example 1f (168 mg, yield: 72%).

Melting point: 152–157° C. $^1$H-NMR(DMSO-d$_6$): 12.1 (1H,s), 9.92(1H,brs), 7.65(1H,d,J=7.5), 7.45–7.59(4H,m), 7.32–7.39(1H,m), 7.17–7.23(1H,m), 4.48(2H,s), 4.20–4.38 (2H,m), 3.3–3.6(4H,m), 2.8–3.0(2H,m), 1.4–2.2(5H,m)

Example 21

(R,S)-5-Bromo-2-[[1-[2-(4-fluorophenyl)-2-acetoxyethyl]piperidin-4-yl]methyl]isoindolin-1-one hydrochloride (Compound 105 in Table 1)

a) (R,S)-5-Bromo-2-[[1-[2-(4-fluorophenyl)-2-acetoxyethyl]piperidin-4-yl]methyl]isoindolin-1-one The compound obtained in Example 17a (360 mg, 0.805 mmol) and dimethylaminopyridine (139 mg, 1.14 mmol) was dissolved in dichloromethane (6 ml). The solution was added with acetic anhydride (100 µl, 1.06 mmol) under ice cooling, and stirring was continued at the same temperature for 2 hours. The reaction mixture was diluted with ethyl acetate, washed with water, an aqueous sodium bicarbonate solution, and then with saturated brine, and then dried over sodium sulfate. Insoluble solids were removed by filtration, the solvent was evaporated under reduced pressure to obtain the title compound as colorless solid (391 mg, yield: 99%).

$^1$H-NMR(CDCl$_3$): 7.71(1H,d,J=8.5), 7.58–7.62(2H,m), 7.27–7.33(2H,m), 6.98–7.05(2H,m), 5.89(1H,dd,J=4.6,8.4), 4.37(2H,s), 3.4–3.5(2H,m), 2.84–3.0(2H,m), 2.80(1H,dd, J=8.4,13.5), 2.52(1H,dd,J=4.6,13.5), 2.11(3H,s), 1.9–2.2(2H,m), 1.7–1.8(1H,m), 1.5–1.7(2H,m), 1.2–1.4(2H,m)

b) (R,S)-5-Bromo-2-[[1-[2-(4-fluorophenyl)-2-acetoxyethyl]piperidin-4-yl]methyl]isoindolin-1-one hydrochloride The compound obtained in Example 21a (387 mg, 0.791 mmol), the title compound was obtained as colorless solid by similar procedures to those of Example 1f (285 mg, yield: 69%).

Melting point: 193–200° C. $^1$H-NMR(DMSO-d$_6$): 11.0 (1H,brs), 7.90(1H,s), 7.69(1H,d,J=8.1), 7.62(1H,d,J=8.1), 7.44–7.53(2H,m), 7.22–7.31(2H,m), 6.0–6.2(1H,m), 4.49–4.52(2H,m), 3.2–3.7(6H,m), 2.8–3.0(2H,m), 2.12(3H, s), 1.4–2.0(5H,m)

Example 22

5-[[1-[2-(4-Fluorophenyl)-2-oxoethyl]piperidin-4-yl] methyl]-4,5-dihydro-6H-thieno[2,3-c]pyrrol-6-one hydrochloride (Compound 776 in Table 2)

a) Ethyl 3-methyl-2-thiophenecarboxylate

By using 3-methyl-2-thiophenecarboxylic acid (1.5 g, 10.55 mmol), the title compound was obtained as pale yellow oil by similar procedures to those of Example 3a (1.20 g). The product was used in the next reaction without purification.

b) Ethyl 3-bromomethyl-2-thiophenecarboxylate

By using the compound obtained in Example 22a (1.20 g), the title compound was obtained as pale brown oil by similar procedures to those of Example 1b (1.88 g). The product was used in the next reaction without purification.

c) Ethyl 3-[[1-(tert-butoxycarbonyl)piperidin-4-yl] methylaminomethyl]-2-thiophenecarboxylate The compound obtained in Example 22b (1.88 g), the title compound was obtained as pale brown solid by similar procedures to those of Example 1c (2.02 g). The product was used in the next reaction without purification.

d) 3-[[1-(tert-Butoxycarbonyl)piperidin-4-yl]methylaminomethyl]-2-thiophenecarboxylic acid The compound obtained in Example 22c (1.0 g) was dissolved in ethanol (15 ml). The solution was added with water (5 ml) and then added with sodium hydroxide (400 mg, 10.0 mmol) under ice cooling, and then the mixture was warmed to room temperature and stirred. After 6 hours, the mixture was added with concentrated hydrochloric acid under ice cooling to adjust its pH to 7.0, and then extracted with dichloromethane. The organic layer was washed with water and dried over magnesium sulfate. Insoluble solids were removed by filtration, and the filtrate was evaporated under reduced pressure. The resulting solid was dissolved in dichloromethane (3 ml). The solution was added with diethyl ether (20 ml) and precipitated solids were collected by filtration to obtain the title compound (416 mg, 35%, 3 steps).

$^1$H-NMR(CDCl$_3$): δ 11.4(s,2H), 7.32(d,1H,J=5.1 Hz), 6.91(d,1H,J=4.5 Hz), 4.21(s,2H), 4.04(s,2H),2.71–2.61(m, 4H), 1.96(br s,1H), 1.79(br d,2H,J=12.6 Hz), 1.41(s,9H), 1.16–1.03(m,2H).

e) tert-Butyl4-[(4,5-dihydro-6H-thieno[2,3-c]pyrrol-6-one)-2-ylmethyl]piperidine-1-carboxylate The compound obtained in Example 22d (500 mg) was dissolved in dichloromethane (14 ml), and added with methanesulfonyl chloride (0.11 ml, 1.41 mmol) under ice cooling. The mixture was stirred at the same temperature for 1 hour, and then warmed to room temperature and stirred for 17 hours. The reaction mixture was added with water (5 ml)

at the same temperature and extracted wit dichloromethane. The organic layer was washed with water and dried over magnesium sulfate. Insoluble solids were removed by filtration and the filtrate was evaporated under reduced pressure. The resulting oil was purified by silica gel column chromatography (methanol-dichloromethane) to obtain the title compound as pale green solid (247 mg, yield: 52%).

$^1$H-NMR(CDCl$_3$): δ 7.63(d,1H,J=4.5 Hz), 7.04(d,1H, J=4.8 Hz), 4.33(s,2H), 4.11(br s,2H), 3.45(br s,2H), 2.69(br dd,2H,J=12.3,12.3 Hz), 1.93–1.87(m,1H), 1.67(br d,2H, J=9.3 Hz), 1.45(s,9H), 1.30–1.16(m,2H).

f) 5-(Piperidin-4-ylmethyl)-4,5-dihydro-6H-thieno[2,3-c]pyrrol-6-one hydrochloride By using the compound obtained in Example 22e (310 mg, 0.90 mmol), the title compound was obtained as pale green solid by similar procedures to those of Example 1d (200 mg, yield: 80%).

$^1$H-NMR(DMSO-d$_6$): δ 8.90(br s,1H), 8.62(br s,1H), 7.98 (d,1H,J=4.7 Hz), 7.24(d,1H,J=4.7 Hz), 4.44(s,2H), 3.38(d, 2H,J=7.4 Hz), 3.24(br d,2H,J=12.6 Hz), 2.80(br dd,2H, J=23.1,12.1 Hz), 2.02–1.91(m,1H), 1.74(br d,2H,J=13.2 Hz), 1.43–1.29(m,2H).

g) 5-[[1-[2-(4-Fluorophenyl)-2-oxoethyl]piperidin-4-yl]methyl]-4,5-dihydro-6H-thieno[2,3-c]pyrrol-6-one By using the compound obtained in Example 22f (193 mg, 0.71 mmol), the title compound was obtained as pale brown solid by similar procedures to those of Example 1e (209 mg, yield: 79%).

$^1$H-NMR(CDCl$_3$): δ 8.10–8.04(m,2H), 7.62(d,1H), 7.15–7.07(m,2H), 7.02(m,1H), 4.32(s,2H), 3.72(s,2H), 3.45 (d,2H,7.1 Hz), 2.96(br d,2H,J=11.5 Hz), 2.20–2.11(m,2H), 1.83–1.76(m,1H), 1.70(br d,2H,J=13.9 Hz), 1.51–1.43(m, 2H).

h) 5-[[1-[2-(4-Fluorophenyl)-2-oxoethyl]piperidin-4-yl]methyl]-4,5-dihydro-6H-thieno[2,3-c]pyrrol-6-one hydrochloride By using the compound obtained in Example 22g (209 mg, 0.56 mmol), the title compound was obtained as colorless solid by similar procedures to those of Example 1f (178 mg, yield: 78%).

Melting point: 167–171° C. $^1$H-NMR(DMSO-d$_6$): δ 9.94 (br s,1H), 8.19–8.06(m,2H), 7.99(d,1H,J=4.8 Hz), 7.58(dd, 2H,J=8.9,8.9 Hz), 7.26(d,1H, J=4.5 Hz), 5.11–5.04(m,2H), 4.47(s,2H), 3.54(br d 2H,J=10.5 Hz), 3.31(Br s,2H), 3.08–3.01(m,2H), 2.09–1.57(m,5H).

Example 23

6-[[1-[2-(4-Fluorophenyl)-2-oxoethyl]piperidin-4-yl]methyl]-6,7-dihydro-5H-pyrrolo[3,4-b]pyridin-5-one dihydrochloride (Compound 796 in Table 2)

a) Ethyl 2-bromomethylpiridine-3-carboxylate

By using 2-bromomethylpyridine-3-carboxylic acid (2.0 g, 12.11 mmol), the title compound was obtained as brown oil by similar procedures to those of Example 1b (1.02 g). The product was used in the next reaction without purification.

b) tert-Butyl 4-[(6,7-dihydro-5H-pyrrolo[3,4-b]pyridin-5-one)-2-ylmethyl]piperidine-1-carboxylate By using the compound obtained in Example 23a (1.01 g), the title compound was obtained as brown oil by similar procedures to those of Example 1c (945 mg). The product was used in the next reaction without purification.

c) 6-(Piperidin-4-ylmethyl)-6,7-dihydro-5H-pyrrolo[3,4-b]pyridin-5-one dihydrochloride By using the compound obtained in Example 23b (811 mg, 1.01 mmol), the title compound was obtained as colorless solid by similar procedures to those of Example 1d (416 mg, yield: 33%).

$^1$H-NMR(DMSO-d$_6$): δ 9.21(s,2H), 8.99(s,2H), 8.10(dd, 1H,J=8.6,1.2 Hz), 7.54(dd,1H, J=7.7,5.0 Hz), 4.57(s,2H), 3.47(d,2H,J=7.4 Hz), 3.24(br d,2H,J=12.3 Hz), 2.79(br dd,2H,J=23.5,12.3 Hz), 2.09–1.99(m,1H), 1.75(br d,2H, J=12.9 Hz), 1.46–1.32(m,2H).

d) 2-[[1-[2-(4-Fluorophenyl)-2-oxoethyl]piperidin-4-yl]methyl]-6,7-dihydro-5H-pyrrolo[3,4-b]pyridin-5-one By using the compound obtained in Example 23c (416 mg, 1.37 mmol), the title compound was obtained as pale brown solid by similar procedures to those of Example 1e (377 mg, yield: 75%).

$^1$H-NMR(CDCl$_3$): δ 8.72(dd,1H,J=4.7,1.4 Hz), 8.13–8.71 (m,3H), 7.40(dd,1H,J=7.6,5.1 Hz), 7.12(dd,2H,J=8.6,8.6 Hz), 4.47(s,2H), 3.73(s,2H), 3.55(d,2H,J=7.1 Hz), 2.97(br d,2H,J=11.5 Hz), 2.15(ddd,2H,J=2.1,11.5,11.5 hz), 1.86–1.80(m,1H), 1.70(br d,2H,J=13.0 Hz), 1.56–1.46(m, 2H).

e) 2-[[1-[2-(4-Fluorophenyl)-2-oxoethyl]piperidin-4-yl]methyl]-6,7dihydro-5H-pyrrolo[3,4-b]pyridin-5-one dihydrochloride By using the compound obtained in Example 23d (377 mg, 1.03 mmol), the title compound was obtained as colorless solid by similar procedures to those of Example 1f (384 mg, yield: 85%).

Melting point: 138–144° C. $^1$H-NMR(DMSO-d$_6$): δ 10.1 (br s,1H), 8.78(dd,1H,=4.7,1.1 Hz), 8.19(m,3H), 7.57–7.45 (m,3H), 5.13–5.05(m,2H), 4.61(s,2H), 3.62(m,3H), 3.32(br s,1H), 3.04(br dd,2H,J=21.8,10.1 Hz), 2.07(br s,1H), 1.89–1.60(m,4H).

Example 24

2-[[1-(3,3-Dimethyl-2-oxobutyl)piperidin-4-yl]methyl]isoindolin-1-one hydrochloride (Compound 126 in Table 1)

a) 2-[[1-(3,3-Dimethyl-2-oxobutyl)piperidin-4-yl]methyl]isoindolin-1-one

The compound obtained in Example 1d (500 mg, 1.87 mmol) was dissolved in DMF (6 ml). The solution was added with triethylamine (0.57 ml, 4.11 mmol) and 1-chloropinacolone (0.24 ml, 1.87 ml), and stirred at room temperature for 30 hours and then heated at 50° C. for 7 hours. After the mixture was stand for cooling, the mixture was added with water (10 ml) and extracted with ethyl acetate. The organic layer was washed three times with water and dried over magnesium sulfate. Insolble solids were removed by filtration and the filtrate was evaporated. The resulting oil was purified by silica gel column chromatography (methanol-dichloromethane) to obtain the title compound as pale brown solid (369 mg, yield: 60%).

$^1$H-NMR(CDCl$_3$): δ 7.84(d,1H,J=7.2 Hz), 7.56–7.42(m, 3H), 4.41(s,2H), 3.50(d,2H,J=7.3 Hz), 3.36(s,2H), 2.88(br d,2H,J=11.3 Hz), 2.05(ddd,2H,J=2.2,11.3,11.3 Hz), 1.87–1.80(m,1H), 1.69(br d,2H,J=12.9 Hz), 1.54–1.46(m, 2H), 1.15(s,9H).

b) 2-[[1-(3,3-Dimethyl-2-oxobutyl)piperidin-4-yl]methyl]isoindolin-1-one hydrochloride By using the compound obtained in Example 24a (369 mg, 1.12 mmol), the title compound was obtained as colorless solid by similar procedures to those of Example 1f (323 mg, yield: 79%).

Melting point: 239–243° C.

$^1$H-NMR(DMSO-d$_6$): δ 9.73(br s,1H), 7.68(d,1H,J=7.5), 7.61(d,2H), 7.53–7.45(m,1H), 4.64–4.52(m,4H), 3.60–3.21(m,4H), 2.95(br d,2H,J=10,5 Hz), 1.97(br s,1H), 1.79(br d,2H,J=13.5 Hz), 1.65–1.52(m,2H), 1.13(s,9H).

Example 25

2-[[1-(2-Methoxybenzyl)piperidin-4-yl]methyl]isoindolin-1-one hydrochloride (Compound 136 in Table 1)

a) 2-Methoxybenzyl chloride

2-Methoxybenzyl alcohol (1.01 g, 7.31 mmol) and triphosgene (757 mg, 2.55 mmol) were dissolved in tetrahydrofuran (5 ml). The solution was added with pyridine (1.18 ml, 14.6 mmol) under ice cooling, and then warmed to room temperature. After 20 minutes, insoluble solids were removed by filtration, and the solvent was evaporated under reduced pressure. The resulting oil was diluted with ethyl acetate and insoluble solids were further removed. The solvent was evaporated under reduced pressure to obtain the title compound as pale yellow oil (1.16 g, yield: 100%).

$^1$H-NMR(CDCl$_3$): 7.25–7.37(2H,m), 6.87–6.97(2H,m), 4.66(2H,s), 3.88(3H,s)

b) 2-[[1-(2-Methoxybenzyl)piperidin-4-yl]methyl]isoindolin-1-one

The compound obtained in Example 25a (339 mg, 2.17 mmol), the compound obtained in Example 1d (563 mg, 2.11 mmol), and triethylamine (700 μl, 5.02 mmol) were added to dimethylformamide (6 ml), and the mixture was stirred at 60° C. for 2 hours. The reaction mixture was allowed to cool to room temperature and then diluted with a mixed solvent of ethyl acetate and hexane. The mixture was washed with water, an aqueous sodium bicarbonate solution, and then with saturated brine, and dried over sodium sulfate. Insoluble solids were removed by filtration, and the solvent was evaporated under reduced pressure. The resulting solid was suspended and washed in a mixed solvent of diethyl ether and hexane, and solid was dried to obtain the title compound as colorless solid (524 mg, yield: 71%).

$^1$H-NMR(CDCl$_3$): 7.84(1H,d,J=7.2), 7.41–7.53(3H,m), 7.35(1H,dd,J=1.4,7.7), 7.10–7.26(1H,m), 6.83–6.95(2H,m), 4.40(2H,s), 3.80(3H,s), 3.55(2H,s), 3.50(2H,d,J=7.2), 2.91–2.96(2H,m), 1.97–2.06(2H,m), 1.5–1.9(3H,m), 1.3–1.5(2H,m)

c) 2-[[1-(2-Methoxybenzyl)piperidin-4-yl]methyl]isoindolin-1-one hydrochloride By using the compound obtained in Example 25b (521 mg, 1.49 mmol), the title compound was obtained as colorless solid by similar procedures to those of Example 1f (470 mg, yield: 82%).

Melting point: 195–203° C. $^1$H-NMR(DMSO-d$_6$): 10.5 (1H,brs), 7.58–7.71(4H,m), 7.41–7.51(2H,m), 7.11(1H,d, J=8.4), 6.98–7.04(1H,m), 4.48–4.52(2H,m), 4.18–4.35(2H, m), 3.82–3.87(3H,m), 3.2–3.5(4H,m), 2.7–2.9(2H,m), 1.5–2.2(5H,m)

Example 26

2-[[1-[2-(2-Methoxyphenyl)ethyl]piperidin-4-yl]methyl]isoindolin-1-one hydrochloride (Compound 146 in Table 1)

a) 2-Methoxyphenethylmethanesulfonate

2-Methoxyphenethyl alcohol (5.29 g, 34.74 mmol) and triethylamine (7.0 ml, 50 mmol) was dissolved in tetrahydrofuran (45 ml). The solution was added with methanesulfonyl chloride (3.0 ml, 39 mmol) under ice cooling, and stirring was continued at the same temperature for 1 hour. The reaction mixture was diluted with ethyl acetate, and washed with water, 10% aqueous citric acid solution, an aqueous sodium bicarbonate solution, and then with saturated brine, and dried over magnesium sulfate. Insoluble solids were removed by filtration, the solvent was evaporated under reduced pressure. The resulting oil was purified by silica gel column chromatography(ethyl acetate-hexane) to obtain the title compound (5.77 g, yield: 72%)

$^1$H-NMR(CDCl$_3$): 7.18–7.29(2H,m), 6.85–6.93(2H,m), 4.42(2H,t,J=7.1), 3.84(3H,s), 3.07(2H,t,J=7.1), 2.83(3H,s)

b) 2-[[1-[2-(2-Methoxyphenyl)ethyl]piperidin-4-yl]methyl]isoindolin-1-one

The compound obtained in Example 26a (530 mg, 2.30 mmol), the compound obtained in Example 1d (563 mg, 2.11 mmol), sodium carbonate (553 mg, 5.22 mmol), and sodium iodide (328 mg, 2.19 mmol) were added to N-methylpyrrolidone (9 ml), and the mixture was stirred at 80° C. for two hours. The reaction mixture was allowed to cool to room temperature, and then the mixture was diluted with ethyl acetate. The mixture was washed with water, an aqueous sodium bicarbonate solution, and the with saturated brine, and dried over sodium sulfate. Insoluble solids were removed by filtration, and then the solvent was evaporated under reduced pressure. The resulting oil was purified by silica gel column chromatography (dichloromethane-methanol) to obtain the title compound as yellow oil (544 mg, yield: 71%).

$^1$H-NMR(CDCl$_3$): 7.85(1H,d,J=7.5), 7.42–7.54(3H,m), 7.12–7.18(2H,m), 6.82–6.90(2H,m), 4.42(2H,s), 3.81(3H,s), 3.52(2H,d,J=7.2), 3.01–3.06(2H,m), 2.79–2.85(2H,m), 2.51–2.58(2H,m), 1.99–2.08(2H,m), 1.6–1.9(3H,m), 1.3–1.5(2H,m)

c) 2-[[1-[2-(2-Methoxyphenyl)ethyl]piperidin-4-yl]methyl]isoindolin-1-one hydrochloride By using the compound obtained in Example 26b (533 mg, 1.46 mmol), the title compound was obtained as pale yellow solid by similar procedures to those of Example 1f (475 mg, yield: 81%).

Melting point: 208–227° C. $^1$H-NMR(DMSO-$d_6$): 10.3 (1H,brs), 7.69(1H,d,J=7.5), 7.60–7.63(2H,m), 7.48–7.53(1H,m), 7.18–7.26(2H,m), 6.88–7.02(2H,m), 4.51 (2H,s),3.79–3.83(3H,m), 3.1–3.6(6H,m), 2.7–3.0(4H,m), 1.7–2.2(3H,m), 1.5–1.7(2H,m)

Example 27

2-(1-Benzylpiperidin-4-ylmethyl)isoindolin-1-one hydrochloride (Compound 176 in Table 1)

a) 2-(1-Benzylpiperidin-4-ylmethyl)isoindolin-1-one

The title compound was obtained by similar procedures to those of Example 25b (yield: 80%).

$^1$H-NMR (CDCl$_3$): δ 7.84 (d, J=7.5 Hz, 1H), 7.41–7.54 (m, 3H), 7.20–7.30 (m, 5H), 4.39 (s, 2H), 3.50 (d, J=6.6 Hz, 2H), 3.49 (s, 2H), 2.88 (br d, J=12 Hz, 2H), 1.96 (dt, J=11.7, 2.4 Hz, 2H), 1.79 (m, 1H), 1.66 (br d, J=12 Hz, 2H), 1.41 (dq, J=11.7, 3.6 Hz, 2H).

b) 2-(1-Benzylpiperidin-4-ylmethyl)isoindolin-1-one hydrochloride

By using the compound obtained in Example 27a, the title compound was obtained by similar procedures to those of Example 1f (yield: 85%).

Melting point: 222–229° C. $^1$H-NMR (DMSO-$d_6$): δ 13.50 (br s, 1H), 7.57–7.60 (m, 4H), 7.46–7.51 (m, 4H), 4.50 (s, 2H), 4.23–4.41 (m, 2H), 3.40–3.65 (m, 2H), 2.79–3.34 (m, 4H), 1.96 (m, 1H), 1.78 (m, 2H), 1.55 (m, 2H).

Example 28

2-[[1-(4-Fluorobenzyl)piperidin-4-yl]methyl]isoindolin-1-one hydrochloride (Compound 186 in Table 1)

a) 2-[[1-(4-Fluorobenzyl)piperidin-4-yl]methyl]isoindolin-1-one

The title compound was obtained by similar procedures to those of Example 25b (yield: 49%).

$^1$H-NMR (CDCl$_3$): δ 7.84 (d, J=7.5 Hz, 1H), 7.42–7.53 (m, 3H), 7.26 (m, 2H), 6.98 (t, J=8.7 Hz, 2H), 4.40 (s, 2H), 3.50 (d, J=7.5 Hz, 2H), 3.45 (s, 2H), 2.86 (br d, J=12 Hz, 2H), 1.94 (dt, J=11.7, 2.1 Hz, 2H), 1.80 (m, 1H), 1.66 (br d, J=12 Hz, 2H), 1.40 (dq, J=12, 4 Hz, 2H).

b) 2-[[1-(4-Fluorobenzyl)piperidin-4-yl]methyl]isoindolin-1-one hydrochloride

By using the compound obtained in Example 28a, the title compound was obtained by similar procedures to those of Example 1f (yield: 85%).

Melting point: 241–249° C. $^1$H-NMR (DMSO-$d_6$): δ 10.30 (br s, 1H), 7.59–7.69 (m, 5H), 7.50 (m, 1H), 7.31 (t, J=9 Hz, 2H), 4.49 (s, 2H), 4.25–4.41 (m, 2H), 3.41–3.64 (m, 2H), 2.77–3.34 (m, 4H), 1.96 (m, 1H), 1.78 (br d, J=12 Hz, 2H), 1.53 (br q, J=12 Hz,2H).

Example 29

2-[[1-[2-(4-Fluorophenyl)ethyl]piperidin-4-yl]methyl]isoindolin-1-one hydrochloride (Compound 196 in Table 1)

a) 2-[[1-[2-(4-Fluorophenyl)ethyl]piperidin-4-yl]methyl]isoindolin-1-one

The title compound was obtained by similar procedures to those of Example 26b (yield: 27%).

$^1$H-NMR (CDCl$_3$): δ 7.85 (d, J=7.8 Hz, 1H), 7.43–7.54 (m, 3H), 7.15 (m, 2H), 6.96 (t, J=8.4 Hz, 2H), 4.42 (s, 2H), 3.52 (d, J=7.2 Hz, 2H), 2.99 (br d, J=12 Hz, 2H), 2.77 (m, 2H), 2.55 (m, 2H), 2.02 (t, J=11 Hz, 2H), 1.83 (m, 1H), 1.73 (br d, J=12 Hz, 2H), 1.40 (dq, J=12, 4 Hz, 2H).

b) 2-[[1-[2-(4-Fluorophenyl)ethyl]piperidin-4-yl]methyl]isoindolin-1-one hydrochloride By using the compound obtained in Example 29a, the title compound was obtained by similar procedures to those of Example 1f (yield: 48%).

Melting point: 230–237° C. $^1$H-NMR (DMSO-$d_6$): δ 10.06 (br s, 1H), 7.69 (d, J=7.5 Hz, 1H), 7.61–7.62 (m, 2H), 7.51 (m, 1H), 7.32 (m, 2H), 7.18 (t, J=8.7 Hz, 2H), 4.52 (s, 2H), 3.54–3.60 (m, 2H), 3.42–3.46 (m, 2H), 2.86–3.34 (m, 6H), 2.86 (m, 1H), 1.83 (br d, J=12 Hz, 2H), 1.54 (br q, J=12 Hz, 2H).

Example 30

2-[[1-[3-Phenyl-3-oxopropyl]piperidin-4-yl]methyl]isoindolin-1-one hydrochloride (Compound 156 in Table 1)

a) 2-[[1-[3-Phenyl-3-oxopropyl]piperidin-4-yl]methyl]isoindolin-1-one

The title compound was obtained by similar procedures to those of Example 26b (yield: 61%).

$^1$H-NMR (CDCl$_3$): δ 7.96 (d, J=6.9 Hz, 2H), 7.85 (d, J=7.2 Hz, 1H), 7.42–7.59 (m, 6H), 4.41 (s, 2H), 3.51 (d, J=6.9 Hz, 2H), 3.19 (t, J=7.4 Hz, 2H), 2.96 (br t, J=12 Hz, 2H), 2.82 (t, J=7.4 Hz, 2H), 2.04 (dt, J=11.7, 1.8 Hz, 2H), 1.81 (m, 1H), 1.71 (br d, J=12 Hz, 2H), 1.40 (dq, J=12, 4 Hz, 2H).

b) 2-[[1-[3-Phenyl-3-oxopropyl]piperidin-4-yl]methyl]isoindolin-1-one hydrochloride By using the compound obtained in Example 30a, the title compound was obtained by similar procedures to those of Example 1f (yield: 66%).

Melting point: 245–261° C. $^1$H-NMR (DMSO-$d_6$): δ 10.38 (br s, 1H), 8.01 (d, J=7.5 Hz, 2H), 7.69 (m, 2H), 7.54–7.62 (m, 4H), 7.49 (m, 1H), 4.52 (s, 2H), 2.88–3.70 (m, 10H), 2.01 (m, 1H), 1.58 (br d, J=12 Hz, 2H), 1.51 (br q, J=12 Hz, 2H).

Example 31

2-[[1-[4-(4-Fluorophenyl)-4-oxobutyl]piperidin-4-yl]methyl]isoindolin-1-one hydrochloride (Compound 166 in Table 1)

a) 2-[[1-[4-(4-Fluorophenyl)-4-oxobutyl]piperidin-4-yl]methyl]isoindolin-1-one

The title compound was obtained by similar procedures to those of Example 26b.

$^1$H-NMR (CDCl$_3$): δ 8.00 (m, 2H), 7.85 (d, J=7.5 Hz, 1H), 7.42–7.54 (m, 3H), 7.12 (t, J=8.4 Hz, 2H), 4.40 (s, 2H), 3.48 (d, J=7.2 Hz, 2H), 2.96 (t, J=7.2 Hz, 2.90 (br d, J=12 Hz, 2H), 2.39 (t, J=7.2 Hz, 2H), 1.90–1.97 (m, 4H), 1.78 (m, 1H), 1.66 (br d, J=12 Hz, 2H), 1.32 (dq, J=12, 4 Hz, 2H).

b) 2-[[1-[4-(4-Fluorophenyl)-4-oxobutyl]piperidin-4-yl]methyl]isoindolin-1-one hydrochloride By using the compound obtained in Example 31a, the title compound was obtained by similar procedures to those of Example 1f (yield: 20%).

Melting point: 195–199° C. $^1$H-NMR (DMSO-d$_6$): δ 9.87 (br s, 1H), 8.06 (m, 2H), 7.69 (d, J=7.4 Hz, 1H), 7.60–7.63 (m, 2H), 7.51 (m, 1H), 7.38 (t, J=8.8 Hz, 2H), 4.51 (s, 2H), 2.85–3.63 (m, 10H), 1.99–2.04 (m, 3H), 1.80 (br d, J=12 Hz, 2H), 1.55 (br q, J=12 Hz, 2H).

Example 32

2-[[1-[2-(4-Fluorophenyloxy)ethyl]piperidin-4-yl]methyl]isoindolin-1-one hydrochloride (Compound 206 in Table 1)

a) 1-(2-Chloroethyloxy)-4-fluorobenzene

4-Fluorophenol (8.92 mmol) and 1-chloro-2-bromoethane (13.4 mmol) were dissolved in acetone (18 mL). The solution was added with potassium carbonate (12.5 mmol) and heated under reflux for 10 hours. The mixture was allowed to cool to room temperature and then filtered. The filtrate was concentrated and the residue was purified by silica gel column chromatography (hexane/ethyl acetate) to obtain the title compound (yield: 31%).

$^1$H-NMR (CDCl$_3$): δ 7.02 (t, J=8.6 Hz, 1H), 6.87 (m, 2H), 4.19 (t, J=5.8 Hz, 2H), 3.80 (t, J=5.8 Hz, 2H).

b) 2-[[1-[2-(4-Fluorophenyloxy)ethyl]piperidin-4-yl]methyl]isoindolin-1-one

By using the compound obtained in Example 32a, the title compound was obtained by similar procedures to those of Example 26b (yield: 61%).

$^1$H-NMR (CDCl$_3$): δ 7.85 (d, J=7.2 Hz, 1H), 7.42–7.54 (m, 3H), 6.93 (t, J=9 Hz, 2H), 6.83 (m, 2H), 4.41 (s, 2H), 4.05 (t, J=6.0 Hz, 2H), 3.51 (d, J=7.2 Hz, 2H), 3.00 (br d, J=12 Hz, 2H), 2.78 (t, J=6.0 Hz, 2H), 2.11 (dt, J=11.7, 2.1 Hz, 2H), 1.81 (m, 1H), 1.69 (m, 2H), 1.43 (dq, J=12.0, 3.6 Hz, 2H).

c) 2-[[1-[2-(4-Fluorophenyloxy)ethyl]piperidin-4-yl]methyl]isoindolin-1-one hydrochloride By using the compound obtained in Example 32b, the title compound was obtained by similar procedures to those of Example 1f (yield: 56%).

Melting point: 198–204° C. $^1$H-NMR (DMSO-d$_6$): δ 10.28 (br s, 1H), 7.68 (d, J=7.5 Hz, 1H), 7.60–7.62 (m, 2H), 7.50 (m, 1H), 7.16 (m, 2H), 7.02 (m, 2H), 4.51 (s, 2H), 4.36 (s, 2H), 2.96–3.61 (m, 8H), 1.99 (m, 1H), 1.80 (m, 2H), 1.59 (m, 2H).

Example 33

2-[[1-[3-(4-Fluorophenyloxy)propyl]piperidin-4-yl]methyl]isoindolin-1-one hydrochloride (Compound 216 in Table 1)

a) 1-(3-Chloropropyloxy)-4-fluorobenzene

The title compound was obtained by similar procedures to those of Example 32a (yield: 94%).

$^1$H-NMR (CDCl$_3$): δ 6.97 (t, J=8.4 Hz, 2H), 6.84 (m, 2H), 4.07 (t, J=6.0 Hz, 2H), 3.74 (t, J=6.3 Hz, 2H), 2.22 (m, 2H).

b) 2-[[1-[3-(4-Fluorophenyloxy)propyl]piperidin-4-yl]methyl]isoindolin-1-one

By using the compound obtained in Example 33a, the title compound was obtained by similar procedures to those of Example 26b (yield: 72%).

$^1$H-NMR (CDCl$_3$): δ 7.85 (d, J=6.9 Hz, 1H), 7.42–7.55 (m, 3H), 6.96 (t, J=8.4 Hz, 2H), 6.82 (m, 2H), 4.41 (s, 2H), 3.96 (t, J=6.3 Hz, 2H), 3.51 (d, J=7.2 Hz, 2H), 2.94 (br d, J=12 Hz, 2H), 2.49 (t, J=7.4 Hz, 2H), 1.90–1.99 (m, 4H), 1.81 (m, 1H), 1.70 (m, 2H), 1.41 (dq, J=12.3, 3.3 Hz, 2H).

c) 2-[[1-[3-(4-Fluorophenyloxy)propyl]piperidin-4-yl]methyl]isoindolin-1-one hydrochloride By using the compound obtained in Example 33b, the title compound was obtained by similar procedures to those of Example 1f (yield: 43%).

Melting point: 164° C. $^1$H-NMR (DMSO-d$_6$): δ 10.14 (br s, 1H), 7.69 (d, J=7.5 Hz, 1H), 7.61–7.62 (m, 2H), 7.51 (m, 1H), 7.13 (t, J=8.7 Hz, 2H), 6.95 (m, 2H), 4.51 (s, 2H), 4.02 (t, J=6 Hz, 2H), 2.85–3.64 (m, 6H), 2.16 (m, 2H), 1.99 (m, 1H), 1.80 (br d, J=12 Hz, 2H), 1.56 (br q, J=12 Hz, 2H).

Example 34

2-[[1-[4-(4-Fluorophenyloxy)butyl]piperidin-4-yl]methyl]isoindolin-1-one hydrochloride (Compound 226 in Table 1)

a) 1-(4-Chlorobutyloxy)-4-fluorobenzene

The title compound was obtained by similar procedures to those of Example 32a (yield: 97%).

$^1$H-NMR (CDCl$_3$): δ 6.96 (t, J=8.7 Hz, 2H), 6.82 (m, 2H), 3.96 (t, J=5.8 Hz, 2H), 3.61 (t, J=6.2 Hz, 2H), 1.89–1.99 (m, 4H).

b) 2-[[1-[4-(4-Fluorophenyloxy)butyl]piperidin-4-yl]methyl]isoindolin-1-one

By using the compound obtained in Example 34a, the title compound was obtained by similar procedures to those of Example 26b (yield: 78%).

$^1$H-NMR (CDCl$_3$): δ 7.85 (d, J=7.5 Hz, 1H), 7.42–7.53 (m, 3H), 6.96 (t, J=8.5 Hz, 2H), 6.81 (m, 2H), 4.41 (s, 2H), 3.92 (t, J=6.3 Hz, 2H), 3.50 (d, J=7.2 Hz, 2H), 2.93 (br d,

J=12 Hz, 2H), 2.38 (t, J=7.5 Hz, 2H), 1.93 (br t, J=12 Hz, 2H), 1.62–1.82 (m, 7H), 1.40 (dq, J=12, 3 Hz, 2H).

c) 2-[[1-[4-(4-Fluorophenyloxy)butyl]piperidin-4-yl]methyl]isoindolin-1-one hydrochloride By using the compound obtained in Example 34b, the title compound was obtained by similar procedures to those of Example 1f (yield: 82%).

Melting point: 145–146° C. $^1$H-NMR (DMSO-$d_6$): δ 10.08 (br s, 1H), 7.69 (d, J=7.5 Hz, 1H), 7.60–7.62 (m, 2H), 7.51 (m, 1H), 7.12 (t, J=9 Hz, 2H), 6.94 (m, 2H), 4.51 (s, 2H), 3.96 (t, J=6 Hz, 2H), 2.81–3.62 (m, 8H), 1.99 (m, 1H), 1.70–1.81 (m, 6H), 1.55 (m, 2H).

Example 35

2-[[1-(1-Benzofuran-2-ylmethyl)piperidin-4-yl]methyl]isoindolin-1-one hydrochloride (Compound 236 in Table 1)

a) 1-Benzofuran-2-ylmethanol

Lithium aluminium hydride (467 mg, 12.3 mmol) was suspended in diethyl ether and the suspension was heated under reflux. The suspension was added dropwise with 1-benzofurane-2-carboxylic acid (2.00 g, 12.3 mmol), dissolved in tetrahydrofuran (10 ml) and further heated under reflux for 20 minutes. The reaction mixture was cooled to 0° C., and then added with water (0.8ml) and stirred at the same temperature for 30 minutes. Insoluble solids were removed by filtration using Celite, and then the solvent was evaporated under reduced pressure to obtain the title compound as yellow oil (1.72 g, yield: 94%).

$^1$H-NMR(CDCl$_3$): 7.54–7.58(1H,m), 7.45–7.49(1H,m), 7.19–7.32(2H,m), 6.67(1H,s), 4.78(2H,d,J=4.5), 1.94(1H, brs)

b) 2-Chloromethyl-1-benzofuran

By using the compound obtained in Example 35a (1.00 g, 6.75 mmol), the title compound was obtained by similar procedures to those of Example 25a (1.17 g, yield: 100%).

$^1$H-NMR(CDCl$_3$): 7.47–7.57(2H,m), 7.20—7.20(2H,m), 6.74(1H,s), 4.71(2H,s)

c) 2-[[1-(1-Benzofuran-2-ylmethyl)piperidin-4-yl]methyl]isoindolin-1-one

By using the compound obtained in Example 35b (538 mg, 3.23 mmol) and the compound obtained in Example 1d (783 mg, 2.94 mmol), the title compound was obtained by similar procedures to those of Example 25b (516 mg, yield: 49%).

$^1$H-NMR(CDCl$_3$): 7.84(1H,d,J=7.2), 7.41–7.55(5H,m), 7.19–7.28(2H,m), 6.57(1H,s), 4.39(2H,s), 3.68(2H,s), 3.50 (2H,d,J=6.9), 2.95–3.00(2H,m), 2.03–2.12(2H,m), 1.6–1.9 (3H,m), 1.4–1.6(2H,m)

d) 2-[[1-(1-Benzofuran-2-ylmethyl)piperidin-4-yl]methyl]isoindolin-1-one hydrochloride By using the compound obtained in Example 35c (277 mg, 0.769 mmol), the title compound was obtained as colorless solid by similar procedures to those of Example 1f (252 mg, yield: 83%).

Melting point: 205–213° C. $^1$H-NMR(DMSO-$d_6$): 10.7 (1H,brs), 7.58–7.75(5H,m), 7.30–7.51(3H,m), 7.21–7.25(1H,m), 4.56–4.72(2H,m), 4.47–4.51(2H,m), 3.2–3.7(4H,m), 2.8–3.0(2H,m), 1.6–2.2(3H,m), 1.4–1.6(2H, m)

Example 36

2-[[1-[2-(Indol-3-yl)ethyl]piperidin-4-yl]methyl]isoindolin-1-one ½.fumarate (Compound 241 in Table 1)

a) 2-(Indol-3-yl)ethyl methanesulfonate

By using 3-indolethanol (2.01 g, 12.5 mmol), the title compound was obtained as brown oil by similar procedures to those of Example 26a (3.10 g, yield: 100%).

$^1$H-NMR(CDCl$_3$): 8.11(1H,brs), 7.60(1H,d,J=7.7), 7.38 (1H,d,J=8.0), 7.10–7.25(3H,m), 4.48(2H,t,J=7.1), 3.23(2H, t,J=7.1), 2.85(3H,s)

b) 2-[[1-[2-(Indol-3-yl)ethyl]piperidin-4-yl]methyl]isoindolin-1-one

The compound obtained in Example 36a (980 mg, 3.40 mmol) and the compound obtained in Example 1d (818 mg, 3.07 mmol), the title compound was obtained as pale yellow solid by similar procedures to those of Example 26b (465 mg, yield: 41%).

$^1$H-NMR(CDCl$_3$): 8.08(1H,brs), 7.86(1H,d,J=7.2), 7.34–7.62(5H,m), 7.03–7.24(3H,m), 4.42(2H,s), 3.53(2H,d, J=7.2), 3.08–3.13(2H,m), 2.97–3.03(2H,m), 2.70–2.76(2H, m), 2.06–2.14(2H,m), 1.7–2.0(3H,m), 1.4–1.6(2H,m)

c) 2-[[1-[2-(Indol-3-yl)ethyl]piperidin-4-yl]methyl]isoindolin-1-one ½.fumarate

By using the compound obtained in Example 36b (181 mg, 0.485 mmol) and fumaric acid (61.5 mg, 0.530 mmol) were added to ethanol (11 ml) and the mixture was heated under reflux for 30 minutes. The precipitated solid was collected by filtration and dried to obtain the title compound as colorless solid (108 mg, yield: 52%).

Melting point: 225–230° C. $^1$H-NMR(DMSO-$d_6$): 10.8 (1H,s), 7.68(1H,d,J=7.5), 7.58–7.61(2H,m), 7.42–7.53(2H, m), 7.33(1H,d,J=7.8), 7.16(1H,s), 7.03–7.09(1H,m), 6.93–6.99(1H,m), 6.53(1H,s,fumaric acid), 4.50(2H,s), 3.43 (2H,d,J=7.2), 3.08–3.13(2H,m), 2.86–2.90(2H,m), 2.69–2.75(2H,m), 2.14–2.23(2H,m), 1.7–1.9(1H,m), 1.5–1.7(2H,m), 1.2–1.4(2H,m)

Example 37

2-[[1-[(6-Fluoro-1,2-benzisoxazol-3-yl)methyl]piperidin-4-yl]methyl]isoindolin-1-one hydrochloride (Compound 246 in Table 1)

a) 2-[[1-[(6-Fluoro-1,2-benzisoxazol-3-yl)methyl]piperidin-4-yl]methyl]isoindolin-1-one The compound obtained in Example 20b (826 mg, 2.07 mmol) was dissolved in N-methylpyrrolidone (7 ml). The solution was added with potassium t-butoxide (243 mg, 2.17 mmol) at room temperature and stirred for 3 hours. The reaction mixture was added with water and precipitated solids were collected by filtration. The solids were washed with water and dried to obtain the title compound as pale yellow solid (573 mg, yield: 73%).

$^1$H-NMR(CDCl$_3$): 7.90–7.94(1H,m), 7.84'1H,d,J=7.8), 7.40–7.55(3H,m), 7.21–7.27(1H,m), 7.03–7.10(1H,m), 4.39 (2H,s), 3.88(2H,s), 3.52(2H,d,J=7.2), 2.89–2.94(2H,m), 2.05–2.15(2H,m), 1.65–1.90(3H,m), 1.3–1.5(2H,m)

b) 2-[[1-[(6-Fluoro-1,2-benzisoxazol-3-yl)methyl]piperidin-4-yl]methyl]isoindolin-1-one hydrochloride By using the compound obtained in Example 37a (303 mg, 0.799 mmol), the title compound was obtained as colorless solid by similar procedures to those of Example 1f (261 mg, yield: 79%).

Melting point: 175–181° C. $^1$H-NMR(DMSO-d$_6$): 11.1 (1H,brs), 8.2–8.3(1H,m), 7.86(1H,d,J=7.5), 7.67(1H,d, J=7.2), 7.58–7.61(2H,m), 7.40–7.50(2H,m), 4.82–5.00(2H, m), 4.48(2H,s), 3.59–3.64(2H,m), 3.2–3.5(2H,m), 2.9–3.1 (2H,m), 1.4–2.2(5H,m)

Example 38

2-[[1-[2-(1,3-Benzodioxol-5-yl)-2-oxoethyl]piperidin-4-yl]methyl]isoindolin-1-one hydrochloride (Compound 251 in Table 1)

a) 1-(1,3-Benzodioxol-5-yl)-2-bromoethan-1-one 1-(1,3-Benzodioxol-5-yl)ethan-1-one (1.05 g, 6.40 mmol) was dissolved in a mixed solvent of dichloromethane (50 ml) and methanol (20 ml). The solution was added with pyridinium perbromide hydrobromide (2.24 g, 7.00 mmol) at room temperature and then heated under reflux. After one hour, the solvent was evaporated under reduced pressure, and the residue was diluted with a mixed solvent of ethyl acetate and hexane. The mixture was washed with water, an aqueous sodium bicarbonate solution, and then with saturated brine, and dried over sodium sulfate. Insoluble solids were removed by filtration, and the solvent was evaporated under reduced pressure. The resulting solid was suspended and washed with hexane and then dried to obtain the title compound as pale yellow solid (1.46 g, yield: 94%).

$^1$HH-NMR(CDCl$_3$): 7.61(1H,dd,J=2.2,8.2), 7.46(1H,d, J=2.2), 6.88(1H,d,J=8.2), 6.08(2H,s), 4.38(2H,s)

b) 2-[[1-[2-(1,3-Benzodioxol-5-yl)-2-oxoethyl]piperidin-4-yl]methyl]isoindolin-1-one By using the compound obtained in Example 38a (491 mg, 2.02 mmol) and the compound obtained in Example 1d (507 mg, 1.90 mmol), the title compound was obtained as pale yellow solid by similar procedures to those of Example 1e (703 mg, yield: 94%).

$^1$H-NMR(CDCl$_3$): 7.84(1H,d,J7.5), 7.67(1H,dd,J=1.8, 8.1), 7.42–7.56(4H,m), 6.84(1H,d,J=8.1), 6.04(2H,s), 4.41 (2H,s), 3.70(2H,s), 3.51(2H,d,J=7.5), 2.95–3.00(2H,m), 2.1–2.2(2H,m), 1.6–2.0(3H,m), 1.4–1.6(2H,m)

c) 2-[[1-[2-(1,3-Benzodioxol-5-yl)-2-oxoethyl]piperidin-4-yl]methyl]isoindolin-1-one hydrochloride By using the compound obtained in Example 38b (690 mg, 1.76 mmol), the title compound was obtained as colorless solid by similar procedures to those of Example 1f (549 mg, yield: 73%).

Melting point: 162–166° C. $^1$H-NMR(DMSO-d$_6$): 9.85 (1H,brs), 7.47—7.74(6H,m), 7.13–7.19(1H,m), 6.19–6.22 (2H,m), 4.95–5.03(2H,m), 4.51–4.54(2H,m), 3.3–3.6(4H, m), 2.9–3.1(2H,m), 2.0–2.2(1H,m), 1.5–1.9(4H,m)

Example 39

2-[[1-[2-(2,3-Dihydro-1,4-benzodioxin-6-yl)-2-oxoethyl]piperidin-4-yl]methyl]isoindolin-1-one hydrochloride (Compound 256 in Table 1)

a) 2-Bromo-1-(2,3-dihydro-1,4-benzodioxin-6-yl)ethan-1-one

By using 1-(2,3-dihydro-1,4-benzodioxin-6-yl)ethan-1-one (1.42 g, 7.97 mmol), the title compound was obtained as pale yellow solid by similar procedures to those of Example 38a (2.05 g, yield: 100%).

$^1$H-NMR(CDCl$_3$): 7.50–7.54(2H,m), 6.93(1H,m), 4.37 (2H,s), 4.32–4.35(2H,m), 4.27–4.31(2H,m)

b) 2-[[1-[2-(2,3-Dihydro-1,4-benzodioxin-6-yl)-2-oxoethyl]piperidin-4-yl]methyl]isoindolin-1-one By using the compound obtained in Example 39a (571 mg, 2.22 mmol) and the compound obtained in Example 1d (576 mg, 2.16 mmol), the title compound was obtained as pale yellow solid by similar procedures to those of Example 1e (627 mg, yield: 71%).

$^1$H-NMR(CDCl$_3$): 7.84(1H,d,J=7.5), 7.42–7.60(5H,m), 6.89(1H,d,J=8.4), 4.41(2H,s), 4.26–4.34(4H,m), 3.69(2H,s), 3.51(2H,d,J=7.2), 2.9–3.0(2H,m), 2.08–2.17(2H,m), 1.6–1.9(3H,m), 1.4–1.6(2H,m)

c) 2-[[1-[2-(2,3-Dihydro-1,4-benzodioxin-6-yl)-2-oxoethyl]piperidin-4-yl]methyl]isoindolin-1-one hydrochloride By using the compound obtained in Example 39b (306 mg, 0.753 mmol), the title compound was obtained as pale yellow solid by similar procedures to those of Example 1f (263 mg, yield: 79%).

Melting point: 142–150° C. $^1$H-NMR(DMSO-d$_6$): 10.0 (1H,brs), 7.69(1H,d,J=7.5), 7.48–7.62(5H,m), 7.06(1H,d, J=8.1), 4.97–5.05(2H,m), 4.53(2H,s), 4.2–4.4(4H,m), 3.4–3.7(4H,m), 2.9–3.1(2H,m), 1.5–2.2(5H,m)

Example 40

2-[[1-[(1-Benzofuran-3-yl)methyl]piperidin-4-yl]methyl]isoindolin-1-one fumarate (Compound 261 in Table 1)

a) 3-Methyl-1-benzofuran-2-yl)carboxylic acid

Sodium phenoxide (15.4 g), prepared from phenol (10.8 g, 114 mmol) and sodium hydroxide (4.80 g, 114 mmol), was added to toluene (160 ml). The mixture was added with ethyl 2-chloroacetoacetate (18.6 g, 113 mmol) dissolved in toluene (20 ml) with heating under reflux, and the mixture was heated with stirring for 3 hours. The reaction mixture was allowed to cool to room temperature, and then added with water and extracted with toluene. The organic layer was washed with saturated brine and dried over magnesium sulfate. Insoluble solids were removed by filtration, the solvent was evaporated under reduced pressure to obtain orange oil (19.7 g). The product was slowly added to concentrated sulfuric acid (20 ml) chilled below 5° C., and stirring was continued for 30 minutes at the same temperature. The reaction mixture was added to ice water and extracted with a mixed solvent of ethyl acetate and hexane. The extract was washed with an aqueous sodium bicarbonate solution and then with saturated brine, and dried over magnesium sulfate. Insoluble solids were removed by filtration and the solvent was evaporated under reduced pressure. The resulting oil was purified by silica gel column chromatography (ethyl acetate-hexane) to obtain orange oil (7.12 g). The product was added to 10% aqueous potassium hydroxide solution (50 ml) and the mixture was heated under reflux for 1 hour. The reaction mixture was allowed to cool to room temperature, and added with 35% sulfuric acid to adjust its pH to 1. The solid precipitated was collected by filtration and washed with water. The resulting solid was dried to obtain the title compound as colorless solid (3.16 g, yield: 16%).

$^1$H-NMR(CDCl$_3$): 7.68(1H,d,J=7.7), 7.58(1H,d,J=8.3), 7.47–7.53(1H,m), 7.30–7.37(1H,m), 2.65(3H,s)

b) 3-Methyl-1-benzofuran

The compound obtained in Example 40a (1.07 g, 6.07 mmol) was dissolved in quinoline (8 ml), and the solution was added with powdered cupper (410 mg, 6.45 mmol). The reaction mixture was heated at 200° C. for 30 minutes, and then allowed to cool to room temperature. Insoluble solids were removed by filtration using Celite and the cake was washed with dichloromethane. The mother liquid was diluted with ethyl ether and washed with 10% hydrochloric acid, water, an aqueous sodium bicarbonate solution, and then with saturated brine, and dried over magnesium sulfate. Insoluble solids were removed by filtration and then the solvent was evaporated under reduced pressure to obtain the title compound as brown oil (819 mg, yield: 100%).

$^1$H-NMR(CDCl$_3$): 7.51–7.55(1H,m), 7.43–7.47(1H,m), 7.40(1H,s), 7.23–7.31(2H,m), 2.25(3H,s)

c) 2-Bromo-3-bromomethyl-1-benzofuran

The compound obtained in Example 40b (771 mg, 5.83 mmol), N-bromosuccinimide (2.07 g, 11.6 mmol), and a catalytic amount of benzoyl peroxide were added to carbon tetrachloride (20 ml), and the mixture was heated under reflux for 5 hours. The reaction mixture was allowed to cool to room temperature, and then insoluble solids were removed by filtration. The solvent was evaporated under reduced pressure to obtain the title compound as yellow oil (1.54 g, yield: 91%).

$^1$H-NMR(CDCl$_3$): 7.61–7.65(1H,m), 7.44–7.48(1H,m), 7.30–7.35(2H,m), 4.56(2H,s)

d) 2-[[1-[(2-Bromo-1-benzofuran-3-yl)methyl]piperidin-4-yl]methyl]isoindolin-1-one By using the compound obtained in Example 40c (1.50 g, 5.17 mmol) and the compound obtained in Example 1d (1.55 g, 5.81 mmol), the title compound was obtained as pale yellow solid by similar procedures to those of Example 25b (1.67 g, yield: 74%).

$^1$H-NMR(CDCl$_3$): 7.83(1H,d,J=7.2), 7.62–7.70(1H,m), 7.38–7.53(4H,m), 7.20–7.27(2H,m), 4.37(2H,s), 3.59(2H,s), 3.49(2H,d,J=7.2), 2.90–2.95(2H,m), 1.99–2.08(2H,m), 1.6–1.9(3H,m), 1.3–1.5(2H,m)

e) 2-[[1-[(1-Benzofuran-3-yl)methyl]piperidin-4-yl]methyl]isoindolin-1-one

The compound obtained in Example 40d (460 mg, 1.05 mmol) was dissolved in a mixed solvent of tetrahydrofuran (5 ml) and ethanol (16 ml). The solution was added with a catalytic amount of Raney nickel, and stirred at room temperature for 5 hours under hydrogen atmosphere. The reaction mixture was filtered using Celite and the cake was washed with a mixed solvent of tetrahydrofuran and ethanol. The solvent was evaporated under reduced pressure to obtain the title compound as yellow solid (290 mg, yield: 77%).

$^1$H-NMR(CDCl$_3$): 7.84(1H,d,J=7.5), 7.68–7.70(1H,m), 7.42–7.54(5H,m), 7.20–7.31(2H,m), 4.39(2H,s), 3.63(2H,s), 3.50(2H,d,J=7.5), 2.94–2.99(2H,m), 1.95–2.05(2H,m), 1.6–1.9(3H,m), 1.3–1.5(2H,m)

f) 2-[[1-[(1-Benzofuran-3-yl)methyl]piperidin-4-yl]methyl]isoindolin-1-one fumarate By using the compound obtained in Example 40e (440 mg, 1.22 mmol), the title compound was obtained as colorless solid by similar procedures to those of Example 36c (413 mg, yield: 71%).

Melting point: 226–237° C. $^1$H-NMR(DMSO-d$_6$): 7.91 (1H,s), 7.77(1H,d,J=6.9), 7.66(1H,d,J=7.5), 7.54–7.59(3H, m), 7.45–7.50(1H,m), 7.24–7.33(2H,m), 6.61(2H,s,fumaric acid), 4.46(2H,s), 3.74(2H,s), 3.40(2H,d,J=7.5), 2.94–2.99 (2H,m), 2.06–2.15(2H,m), 1.7–1.9(1H,m), 1.5–1.6(2H,m), 1.1–1.3(2H,m)

Example 41

2-[[1-[(2-Bromo-1-benzofuran-3-yl)methyl]piperidin-4-yl]methyl]isoindolin-1-one fumarate (Compound 266 in Table 1)

By using the compound obtained in Example 40d (336 mg, 0.765 mmol), the title compound was obtained as pale yellow solid by similar procedures to those of Example 36c (305 mg, yield: 72%).

Melting point: 200–211° C. $^1$H-NMR(DMSO-d$_6$): 7.73–7.78(1H,m), 7.66(1H,d,J=7.5), 7.55–7.60(3H,m), 7.40–7.49(1H,m), 7.26–7.34(2H,m), 6.63(2H,s,fumaric acid), 4.46(2H,s), 3.62(2H,s), 3.39(2H,d,J=7.5), 2.87–2.92 (2H,m), 2.00–2.09(2H,m), 1.6–1.8(1H,m), 1.5–1.6(2H,m), 1.1–1.3(2H,m)

Example 42

2-[[1-[2-(4-Fluoroanilino)-2-oxoethyl]piperidin-4-yl]methyl]isoindolin-1-one hydrochloride (Compound 271 in Table 1)

a) 2-Chloro-N-(4-fluorophenyl)acetamide

Chloroacetyl chloride (0.60 ml, 7.54 mmol) was dissolved in toluene (6 ml), and the solution was added with 4-fluoroaniline (0.72 ml, 7.52 mmol) at room temperature and stirred at the same temperature for 1 hour. The reaction mixture was added with water and extracted with ethyl acetate, and the extract was washed with saturated brine and dried over magnesium sulfate. Insoluble solids were removed by filtration and the filtrate was evaporated under reduced pressure to obtain the title compound as pale yellow solid (1.07 g, yield: 76%).

¹H-NMR(CDCl₃): 8.23(1H,brs,NH), 7.47–7.55(2H,m), 7.02–7.11(2H,m), 4.20(2H,s)

b) 2-[[1-[2-(4-Fluoroanilino)-2-oxoethyl]piperidin-4-yl]methyl]isoindolin-1-one

The compound obtained in Example 42a (354 mg, 1.89 mmol), the compound obtained in Example 1d (501 mg, 1.88 mmol), and triethylamine (0.65 ml, 4.66 mmol) was added to dimethylformamide (6 ml), and the mixture was stirred at 60° C. for 3 hours. The reaction mixture was allowed to cool to room temperature, and then added with water. The solid precipitated was collected by filtration and dried under reduced pressure to obtain the title compound as pale yellow solid (577 mg, yield: 81%).

¹H-NMR(CDCl₃): 9.14(1H,brs,NH), 7.86(1H,d,J=7.5), 7.43–7.57(5H,m), 6.99–7.07(2H,m), 4.42(2H,s), 3.57(2H,d,J=7.2), 3.10(2H,s), 2.86–2.97(2H,m), 2.19–2.30(2H,m), 1.7–1.9(3H,m), 1.3–1.5(2H,m)

c) 2-[[1-[2-(4-Fluoroanilino)-2-oxoethyl]piperidin-4-yl]methyl]isoindolin-1-one hydrochloride By using the compound obtained in Example 42b, the title compound was obtained as colorless solid by similar procedures to those of Example 1f (yield: 70%).

Melting point: 201–219° C.

¹H-NMR(DMSO-d₆): 10.9(1H,brs,NH), 9.9(1H,brs,HCl), 7.58–7.71(5H,m), 7.46–7.54(1H,m), 7.21(2H,t,J=8.7), 4.52(2H,s), 4.25(0.4H,s), 4.14(1.6H,s), 3.3–3.7(4H,m), 2.9–3.1(2H,m), 1.9–2.1(1H,m), 1.7–1.9(2H,m), 1.4–1.6(2H,m)

Example 43

2-[[1-[2-(Diphenylamino)-2-oxoethyl]piperidin-4-yl]methyl]isoindolin-1-one hydrochloride (Compound 278 in Table 1)

a) 2-Chloro-N,N-diphenylacetamide

Chloroacetyl chloride (0.32 ml, 4.02 mmol) was dissolved in a mixed solvent of toluene (6 ml) and tetrahydrofuran (2 ml). The solution was added with diphenylamine (690 mg, 4.08 mmol) at room temperature, and the heated at 100° C. for 80 minutes. The solvent was evaporated under reduced pressure, and the solid precipitated was suspended and washed in ethyl ether. The solid was collected by filtration and dried under reduced pressure to obtain the title compound as colorless solid (746 mg, yield: 75%).

¹H-NMR(CDCl₃): 7.0–7.5(10H,m), 4.03(2H,s)

b) 2-[[1-[2-(Diphenylamino)-2-oxoethyl]piperidin-4-yl]methyl]isoindolin-1-one

By using the compound obtained in Example 43a, the title compound was obtained as pale yellow solid by similar procedures to those of Example 42b (yield: 67%).

¹H-NMR(CDCl₃): 7.84(1H,d,J=7.2), 7.1–7.6(13H,m), 4.38(2H,s), 3.48(2H,d,J=7.2), 3.10(2H,s), 2.82–2.90(2H,m), 2.04–2.18(2H,m), 1.5–1.8(3H,m), 1.2–1.4(2H,m)

c) 2-[[1-[2-(Diphenylamino)-2-oxoethyl]piperidin-4-yl]methyl]isoindolin-1-one hydrochloride By using the compound obtained in Example 43b, the title compound was obtained as colorless solid by similar procedures to those of Example 1f (yield: 84%).

Melting point: 197–209° C. ¹H-NMR(DMSO-d₆): 9.7(1H,brs,HCl), 7.68(1H,d,J=7.4), 7.2–7.6(13H,m), 4.49(2H,s), 4.10(0.4H,s), 4.02(1.6H,s), 3.3–3.6(4H,m), 2.8–3.0(2H,m), 1.7–1.9(1H,m), 1.6–1.7(2H,m), 1.4–1.6(2H,m)

Example 44

2-[[1-[2-(N-Methylanilino)-2-oxoethyl]piperidin-4-yl]methyl]isoindolin-1-one hydrochloride (Compound 284 in Table 1)

a) 2-[[1-[2-(N-Methylanilino)-2-oxoethyl]piperidin-4-yl]methyl]isoindolin-1-one

By using N-methylaniline, 2-chloro-N-methyl-N-phenylacetamide was obtained as crude product by similar procedures to those of Example 43a. By using the resulting product, the title compound was obtained as colorless oil by similar procedures to those of Example 42b(yield: 69%).

¹H-NMR(CDCl₃): 7.83(1H,d,J=7.3), 7.16–7.54(8H,m), 4.38(2H,s), 3.46(2H,d,J=7.2), 3.26(3H,s), 2.92(2H,s), 2.75–2.85(2H,m), 1.9–2.1(2H,m), 1.5–1.8(3H,m), 1.2–1.4(2H,m)

b) 2-[[1-[2-(N-Methylanilino)-2-oxoethyl]piperidin-4-yl]methyl]isoindolin-1-one hydrochloride By using the compound obtained in Example 44a, the title compound was obtained as colorless solid by similar procedures to those of Example 1f (yield: 92%).

Melting point: 199–213° C. ¹H-NMR(DMSO-d₆): 9.6(1H,brs,HCl), 7.68(1H,d,J=7.2), 7.56–7.62(2H,m), 7.2–7.55(6H,m), 4.49(2H,s), 3.9–4.0(2H,m), 3.37(3H,s), 3.1–3.7(4H,m), 2.8–3.0(2H,m), 1.6–1.9(3H,m), 1.3–1.6(2H,m)

Example 45

2-[[1-[3-(4-Fluoroanilino)-3-oxopropyl]piperidin-4-yl]methyl]isoindolin-1-one hydrochloride (Compound 274 in Table 1)

a) 3-Chloro-N-(4-fluorophenyl)propanamide

By using 4-fluoroaniline and 3-chloropropionyl chloride, the title compound was obtained by similar procedures to those of Example 42a (yield: 57%).

¹H-NMR(CDCl₃): 7.3–7.5(3H,m), 6.98–7.05(2H,m), 3.88(2H,t,J=6.2), 2.81(2H,t,J=6.2)

b) 2-[[1-[3-(4-Fluoroanilino)-3-oxopropyl]piperidin-4-yl]methyl]isoindolin-1-one By using the compound obtained in Example 45a, the title compound was obtained as pale yellow solid by similar procedures to those of Example 26b (yield: 86%).

¹H-NMR(CDCl₃): 11.04(1H,s,NH), 7.87(1H,d,J=7.2), 7.44–7.60(5H,m), 6.96–7.03(2H,m), 4.43(2H,s), 3.58(2H,d,J=6.9), 3.06–3.12(2H,m), 2.69(2H,t,J=6.0), 2.51(2H,t,J=6.0), 2.03–2.14(2H,m), 1.7–2.0(3H,m), 1.3–1.5(2H,m)

c) 2-[[1-[3-(4-Fluoroanilino)-3-oxopropyl]piperidin-4-yl]methyl]isoindolin-1-one hydrochloride By using the compound obtained in Example 45b, the title compound was obtained as colorless solid by similar procedures to those of Example 1f (yield: 91%).

Melting point: 211–223° C. $^1$H-NMR(DMSO-d$_6$): 10.4 (1H,s,NH), 10.2(1H,brs,HCl), 7.59–7.71(5H,m), 7.45–7.53 (1H,m), 7.12–7.20(2H,m), 4.51(2H,s), 3.1–3.6(6H,m), 2.8–3.0(4H,m), 1.9–2.1(1H,m), 1.6–1.8(2H,m), 1.4–1.6(2H, m)

Example 46

2-[[1-[3-(Diphenylamino)-3-oxopropyl]piperidin-4-yl]methyl]isoindolin-1-one hydrochloride (Compound 281 in Table 1)

a) 2-[[1-[3-(Diphenylamino)-3-oxopropyl]piperidin-4-yl]methyl]isoindolin-1-one

By using diphenylamine, 3-chloro-N,N-diphenylpropanamide was obtained as crude product by similar procedures to those of Example 43a. By using the resulting product, the title compound was obtained as colorless solid by similar procedures to those of Example 26b (yield: 89%).

$^1$H-NMR(CDCl$_3$): 7.84(1H,d,J=7.4), 7.0–7.6(13H,m), 4.38(2H,s), 3.48(2H,d,J=7.1), 2.74–2.84(2H,m), 2.73(2H,t, J=7.5), 2.45(2H,t,J=7.5), 1.86–1.96(2H,m), 1.5–1.8(3H,m), 1.2–1.4(2H,m)

b) 2-[[1-[3-(Diphenylamino)-3-oxopropyl]piperidin-4-yl]methyl]isoindolin-1-one hydrochloride By using the compound obtained in Example 46a, the title compound was obtained as colorless solid by similar procedures to those of Example 1f (yield: 82%).

Melting point: 200–205° C. $^1$H-NMR(DMSO-d$_6$): 9.6–10.2(1H,broad,HCl), 7.68(1H,d,J=7.5), 7.1–7.65(13H,m 4.49(2H,s), 3.0–3.6(6H,m), 3.6–3.9(4H,m), 1.8–2.0(1H,m), 1.6–1.8(2H,m), 1.3–1.6(2H, m)

Example 47

2-[[1-[3-(N-Methylanilino)-3-oxopropyl]piperidin-4-yl]methyl]isoindolin-1-one hydrochloride (Compound 287 in Table 1)

a) 2-[[1-[3-(N-Methylanilino)-3-oxopropyl]piperidin-4-yl]methyl]isoindolin-1-one By using N-methylaniline, 3-chloro-N-methyl-N-phenylpropanamide was obtained as crude product by similar procedures to those of Example 43a. By using the resulting product, the title compound was obtained as colorless solid by similar procedures to those of Example 26b (yield: 57%).

$^1$H-NMR(CDCl$_3$): 7.83(1H,d,J=7.2), 7.3–7.5(6H,m), 7.18 (2H,dd,J=1.4,7.2), 4.37(2H,s), 3.46(2H,d,J=7.2), 3.26(3H, s), 2.70–2.78(2H,m), 2.65(2H,t,J=7.5), 2.26(2H,t,J=7.5), 1.8–2.0(2H,m), 1.5–1.8(3H,m), 1.2–1.4(2H,m)

b) 2-[[1-[3-(N-Methylanilino)-3-oxopropyl]piperidin-4-yl]methyl]isoindolin-1-one hydrochloride By using the compound obtained in Example 47a, the title compound was obtained as colorless solid by similar procedures to those of Example 1f (yield: 91%).

Melting point: 206–214° C. $^1$H-NMR(DMSO-d$_6$): 9.5–10.1(1H,broad,HCl), 7.67(1H,d,J=7.5), 7.55–7.62(2H, m), 7.1–7.5(6H,m), 4.48(2H,s), 3.0–3.6(9H,m), 2.7–2.9(2H, m), 2.5–2.6(2H,m), 1.8–2.0(1H,m), 1.6–1.8(2H,m), 1.3–1.6 (2H,m)

Example 48

2-[[1-[2-(1,2,3,4-Tetrahydroquinolin-1-yl)-2-oxoethyl]piperidin-4-yl]methyl]isoindolin-1-one hydrochloride (Compound 320 in Table 1)

a) 2-[[1-[2-(1,2,3,4-Tetrahydroquinolin-1-yl)-2-oxoethyl]piperidin-4-yl]methyl]isoindolin-1-one By using 1,2,3,4-tetrahydroquinoline, 2-chloro-1-(1,2,3, 4-tetrahydroquinolin-1-yl)ethan-1-one was obtained as crude product by similar procedures to those of Example 43a. By using the resulting product, the title compound was obtained as pale yellow oil by similar procedures to those of Example 42b (yield: 82%).

$^1$H-NMR(CDCl$_3$): 7.84(1H,d,J=7.2), 7.40–7.54(4H,m), 7.06–7.17(3H,m), 4.38(2H,s), 3.80(2H,t,J=6.6), 3.48(2H,d, J=7.2), 3.27(2H,s), 2.86–2.94(2H,m), 2.7(2H,t,J=6.6), 2.04–2.14(2H,m), 1.92–2.02(2H,m), 1.5–1.8(3H,m), 1.2–1.4(2H,m)

b) 2-[[1-[2-(1,2,3,4-Tetrahydroquinolin-1-yl)-2-oxoethyl]piperidin-4-yl]methyl]isoindolin-1-one hydrochloride By using the compound obtained in Example 48a, the title compound was obtained as colorless solid by similar procedures to those of Example 1f (yield: 94%).

Melting point: 208–221° C. $^1$H-NMR(DMSO-d$_6$): 9.6 (1H,brs,HCl), 7.68(1H,d,J=7.4), 7.55–7.62(2H,m), 7.45–7.54(1H,m), 7.0–7.4(4H,broad), 4.51 (2H,s), 4.1–4.6 (2H,broad), 3.2–3.8(8H,m), 2.8–3.0(2H,m), 2.6–2.8(2H,m), 1.5–2.0(7H,m)

Example 49

2-[[1-[3-(1,2,3,4-Tetrahydroquinolin-1-yl)-3-oxopropyl]piperidin-4-yl]methyl]isoindolin-1-one hydrochloride (Compound 324 in Table 1)

a) 2-[[1-[3-(1,2,3,4-Tetrahydroquinolin-1-yl)-3-oxopropyl]piperidin-4-yl]methyl]isoindolin-1-one By using 1,2,3,4-tetrahydroquinoline, 3-chloro-1-(1,2,3, 4-tetrahydroquinolin-1-yl)propan-1-one was obtained as crude product by similar procedures to those of Example 43a. By using the resulting product, the title compound was obtained as colorless solid by similar procedures to those of Example 26b (yield: 79%).

$^1$H-NMR(CDCl$_3$): 7.84(1H,d,J=7.2), 7.40–7.55(3H1,m), 7.07–7.25(4H,m), 4.38(2H,s), 3.78(2H,t,J=6.6), 3.47(2H,d, J=7.2), 2.6–2.9(8H,m), 1.8–2.0(4H,m), 1.5–1.8(3H,m), 1.2–1.4(2H,m)

b) 2-[[1-[3-(1,2,3,4-Tetrahydroquinolin-1-yl)-3-oxo-propyl]piperidin-4-yl]methyl]isoindolin-1-one hydrochloride By using the compound obtained in Example 49a, the title compound was obtained as colorless solid by similar procedures to those of Example 1f (yield: 97%).

Melting point: 227–232° C.

$^1$H-NMR(DMSO-$d_6$): 9.6(1H,brs,HCl), 7.4–7.7(5H,m), 7.0–7.3(3H,m), 4.50(2H,s), 3.6–3.7(2H,m), 3.2–3.6(8H,m), 3.0–3.2(2H,m), 2.8–3.0(2H,m), 2.6–2.8(2H,m), 1.7–2.0(5H, m), 1.3–1.6(2H,m)

Example 50

2-[[1-[2-Oxo-2-(piperidin-1-yl)ethyl]piperidin-4-yl]methyl]isoindolin-1-one fumarate (Compound 328 in Table 1)

a) 2-[[1-[2-Oxo-2-(piperidin-1-yl)ethyl]piperidin-4-yl]methyl]isoindolin-1-one By using piperidine, 2-chloro-1-(piperidin-1-yl)ethan-1-one was obtained as crude product by similar procedures to those of Example 42a. By using the resulting product, the title compound was obtained as pale yellow oil by similar procedures to those of Example 42b (yield: 73%).

$^1$H-NMR(CDCl$_3$): 7.85(1H,d,J=7.5), 7.42–7.54(3H,m), 4.39(2H,s), 3.48–3.55(6H,m), 3.13(2H,s), 2.84–2.91(2H,m), 1.97–2.08(2H,m), 1.4–1.8(9H,m), 1.2–1.4(2H,m)

b) 2-[[1-[2-Oxo-2-(piperidin-1-yl)ethyl]piperidin-4-yl]methyl]isoindolin-1-one fumarate By using the compound obtained in Example 50a, the title compound was obtained as colorless solid by similar procedures to those of Example 36c (yield: 83%).

Melting point: 201–204° C. $^1$H-NMR(DMSO-$d_6$): 7.67 (1H,d,J=7.5), 7.56–7.61(2H,m), 7.45–7.52(1H,m), 6.59(2H, s,fumaric acid), 4.48(2H,s), 3.3–3.5(6H,m), 3.23(2H,s), 2.83–3.00(2H,m), 2.03–2.14(2H,m), 1.6–1.8(1H,m), 1.3–1.6(8H,m), 1.1–1.3(2H,m)

Example 51

2-[[1-[2-(Indolin-1-yl)-2-oxoethyl]piperidin-4-yl]methyl]isoindolin-1-one fumarate (Compound 333 in Table 1)

a) 2-[[1-[2-(Indolin-1-yl)-2-oxoethyl]piperidin-4-yl]methyl]isoindolin-1-one By using indoline, 2-chloro-1-(indolin-1-yl)ethan-1-one was obtained as crude product by similar procedures to those of Example 43a. By using the resulting product, the title compound was obtained as pale yellow solid by similar procedures to those of Example 42b (yield: 84%).

$^1$H-NMR(CDCl$_3$): 8.22(1H,d,J=8.4), 7.84(1H,d,J=7.2), 7.42–7.56(3H,m), 7.14–7.23(2H,m), 7.14(1H,t,J=7.7), 4.40 (2H,s), 4.19(2H,t,J=8.4), 3.51(2H,d,J=7.2), 3.24(2H,s), 3.18 (2H,t,J=8.4), 2.94–3.01(2H,m), 2.12–2.22(2H,m), 1.7–1.9 (1H,m), 1.5–1.7(3H,m), 1.3–1.5(2H,m)

b) 2-[[1-[2-(Indolin-1-yl)-2-oxoethyl]piperidin-4-yl]methyl]isoindolin-1-one fumarate By using the compound obtained in Example 51a, the title compound was obtained as colorless solid by similar procedures to those of Example 36c (yield: 54%).

Melting point: 168–171° C. $^1$H-NMR(DMSO-$d_6$): 8.05 (1H,d,J=7.9), 7.67(1H,d,J=7.4), 7.55–7.62(2H,m), 7.45–7.52(1H,m), 7.24(1H,d,J=7.3), 7.12–7.18(1H,m), 6.97–7.03(1H,m), 6.61(2H,s,fumaric acid), 4.49(2H,s), 4.17 (2H,t,J=8.4), 3.42(2H,d,J=7.2), 3.35(2H,s), 3.13(2H,t, J=8.4), 2.91–2.98(2H,m), 2.15–2.26(2H,m), 1.6–1.8(1H,m), 1.5–1.6(2H,m), 1.1–1.3(2H,m)

Example 52

2-[[1-[2-(1,2,3,4-Tetrahydoisoquinolin-2-yl)-2-oxoethyl]piperidin-4-yl]methyl]isoindolin-1-one fumarate (Compound 229 in Table 1)

By using 1,2,3,4-tetrahydoroisoquinoline, 2-chloro-1-(1, 2,3,4-tetrahydroisoquinolin-2-yl)ethan-1-one was obtained as crude product by similar procedures to those of Example 42a. By using the resulting product, 2-[[1-[2-(1,2,3,4-tetrahydroisoquinolin-2-yl)-2-oxoethyl]piperidin-4-yl]methyl] isoindolin-1-one was obtained as crude product by similar procedures to those of Example 42b. By using the resulting product, the title compound was obtained as colorless solid by similar procedures to those of Example 36c (yield: 38%).

Melting point: 171–173° C. $^1$H-NMR(DMSO-$d_6$): 7.67 (1H,d,J=7.5), 7.55–7.61(2H,m), 7.45–7.52(1H,m), 7.0–7.2 (4H,m), 6.60(2H,s,fumaric acid), 4.73(0.8H,s), 4.59(1.2H, s), 4.48(1.2H,s), 4.46(0.8H,s), 3.74(1.2H,t,J=5.7), 3.66 (0.8H,t,J=6.0), 3.32–3.43(4H,m), 2.6–3.0(4H,m), 2.0–2.2(2H,m), 1.6–1.8(1H,m), 1.4–1.6(2H,m), 1.1–1.3(2H, m)

Example 53

2-[[1-[2-(Indolin-1-yl)ethyl]piperidin-4-yl]methyl]isoindolin-1-one fumarate (Compound 338 in Table 1)

a) Ethyl 2-(indolin-1-yl)acetate

Indoline (1.07 g, 8.98 mmol), ethyl bromoacetate (1.20 ml, 10.8 mmol), potassium carbonate (2.10 g, 15.2 mmol) were added to dimethylformamide (14 ml), and the mixture was heated at 80° C. for 30 minutes. The reaction mixture was cooled to room temperature and diluted with ethyl acetate, and then washed with water and dried over sodium sulfate. Insoluble solids were removed by filtration and the filtrate was evaporated under reduced pressure. The resulting oil was purified by silica gel column chromatography (ethyl acetate-hexane) to obtain the title compound as yellow oil (1.35 g, yield: 73%).

$^1$H-NMR(CDCl$_3$): 7.01–7.11(2H,m), 6.68(1H,t,J=7.4), 6.40(1H,d,J=7.8), 4.20(2H,q,J=7.2), 3.88(2H,s), 3.54(2H,t, J=8.4), 3.03(2H,t,J=8.4), 1.27(3H,t,J=7.2)

b) 2-(Indolin-1-yl)ethan-1-ol

Lithium aluminum hydride (300 mg, 7.91 mmol) was added with tetrahydrofuran (9 ml) and the suspension was stirred with ice cooling. The mixture was added slowly with the compound obtained in Example 53a (1.33 g, 6.48 mmol) which was dissolved in tetrahydrofuran (3 ml), and then the mixture was stirred at the same temperature for 15 minutes. The reaction mixture was added successively with water (0.3 ml), 15% aqueous sodium hydroxide solution (0.3 ml), water (0.9 ml), and sodium sulfate. Insoluble solids were removed by filtration and the filtrate was evaporated under reduced pressure. The resulting oil was purified by silica gel column chromatography (ethyl acetate-hexane) to obtain the title compound as colorless oil (873 mg, yield: 83%).

$^1$H-NMR(CDCl$_3$): 7.04–7.13(2H,m), 6.71(1H,t,J=7.4), 6.57(1H,d,J=7.8), 3.79–3.84(2H,m), 3.39(2H,t,J=8.4), 3.21–3.28(2H,m), 3.00(2H,t,J=8.4), 2.08(1H,brs.OH)

c) 2-[[1-[2-(Indolin-1-yl)ethyl]piperidin-4-yl]methyl]isoindolin-1-one fumarate

By using the compound obtained in Example 53b, 2-(indolin-1-yl)ethan-1-ol methanesulfonate was obtained as crude product by similar procedure to those of Example 26a. By using the resulting product, 2-[[1-[2-(indolin-1-yl)ethyl]piperidin-4-yl]methyl]isoindolin-1-one was obtained as crude product by similar procedures to those of Example 26b. By using the resulting product, the title compound was obtained by similar procedures to those of Example 36c (yield: 66%).

Melting point: 216–224° C. $^1$H-NMR(DMSO-d$_6$): 7.67 (1H,d,J=7.5), 7.55–7.61(2H,m), 7.45–7.52(1H,m), 6.94–7.03(2H,m), 6.58(2H,s,fumaric acid), 6.50–6.56(2H, m), 4.48(2H,s), 3.42(2H,d,J=7.2), 3.34(2H,t,J=8.3), 3.22 (2H,t,J=6.9), 3.04–3.11(2H,m), 2.86(2H,t,J=8.3), 2.70(2H,t, J=6.9), 2.1–2.3(2H,m), 1.7–1.9(1H,m), 1.5–1.7(2H,m), 1.1–1.4(2H,m)

Example 54

2-[[1-[2-(1,2,3,4-Tetrahydroquinolin-1-yl)ethyl]piperidin-4-yl]methyl]isoindolin-1-one fumarate (Compound 325 in Table 1)

By using 1,2,3,4-tetrahydroquinoline, ethyl 2-[1,2,3,4-tetrahydroquinolin-1-yl]acetate was obtained as crude product by similar procedures to those of Example 53a. By using the resulting product, 2-[1,2,3,4-tetrahydroquinolin-1-yl] ethan-1-ol was obtained as crude product by similar procedures to those of Example 53b. By using the resulting product, 2-[1,2,3,4-tetrahydroquinolin-1-yl]ethan-1-ol methanesulfonate was obtained as crude product by similar procedures to those of Example 26a. By using the resulting product, 2-[[1-[2-(1,2,3,4-tetrahydroquinolin-1-yl)ethyl]-piperidin-4-yl]methyl]isoindolin-1-onewas obtained as crude product by similar procedures to those of Example 26b. By using the resulting product, the title compound was obtained as pale yellow solid by similar procedures to those of Example 36c (yield: 46%).

Melting point: 196–200° C. $^1$H-NMR(DMSO-d$_6$): 7.67 (1H,d,J=7.5), 7.55–7.61(2H,m), 7.45–7.52(1H,m), 6.90–6.97(1H,m), 6.84(1H,d,J=6.4), 6.59(2H,s,fumaric acid), 6.56(1H,d,J=8.3), 6.41–6.48(1H,m), 4.48(2H,s), 3.37–3.44(4H,m), 3.26(2H,t,J=5.5), 3.00–3.07(2H,m), 2.56–2.68(4H,m), 2.1–2.3(2H,m), 1.7–1.9(3H,m), 1.5–1.7 (2H,m), 1.1–1.4(2H,m)

Example 55

5-Methoxy-2-[[1-[2-(4-fluorophenyl)-2-(Z)-hydroxyiminoethyl]piperidin-4-yl]methyl]isoindolin-1-one hydrochloride (Z-isomer of Compound 99 in Table 1)

a) 5-Methoxy-2-[[1-[2-(4-fluorophenyl)-2-(E,Z)-hydroxyiminoethyl]piperidin-4-yl]methyl]isoindolin-1-one By using the compound obtained in Example 3e (443 mg, 1.12 mmol), Z-isomer of the title compound (239 mg, yield: 52%) and E-isomer (187mg, yield: 41%) were obtained as colorless solids by similar procedures to those of Example 18a.

(Z-isomer)
$^1$H-NMR(CDCl$_3$): 12–13(1H,br,OH), 7.75(1H,d,J=8.4), 7.56–7.65(2H,m), 6.96–7.08(3H,m), 6.92(1H,d,J=2.1), 4.35 (2H,s), 3.87(3H,s), 3.74(2H,s), 3.48(2H,d,J=7.2), 3.00–3.07 (2H,m), 2.12–2.23(2H,m), 1.8–2.0(1H,m), 1.6–1.8(2H,m), 1.3–1.5(2H,m)

(E-isomer) $^1$H-NMR(CDCl$_3$): 7.74(1H,d,J=8.4), 7.60–7.68 (2H,m), 7.05–7.12(2H,m), 6.98(1H,dd,J=2.1,8.4), 6.91(1H, d,J=2.1), 4.32(2H,s), 3.86(3H,s),3.44(2H,d,J=7.5), 3.31(2H, s), 2.88–2.95(2H,m), 1.95–2.05(2H,m), 1.5–1.9(3H,m), 1.2–1.4(2H,m)

b) 5-Methoxy-2-[[1-[2-(4-fluorophenyl)-2-(Z)-hydroxyiminoethyl]piperidin-4-yl]methyl]isoindolin-1-one hydrochloride By using the Z-isomer obtained in Example 55a (232 mg, 0.564 mmol), the title compound was obtained as colorless solid by similar procedures to those of Example 1f (208 mg, yield: 82%).

Melting point: 173–178° C. $^1$H-NMR(DMSO-d$_6$): 12.61 (1H,s,OH), 10.6(1H,brs,HCl), 7.81–7.87(2H,m), 7.56(1H,d, J=8.4), 7.27–7.34(2H,m), 7.15(1H,d,J=1.8), 7.02(1H,dd, J=1.8,8.4), 4.53(0.4H,s), 4.42(2H,s), 4.39(1.6H,s), 3.83(3H, s), 2.9–3.6(6H,m), 1.4–2.0(5H,m)

Example 56

5-Methoxy-2-[[1-[2-(4-fluorophenyl)-2-(E)-hydroxyiminoethyl]piperidin-4-yl]methyl]isoindolin-1-one hydrochloride (E-isomer of Compound 99 in Table 1)

By using the E-isomer obtained in Example 55a (180 mg, 0.438 mmol), the title compound was obtained as colorless solid by similar procedures to those of Example 1f (140 mg, yield: 71%).

Melting point: 192–195° C. $^1$H-NMR(DMSO-d$_6$): 11.86 (1H,s,OH), 10.7(1H,brs,HCl), 7.68–7.74(2H,m), 7.57(1H,d, J=8.4), 7.29–7.37(2H,m), 7.15(1H,d,J=1.8), 7.03(1H,dd, J=1.8,8.4), 4.43(2H+0.4H,s), 4.30(1.6H,s), 3.83(3H,s), 3.48–3.55(2H,m), 3.37(2H,J=6.9), 2.90–3.01(2H,m), 1.8–2.0(1H,m), 1.3–1.8(4H,m)

Example 57

5-Bromo-2-[[1-[2-(4-fluorophenyl)-2-(Z)-hydroxyiminoethyl]piperidin-4-yl]methyl]isoindolin-1-one fumarate (Z-isomer of Compound 92 in Table 1)

a) 5-Bromo-2-[[1-[2-(4-fluorophenyl)-2-(E,Z)-hydroxyiminoethyl]piperidin-4-yl]methyl]isoindolin-1-one By using the compound obtained in Example 3e (481 mg, 1.08 mmol), Z-isomer of the title compound (217 mg, yield: 44%) and E-isomer (112 mg, yield: 23%) were obtained as colorless solids by similar procedures to those of Example 18a.

(Z-isomer)
$^1$H-NMR(CDCl$_3$): 7.71(1H,d,J=8.5), 7.56–7.65(4H,m), 7.00–7.08(2H,m), 4.38(2H,s), 3.74(2H,s), 3.49(2H,d,J=7.3), 3.00–3.07(2H,m), 2.12–2.22(2H,m), 1.8–2.01(1H,m), 1.6–1.8(2H,m), 1.3–1.5(2H,m)

(E-isomer)
$^1$H-NMR(CDCl$_3$): 7.70(1H,d,J=8.4), 7.56–7.66(4H,m), 7.04–7.12(2H,m), 4.36(2H,s), 3.46(2H,d,J=7.5), 3.32(2H,s), 2.90–2.96(2H,m), 1.96–2.07(2H,m), 1.5–1.9(3H,m), 1.2–1.4(2H,m)

b) 5-Bromo-2-[[1-[2-(4-fluorophenyl)-2-(Z)-hydroxyiminoethyl]piperidin-4-yl]methyl]isoindolin-1-one fumarate By using the Z-isomer compound obtained in Example 57a (212 mg, 0.461 mmol), the title compound was obtained as colorless solid by similar procedures to those of Example 36c (114 mg, yield: 43%).

Melting point: 171–174° C. $^1$H-NMR(DMSO-d$_6$): 7.83 (1H,s), 7.75–7.82(2H,m), 7.66(1H,d,J=8.1), 7.58(1H,d,J=8.1), 7.15–7.22(2H,m), 6.62(2H,s,fumaric acid), 4.45(2H,s), 3.60(2H,s), 3.34(2H,d,J=7.2), 2.75–2.80(2H,m), 1.96–2.05(2H,m), 1.6–1.8(1H,m), 1.4–1.6(2H,m), 1.0–1.2(2H,m)

Example 58

5-Bromo-2-[[1-[2-(4-fluorophenyl)-2-(E)-hydroxyiminoethyl]piperidin-4-yl]methyl]isoindolin-1-one fumarate (E-isomer of Compound 92 in Table 1)

By using the E-isomer compound obtained in Example 57a (109 mg, 0.237 mmol), the title compound was obtained as colorless solid by similar procedures to those of Example 36c (36 mg, yield: 26%).

Melting point: 186–188° C. $^1$H-NMR(DMSO-d$_6$): 10.98 (1H,brs,OH), 7.83(1H,s), 7.61–7.70(3H,m), 7.59(1H,d,J=8.1), 7.15–7.25(2H,m), 6.62(2H,s,fumaric acid), 4.45(2H,s), 3.35(2H,d,J=7.2), 3.30(2H,s), 2.77–2.85(2H,m), 1.86–1.97(2H,m), 1.6–1.8(1H,m), 1.4–1.6(2H,m), 1.0–1.2 (2H,m)

Example 59

2-[[1-(2-phenylbenzyl)piperidin-4-yl]methyl]isoindolin-1-one fumarate (Compound 456 in Table 1)

a) 2-[[1-(2-Phenylbenzyl)piperidin-4-yl]methyl]isoindolin-1-one

2-Phenylbenzylbromide (462 mg,1.87 mmol) and the compound obtained in Example 1d were dissolved in dimethylformamide (6 ml). The solution was added with potassium carbonate (517 mg, 1.87 mmol) and heated at 80° C. with stirring. The reaction mixture was added with water (10 ml) and precipitated solids were collected by filtration to obtain the title compound as colorless solid (633 mg, yield: 85%).

$^1$H-NMR(CDCl$_3$): 7.84(1H,d,J=7.5 Hz), 7.53–7.24(12H,m), 4.36(2H,s), 3.47(2H,d,J=7.2 Hz), 3.37(2H,s),2.78(2H,brd,J=11.4 Hz), 1.83(2H,brdd,J=11.6,11.6 Hz), 1.74–1.68 (1H,m), 1.63–1.57(2H,m), 1.39–1.30(2H,m).

b) 2-[[1-(2-Phenylbenzyl)piperidin-4-yl]methyl]isoindolin-1-one fumarate

By using the compound obtained in Example 59a (620 mg, 1.56 mmol), the title compound was obtained as colorless solid by similar procedures to those of Example 36c (331 mg, yield: 41%).

Melting point: 188–193° C. $^1$H-NMR(DMSO-d$_6$): 7.67–7.23(13H,m), 6.62(2H,s), 4.45(2H,s), 3.42(2H,s), 3.37 (2H,d,J=6.9 Hz), 2.74(2H,brd,J=11.4 Hz), 1.86(2H,brdd,J=10.8,10.8 Hz), 1.69–1.65(1H,m), 1.52(2H,brd,J=12.6 Hz), 1.17(2H,brdd,J=22.4,10.4 Hz).

Example 60

2-[[1-[2-(2-Propoxyphenyl)ethyl]piperidin-4-yl]methyl]isoindolin-1-one hydrochloride (Compound 501 in Table 1)

a) Ethyl 2-hydroxyphenylacetate

2-Hydroxyphenylacetic acid (6.06 g, 39.8 mmol) was dissolved in ethanol (180 ml) and the solution was added with concentrated sulfuric acid (2 ml) and heated under reflux for 90 minutes. The reaction mixture was concentrated under reduced pressure and diluted with ethyl acetate. The mixture was washed with water and saturated brine, and dried over sodium sulfate. Insoluble solids were removed by filtration, and the filtrate was concentrated under reduced pressure to obtain the title compound as orange oil (7.67 g, yield: quantitative).

$^1$H-NMR(CDCl$_3$): 7.56(1H,s,OH), 7.15–7.26(1H,m), 7.09(1H,dd,J=1.5,7.5), 4.20(2H,q,J=7.2), 3.67(2H,s), 1.29 (3H,t,J=7.2)

b) Ethyl 2-propoxyphenylacetate

The compound obtained in Example 60a (1.12 g, 6.22 mmol), iodopropane (0.635 ml, 6.54 mmol), and potassium carbonate (1.27 g, 9.19 mmol) were added to dimethylformamide (10 ml), and the mixture was heated at 70° C. for 2 hours. The reaction mixture was added with water and extracted with ethyl acetate. The extract was washed with saturated aqueous sodium bicarbonate solution, water, and then with saturated brine, and dried over magnesium sulfate. Insoluble solids were removed by filtration and the filtrate was concentrated under reduced pressure to obtain the title compound as yellow oil (1.15 g, yield: 83%).

$^1$H-NMR(CDCl$_3$): 7.15–7.26(2H,m), 6.82–6.93(2H,m), 4.15(2H,q,J=7.2), 3.92(2H,t,J=6.4), 3.62(2H,s), 1.72–1.84 (2H,m), 1.25(3H,t,J=7.2), 1.03(3H,t,J=7.4)

c) 2-[[1-[2-(2-Propoxyphenyl)ethyl]piperidin-4-yl]methyl]isoindolin-1-one

By using the compound obtained in Example 60b (1.00 g, 4.50 mmol), 2-(2-propoxyphenyl)ethanol (834 mg) was obtained as crude product by similar procedures to those of Example 53b. By using the resulting product, 2-(2-propoxyphenyl)ethanol methanesulfonate (1.13 g) was obtained as crude product by similar procedures to those of Example 26a. By using the resulting product, the title compound was obtained as pale yellow solid by similar procedures to those of Example 26b (yield: 68%).

$^1$H-NMR(CDCl$_3$): 7.85(1H,d,J=7.5), 7.41–7.55(3H,m), 7.11–7.19(2H,m), 6.78–6.89(2H,m), 4.42(2H,s), 3.91(2H,t, J=6.3), 3.52(2H,d,J=6.9), 3.00–3.08(2H,m), 2.80–2.88(2H, m), 2.53–2.61(2H,m), 2.0–2.1(2H,m), 1.6–1.9(5H,m), 1.3–1.5(2H,m), 1.04(3H,t,J=7.4)

d) 2-[[1-[2-(2-Propoxyphenyl)ethyl]piperidin-4-yl] methyl]isoindolin-1-one hydrochloride By using the compound obtained in Example 60c, the title compound was obtained as colorless solid by similar procedures to those of Example 1f (yield: 61%).

Melting point: 169–180° C. $^1$H-NMR(DMSO-d$_6$): 10.3–10.7(1H,brs,HCl), 7.69(1H,d,J=7.4), 7.60–7.63(2H,m) 7.47–7.53(1H,m), 7.18–7.26(2H,m), 6.87–7.00(2H,m), 4.52 (2H,s), 3.94(2H,t,J=6.4), 2.8–3.7(10H,m), 1.9–2.2(1H,m), 1.6–1.9(4H,m), 1.4–1.6(2H,m), 1.01(3H,t,J=7.4)

Example 61

2-[[1-[2-(2-Benzyloxyphenyl)ethyl]piperidin-4-yl] methyl]isoindolin-1-one fumarate (Compound 506 in Table 1)

a) 2-[[1-[2-(2-Benzyloxyphenyl)ethyl]piperidin-4-yl]methyl]isoindolin-1-one

By using the compound obtained in Example 60a and benzyl bromide, ethyl 2-benzyloxyphenylacetate was obtained as crude product by similar procedures to those of Example 60b. By using the resulting product, 2-(2-benzyloxyphenyl)ethanol was obtained as crude product by similar procedures to those of Example 53b. By using the resulting product, 2-(2-benzyloxyphenyl)ethanol methanesulfonate was obtained as crude product by similar procedures to those of Example 26a. By using the resulting product, the title compound was obtained as yellow oil by similar procedures to those of Example 26b (yield: 72%).

$^1$H-NMR(CDCl$_3$): 7.85(1H,d,J=7.2), 7.28–7.55(8H,m), 7.11–7.19(2H,m), 6.86–6.93(2H,m), 5.07(2H,s), 4.41(2H,s), 3.50(2H,d,J=7.2), 2.95–3.02(2H,m), 2.83–2.92(2H,m), 2.55–2.63(2H,m), 1.9–2.1(2H,m), 1.5–1.8(3H,m), 1.3–1.5 (2H,m)

b) 2-[[1-[2-(2-Benzyloxyphenyl)ethyl]piperidin-4-yl]methyl]isoindolin-1-one fumarate By using the compound obtained in Example 61a, the title compound was obtained as colorless solid by similar procedures to those of Example 36c (yield: 56%).

Melting point: 184–188° C. $^1$H-NMR(DMSO-d$_6$): 7.68 (1H,d,J=7.5), 7.58–7.62(2H,m), 7.2–7.5(6H,m), 7.1–7.2(2H,m), 7.04(1H,d,J=8.4), 6.8–6.9(1H,m), 6.57(2H, s,fumaric acid), 5.12(2H,s), 4.48(2H,s), 3.41(2H,d,J=7.1), 3.0–3.1(2H,m), 2.8–2.9(2H,m), 2.6–2.7(2H,m), 2.1–2.3(2H, m), 1.7–1.9(1H,m), 1.5–1.6(2H,m), 1.2–1.4(2H,m)

Example 62

2-[[1-(2-[1,1'-Biphenyl]-2-ylethyl)piperidin-4-yl] methyl]isoindolin-1-one fumarate (Compound 511 in Table 1)

a) 2-[1,1'-Biphenyl]-2-ylacetonitrile 2-(Bromomethyl)biphenyl (1.35 g, 5.48 mmol), potassium cyanide (368 mg, 5.65 mmol), and a catalytic amount of 18-crown-6 ether were added to acetonitrile (10 ml), and the mixture was heated under reflux for 5 days. The reaction mixture was added with water and extracted with ethyl acetate. The extract was washed with saturated aqueous sodium bicarbonate solution and saturated brine, and dried over magnesium sulfate. Insoluble solids were removed by filtration, and the filtrate was concentrated under reduced pressure. The resulting oil was purified by silica gel column chromatography (ethyl acetate-hexane) to obtain the title compound as colorless solid (1.07 g, yield: quantitative).

$^1$H-NMR(CDCl$_3$): 7.3–7.5(6H,m), 7.2–7.3(3H,m), 3.63 (2H,s)

b) 2-[1,1'-Biphenyl]-2-ylacetic acid

The compound obtained in Example 62a (1.06 g, 5.48 mmol) was dissolved in ethyleneglycol (30 ml). The solution was added with potassium hydroxide (5.98 g, 90.6 mmol) and heated at 190° C. for 2 hours. The reaction mixture was allowed to cool to room temperature, and then pored into 1N hydrochloric acid (200 ml). The precipitated solids were collected by filtration and washed with water, and then dried under reduced pressure to obtain the title compound as colorless solid (1.05 g, yield: 91%).

$^1$H-NMR(CDCl$_3$): 7.25–7.42(9H,m), 3.63(2H,s)

c) 2-[[1-[2-(1,1'-Biphenyl)-2-ylethyl]piperidin-4-yl] methyl]isoindolin-1-one

By using the compound obtained in Example 62b, 2-[1, 1'-biphenyl]-2-ylethanol was obtained as crude product by similar procedures to those of Example 53b. By using the resulting product, 2-[1,1'-biphenyl]-2-ylethanol methanesulfonate was obtained as crude product by similar procedures to those of Example 26a. By using the resulting product, the title compound was obtained as yellow oil by similar procedures to those of Example 26b (yield: 70%).

$^1$H-NMR(CDCl$_3$): 7.84(1H,d,J=7.4), 7.1–7.5(12H,m), 4.37(2H,s), 3.45(2H,d,J=7.0), 2.6–2.8(4H,m), 2.36–2.46(2H,m), 1.5–1.9(7H,m), 1.2–1.4(2H,m)

d) 2-[[1-[2-(1,1'-Biphenyl)-2-ylethyl]piperidin-4-yl] methyl]isoindolin-1-one fumarate By using the compound obtained in Example 62c, the title compound was obtained as colorless solid by similar procedures to those of Example 36c (yield: 68%).

Melting point: 198–206° C. $^1$H-NMR(DMSO-d$_6$): 7.66 (1H,d,J=7.5), 7.56–7.66(2H,m), 7.1–7.5(10H,m), 6.57(2H, s,fumaric acid), 4.45(2H,s), 3.37(2H,d,J=7.3), 2.71–2.85 (4H,m), 2.50–2.59(2H,m), 1.95–2.10(2H,m), 1.6–1.8(1H, m), 1.4–1.6(2H,m), 1.1–1.3(2H,m)

Example 63

2-[[1-[2-(2-Phenethyloxyphenyl)ethyl]piperidin-4-yl]methyl]isoindolin-1-one fumarate (Compound 516 in Table 1)

a) 2-[[1-[2-(2-Phenethyloxyphenyl)ethyl]piperidin-4-yl]methyl]isoindolin-1-one By using the compound obtained in Example 60a and phenethyl bromide, ethyl 2-phenethyloxyphenylacetate was obtained as crude product by similar procedures to those of Example 60b. By using the resulting product, 2-(2-phenethyloxyphenyl)ethanol was obtained as crud product by similar procedures to those of Example 53b. By using the resulting product, 2-(2-phenethyloxyphenyl)-ethanol methanesulfonate was obtained as crude product by similar procedures to those of Example 26a. By using the resulting product, the title compound was obtained as yellow oil by similar procedures to those of Example 26b (yield: 70%).

$^1$H-NMR(CDCl$_3$): 7.86(1H,d,J=7.1), 7.42–7.55(3H,m), 7.11–7.33(7H,m), 6.78–6.89(2H,m), 4.42(2H,s), 4.19(2H,t, J=6.8), 3.52(2H,d,J=7.0), 3.10(2H,t,J=6.8), 2.94–3.01(2H, m), 2.75–2.83(2H,m), 2.46–2.54(2H,m), 1.8–2.0(2H,m), 1.5–1.8(3H,m), 1.3–1.5(2H,m)

b) 2-[[1-[2-(2-Phenethyloxyphenyl)ethyl]piperidin-4-yl]methyl]isoindolin-1-one fumarate By using the compound obtained in Example 63a, the title compound was obtained as colorless solid by similar procedures to those of Example 36c (yield: 56%).

Melting point: 178–180° C. $^1$H-NMR(DMSO-d$_6$): 7.68 (1H,d,J=7.5), 7.57–7.62(2H,m), 7.4–7.5(1H,m), 7.10–7.33 (7H,m), 6.95(1H,d,J=8.1), 6.80–6.87(1H,m), 6.57(2H,s,fumaric acid), 4.49(2H,s), 4.20(2H,t,J=6.3), 3.42(2H,d,J=7.2), 3.05(2H,t,J=6.3), 2.94–3.00(2H,m), 2.65–2.72(2H,m), 2.4–2.55(2H,m), 2.0–2.2(2H,m), 1.7–1.8(1H,m), 1.5–1.6(2H,m), 1.2–1.3(2H,m)

Example 64

2-[[1-(2-Furylbenzyl)piperidin-4-yl]methyl]isoindolin-1-one fumarate (Compound 461 in Table 1)

a) 2-Bromofuran

Dimethylformamide (35 ml) was cooled to –20° C. and then added dropwise with bromine (13 ml, 253 mmol) over 25 minutes to prepare solution of bromine in dimethylformamide. Furan (25 ml, 345 mmol) was dissolved in dimethylformamide (35 ml) and then added dropwise with the already prepared solution of bromine in dimethylformamide over 1 hour while the temperature was kept at 25 to 30° C. The reaction mixture was kept at 30 to 35° C. and stirred for 1 hour. The reaction mixture was pored in ice water (230 ml), and then the mixture was stirred for 2 minutes and extracted with diethyl ether. The extract was washed with water, and then added with diethylphenylamine (2 ml) and dried over sodium sulfate. Insoluble solids were removed by filtration, and the residue was distilled under atmospheric pressure to obtain the title compound as colorless liquid as a fraction of internal temperature of 95 to 105° C. (yield: 23%).

$^1$H-NMR(CDCl$_3$): 7.42(1H,d,J=2.4 Hz), 6.37(1H,d,J=2.9 Hz), 6.30(1H,d,J=4.0 Hz).

b) 2-Furylbenzaldehyde

2-Formylphenylboric acid (300 mg, 2.0 mmol), 2-bromofuran obtained in Example 64a (588 mg, 4.0 mmol), and tetrakis triphenylphosphine palladium (15 mg) were dissolved in a mixed solvent of toluene (38 ml) and methanol (5 ml). The solution was added with 2M aqueous sodium carbonate solution (20 ml) and heated at 80° C. with stirring for 6 hours. The reaction mixture was stand for cooling, and then the solvent was evaporated. The mixture was extracted with dichloromethane, and the extract was washed with a mixture of 2M aqueous sodium carbonate solution (10 ml) and aqueous solution of ammonia (2 ml), and dried over sodium sulfate. Insoluble solids were removed by filtration, and the filtrate was evaporated under reduced pressure to obtain the title compound as crude yellow oil (126 mg). The resulting crude product was used in the next reaction without purification.

c) 2-[[1-(2-Furylbenzyl)piperidin-4-yl]methyl]isoindolin-1-one

The compound obtained in Example 1d (267 mg, 1.0 ml) was dissolved in methanol. The solution was added with the crude product obtained in Example 64b (126 mg) and sodium cyanoborohydride (157 mg, 2.5 mmol), and the reaction mixture was added with acetic acid (57 μl, 1.0 mmol) to adjust is pH to about 6 and then heated at 40° C. for 8 hours with stirring. The solvent was evaporated and then the residue was diluted with ethyl acetate. The mixture was washed with saturated aquesous sodium bicarbonate solution and saturated brine, and dried over sodium sulfate. Insoluble solids were removed by filtration, and the filtrate was evaporated under reduced pressure. The resulting crude product was purified by silica gel column chromatography (methanol-dichloromethane) to obtain the title compound as yellow oil (165 mg, yield: 21%,2 steps).

$^1$H-NMR(CDCl$_3$): 7.84(1H,d,J=7.5 Hz), 7.66(1H,dd, J=7.4,1.7 Hz), 7.53–7.43(5H,m), 7.31–7.25(2H,m), 6.75 (1H,d,J=3.0 Hz), 6.48(1H,dd,J=3.3,1.8 Hz), 4.39(2H,s), 3.57(2H,s), 3.50(2H,d.J=7.5 Hz), 2.91(2H,brd,J=11.7 Hz), 1.98(2H,ddd,J=2.1,11.6,11.6 Hz), 1.81–1.76(1H,m), 1.65 (2H,brd,J=12.9 Hz), 1.41(2H,ddd,J=3.6,12.0,12.0 Hz).

d) 2-[[1-(2-Furylbenzyl)piperidin-4-yl]methyl]isoindolin-1-one fumarate

By using the compound obtained in Example 64c (165 mg), the title compound was obtained as colorless solid by similar procedures to those of Example 36c (127 mg, yield: 59%).

Melting point: 140–153° C. $^1$H-NMR(DMSO-d$_6$): 7.79 (1H,d,J=1.5 Hz), 7.65(2H,d,J=7.9,7.9 Hz), 7.59–7.58(2H, m), 7.49–7.46(2H,m), 7.36–7.32(2H,m), 6.85(1H, d,J=3.2 Hz), 6.63–6.62(3H,m), 4.48(2H,s), 3.64(2H,s), 3.40(2H,d, J=7.3 Hz), 2.84(2H,d,J=11.5 Hz), 2.03(2H,brdd,J=10.9, 10.9 Hz), 1.78–1.73(1H,m), 1.58(2H,brdd,J=11.0 Hz), 1.27–1.15(2H,m).

Example 65

2-[[1-(2-Benzoylbenzyl)piperidin-4-yl]methyl]isoindolin-1-one fumarate (Compound 466 in Table 1)

a) 2-Benzoylbenzyl bromide

By using 2-methylbenzophenone (1.18 g, 6.0 mmol), the title compound was obtained as crude yellow oil by similar procedures to those of Example 1b (1.74 g). The resulting crude product was used in the next reaction without purification.

b) 2-[[1-(2-Benzoylbenzyl)piperidin-4-yl]methyl]isoindolin-1-one

The compound obtained in Example 65a (1.74 g) was dissolved in dimethylformamide (15 ml). The solution was added with the compound obtained in Example 1d (1.07 g, 4.0 mmol) and potassium carbonate (1.10 g, 8.0 mmol), and the mixture was stirred at room temperature for 16 hours. The reaction mixture was added with water (30 ml) and extracted with ethyl acetate. The extract was washed with water and saturated brine, and dried over sodium sulfate. Insoluble solids were removed by filtration, and the filtrate was evaporated under reduced pressure. The resulting crude product was purified by silica gel column chromatography (methanol-dichloromethane) to obtain the title compound as brown semi-solid (1.07 g, yield: 63%).

$^1$H-NMR(CDCl$_3$): 7.78–7.75(3H,m), 7.51–7.26(10H,m), 4.28(2H,s), 3.40(2H,s), 3.28(2H,d,J=6.9 Hz), 2.46(2H,d, J=11.4 Hz), 1.79(2H,brdd,J=11.4,11.4 Hz), 1.59–1.56(1H, m), 1.34(2H,brd,J=13.2 Hz), 0.86–0.82(2H,m).

c) 2-[[1-(2-Benzoylbenzyl)piperidin-4-yl]methyl]isoindolin-1-one fumarate

By using the compound obtained in Example 65b (1.00 g, 2.36 mmol), the title compound was obtained as colorless solid by similar procedures to those of Example 36c (971 mg, yield: 76%).

Melting point: 166–169° C. $^1$H-NMR(DMSO-d$_6$): 7.67–7.29(13H,m), 6.63(2H,s), 4.36(2H,s), 3.54(2H,s), 3.18 (2H,d,J=6.9 Hz), 2.32(2H,brd,J=11.1 Hz), 1.77(2H,brdd, J=10.5,10.5 Hz), 1.50–1.48(1H,m), 1.25(2H,brd,J=11.7 Hz), 0.67(2H,brdd,J=20.1,11.7 Hz).

Example 66

2-[[1-[3-(2-Phenethylphenyloxy)propyl]piperidin-4-yl]methyl]isoindolin-1-one fumarate (Compound 691 in Table 1)

a) 2-[3-(Tetrahydro-2H-pyran-2-yloxy)propoxy]benzaldehyde

By using 2-(3-bromopropoxy)tetrahydro-2H-pyran and salicylaldehyde, the title compound was obtained as colorless oil by similar procedures to those of Example 60b (yield: quantitative).

$^1$H-NMR(CDCl$_3$): 10.52(1H,s,OH), 7.83(1H,dd,J=1.8, 7.8), 7.50–7.57(1H,m), 6.98–7.05(2H,m), 4.56–4.61(1H,m), 4.22(2H,t,J=6.3), 3.91–4.00(1H,m), 3.75–3.85(1H,m), 3.56–3.66(1H,m), 3.38–3.50(1H,m), 2.05–2.22(2H,m), 1.4–1.9(8H,m)

b) 3-(2-Phenethylphenyloxy)propanol

Benzyltriphenylphosphonium bromide (2.25 g, 5.19 mmol) was suspended in tetrahydrofuran (20 ml) and the suspension was stirred with ice cooling. The suspension was added with potassium t-butoxide (596 mg, 5.31 mol), and the mixture was stirred at the same temperature. The reaction mixture was added with the compound obtained in Example 66a (1.09 g, 4.12 mmol) which was dissolved in tetrahydrofuran (4 ml), and then the mixture was stirred for 1 hour. The reaction mixture was diluted with 10% aqueous citric acid solution and extracted with ethyl acetate. The extract was washed with water, saturated aqueous sodium bicarbonate solution, and then with saturated brine, and dried over magnesium sulfate. Insoluble solids were removed by filtration, and the filtrate was evaporated under reduced pressure to obtain 2-[3-[2-[(E,Z)-2-phenylethenyl] phenoxy]propoxy]tetrahydro-2H-pyran as crude product. The product was dissolved in methanol (50 ml), and the solution was added with a catalytic amount of p-toluenesulfonic acid and then heated under reflux for 4 hours. The reaction mixture was concentrated under reduced pressure, and the resulting oil was purified by silica gel column chromatography (ethyl acetate-hexane) to obtain 3-[2-[(E, Z)-2-phenylethenyl]phenoxy]propanol. The product was dissolved in ethanol (12 ml) and the solution was added with a catalytic amount of 10% palladium carbon and the mixture was stirred under hydrogen atmosphere to give the title compound as colorless oil (464 mg, yield: 45%).

$^1$H-NMR(CDCl$_3$): 7.10–7.32(7H,m), 6.85–6.92(2H,m), 4.12(2H,t,J=5.9), 3.90(2H,t,J=5.9), 2.8–3.0(4H,m), 2.0–2.2 (2H,m)

c) 2-[[1-[3-(2-Phenethylphenyloxy)propyl]piperidin-4-yl]methyl]isoindolin-1-one

By using the compound obtained in Example 66b, 3-(2-phenethylphenyloxy)propanol methanesulfonate was obtained as crude product by similar procedures to those of Example 26a. By using the resulting product, the title compound was obtained as yellow oil by similar procedures to those of Example 26b (yield: 86%).

$^1$H-NMR(CDCl$_3$): 7.85(1H,d,J=7.5), 7.40–7.55(3H,m), 7.07–7.29(7H,m), 6.83–6.89(2H,m), 4.41(2H,s), 4.01(2H,t, J=6.2), 3.51(2H,d,J=7.2), 2.82–3.00(6H,m), 2.51–2.59(2H, m), 1.9–2.1(4H,m), 1.6–1.9(3H,m), 1.3–1.5(2H,m)

d) 2-[[1-[3-(2-Phenethylphenyloxy)propyl]piperidin-4-yl]methyl]isoindolin-1-one fumarate By using the compound obtained in Example 66c, the title compound was obtained as colorless solid by similar procedures to those of Example 36c (yield: 60%).

Melting point: 166–169° C. $^1$H-NMR(DMSO-d$_6$): 7.68 (1H,d,J=7.3), 7.57–7.61(2H,m), 7.4–7.5(1H,m), 7.11–7.27 (7H,m), 6.93(1H,d,J=8.0), 6.8–6.9(1H,m), 6.57(2H,s,fumaric acid), 4.48(2H,s), 4.00(2H,t,J=5.9), 3.42(2H,d,J=7.3), 3.00–3.07(2H,m), 2.81(4H,s), 2.6–2.7(2H,m), 2.1–2.3(2H, m), 1.9–2.0(2H,m), 1.7–1.9(1H,m), 1.5–1.7(2H,m), 1.2–1.4 (2H,s),

Example 67

2-[[1-[3-(2-Benzylphenyloxy)propyl]piperidin-4-yl]methyl]isoindolin-1-one fumarate (Compound 696 in Table 1)

a) 3-(2-Benzylphenyloxy)propanol

By using 2-hydroxydiphenylmethane and 3-bromopropanol, the title compound was obtained as colorless oil by similar procedures to those of Example 60b (yield: 28%).

$^1$H-NMR(CDCl$_3$): 7.08–7.28(7H,m), 6.86–6.94(2H,m), 4.08(2H,t,J=5.7), 3.98(2H,s), 3.71(2H,t,J=6.0), 1.93–2.03 (2H,m), 1.49(1H,brs,OH)

b) 2-[[1-[3-(2-Benzylphenyloxy)propyl]piperidin-4-yl]methyl]isoindolin-1-one By using the compound obtained in Example 67a, 3-(2-benzylphenyloxy)propanol methanesulfonate was obtained as crude product by similar procedures to those of Example 26a. By using the resulting product, the title compound was obtained as pale yellow solid by similar procedures to those of Example 26b (yield: 87%).

$^1$H-NMR(CDCl$_3$): 7.85(1H,d,J=7.3), 7.41–7.55(3H,m), 7.0–7.3(7H,m), 6.81–6.90(2H,m), 4.40(2H,s), 3.97(2H,t, J=6.1), 3.96(2H,s), 3.50(2H,d,J=7.1), 2.84–3.92(2H,m), 2.36–2.44(2H,m), 1.8–2.0(4H,m), 1.5–1.8(3H,m), 1.2–1.4 (2H,m)

c) 2-[[1-[3-[2-[2-(3-Methoxyphenyl)ethyl]phenyloxy]propyl]piperidin-4-yl]methyl]isoindolin-1-one fumarate By using the compound obtained in Example 67b, the title compound was obtained as colorless solid by similar procedures to those of Example 36c (yield: 80%).

Melting point: 185–191° C. $^1$H-NMR(DMSO-d$_6$): 7.67 (1H,d,J=7.2), 7.56–7.60(2H,m), 7.46–7.52(1H,m), 7.13–7.27(7H,m), 6.93(1H,d,J=7.8), 6.83–6.89(1H,m), 6.57 (2H,s,fumaric acid), 4.48(2H,s), 3.97(2H,t,J=6.0), 3.88(2H, s), 3.41(2H,d,J=7.2), 2.90–2.97(2H,m), 2.48–2.52(2H,m), 2.0–2.15(2H,m), 1.6–1.9(3H,m), 1.5–1.6(2H,m), 1.2–1.3(2H,m)

Example 68

2-[[1-[3-[2-[2-(3-Methoxyphenyl)ethyl]phenyloxy]propyl]piperidin-4-yl]methyl]isoindolin-1-one fumarate (Compound 701 in Table 1)

a) 3-Methoxybenzyltriphenylphosphonium chloride

3-Methoxybenzyl chloride (1.05 g, 6.69 mmol), triphenylphosphine (1.75 g, 6.67 mmol) was dissolved in dimethylformamide (10 ml) and heated at 150° C. for 40 minutes. The reaction mixture was cooled to room temperature, and the solid precipitated was collected by filtration and washed and ethyl ether, and then dried under reduced pressure to obtain the title compound as colorless solid 1.70 g (yield: 61%).

$^1$H-NMR(DMSO-d$_6$): 7.87–7.95(3H,m), 7.64–7.79(12H, m), 7.16(1H,t,J=7.9), 6.86(1H,d,J=8.3), 6.61(1H,d,J=7.4), 6.49(1H,s), 5.1–5.3(2H,m), 3.50(3H,s)

b) 3-[2-[2-(3-Methoxyphenyl)ethyl]phenyloxy]propanol

By using the compound obtained in Example 68a and the compound obtained in Example 66a, the title compound was obtained as colorless oil by similar procedures to those of Example 66b (yield: 50%).

$^1$H-NMR(CDCl$_3$): 7.10–7.24(3H,m), 6.70–6.93(5H,m), 4.12(2H,t,J=5.9), 3.90(2H,t,J=5.9), 3.78(3H,s), 2.8–3.0(4H, m), 2.0–2.2(2H,m), 1.72(1H,brs,OH)

c) 2-[[1-[3-[2-[2-(3-Methoxyphenyl)ethyl]phenyloxy]propyl]piperidin-4-yl]methyl]isoindolin-1-one By using the compound obtained in Example 68b, 3-[2-[2-(3-methoxyphenyl)ethyl]phenyloxy]propanol methanesulfonate was obtained as crude product by similar procedures to those of Example 26a. By using the resulting product, the title compound was obtained as yellow oil by similar procedures to those of Example 26b (yield: 84%).

$^1$H-NMR(CDCl$_3$): 7.85(1H,d,J=7.5), 7.42–7.55(3H,m), 7.07–7.22(3H,m), 6.70–6.89(5H,m), 4.41(2H,s), 4.01(2H,t, J=6.1), 3.77(3H,s), 3.50(2H,d,J=7.2), 2.80–3.00(6H,m), 2.51–2.59(2H,m), 1.9–2.1(4H,m), 1.6–1.9(3H,m), 1.3–1.5 (2H,m)

d) 2-[[1-[3-[2-[2-(3-Methoxyphenyl)ethyl]phenyloxy]propyl]piperidin-4-yl]methyl]isoindolin-1-one fumarate By using the compound obtained in Example 68c, the title compound was obtained as colorless solid by similar procedures to those of Example 36c (yield: 73%).

Melting point: 181–184° C. $^1$H-NMR(DMSO-d$_6$): 7.67 (1H,d,J=7.4), 7.58–7.60(2H,m), 7.47–7.51(1H,m), 7.12–7.20(3H,m), 6.93(1H,d,J=8.0), 6.70–6.87(4H,m), 6.57 (2H,s,fumaric acid), 4.48(2H,s), 4.00(2H,t,J=5.8), 3.70(3H, s), 3.41(2H,d,J=7.2), 2.98–3.05(2H,m), 2.7–2.9(4H,m), 2.6–2.7(2H,m), 2.0–2.2(2H,m), 1.9–2.0(2H,m), 1.7–1.8(1H, m), 1.5–1.7(2H,m), 1.2–1.4(2H,m)

Example 69

2-[[1-[4-Phenyl-2-oxobutyl]piperidin-4-yl]methyl]isoindolin-1-one hydrochloride (Compound 344 in Table 1)

2M LDA/heptane, THF, EtPh solution (3.07 mL, 6.14 mmol) was added to DME (3 mL) cooled at −78° C., and then the mixture was added dropwise with benzylacetone 0.700 g (4.72 mmol)/DME (5 mL). After stirring for 1 hour, the mixture was added dropwise with chlorotrimethylsilane (0.779 mL, 6.14 mmol) and then warmed to room temperature. The reaction mixture was diluted with hexane, and washed twice with water, twice with saturated aqueous NH$_4$Cl solution, and then with brine, and dried over Na$_2$SO$_4$.

The solvent was evaporated, and the residual oil was dissolved in THF (18 mL) and cooled to 0° C. and added with NBS (0.924 g, 5.19 mmol). The reaction mixture was warmed to room temperature and stirred for 1 hour, the reaction mixture was poured in aqueous Na$_4$S$_2$O$_3$ solution and extracted three times with ether. The combined organic layer was dried over Na$_2$SO$_4$.

After the solvent was evaporated, the resulting oil was dissolved in DMF (10 mL), and the solution was added with the compound obtained in Example 1d (1.26 g, 4.72 mmol)

and triethylamine (1.64 mL, 11.8 mmol). After stirring at room temperature, the reaction mixture was diluted with ethyl acetate and washed four times with water and then with brine, and dried over $Na_2SO_4$.

The drying agent was removed by filtration, the filtrate was made into a solution of ethanol (1.5 ml) and ethyl acetate (3 mL). The solution was added with 4N HCl—AcOEt (1.08 mL, (4.31 mmol). After stirring, the mixture was added with ethyl acetate (10 mL) and precipitated crystals were collected by filtration and dried to obtain the title compound (yield: 39%).

Melting point: 183–187° C. $^1$H-NMR (DMSO-$d_6$): δ 9.93 (br s, 1H), 7.68 (d, J=7.4 Hz, 1H), 7.61 (m, 2H), 7.49 (m, 1H), 7.16–7.31 (m, 5H), 4.51 (s, 2H), 4.33–4.50 (m, 2H), 2.84–3.57 (m, 10H), 1.99 (m, 1H), 1.78 (br d, J=13 Hz, 2H), 1.58 (m, 2H).

Example 70

2-[[1-[3-Phenyl-2-oxopropyl]piperidin-4-yl]methyl]isoindolin-1-one hydrochloride (Compound 349 in Table 1)

a) 2-[[1-[3-Phenyl-2-hydroxypropyl]piperidin-4-yl]methyl]isoindolin-1-one

The compound obtained in Example 1d (994 mg, 3.73 mmol) and (2,3-epoxypropyl)benzene (0.500 g, 3.73 mmol), and triethylamine (0.78 mL, 5.60 mmol) were dissolved in ethanol (8 mL), and the mixture was heated at 50° C. After completion of the reaction, the reaction mixture was diluted with ethyl acetate and washed four times with water and then with brine, and dried over $Na_2SO_4$. After the drying agent was removed by filtration, the filtrate was concentrated and the residue was purified by silica gel chromatography (acetone) to obtain the title compound (yield: 44%).

$^1$H-NMR (CDCl$_3$): δ 7.85 (d, J=7.2 Hz, 1H), 7.42–7.56 (m, 3H), 7.21–7.32 (m, 5H) 4.39 (s, 2H), 3.90 (m,1H), 3.49 (d, J=9.6 Hz, 2H), 2.96 (br d, J=9 Hz, 1H), 2.76–2.86 (m, 2H), 2.65 (m, 1H), 2.20–2.31 (m, 3H), 1.87 (dt, J=12, 2 Hz, 1H), 1.79(m, 1H), 1.67 (br d, J=13 Hz, 2H), 1.36 (dq, J=12, 4 Hz, 2H).

b) 2-[[1-[3-Phenyl-2-oxopropyl]piperidin-4-yl]methyl]isoindolin-1-one (COCl)$_2$ (0.125 g, 0.998 mmol)/CH$_2$Cl$_2$ (3 mL) was cooled to −78° C., and solution was added dropwise with DMSO (0.121 g, 1.55 mmol), and after stirring for 10 minutes, the mixture was added dropwise with the compound obtained in Example 70a) (180 mg, 0.494 mmol)/CH$_x$Cl$_2$ (1 mL). After stirring for 30 minutes, the reaction mixture was added dropwise with triethylamine (0.491 mL, 3.52 mmol), and after stirring for 4 hours, the reaction mixture was warmed up to room temperature. The reaction mixture was diluted with ethyl acetate (40 mL) and washed four times with water and then with brine, and dried over $Na_2SO_4$. After the drying agent was removed by filtration and the filtration was concentrated, the residue was purified by silica gel chromatography (acetone/hexane) to obtain the title compound (yield: 50%).

$^1$H-NMR (CDCl$_3$): δ 7.85 (d, J=7.5 Hz, 1H), 7.42–7.54 (m, 3H), 7.22–7.35 (m, 5H), 4.40 (s, 2H), 3.75 (s, 2H), 3.51 (d, J=7.2 Hz, 2H), 3.16 (s, 2H), 2.79 (br d, J=12 Hz, 2H), 2.03 (dt, J=11.4, 2.1 Hz, 2H), 1.78 (m, 1H), 1.67 (br d, J=10 Hz, 2H), 1.47 (dq, J=12, 4 Hz, 2H).

c) 2-[[1-[3-Phenyl-2-oxopropyl]piperidin-4-yl]methyl]isoindolin-1-one hydrochloride By using the compound obtained in Example 70b, the title compound was obtained by similar procedures to those of Example 1f (yield: 59%).

Melting point: 198–204° C. $^1$H-NMR (DMSO-$d_6$): δ 9.84 (br s, 1H), 7.68 (d, J=7.5 Hz, 1H), 7.61 (m, 2H), 7.50 (m, 1H), 7.22–7.37 (m, 5H), 4.40–4.54 (m, 4H), 3.88 (s, 2H), 2.94–3.56 (m, 6H), 1.99 (m, 1H), 1.78 (br d, J=14 Hz, 2H), 1.56 (m, 2H).

Example 71

2-[[1-[4-Phenyl-3-oxobutyl]piperidin-4-yl]methyl]isoindolin-1-one hydrochloride (Compound 354 in Table 1)

a) 1-Tosyloxy-3-hydroxy-4-phenylpropane

A solution of methyl(phenylacetyl)acetic acid (0.700 g, 3.64 mmol), prepared according to the method described in literature (Yonemitsu, O, et al, Org. Synth., 1984, 63, 198) in 24 mL of ethanol was cooled to 0° C., and the solution was added with NaBH$_4$ (1.10 g, 29.1 mmol) and stirred at room temperature. The reaction mixture was added with concentrated hydrochloric acid to become acidic, and then diluted with brine and extracted four times with dichloromethane. The combined organic layer was dried over $Na_2SO_4$.

After the drying agent was removed by filtration and the filtrate was concentrated, the resulting oil was dissolved in dichloromethane (8 mL). The solution was added with pyridine (0.61 mL, 7.54 mmol) and cooled to 0° C. The solution with stirring was added with tosyl chloride (0.694 g, 3.64 mmol) and stirred for 2 hours. Then the reaction mixture was diluted with ether and washed twice with water, and dried over $Na_2SO_4$. After the drying agent was removed by filtration and the filtrate was concentrated, the residue was purified by silica gel chromatography (ethyl acetate/hexane) to obtain the title compound (yield: 32%).

$^1$H-NMR (CDCl$_3$): δ 7.78 (d, J=8.1 Hz, 2H), 7.15–7.34 (m, 7H), 4.26 (m, 1H), 4.17 (m, 1H), 3.94 (m, 1H), 2.78 (m, 1H), 2.64 (m, 1H), 2.44 (s, 3H), 1.93 (m, 1H), 1.75 (m, 1H).

b) 2-[[1-[4-Phenyl-3-oxobutyl]piperidin-4-yl]methyl]isoindolin-1-one

By using the compound obtained in Example 71a, a product was obtained by similar procedures to those of Example 26b, which was subjected without purification to procedures similar to those of Example 70b to obtain the title compound (yield: 27%).

$^1$H-NMR (CDCl$_3$): δ 7.84 (d, J=7.2 Hz, 1H), 7.44–7.53 (m, 3H), 7.18–7.32 (m, 5H), 4.39 (s, 2H), 3.70 (s, 2H), 3.48 (d, J=7.2 Hz, 2H), 2.82 (br d, J=12 Hz, 2H), 2.05–2.65 (m, 4H), 1.91 (dt, J=11.7, 2.1 Hz, 2H), 1.75 (m, 1H), 1.66 (m, 2H), 1.33 (dq, J=12, 3 Hz, 2H).

c) 2-[[1-[4-Phenyl-3-oxobutyl]piperidin-4-yl]methyl]isoindolin-1-one hydrochloride By using the compound obtained in Example 71b, the title compound was obtained by similar procedures to those of Example 1f (yield: 61%).

Melting point: 163–166° C. $^1$H-NMR (DMSO-$d_6$): δ 9.89 (br s, 1H), 7.68 (d, J=7.5 Hz, 1H), 7.61 (m, 2H), 7.49 (m, 1H), 7.19–7.35 (m, 5H), 4.50 (s, 2H), 3.84 (s, 2H), 2.81–3.62 (m, 10H), 1.97(m, 1H), 1.78 (br d, J=13 Hz, 2H), 1.49 (m, 2H).

Example 72

2-[[1-[2-(2-Methoxyphenyl)-2-oxoethyl]piperidin-4-yl]methyl]isoindolin-1-one fumarate (Compound 376 in Table 1)

a) 2-[[1-[2-(2-Methoxyphenyl)-2-oxoethyl]piperidin-4-yl]methyl]isoindolin-1-one

2'-Methoxyacetophenone (1.11 g, 7.39 mmol) and pyridinium perbromide hydrobromide (2.61 g, 8.16 mmol) were dissolved in a mixed solvent of dichloromethane (50 ml) and methanol (20 ml), and the mixture was heated under reflux for 1 hour. The reaction solvent was evaporated under reduced pressure, and the residue was diluted with ethyl acetate. The mixture was washed with water and saturated brine, and dried over magnesium sulfate. Insoluble solids were removed by filtration and the filtrate was evaporated under reduced pressure to obtain 2-bromo-1-(2-methoxyphenyl)ethan-1-one as crude product. By using the product, the title compound was obtained as yellow oil by similar procedures to those of Example 1e (yield: 63%).
$^1$H-NMR(CDCl$_3$): 7.84(1H,d,J=7.5), 7.70(1H,dd,J=2.0, 7.7), 7.42–7.55(4H,m), 6.93–7.03(2H,m), 4.41(2H,s), 3.89 (3H,s), 3.80(2H,s), 3.50(2H,d,J=7.2), 2.92–3.00(2H,m), 2.14–2.26(2H,m), 1.6–1.9(3H,m), 1.4–1.55(2H,m)

b) 2-[[1-[2-(2-Methoxyphenyl)-2-oxoethyl]piperidin-4-yl]methyl]isoindolin-1-one fumarate By using the compound obtained in Example 72a, the title compound was obtained as colorless solid by similar procedures to those of Example 36c (yield: 50%).
Melting point: 180–190° C. $^1$H-NMR(DMSO-d$_6$): 7.67 (1H,d,J=7.5), 7.44–7.61(5H,m), 7.17(1H,d,J=8.2), 7.03(1H, t,J=7.4), 6.60(2H,s,fumaric acid), 4.48(2H,s), 3.88(3H,s), 3.84(2H, s), 3.40(2H,d,J=7.3), 2.88–2.95(2H,m), 2.21–2.31 (2H,m), 1.6–1.8(1H,m), 1.4–1.6(2H,m), 1.1–1.3(2H,m)

Example 73

2-[[1-[2-(4-Tolyl)-2-oxoethyl]piperidin-4-yl]methyl]isoindolin-1-one hydrochloride (Compound 396 in Table 1)

a) 2-[[1-[2-(4-Tolyl)-2-oxoethyl]piperidin-4-yl]methyl]isoindolin-1-one

By using 2-bromo-1-(4-methylphenyl)ethan-1-one, the title compound was obtained as pale yellow solid by similar procedures to those of Example 1e (yield: 83%).
$^1$H-NMR(CDCl$_3$): 7.91(2H,d,J=8.2), 7.84(1H,d,J=7.5), 7.41–7.59(3H,m), 7.24(2H,d,J=8.2), 4.41(2H,s), 3.76(2H,s), 3.51(2H,d,J=7.1), 2.95–3.03(2H,m), 2.41(3H,s), 2.09–2.21 (2H,m), 1.6–1.9(3H,m), 1.4–1.6(2H,m)

b) 2-[[1-[2-(4-Tolyl)-2-oxoethyl]piperidin-4-yl]methyl]isoindolin-1-one hydrochloride By using the compound obtained in Example 73a, the title compound was obtained as colorless solid by similar procedures to those of Example 1f (yield: 90%).

Melting point: 169–185° C. $^1$H-NMR(DMSO-d$_6$): 9.8–10.0(1H,brs,HCl), 7.80(0.5H,d,J=7.9), 7.89(1.5H,d, J=7.9), 7.69(1H,d,J=7.4), 7.57–7.63(2H,m), 7.40–7.52(3H, m), 5.09(0.5H,s), 5.02(1.5H,s), 4.53(2H,s), 3.51–3.58(2H, m), 3.47(2H,d,J=7.0), 2.9–3.1(2H,m), 2.41(3H,s), 1.9–2.1 (1H,m), 1.4–1.9(4H,m)

Example 74

2-[[1-[2-(3,4-Difluorophenyl)-2-oxoethyl]piperidin-4-yl]methyl]isoindolin-1-one fumarate (Compound 401 in Table 1)

a) 2-[[1-[2-(3,4-Difluorophenyl)-2-oxoethyl]piperidin-4-yl]methyl]isoindolin-1-one By using 3',4'-difluoroacetophenone, the title compound was obtained as yellow solid by similar procedures to those of Example 72a and Example 1e (yield: 84%).
$^1$H-NMR(CDCl$_3$): 7.8–8.0(3H,m), 7.40–7.57(3H,m), 7.10–7.26(1H,m), 4.40(2H,s), 3.67(2H,s), 3.51(2H,d,J=7.2), 2.86–2.97(2H,m), 2.08–2.20(2H,m), 1.6–1.9(3H,m), 1.3–1.5(2H,m)

b) 2-[[1-[2-(3,4-Difluorophenyl)-2-oxoethyl]piperidin-4-yl]methyl]isoindolin-1-one funarate By using the compound obtained in Example 74a, the title compound was obtained as colorless solid by similar procedures to those of Example 36c (yield: 79%).
Melting point: 186–193° C. $^1$H-NMR(DMSO-d$_6$): 8.00–8.09(1H,m), 7.85–7.95(1H,m), 7.54–7.69(4H,m), 7.4–7.5(1H,m), 6.62(2H,s,fumaric acid), 4.48(2H,s), 3.83 (2H,s), 3.40(2H,d,J=7.2), 2.84–2.90(2H,m), 2.08–2.18(2H, m), 1.6–1.8(1H,m), 1.4–1.6(2H,m), 1.1–1.3(2H,m)

Example 75

2-[[1-[2-(2-Naphthyl)-2-oxoethyl]piperidin-4-yl]methyl]isoindolin-1-one hydrochloride (Compound 411 in Table 1)

a) 2-[[1-[2-(2-Naphthyl)-2-oxoethyl]piperidin-4-yl]methyl]isoindolin-1-one

By using 2-bromo-1-(2-naphthyl)ethan-1-one, the title compound was obtained as pale yellow solid by similar procedures to those of Example 1e (yield: 83%).
$^1$H-NMR(CDCl$_3$): 8.57(1H,s), 7.83–8.05(4H,m), 7.41–7.66(6H,m), 4.42(2H,s), 3.96(2H,s), 3.53(2H,d,J=7.2), 3.04–3.13(2H,m), 2.20–2.31(2H,m), 1.6–1.9(3H,m), 1.4–1.6(2H,m)

b) 2-[[1-[2-(2-Naphthyl)-2-oxoethyl]piperidin-4-yl]methyl]isoindolin-1-one hydrochloride By using the compound obtained in Example 75a, the title compound was obtained as pale yellow solid by similar procedures to those of Example 1f (yield: 61%).
Melting point: 192–201° C. $^1$H-NMR(DMSO-d$_6$): 9.8–10.2(1H,brs,HCl), 8.81(0.2H,s), 8.72(0.8H,s), 7.97–8.19(4H,m), 7.4–7.8(6H,m), 5.26(0.4H,s), 5.19(1.6H, s), 4.55(2H,s), 3.57–3.64(2H,m), 3.49(2H,d,J=6.9), 3.0–3.2 (2H,m), 2.0–2.2(1H,m), 1.5–1.9(4H,m)

Example 76

2-[[1-[2-(3-Chlorophenyl)-2-oxoethyl]piperidin-4-yl]methyl]isoindolin-1-one fumarate (Compound 406 in Table 1)

a) 2-[[1-[2-(3-Chlorophenyl)-2-oxoethyl]piperidin-4-yl]methyl]isoindolin-1-one

By using 3'-chloroacetophenone, the title compound was obtained as orange oil by similar procedures to those of Example 72a and Example 1e (yield: 79%).

$^1$H-NMR(CDCl$_3$): 7.98–8.00(1H,m), 7.90(1H,d,J=8.1), 7.85(1H,d,J=7.5), 7.3–7.6(5H,m), 4.41(2H,s), 3.74(2H,s), 3.52(2H,d,J=7.4), 2.94–3.02(2H,m), 2.08–2.20(2H,m), 1.6–1.9(3H,m), 1.3–1.5(2H,m)

b) 2-[[1-[2-(3-Chlorophenyl)-2-oxoethyl]piperidin-4-yl]methyl]isoindolin-1-one fumarate By using the compound obtained in Example 76a, the title compound was obtained as colorless solid by similar procedures to those of Example 36c (yield: 64%).

Melting point: 187–193° C. $^1$H-NMR(DMSO-d$_6$): 8.00 (1H,d,J=1.5), 7.97(1H,d,J=8.4), 7.64–7.74(2H,m), 7.4–7.6 (4H,m), 6.61(2H,s,fumaric acid), 4.48(2H,s), 3.88(2H,s), 3.40(2H,d,J=7.2), 2.86–2.92(2H,m), 2.10–2.21(2H,m), 1.6–1.8(1H,m), 1.5–1.6(2H,m), 1.1–1.3(2H,m)

Example 77

2-[[1-[2-(2-Tolyl)-2-oxoethyl]piperidin-4-yl]methyl]isoindolin-1-one fumarate (Compound 386 in Table 1)

a) 2-[[1-[2-(2-Tolyl)-2-oxoethyl]piperidin-4-yl]methyl]isoindolin-1-one

By using 2'-methylacetophenone, the title compound was obtained as orange oil by similar procedures to those of Example 72a and Example 1e (yield: 78%).

$^1$H-NMR(CDCl$_3$): 7.84(1H,d,J=7.5), 7.33–7.66(5H,m), 7.20–7.27(2H,m), 4.41(2H,s), 3.75(2H,s), 3.52(2H,d,J=7.2), 2.99–3.07(2H,m), 2.48(3H,s), 2.1–2.3(2H,m), 1.8–2.0(1H, m), 1.6–1.8(2H,m), 1.4–1.6(2H,m)

b) 2-[[1-[2-(2-Tolyl)-2-oxoethyl]piperidin-4-yl]methyl]isoindolin-1-one fumarate By using the compound obtained in Example 77a, the title compound was obtained as colorless solid by similar procedures to those of Example 36c (yield: 56%).

Melting point: 186–194° C. $^1$H-NMR(DMSO-d$_6$): 7.75 (1H,d,J=7.2), 7.66(1H,d,J=7.5), 7.55–7.60(2H,m), 7.39–7.51(2H,m), 7.30(2H,t,J=7.1), 6.61(2H,s,fumaric acid), 4.47(2H,s), 3.79(2H,s), 3.39(2H,d,J=7.2), 2.86–2.93 (2H,m), 2.38(3H,s), 2.12–2.23(2H,m), 1.6–1.8(1H,m), 1.5–1.6(2H,m), 1.1–1.3(2H,m)

Example 78

2-[[1-[2-(3-Tolyl)-2-oxoethyl]piperidin-4-yl]methyl]isoindolin-1-one fumarate (Compound 391 in Table 1)

a) 2-[[1-[2-(3-Tolyl)-2-oxoethyl]piperidin-4-yl]methyl]isoindolin-1-one

By using 3'-methylacetophenone, the title compound was obtained as yellow oil by similar procedures to those of Example 72a and Example 1e (yield: 58%).

$^1$H-NMR(CDCl$_3$): 7.84(1H,d,J=7.5), 7.77–7.82(2H,m), 7.26–7.56(5H,m), 4.41(2H,s), 3.82(2H,s), 3.52(2H,d,J=7.2), 2.99–3.06(2H,m), 2.40(3H,s), 218–2.30(2H,m), 1.8–2.0(1H,m), 1.6–1.8(2H,m), 1.4–1.6(2H,m)

b) 2-[[1-[2-(3-Tolyl)-2-oxoethyl]piperidin-4-yl]methyl]isoindolin-1-one fumarate By using the compound obtained in Example 78a, the title compound was obtained as colorless solid by similar procedures to those of Example 36c (yield: 55%).

Melting point: 185–193° C. $^1$H-NMR(DMSO-d$_6$): 7.77–7.82(2H,m), 7.67(1H,d,J=7.5), 7.55–7.60(2H,m), 7.35–7.52(3H,m), 6.61(2H,s,fumaric acid), 4.48(2H,s), 3.88 (2H,s), 3.41(2H,d,J=7.3), 2.8–3.0(2H,m), 2.37(3H,s), 2.0–2.2(2H,m), 1.6–1.8(1H,m), 1.5–1.6(2H,m), 1.1–1.3(2H, m)

Example 79

2-[[1-[2-(3-Methoxyphenyl)-2-oxoethyl]piperidin-4-yl]methyl]isoindolin-1-one fumarate (Compound 381 in Table 1 a) 2-[[1-[2-(3-Methoxyphenyl)-2-oxoethyl]piperidin-4-yl]methyl]isoindolin-1-one

By using 2-bromo-1-(3-methoxyphenyl)ethan-1-one, the title compound was obtained as yellow oil by similar procedures to those of Example 1e (yield: 90%).

$^1$H-NMR(CDCl$_3$): 7.84(1H,d,J=7.2), 7.40–7.65(5H,m), 7.35(1H,t,J=8.0), 7.08–7.19(1H,m), 4.41(2H,s), 3.85(3H,s), 3.80(2H,s), 3.52(2H,d,J=7.2), 2.97–3.06(2H,m), 2.15–2.29 (2H,m), 1.6–1.9(3H,m), 1.4–1.6(2H,m)

b) 2-[[1-[2-(3-Methoxyphenyl)-2-oxoethyl]piperidin-4-yl]methyl]isoindolin-1-one fumarate By using the compound obtained in Example 79a, the title compound was obtained as colorless solid by similar procedures to those of Example 36c (yield: 71%).

Melting point: 178–188° C. $^1$H-NMR(DMSO-d$_6$): 7.67 (1H,d,J=7.5), 7.55–7.61(3H,m), 7.40–7.52(3H,m), 7.21(1H, dd,J=2.3,8.1), 6.61(2H,s,fumaric acid), 4.48(2H,s), 3.87(2H, s), 3.81(3H,s), 3.41(2H,d,J=7.2), 2.8–3.0(2H,m), 2.0–2.2 (2H,m), 1.6–1.8(1H,m), 1.5–1.6(2H,m), 1.1–1.3(2H,m)

Example 80

5-Methoxy-2-[[1-(2-phenyl-2-oxoethyl)piperidin-4-yl]methyl]isoindolin-1-one fumarate (Compound 42 in Table 1)

a) 5-Methoxy-2-[[1-(2-phenyl-2-oxoethyl)piperidin-4-yl]methyl]isoindolin-1-one By using the compound obtained in Example 9c and phenacyl bromide, the title compound was obtained as pale yellow oil by similar procedures to those of Example 1e (yield: 55%).

$^1$H-NMR(CDCl$_3$): 8.01(2H,d,J=7.2), 7.75(1H,dd,J=2.6, 8.7), 7.53–7.61(1H,m), 7.45(2H,t,J=7.5), 6.96–7.00(1H,m), 6.92(1H,s), 4.36(2H,s), 3.88(3H,s), 3.82(2H,s), 3.48(2H,d, J=7.2), 2.97–3.05(2H,m), 2.15–2.27(2H,m), 1.6–1.9(3H,m), 1.4–1.6(2H,m)

b) 5-Methoxy-2-[[1-(2-phenyl-2-oxoethyl)piperidin-4-yl]methyl]isoindolin-1-one fumarate By using the compound obtained in Example 80a, the title compound was obtained as colorless solid by similar procedures to those of Example 36c (yield: 74%).

Melting point: 186–193° C. $^1$H-NMR(DMSO-d$_6$): 7.99 (2H,d,J=7.5), 7.66(1H,t,J=7.5), 7.49–7.62(3H,m), 7.13(1H, d,J=1.5), 7.02(1H,dd,J=2.1,8.4), 6.61(2H,s,fumaric acid), 4.41(2H,s), 3.89(2H,s), 3.83(3H,s), 3.36(2H,d,J=7.2), 2.88–2.95(2H,m), 2.12–2.23(2H,m), 1.6–1.8(1H,m), 1.5–1.6(2H,m), 1.1–1.3(2H,m)

Example 81

2-[[1-[2-(2-Furyl)-2-oxoethyl]piperidin-4-yl]methyl]isoindolin-1-one hydrochloride (Compound 416 in Table 1)

a) 2-Bromo-1-(2-furyl)-ethan-1-one

By using 2-acetylfuran (500 mg, 4.54 mmol), the title compound was obtained as colorless semisolid by similar procedures to those of Example 72a (119 mg, yield: 14%).

$^1$H-NMR(CDCl$_3$): 7.65(1H,s), 7.35(1H,d,J=3.9 Hz), 4.33 (2H,s).

b) 2-[[1-[2-(2-Furyl)-2-oxoethyl]piperidin-4-yl]methyl]-isoindolin-1-one

By using the compound obtained in Example 81a (119 mg, 0.63 mmol) and the compound obtained in Example 1d (160 mg, 0.60 mmol), the title compound was obtained as crude product by similar procedures to those of Example 1e (131 mg). The crude product was used in the next reaction without purification.

c) 2-[[1-[2-(2-Furyl)-2-oxoethyl]piperidin-4-yl]methyl]-isoindolin-1-one hydrochloride By using the crude compound obtained in Example 81b (131 mg), the title compound was obtained as colorless solid by similar procedures to those of Example 1f 40 mg (yield: 18%, 2 steps). 209–216 (dec.)

$^1$H-NMR(DMSO-d$_6$): 9.98(1H,brs), 8.17(1H,s), 7.74–7.58(4H,m), 7.53–7.47(1H,m), 6.85(1H,d,J=3.5 Hz), 4.87–4.78(2H,m), 4.52(2H,s), 3.60–3.44(4H,m), 3.05–2.98 (2H,m), 2.01(1H,brs), 1.83(2H,brd,J=13.9 Hz), 1.64(2H, brdd,J=11.1,11.1 Hz).

Example 82

2-[[1-[2-(2-Thienyl)-2-oxoethyl]piperidin-4-yl]methyl]-isoindolin-1-one hydrochloride (Compound 421 in Table 1)

a) 2-Bromo-1-(2-thienyl)-ethan-1-one and 2-bromo-1-(5-bromo2-thienyl)-ethan-1-one By using 2-acetylthiophene (500 mg, 3.96 mmol), a reaction similar to that of Example 72a was carried out. The product was purified by silica gel column chromatography to obtain 2-bromo-1-(2-thienyl)-ethan-1-one as pale yellow oil (618 mg, yield: 76%) and 2-bromo-1-(5-bromo2-thienyl)-ethan-1-one as pale yellow oil (171 mg, yield: 15%).

2-Bromo-1-(2-thienyl)-ethan-1-one $^1$H-NMR(CDCl$_3$): 7.82(1H,d,J=3.6 Hz), 7.73(1H,d,J=4.0 Hz), 7.18(1H,dd, J=5.2,3.8 Hz), 4.37(2H,s). 2-Bromo-1-(5-bromo2-thienyl)-ethan-1-one $^1$H-NMR(CDCl$_3$): 7.55(1H,g,J=3.8 Hz), 7.14 (1H,d,J=3.8 Hz), 4.28(2H,s).

b) 2-[[1-[2-(2-Thienyl)-2-oxoethyl]piperidin-4-yl]methyl]-isoindolin-1-one

By using 2-bromo-1-(2-thienyl)-ethan-1-one obtained in Example 82a (300 mg, 1.46 mmol) and the compound obtained in Example 1d (389 mg, 1.46 mmol), a reaction similar to that of Example 1e was carried out to obtain the title compound as colorless solid (441 mg, yield: 85%).

$^1$H-NMR(CDCl$_3$): 7.98(1H,dd,J=3.8,1.1 Hz), 7.85(1H, J=7.5 Hz), 7.62–7.61(1H,m), 7.56–7.43(3H,m), 7.13–7.10 (1H,m), 4.41(2H,s), 3.58(2H,s), 3.53(2H,d,J=7.3 Hz), 2.96 (2H,brd,J=11.5 Hz), 2.17(2H,ddd,J=2.4,11.5,11.5 Hz), 1.84–1.78(1H,m),1.70–1.67(2H,m),1.53(2H,ddd,J=3.6, 12.0,12.0 Hz).

c) 2-[[1-[2-(2-Thienyl)-2-oxoethyl]piperidin-4-yl]methyl]-isoindolin-1-one hydrochloride By using the compound obtained in Example 82b (435 mg, 1.23 mmol), a reaction similar to that of Example 1f was carried out to obtain the title compound as colorless solid (418 mg, yield: 87%).

Melting point: 182–186° C. $^1$H-NMR(DMSO-d$_6$): 10.1 (1H,brs), 8.18(1H,d,J=1.8 Hz), 8.05(1H,d,J=3.3 Hz), 7.69 (1H,d,J=7.2 Hz), 7.62–7.58(2H,m), 7.53–7.47(1H,m), 7.36–7.34(1H,m), 5.04–4.95(2H,m), 4.53(2H,s), 3.55(2H, brd,J=11.7 Hz), 3.46(2H,brd,J=6.9 Hz), 3.05(2H,brs), 2.03 (1H,brs), 1.86–1.63(4H,m).

Example 83

2-[[1-[2-(5-Bromo-2-thienyl)-2-oxoethyl]piperidin-4-yl]methyl]-isoindolin-1-one hydrochloride (Compound 426 in Table 1)

a) 2-[[1-[2-(5-Bromo-2-thienyl)-2-oxoethyl]piperidin-4-yl]methyl]-isoindolin-1-one By using 2-bromo-1-(5-bromo2-thienyl)-ethan-1-one obtained in Example 82a (171 mg, 0.602 mmol), a reaction similar to that of Example 1e was carried out to obtain crude product of the title compound as pale brown solid (210 mg). The crude product obtained was used in the next reaction without purification.

b) 2-[[1-[2-(5-Bromo-2-thienyl)-2-oxoethyl]piperidin-4-yl]methyl]-isoindolin-1-one hydrochloride By using the crude product obtained in Example 83a (171 mg), a reaction similar to that of Example 1f was carried out to obtain the title compound as pale brown solid (99 mg, yield: 38%, 2 steps).
Melting point: 195–208° C.(dec.) $^1$H-NMR(DMSO-$d_6$): 10.1(1H,brs), 8.03–7.89(1H,m), 7.70–7.47(5H,m), 5.01–4.90(2H,m), 4.52(2H,s), 3.58–3.44(4H,m), 3.04–2.97 (2H,m), 2.03–1.60(5H,m).

Example 84

2-[[1-(2-Cyclohexyl-2-oxoethyl)piperidin-4-yl]methyl]isoindolin-1-one fumarate (Compound 446 in Table 1)

a) 2-Chloro-1-(1-cyclohexyl)ethan-1-one

By using methyl cyclohexanecarboxylate, the title compound was obtained according to the preparation method for haloketones described in the International Publication No WO/23756 (yield: 79%).
$^1$H-NMR(CDCl$_3$): 4.16(2H,s), 2.58–2.69(1H,m), 1.6–1.9 (4H,m), 1.1–1.5(6H,m)

b) 2-[[1-(2-Cyclohexxyl-2-oxoethyl)piperidin-4-yl]methyl]isoindolin-1-one

By using the compound obtained in Example 84a, the title compound was obtained as colorless oil by similar procedures to those of Example 1e (yield: 51%).
$^1$H-NMR(CDCl$_3$): 7.84(1H,d,J=7.2), 7.41–7.56(3H,m), 4.40(2H,s), 3.50(2H,d,J=7.2), 3.20(2H,s), 2.81–2.88(2H,m), 2.41–2.50(1H,m), 1.98–2.09(2H,m), 1.6–1.9(7H,m), 1.1–1.5(8H,m)

c) 2-[[1-(2-Cyclohexyl-2-oxoethyl)piperidin-4-yl]methyl]isoindolin-1-one fumarate By using the compound obtained in Example 84b, the title compound was obtained as colorless solid by similar procedures to those of Example 36c (yield: 89%).
Melting point: 186–196° C. $^1$H-NMR(DMSO-$d_6$): 7.67 (1H,d,J=7.5), 7.55–7.60(2H,m), 7.45–7.52(1H,m), 6.61(2H, s,fumaric acid), 4.48(2H,s), 3.41(2H,d,J=7.4), 3.29(2H,s), 2.75–2.81(2H,m), 2.4–2.6(1H,m), 2.0–2.2(2H,m), 1.53–1.76(8H,m), 1.0–1.3(7H,m)

Example 85

2-[[1-(2-Cyclohexyl-2-hydroxyethyl)piperidin-4-yl]methyl]isoindolin-1-one fumarate (Compound 451 in Table 1)

a) 2-[[1-(2-Cyclohexyl-2-hydroxyethyl)piperidin-4-yl]methyl]isoindolin-1-one

By using the compound obtained in Example 84b, the title compound was obtained as colorless solid by similar procedures to those of Example 16a (yield: 77%).

$^1$H-NMR(CDCl$_3$): 7.85(1H,d,J=7.5), 7.42–7.57(3H,m), 4.40(2H,s), 3.48–3.53(2H,m), 3.35–3.45(1H,m), 3.0–3.1(1H,m), 2.7–2.8(1H,m), 2.2–2.4(3H,m), 1.5–2.0(9H, m), 0.9–1.5(8H,m)

b) 2-[[1-(2-Cyclohexyl-2-hydroxyethyl)piperidin-4-yl]methyl]isoindolin-1-one fumarate By using the compound obtained in Example 85a, the title compound was obtained as colorless solid by similar procedures to those of Example 36c (yield: 85%).
Melting point: 180–183° C. $^1$H-NMR(DMSO-$d_6$): 7.67 (1H,d,J=7.2), 7.55–7.62(2H,m), 7.44–7.52(1H,m), 6.53(2H, s,fumaric acid), 4.49(2H,s), 3.45–3.60(1H,m), 3.42(2H,d, J=7.2), 3.0–3.2(2H,m), 2.5–2.7(2H,m), 2.2–2.4(2H,m), 0.90–2.0(17H,m)

Example 86

2-[[1-[[5-(4-Chlorophenyl)]furfuryl]piperidin-4-yl]methyl]isoindolin-1-one hydrochloride (Compound 471 in Table 1)

a) 2-[[1-[[5-(4-Chlorophenyl)]furfuryl]piperidin-4-yl]methyl]isoindolin-1-one

A solution of the compound obtained in Example 1d (334 mg, 1.45 mmol) and 5-(4-chlorophenyl)furfural (300 mg, 1.45 mmol) in methanol (5 mL) was added with acetic acid to adjust its pH to 6. The mixture was added wit NaCNBH$_3$ (0.25 g, 3.58 mmol) and stirred at room temperature for 4 hours. Then methanol was evaporated and the residue was diluted with ethyl acetate. The mixture was washed twice with saturated aqueous NaHCO$_3$ solution and then with brine, and dried over Na$_2$SO$_4$. After the drying agent was removed by filtration, the filtrate was concentrated and the residue was purified by silica gel chromatography to (dichloromethane/methanol) to obtain the title compound (yield: 55%).
$^1$H-NMR (CDCl$_3$): δ 7.84 (d, J=7.2 Hz, 1H), 7.57 (d, J=8.7 Hz, 2H), 7.43–7.53(m, 3H), 7.32 (d, J=8.7 Hz, 2H), 6.56 (d, J=3.5 Hz, 1H), 6.26 (d, J=3.5 Hz, 1H), 4.39 (s, 2H), 3.61 (s, 2H), 3.50 (d, J=6.9 Hz, 2H), 2.96 (br d, J=11.4 Hz, 2H), 2.07 (dt, J=11.4, 2.1 Hz, 2H), 1.78 (m, 1H), 1.70 (br d, J=12 Hz, 2H), 1.43 (dq, J=11.4, 3.3 Hz, 2H).

b) 2-[[1-[[5-(4-Chlorophenyl)]furfuryl]piperidin-4-yl]methyl]isoindolin-1-one hydrochloride By using the compound obtained in Example 86a, the title compound was obtained by similar procedures to those of Example 1f (yield: 82%).
Melting point: 218–226° C. $^1$H-NMR (DMSO-$d_6$): δ 10.6 (br s, 1H), 7.78 (d, J=8.4 Hz, 2H), 7.67 (d, J=7.5 Hz, 1H), 7.58 (m, 2H), 7.46–7.54 (m, 3H), 7.08 (d, J=3 Hz, 1H), 6.83 (d, J=3 Hz, 1H), 4.41–4.49 (m, 4H), 2.88–3.43 (m, 6H), 1.98 (m, 1H), 1.80 (br d, J=13 Hz, 2H), 1.56 (br q, J=12 Hz, 2H).

Example 87

2-[[1-[[2-(1-Phenyl)pyrrolyl]methyl]piperidin-4-yl]methyl]isoindolin-1-one fumarate (Compound 476 in Table 1)

a) 2-Formyl-1-phenylpyrrole, 3-formyl-1-phenylpyrrole

DMF 561 mg (7.68 mmol) was cooled to 0° C., and added dropwise with $POCl_3$ (1.18 g, 7.68 mmol). The mixture was stirred at room temperature for 15 minutes, and added dropwise with a solution of 1-phenylpyrrole (1.00 g, 6.98 mmol)/DMF (1.6 mL). After stirring at 50° C. for 1.5 hours, the mixture was cooled to 0° C. and added with saturated aqueous $Na_2CO_3$ solution to adjust it pH to 8. The mixture was diluted with ethyl acetate and the organic layer was separated. The layer was washed three times with water and dried over $Na_2SO_4$. The drying agent was removed by filtration and then the filtrate was concentrated. The residue was separated and purified by silica gel chromatography (dichloromethane/hexane) to obtain the title compound.

2-Formyl-1-phenylpyrrole (yield: 86%) $^1$H-NMR ($CDCl_3$): δ 9.57 (s, 1H), 7.43–7.47 (m, 5H), 7.17 (dd, J=3.9, 1.5 Hz, 1H), 7.08 (t, J=1.8 Hz, 1H), 6.41 (dd, J=3.9, 2.6 Hz, 1H).

3-Formyl-1-phenylpyrrole (yield: 14%) $^1$H-NMR ($CDCl_3$): δ 9.86 (s, 1H), 7.67 (t, J=1.8 Hz, 1H), 7.37–7.49 (m, 5H), 7.09 (t, J=2.4 Hz, 1H), 6.81 (dd, J=3.0, 1.5 Hz, 1H).

b) 2-[[1-[[2-(1-Phenyl)pyrrolyl]methyl]piperidin-4-yl]methyl]isoindolin-1-one

By using the compound obtained in Example 87a, i.e., 2-formyl-1-phenylpyrrole, the title compound was obtained by similar procedures to those of Example 86a (yield: 64%).

$^1$H-NMR ($CDCl_3$): δ 7.85 (d, J=7.5 Hz, 1H), 7.31–7.56 (m, 8H), 6.84 (t, J=2.4 Hz, 1H), 6.22 (t, J=3.0 Hz, 1H), 6.17 (dd, J=3.3, 1.8 Hz, 1H), 4.38 (s, 2H), 3.48 (d, J=7.2 Hz, 2H), 3.31 (s, 2H), 2.86 (d, J=11.4 Hz, 2H), 1.86 (dt, J=11.4, 1.8 Hz, 2H), 1.74 (m, 1H), 1.61 (br d, J=12.9 Hz, 2H), 1.30 (dq, J=12, 3.6 Hz, 2H).

c) 2-[[1-[[2-(1-Phenyl)pyrrolyl]methyl]piperidin-4-yl]methyl]isoindolin-1-one fumarate By using the compound obtained in Example 87b, the title compound was obtained by similar procedures to those of Example 40f (yield: 75%).

Melting point: 281–284° C. $^1$H-NMR (DMSO-$d_6$): δ 7.66 (d, J=7.5 Hz, 1H), 7.45–7.62 (m, 7H), 7.36 (t, J=7 Hz, 1H), 6.96 (t, J=2 Hz, 1H), 6.62 (s, 2H), 6.16 (br s, 2H), 4.46 (s, 2H), 3.37–3.39 (m, 4H), 2.81 (d, J=11 Hz, 2H), 1.93 (m, 2H), 1.71 (m, 1H), 1.55 (br d, J=12 Hz, 2H), 1.15 (br q, J=11 Hz, 2H).

Example 88

2-[[1-[[3-(1-Phenyl)pyrrolyl]methyl]piperidin-4-yl]methyl]isoindolin-1-one fumarate (Compound 481 in Table 1)

a) 2-[[1-[[3-(1-Phenyl)pyrrolyl]methyl]piperidin-4-yl]methyl]isoindolin-1-one

By using the compound obtained in Example 87a, i.e., 3-formyl-1-phenylpyrrole, the title compound was obtained in similar procedures to those of Example 86a (yield: 85%).

$^1$H-NMR ($CDCl_3$): δ 7.84 (d, J=7.2 Hz, 1H), 7.35–7.54 (m, 7H), 7.21 (m,1H), 7.01 (m, 2H), 6.27 (m, 1H), 4.40 (s, 2H), 3.50–3.52 (m, 4H), 3.02 (br d, J=11.7 Hz, 2H), 2.03 (dt, J=11.7, 2.1 Hz, 2H), 1.83 (m, 1H), 1.71 (br d, J=12 Hz, 2H), 1.45 (dq, J=11.7, 3.6 Hz, 2H).

b) 2-[[1-[[3-(1-Phenyl)pyrrolyl]methyl]piperidin-4-yl]methyl]isoindolin-1-one fumarate By using the compound obtained in Example 88b, the title compound was obtained by similar procedures to those of Example 40f (yield: 81%).

Melting point: 222–227° C. $^1$H-NMR (DMSO-$d_6$): δ 7.67 (d, J=7.4 Hz, 1H), 7.42–7.58 (m, 7H), 7.35 (s, 2H), 7.24 (t, J=7.2 Hz, 1H), 6.55 (s, 2H), 6.26 (s, 1H), 4.48 (s, 2H), 3.66 (s, 2H), 3.42 (d, J=7.2 Hz, 2H), 3.08 (d, J=11.7 Hz, 2H), 2.28 (br t, J=11 Hz, 2H), 1.82 (m, 1H), 1.65 (br d, J=12 Hz, 2H), 1.33 (br q, J=11 Hz, 2H).

Example 89

2-[[1-[[2-(1-Benzyl)pyrrolyl]methyl]piperidin-4-yl]methyl]isoindolin-1-one hydrochloride (Compound 486 in Table 1)

a) 2-Formyl-1-benzylpyrrole

A suspension of 60% NaH (252 mg, 6.31 mmol) in DMF (8 mL) with stirring was added dropwise with pyrrole-2-carboxyaldehyde (0.500 g, 5.26 mmol)/DMF 4 mL under nitrogen at 0° C. After stirring for 10 minutes, the mixture was added dropwise with benzyl bromide (0.75 mL, 6.31 mmol). After stirring for 30 minutes, the reaction mixture was diluted with ethyl acetate and washed four times with water and the with brine, and dried over $Na_2SO_4$. The drying agent was removed by filtration and then the filtrate was concentrated, the residue was purified by silica gel chromatography (dichloromethane/hexane) to obtain the title compound (yield: 99%).

$^1$H-NMR ($CDCl_3$): δ 9.56 (s, 1H), 7.23–7.34 (m, 3H), 7.15 (d, J=7.2 Hz, 2H), 6.98 (m, 2H), 6.27 (m, 1H), 5.57 (s, 2H).

b) 2-[[1-[[2-(1-Benzyl)pyrrolyl]methyl]piperidin-4-yl]methyl]isoindolin-1-one

By using the compound obtained in Example 89a, the title compound was obtained by similar procedures to those of Example 86a (yield: 52%).

$^1$H-NMR ($CDCl_3$): δ 7.85 (d, J=7.2 Hz, 1H), 7.42–7.55 (m, 3H), 7.21–7.31 (m, 3H), 7.03 (d, J=7.2 Hz, 2H), 6.66 (m, 1H), 6.08 (m, 1H), 6.00 (dd, J=3.0, 1.5 Hz, 1H), 5.22 (s, 2H), 4.37 (s, 2H), 3.46 (d, J=7.5 Hz, 2H), 3.26 (s, 2H), 2.79 (d, J=11.7 Hz, 2H), 1.82 (dt, J=11.7, 1.8 Hz, 2H), 1.72 (m, 1H), 1.58 (br d, J=12 Hz, 2H), 1.23 (dq, J=12.0, 3.6 Hz, 2H).

c) 2-[[1-[[2-(1-Benzyl)pyrrolyl]methyl]piperidin-4-yl]methyl]isoindolin-1-one hydrochloride By using the compound obtained in Example 89b, the title compound was obtained by similar procedures to those of Example 1f (yield: 84%).

Melting point: 171° C. ¹H-NMR (DMSO-d$_6$): δ 10.33 (br s, 1H), 7.68 (d, J=7.5 Hz, 1H), 7.60 (m, 2H), 7.49 (m, 1H), 7.26–7.35 (m, 3H), 7.02–7.08 (m, 2H), 6.95 (s, 1H), 6.42 (m, 1H), 6.14 (m, 1H), 5.35–5.40 (m, 2H), 4.50 (s, 2H), 4.14–4.29 (m, 2H), 2.79–3.64 (m, 4H), 1.94 (m, 1H), 1.76 (m, 2H), 1.59 (m, 2H).

Example 90

2-[[1-[[2-(1-Butyl)pyrrolyl]methyl]piperidin-4-yl]methyl]isoindolin-1-one hydrochloride (Compound 491 in Table 1)

a) 2-Formyl-1-butylpyrrole

By using n-butyl iodide, the title compound was obtained by similar procedures to those of Example 89a (yield: 92%).

¹H-NMR (CDCl$_3$): δ 9.53 (s, 1H), 6.91–6.94 (m, 2H), 6.21 (dd, J=3.9, 2.4 Hz, 1H), 4.31 (t, J=7.2 Hz, 2H), 1.74 (m, 2H), 1.29 (m, 2H), 0.93 (t, J=7.2 Hz, 3H).

b) 2-[[1-[[2-(1-Butyl)pyrrolyl]methyl]piperidin-4-yl]methyl]isoindolin-1-one

By using the compound obtained in Example 90a, the title compound was obtained by similar procedures to those of Example 86a (yield: 29%).

¹H-NMR (CDCl$_3$): δ 7.84 (d, J=7.5 Hz, 1H), 7.42–7.55 (m, 3H), 6.62 (t, J=1.8 Hz, 1H), 6.02 (t, J=3.3 Hz, 1H), 5.93 (dd, J=3.3, 1.8 Hz, 1H), 4.39 (s, 2H), 3.92 (t, J=7.5 Hz, 2H), 3.49 (d, J=7.5 Hz, 2H), 3.39 (s, 2H), 2.85 (br d, J=11.7 Hz, 2H), 1.87 (dt, J=11.7, 2.1 Hz, 2H), 1.63–1.75 (m, 5H), 1.28–1.38 (m, 4H), 0.94 (t, J=7.5 Hz, 3H).

c) 2-[[1-[[2-(1-Butyl)pyrrolyl]methyl]piperidin-4-yl]methyl]isoindolin-1-one hydrochloride By using the compound obtained in Example 90b, the title compound was obtained by similar procedures to those of Example 1f (yield: 78%).

Melting point: 179° C. ¹H-NMR (DMSO-d$_6$): δ 10.04 (br s, 1H), 7.68 (d, J=7.5 Hz, 1H), 7.59–7.61 (m, 2H), 7.49 (m, 1H), 6.90 (s, 1H), 6.35 (m, 1H), 6.07 (m, 1H), 4.50 (s, 2H), 4.23–4.37 (m, 2H), 3.96–4.04 (m, 2H), 2.84–3.66 (m, 6H), 1.95 (m, 1H), 1.78 (br d, J=12 Hz, 2H), 1.54–1.62 (m, 4H), 1.21 (m, 2H), 0.87 (t, J=7.5 Hz, 3H).

Example 91

2-[[1-[(2-Pyrrolyl)methyl]piperidin-4-yl]methyl]isoindolin-1-one hydrochloride (Compound 496 in Table 1)

By similar procedures to those of Example 86a and Example 1f, the title compound was obtained (60%).

Melting point: 186° C.

¹H-NMR (DMSO-d$_6$): δ 11.09 (br s, 1H), 9.99 (br s, 1H), 7.65 (d, J=7.5 Hz, 1H), 7.59 (m, 2H), 7.48 (m, 1H), 6.89 (s, 1H), 6.23 (m, 1H), 6.08 (s, 1H), 4.49 (s, 2H), 4.18–4.33 (m, 2H), 2.73–3.60 (m, 6H), 1.94 (m, 1H), 1.76 (br d, J=12 Hz, 2H), 1.48 (br q, J=12 Hz, 2H).

Example 92

2-[[1-[2-(2-Phenyl-1H-imidazol-1-yl)ethyl]piperidin-4-yl]methyl]-isoindolin-1-one dihydrochloride (Compound 591 in Table 1)

a) t-Butyldimethylsilyl 2-(2-phenyl-1H-imidazol-1-yl)ethyl ether

2-Bromoethanol (3.44 g, 27.53 mmol), t-butyldimethylchlorosilane (4.23 g, 28.07 mmol), and imidazole (3.97 g, 58.31 mmol) was dissolved in dimethylformamide (20 ml) and the solution was stirred at room temperature for 3 hours. The reaction mixture was diluted with ethyl acetate and washed with water and then with saturated brine, and dried over magnesium sulfate. Insoluble solids were removed by filtration, and then the filtrate was concentrated under reduced pressure to obtain t-butyldimethylsilyl 2-bromoethyl ether (6.05 g) as crude product. The crude product (1.83 g), 2-phenylimidazole (1.11 g, 7.70 mmol), and potassium carbonate (1.50 g, 10.9 mmol) was added in dimethylformamide (10 ml), and the mixture was heated at 80° C. for 10 hours. The reaction mixture was diluted with water and extracted with ethyl acetate. The extract was washed with water and then with saturated brine, and dried over sodium sulfate. Insoluble solids were removed by filtration and the filtrate was evaporated under reduced pressure. The resulting oil was purified by silica gel column chromatography (ethyl acetate-hexane) to obtain the title compound as pale yellow oil (1.16 g, yield: 50%).

¹H-NMR(CDCl$_3$): 7.62–7.68(2H,m), 7.43–7.49(3H,m), 7.18(1H,d,J=1.2), 7.13(1H,d,J=1.2), 4.14(2H,t,J=5.4), 3.87(2H,t,J=5.4), 0.84(9H,s), −0.04(6H,s)

b) 2-(2-Phenyl-1H-imidazol-1-yl)ethan-1-ol

The compound obtained in Example 92a (1.11 g, 3.67 mmol) was dissolved in ethanol (8 ml) and the solution was stirred with ice cooling. The solution was added with 18% aqueous hydrochloric acid solution (10 ml) and stirred for 2 hours. The reaction mixture was washed with hexane and the aqueous layer was added with sodium hydroxide to adjust its pH over 11. The mixture was extracted with dichloromethane and dried over sodium sulfate. Insoluble solids were removed by filtration and the filtrate was concentrated under reduced pressure. The resulting solid was suspended and washed in ethyl ether to obtain the title compound as colorless solid (636 mg, yield: 92%).

¹H-NMR(CDCl$_3$): 7.55–7.61(2H,m), 7.38–7.42(3H,m), 7.07(1H,s), 7.05(1H,s), 4.11(2H,t,J=5.4), 3.87(2H,t,J=5.4), 2.85(1H,brs,OH)

c) 2-[[1-[2-(2-Phenyl-1H-imidazol-1-yl)ethyl]piperidin-4-yl]methyl]isoindolin-1-one By using the compound obtained in Example 92b, 2-(2-phenyl-1H-imidazol-1-yl)ethan-1-ol methanesulfonate was obtained as crude product by similar procedures to those of Example 26a. By using the resulting product, the title compound was obtained as yellow oil by similar procedures to those of Example 26b (yield: 50%).

¹H-NMR(CDCl$_3$): 7.84(1H,d,J=7.2), 7.37–7.62(8H,m), 7.11(1H,d,J=0.9), 7.10(1H,d,J=0.9), 4.38(2H,s), 4.08(2H,t,J=6.8), 3.47(2H,d,J=7.2), 2.75–2.82(2H,m), 2.64(2H,t,J=6.8), 1.9–2.0(2H,m), 1.5–1.9(3H,m), 1.2–1.4(2H,m)

d) 2-[[1-[2-(2-Phenyl-1H-imidazol-1-yl)ethyl]piperidin-4-yl]methyl]isoindolin-1-one dihydrochloride By using the compound obtained in Example 92c, the title compound was obtained as colorless solid by similar procedures to those of Example 1f (yield: 90%).
Melting point: 155–168° C. $^1$H-NMR(DMSO-d$_6$): 13.0 (1H,brs,HCl), 11.5(1H,brs,HCl), 8.04–8.10(1H,m), 7.81–7.89(3H,m), 7.57–7.76(6H,m), 7.45–7.54(1H,m), 4.60–4.69(2H,m), 4.49(2H,s), 3.0–3.7(6H,m), 2.7–2.9(2H, m), 1.4–1.8(5H,m)

Example 93

2-[[1-[2-[2-(1-Benzyl)pyrrolyl]-2-oxoethyl]piperidin-4-yl]methyl]-isoindolin-1-one hydrochloride (Compound 431 in Table 1)

By using 2-acethylpyrrole, 1-benzyl-2-acetylpyrrol was synthesized by similar procedures to those of Example 89a, and then the product was subjected to procedures similar to those of Example 69 without purification to obtain the title compound (yield: 8%).
Melting point: 196–200° C. $^1$H-NMR (DMSO-d$_6$): δ 9.71 (br s, 1H), 7.68 (d, J=7.8 Hz, 1H), 7.61 (m, 2H), 7.57 (m, 1H), 7.49 (m, 1H), 7.23–7.33 (m, 4H), 7.08 (m, 2H), 6.35 (m, 1H), 5.59 (s, 2H), 4.69–4.78 (m, 2H), 4.51 (s, 2H), 2.89–3.56 (m, 6H), 1.97 (m, 1H), 1.79 (m, 2H), 1.58 (m, 2H).

Example 94

2-[[1-[2-[2-(1-Butyl)pyrrolyl]-2-oxoethyl]piperidin-4-yl]methyl]isoindolin-1-one hydrochloride (Compound 436 in Table 1)

By using 2-acetylpyrrole, 1-butyl-2-acetylpyrrole was synthesized by simlar procedures to those of Example 90a, and then the product was subjected to procedures similar to those of Example 69 without purification to obtain the title compound (yield: 67%).
Melting point: 200–207° C. $^1$H-NMR (DMSO-d$_6$): δ 9.78 (br s, 1H), 7.69 (d, J=7.5 Hz, 1H), 7.61 (m, 2H), 7.51 (m, 1H), 7.40 (m, 1H), 7.20 (m, 1H), 6.25 (m, 1H), 4.70–4.78 (m, 2H), 4.53 (s, 2H), 4.30 (t, J=7.2 Hz, 2H), 2.52–3.51 (m, 6H), 1.94 (m, 1H), 1.82 (br d, J=12 Hz, 2H), 1.25 (m, 2H), 0.88 (t, J=7.5 Hz, 3H).

Example 95

2-[[1-[2-[2-(1-Phenyl)pyrrolyl]-2-oxoethyl]piperidin-4-yl]methyl]-isoindolin-1-one hydrochloride (Compound 441 in Table 1)

a) 2-[[1-[2-[2-(1-Phenyl)pyrrolyl]-2-oxoethyl]piperidin-4-yl]methyl]isoindolin-1-one By using 1-phenyl-2-chloroacetylpyrrole prepared according to the method described in literature (P. D. Croce, C. L. Rosa, A. Ritieni, Synthesis, 1989, 783.), the title compound was obtained in similar procedures to those of Example 1e (yield: 52%).
$^1$H-NMR (CDCl$_3$): δ 7.84 (d, J=7.2 Hz, 1H), 7.34–7.57 (m, 6H), 7.21–7.25 (m,3H), 6.95 (m, 1H), 6.29 (m, 1H), 4.38 (s, 2H), 3.61 (s, 2H), 3.48 (d, J=7.2 Hz, 2H), 2.94 (br d, J=11 Hz, 2H), 2.12 (dt, J=11.4, 2.4 Hz, 2H), 1.80 (m, 1H), 1.65 (br d, J=12 Hz, 2H), 1.45 (dq, J=12, 3 Hz, 2H).

b) 2-[[1-[2-[2-(1-Phenyl)pyrrolyl]-2-oxoethyl]piperidin-4-yl]methyl]isoindolin-1-one hydrochloride By using the compound obtained in Example 95a, the title compound was obtained by similar procedures to those of Example 1f (yield: 89%).
Melting point: 193–197° C. $^1$H-NMR (DMSO-d$_6$): δ 9.75 (br s, 1H), 7.65 (d, J=7.5 Hz, 1H), 7.33–7.50 (m, 8H), 6.46 (m, 1H), 4.76–4.86 (m, 2H), 4.51 (s, 2H), 2.98–3.61 (m, 6H), 1.99 (m, 1 H), 1.78 (m, 2H), 1.56 (m, 2H).

Example 96

2-[[1-[2-(2-Trifluoromethylphenyl)ethyl]piperidin-4-yl]methyl]-isoindolin-1-one fumarate (Compound 521 in Table 1)

By using 2-trifluoromethylphenethylalcohol, the title compound was obtained as colorless solid by similar procedures to those of Examples 26a, 26b, and 36c (yield: 29%).
Melting point: 204–220° C. $^1$H-NMR(DMSO-d$_6$): 7.68 (1H,d,J=7.8), 7.57–7.66(4H,m), 7.38–7.53(3H,m), 6.59(2H, s), 4.49(2H,s), 3.42(2H,d,J=7.2), 3.00–3.05(2H,m), 2.90–2.99(2H,m), 2.62–2.69(2H,m), 2.14–2.25(2H,m), 1.7–1.9(1H,m), 1.5–1.7(2H,m), 1.1–1.3(2H,m)

Example 97

2-[[1-[2-(1-Naphthyl)ethyl]piperidin-4-yl]methyl]isoindolin-1-one fumarate (Compound 526 in Table 1)

By using 1-naphthalenethanol, the title compound was obtained as colorless solid by similar procedures to those of Examples 26a, 26b, and 36c (yield: 60%).
Melting point: 222–229° C. $^1$H-NMR(DMSO-d$_6$): 8.08 (1H,d,J=7.9), 7.91–7.95(1H,m), 7.78–7.80(1H,m), 7.69(1H, d,J=7.4), 7.41–7.62(7H,m), 6.59(2H,s,fumaric acid), 4.51 (2H,s), 3.45(2H,d,J=7.3), 3.26–3.34(2H,m), 3.15–3.29(2H, m), 2.80–2.87(2H,m), 2.27–2.39(2H,m), 1.7–1.9(1H,m), 1.6–1.7(2H,m), 1.2–1.4(2H,m)

Example 98

2-[[1[2-(2-Naphthyl)ethyl]piperidin-4-yl]methyl]isoindolin-1-one fumarate (Compound 531 in Table 1)

a) 2-[[1[2-(2-Naphthyl)ethyl]piperidin-4-yl]methyl]isoindolin-1-one

By using 2-naphthalenethanol, the title compound was obtained as colorless solid by similar procedures to those of Examples 26a and 26b (yield: 77%).
$^1$H-NMR(CDCl$_3$): 7.85(1H,d,J=7.5), 7.73–7.81(3H,m), 7.63(1H,s), 7.21–7.56(6H,m), 4.42(2H,s), 3.52(2H,d,J=7.2), 2.93–3.07(4H,m), 2.62–2.71(2H,m), 1.99–2.10(2H,m), 1.6–1.9(3H,m), 1.3–1.5(2H,m)

b) 2-[[1[2-(2-Naphthyl)ethyl]piperidin-4-yl]methyl]isoindolin-1-one fumarate

By using the compound obtained in Example 98a, the title compound was obtained as colorless solid by similar procedures to those of Example 36c (yield: 81%).

Melting point: 223–233° C. $^1$H-NMR(DMSO-d$_6$): 7.83–7.87(3H,m), 7.73(1H,s), 7.68(1H,d,J=7.5), 7.56–7.62(2H,m), 7.39–7.49(4H,m), 6.58(2H,s), 4.49(2H,s), 3.43(2H,d,J=7.2), 3.0–3.2(2H,m), 2.8–3.0(2H,m), 2.7–2.8(2H,m), 2.1–2.3(2H,m), 1.7–1.9(1H,m), 1.5–1.7(2H,m), 1.2–1.4(2H,m)

Example 99

2-[[1-[2-(3-Tolyl)ethyl]piperidin-4-yl]methyl]isoindolin-1-one fumarate (Compound 536 in Table 1)

By using 3-tolylacetic acid, 3-methylphenethylalcohol was obtained as crude product by similar procedures to those of Example 53b. By using the resulting product, the title compound was obtained as colorless solid by similar procedures to those of Examples 26a, 26b, and 36c (yield: 55%).

Melting point: 214–220° C. $^1$H-NMR(DMSO-d$_6$): 7.68 (1H,d,J=7.5), 7.55–7.61(2H,m), 7.44–7.52(1H,m), 7.17(1H,t,J=7.4), 6.98–7.05(3H,m), 6.57(2H,s,fumaric acid), 4.49 (2H,s), 3.43(2H,d,J=7.2), 3.07–3.15(2H,m), 2.6–2.8(4H,m), 2.27(3H,s), 2.1–2.3(2H,m), 1.7–1.9(1H,m), 1.5–1.7(2H,m), 1.2–1.4(2H,m)

Example 100

2-[[1-[2-(3-Fluorophenyl)ethyl]piperidin-4-yl]methyl]isoindolin-1-one fumarate (Compound 541 in Table 1)

By using 3-fluorophenylacetic acid, 3-fluorophenethylalcohol was obtained as crude product by similar procedures to those of Example 53b. By using the resulting product, the title compound was obtained as colorless solid by similar procedures to those of Examples 26a, 26b, and 36c (yield: 48%).

Melting point: 208–213° C. $^1$H-NMR(DMSO-d$_6$): 7.67 (1H,d,J=7.2), 7.55–7.61(2H,m), 7.45–7.52(1H,m), 7.27–7.35(1H,m), 7.00–7.12(3H,m), 6.58(2H,s,fumaric acid), 4.49(2H,s), 3.42(2H,d,J=7.2), 3.03–3.10(2H,m), 2.6–2.9(4H,m), 2.1–2.3(2H,m), 1.7–1.9(1H,m), 1.5–1.7(2H,m), 1.1–1.3(2H,m)

Example 101

2-[[1-[2-(4-Methoxyphenyl)ethyl]piperidin-4-yl]methyl]isoindolin-1-one fumarate (Compound 546 in Table 1)

By using 4-methoxyphenethylalcohol, the title compound was obtained as colorless solid by similar procedures to those of Examples 26a, 26b, and 36c (yield: 68%).

Melting point: 220–227° C. $^1$H-NMR(DMSO-d$_6$): 7.67 (1H,d,J=7.5), 7.56–7.61(2H,m), 7.45–7.51(1H,m), 7.13(2H,d,J=7.8), 6.84(2H,d,J=7.8), 6.57(2H,s,fumaric acid), 4.49 (2H,s), 3.71(3H,s), 3.42(2H,d,J=7.2), 3.03–3.10(2H,m), 2.6–2.8(4H,m), 2.14–2.26(2H,m), 1.7–1.9(1H,m), 1.5–1.7 (2H,m), 1.2–1.4(2H,m)

Example 102

2-[[1-[2-(3-Methoxyphenyl)ethyl]piperidin-4-yl]methyl]isoindolin-1-one fumarate (Compound 551 in Table 1)

By using 3-methoxyphenethylalcohol, the title compound was obtained as colorless solid by similar procedures to those of Examples 26a, 26b, and 36c (yield: 43%).

Melting point: 200–206° C. $^1$H-NMR(DMSO-d$_6$): 7.67 (1H,d,J=7.5), 7.56–7.61(2H,m), 7.45–7.52(1H,m), 7.19(1H,t,J=8.0), 6.73–6.82(3H,m), 6.57(2H,s,fumaric acid), 4.49 (2H,s), 3.73(3H,s), 3.42(2H,d,J=7.2), 3.0–3.1(2H,m), 2.6–2.8(4H,m), 2.1–2.3(2H,m), 1.7–1.9(1H,m), 1.6–1.7(2H,m), 1.1–1.3(2H,m)

Example 103

2-[[1-[2-(2-Nitrophenyl)ethyl]piperidin-4-yl]methyl]isoindolin-1-one hydrochloride (Compound 556 in Table 1)

a) 2-[[1-[2-(2-Nitrophenyl)ethyl]piperidin-4-yl]methyl]isoindolin-1-one

By using 2-nitrophenethylalcohol, 2-nitrophenethyl methanesulfonate was prepared by similar procedures to those of Example 26a. By using the resulting product, the title compound was obtained by similar procedures to those of Example 26b (52%).

$^1$H-NMR (CDCl$_3$): δ 7.97 (d, J=8.1 Hz, 1H), 7.84 (d, J=7.5 Hz, 1H), 7.39–7.59 (m, 6H), 4.44 (s, 2H), 3.57 (d, J=7.5 Hz, 2H), 3.33–3.42 (m, 4H), 3.03 (m, 2H), 2.10 (m, 1H), 1.63–1.98 (m, 4H).

b) 2-[[1-[2-(2-Nitrophenyl)ethyl]piperidin-4-yl]methyl]isoindolin-1-one hydrochloride By using the compound obtained in Example 103a, the title compound was obtained by similar procedures to those of Example 1f (yield: 84%).

Melting point: 248–252° C. $^1$H-NMR (DMSO-d$_6$): δ 11.60 (br s, 1H), 8.03 (d, J=7.7 Hz, 1H), 7.68–7.75 (m, 2H), 7.50–7.62 (m, 5H), 4.52 (s, 2H), 2.84–3.59 (m, 10H), 2.28 (m, 1H), 1.87 (m, 2H), 1.62 (m, 2H).

Example 104

2-[[1-[2-(2-Aminophenyl)ethyl]piperidin-4-yl]methyl]isoindolin-1-one hydrochloride (Compound 561 in Table 1)

a) 2-[[1-[2-(2-Aminophenyl)ethyl]piperidin-4-yl]methyl]isoindolin-1-one

To 10% Pd-C (89 mg)/MeOH (12 mL) were added the compound obtained in Example 103a 0.500 g (1.32 mmol) and HCO$_2$NH$_4$ (208 mg, 3.30 mmol)/H$_2$O (3 mL), and the mixture was heated under reflux, and then Pd was removed by filtration and the filtrate was concentrated. The residue was added with water and extracted three times with dichloromethane, and the combined organic layer was dried over Na$_2$SO$_4$. The drying agent was removed by filtration and then the filtrate was concentrated to obtain the title compound (yield: 93%).

$^1$H-NMR (CDCl$_3$): δ 7.85 (d, J=7.3 Hz, 1H), 7.42–7.53 (m, 3H), 6.97–7.04 (m, 2H), 6.65–6.70 (m, 2H), 4.40 (s, 2H), 3.51 (d, J=7.2 Hz, 2H), 3.02 (br d, J=11.6 Hz, 2H), 2.70 (dd, J=7.1, 6.5 Hz, 2H), 2.56 (dd, J=7.1, 6.5 Hz, 2H), 2.00 (dt, J=11.6, 2.0 Hz, 2H), 1.81 (m, 1H), 1.71 (br d, J=12 Hz, 2H), 1.40 (dq, J=12, 3 Hz, 2H).

b) 2-[[1-[2-(2-Aminophenyl)ethyl]piperidin-4-yl]methyl]isoindolin-1-one hydrochloride By using the compound obtained in Example 104a, the title compound was obtained by similar procedures to those of Example 1f (yield: 93%).

Melting point: 239–243° C. $^1$H-NMR (DMSO-$d_6$): δ 7.69 (d, J=7.2 Hz, 1H), 7.61 (m, 1H), 7.49 (m, 1H), 7.16–7.32 (m, 4 H), 4.52 (s, 2H), 2.87–3.75 (m, 10H), 2.04 (m, 1H), 1.84 (m, 2H), 1.59 (m, 2H).

Example 105

2-[[1-[2-(2-Acetylaminophenyl)ethyl]piperidin-4-yl]methyl]isoindolin-1-one hydrochloride (Compound 566 in Table 1)

a) 2-[[1-[2-(2-Acetylaminophenyl)ethyl]piperidin-4-yl]methyl]isoindolin-1-one

The compound obtained in Example 104a (246 mg, 0.704 mmol) was dissolved in pyridine (1 mL), and the solution was added with acetic anhydride (144 mg, 1.41 mmol) and heated at 60° C. After one our, the reaction mixture was diluted with brine and extracted with three times with dichloromethane, and then the combined organic layer was dried over $Na_2SO_4$. The drying agent was removed by filtration and the filtrate was concentrated, and then the residue was purified by silica gel chromatography (dichloromethane/methanol) to obtain the title compound (yield: 47%).

$^1$H-NMR (CDCl$_3$): δ 10.01 (br s, 1H), 7.93 (d, J=7.8 Hz, 1H), 7.85 (d, J=7.2 Hz, 1H), 7.43–7.55 (m, 3H), 7.22 (m, 1H), 6.95–7.09 (m, 2H), 4.41 (s, 2H), 3.54 (d, J=7.2 Hz, 2H), 3.06 (br d, J=12 Hz, 2H), 2.81 (m, 2H), 2.66 (m, 2H), 2.23 (s, 3H), 2.18 (m, 2H), 1.91 (m, 1H), 1.78 (m, 2H), 1.50 (m, 2H).

b) 2-[[1-[2-(2-Acetylaminophenyl)ethyl]piperidin-4-yl]methyl]isoindolin-1-one hydrochloride By using the compound obtained in Example 105a, the title compound was obtained by similar procedures to those of Example 1f (yield: 77%).

Melting point: 134° C. $^1$H-NMR (DMSO-$d_6$): δ 10.36 (br s, 1H), 9.53 (br s, 1H), 7.67 (d, J=7.8 Hz, 1H), 7.59 (m, 2H), 7.15–7.35 (m, 4H), 4.50 (s, 2H), 2.81–3.58 (m, 10H), 2.09 (s, 3H), 2.00 (m, 1H), 1.80 (m, 2H), 1.56 (m, 2H).

Example 106

2-[[1-[2-(2-Methylaminophenyl)ethyl]piperidin-4-yl]methyl]isoindolin-1-one ¼.fumarate (Compound 571 in Table 1)

a) 2-[[1-[2-(2-Methylaminophenyl)ethyl]piperidin-4-yl]methyl]isoindolin-1-one

Acetic anhydride (0.241 g, 2.36 mmol) was added dropwise with formic acid (0.133 g, 2.83 mmol) and heated at 50° C. After 2 hours, the reaction mixture was diluted with THF (1 ml) and cooled to 0° C., and then added dropwise with a solution of the compound obtained in Example 104a (411 mg, 1.18 mmol) in THF (3 ml). After stirring for 30 minutes, the reaction mixture was added with brine and extracted four times with dichloromethane, and the combined organic layer was dried over $Na_2SO_4$.

The drying agent was removed by filtration and the filtrate was concentrated, the residue was dissolved in THF (1 mL). The solution was cooled to 0° C., and added dropwise with BH3SMe$_2$ (90 μl, 0.952 mmol). The reaction mixture was warmed to room temperature and stirred for 3 hours, and then cooled to 0° C. and added dropwise with methanol (0.5 mL). The reaction mixture was further added with 1N aqueous solution of NaOH (3 mL) and stirred for 30 minutes, and then added with brine and extracted four times with dichloromethane, and the combined organic layer was dried over $Na_2SO_4$. The drying agent was removed by filtration and the filtrate was concentrated, the residue was purified by silica gel chromatography (dichloromethane/methanol) to obtain the title compound (yield: 72%)

$^1$H-NMR (CDCl$_3$): δ 7.85 (d, J=7.5 Hz, 1H), 7.45–7.55 (m, 3H), 7.18 (m, 1H), 6.97 (m, 1H), 6.60–6.65 (m, 2H), 4.44 (s, 2H), 3.57 (d, J=6.9 Hz, 2H), 3.21 (br d, J=12 Hz, 2H), 3.07 (m, 2H), 2.88 (s, 3H), 2.78 (m, 2H), 2.42 (br t, J=12 Hz, 2H), 2.16 (m, 2H), 2.02 (m, 1H), 1.64 (m, 2H).

b) 2-[[1-[2-(2-Methylaminophenyl)ethyl]piperidin-4-yl]methyl]isoindolin-1-one ¼.fumarate By using the compound obtained in Example 106a, the title compound was obtained by similar procedures to those of Example 40f (yield: 77%).

Melting point: 155° C. $^1$H-NMR (DMSO-$d_6$): δ 7.69 (d, J=7.5 Hz, 1H), 7.60 (m, 2H), 7.49 (m, 1H), 7.07 (t, J=7.7 Hz, 1H), 6.95 (d, J=7.2 Hz, 1H), 6.62 (s, 0.5H), 6.50–6.58 (m, 2H), 4.50 (s, 2H), 3.48 (d, J=6.1 Hz, 2H), 2.92–3.02 (m, 4H), 2.78 (m, 2 H), 2.72 (s, 3H), 2.63 (br t, J=11 Hz, 2H), 1.79–1.89 (m, 3H), 1.52 (m, 2H).

Example 107

2-[[1-[2-(4-Fluorophenylthio)ethyl]piperidin-4-yl]methyl]isoindolin-1-one hydrochloride (Compound 706 in Table 1)

a) 2-[[1-[2-(4-Fluorophenylthio)ethy]piperidin-4-yl]methyl]isoindolin-1-one

4-Fluorobenzenethiol (0.50 ml, 4.69 mmol) and 2-bromoethanol (0.345 ml, 4.87 mmol) was dissolved in tetrahydrofuran (12 ml). The solution was added with 1N aqueous solution of sodium hydroxide (4.8 ml, 4.8 mmol) and heated at 80° C. for 80 minutes with stirring. The reaction mixture was diluted with a mixed solvent of ethyl acetate-hexane, and washed with diluted aqueous solution of sodium hydroxide, water, and then with saturated brine, and dried over magnesium sulfate. Insoluble solids were removed by filtration and the filtrate was concentrated under reduced pressure to obtain 2-(4-fluorophenylthio)ethanol as crude product. By using the resulting product, 2-(4-fluorophenylthio)ethanol ethanesulfonate was obtained as crude product by similar procedures to those of Example 26a. By using the resulting product, the title compound was obtained as colorless solid by similar procedures to those of Example 26b (yield: 64%).

$^1$H-NMR(CDCl$_3$): 7.84(1H,d,J=7.5), 7.40–7.55(3H,m), 7.31–7.39(2H,m), 6.98(2H,t,J=8.9), 4.39(2H,s), 3.49(2H,d,J=7.2), 2.95–3.02(2H,m), 2.85–2.94(2H,m), 2.54–2.61(2H, m), 1.94–2.04(2H,m), 1.5–1.8(3H,m), 1.2–1.4(2H,m)

b) 2-[[1-[2-(4-Fluorophenylthio)ethyl]piperidin-4-yl]methyl]isoindolin-1-one hydrochloride By using the compound obtained in Example 107a, the title compound was obtained by similar procedures to those of Example 1f (yield: 86%).

Melting point: 185–192° C. $^1$H-NMR(DMSO-d$_6$): 10.55 (1H,brs,HCl), 7.68(1H,d,J=7.5), 7.59–7.62(2H,m), 7.46–7.52(3H,m), 7.18–7.25(2H,m), 4.50(2H,s), 3.1–3.7(8H,m), 2.7–2.9(2H,m), 1.7–2.0(3H,m), 1.4–1.6(2H,m)

Example 108

2-[[1-[3-(4-Fluorophenylthio)propyl]piperidin-4-yl]methyl]isoindolin-1-one hydrochloride (Compound 711 in Table 1)

a) 3-(4-Fluorophenylthio)propanol

4-Fluorobenzenethiol (788 mg, 6.15 mmol) and 3-bromopropanol (0.535 ml, 6.16 mmol) was dissolved in tetrahydrofuran (20 ml). The solution was added with 1N aqueous solution of sodium hydroxide (6.2 ml, 6.2 mmol) and heated at 80° C. for 3 hours with stirring. The reaction mixture was diluted with a mixed solvent of ethyl acetate-hexane and washed with diluted aqueous solution of sodium hydroxide, water, and then with saturated brine, and dried over magnesium sulfate. Insoluble solids were moved by filtration and the filtrate was concentrated under reduced pressure. The resulting oil was purified by silica gel column chromatography (ethyl acetate-hexane) to obtain the title compound as colorless oil (592 mg, yield: 52%).

$^1$H-NMR(CDCl$_3$): 7.33–7.39(2H,m), 6.97–7.03(2H,m), 3.77(2H,t,J=6.0), 2.99(2H,t,J=7.3), 1.80–1.91(2H,m), 1.49 (1H,brs,OH)

b) 2-[[1-[3-(4-Fluorophenylthio)propyl]piperidin-4-yl]methyl]isoindolin-1-one

By using the compound obtained in Example 108a, 3-(4-fluorophenylthio)propanol methanesulfonate was obtained as crude product by similar procedures to those of Example 26a. By using the resulting product, the title compound was obtained as pale yellow solid by similar procedures to those of Example 26b (yield: 86%).

$^1$H-NMR(CDCl$_3$): 7.85(1H,d,J=7.5), 7.41–7.55(3H,m), 7.30–7.37(2H,m), 6.98(2H,t,J=8.6), 4.40(2H,s), 3.40(2H,d,J=7.3), 2.83–2.92(4H,m), 2.41(2H,t,J=7.5), 1.86–1.96(2H,m), 1.5–1.8(5H,m), 1.2–1.4(2H,m)

c) 2-[[1-[3-(4-Fluorophenylthio)propyl]piperidin-4-yl]methyl]isoindolin-1-one hydrochloride By using the compound obtained in Example 108b, the title compound was obtained as colorless solid by similar procedures to those of Example 1f (yield: 52%).

Melting point: 162–164° C. $^1$H-NMR(DMSO-d$_6$): 9.8–10.6(1H,brs,HCl), 7.68(1H,d,J=7.5), 7.60–7.62(2H,m), 7.42–7.52(3H,m), 7.17–7.24(2H,m), 4.50(2H,s), 2.9–3.7(8H,m), 2.6–2.8(2H,m), 1.8–2.0(3H,m), 1.6–1.8(2H,m), 1.4–1.6(2H,m)

Example 109

2-[[1-[2-(Phenylthio)ethyl]piperidin-4-yl]methyl]isoindolin-1-one fumarate (Compound 726 in Table 1)

By using thiophenol, 2-[[1-[2-(phenylthio)ethyl]piperidin-4-yl]methyl]isoindolin-1-one was obtained as crude product by similar procedures to those of Example 107a. By using the resulting product, the title compound was obtained as colorless solid by similar procedures to those of Example 36c (yield: 62%).

Melting point: 188–192° C. $^1$H-NMR(DMSO-d$_6$): 7.67 (1H,d,J=7.5), 7.55–7.60(2H,m), 7.45–7.52(1H,m), 7.27–7.35(4H,m), 7.14–7.20(1H,m), 6.60(2H,s,fumaric acid), 4.47(2H,s), 3.40(2H,d,J=7.2), 3.06–3.18(2H,m), 2.88–2.95(2H,m), 2.5–2.6(2H,m), 1.9–2.1(2H,m), 1.6–1.8 (1H,m), 1.5–1.6(2H,m), 1.1–1.3(2H,m)

Example 110

2-[[1-[2-(2-Methoxyphenylthio)ethyl]piperidin-4-yl]methylisoindolin-1-one fumarate (Compound 731 in Table 1)

By using 2-methoxybenzenethiol, 2-[[1-[2-(2-methoxyphenylthio)ethyl]piperidin-4-yl]methyl]isoindolin-1-one was obtained as crude product by similar procedures to those of Example 107a. By using the resulting product, the title compound was obtained as colorless solid by similar procedures to those of Example 36c (yield: 53%).

Melting point: 166–169° C. $^1$H-NMR(DMSO-d$_6$): 7.67 (1H,d,J=7.5), 7.55–7.60(2H,m), 7.45–7.52(1H,m), 7.14–7.25(2H,m), 6.90–6.99(2H,m), 6.60(2H,s,fumaric acid), 4.48(2H,s), 3.80(3H,s), 3.41(2H,d,J=7.3), 2.99–3.06 (2H,m), 2.91–2.98(2H,m), 2.55–2.64(2H,m), 2.01–2.11(2H,m), 1.6–1.8(1H,m), 1.5–1.6(2H,m), 1.1–1.3(2H,m)

Example 111

2-[[1-[2-(3-Methoxyphenylthio)ethyl]piperidin-4-yl]methyl]isoindolin-1-one fumarate (Compound 736 in Table 1)

By using 3-methoxybenzenethiol, 2-[[1-[2-(3-methoxyphenylthio)ethyl]piperidin-4-yl]methyl]isoindolin-1-one was obtained as crude product by similar procedures to those of Example 107a. By using the resulting product, the title compound was obtained as colorless solid by similar procedures to those of Example 36c (yield: 40%).

Melting point: 156–159° C. $^1$H-NMR(DMSO-d$_6$): 7.67 (1H,d,J=7.4), 7.56–7.61(2H,m), 7.45–7.52(1H,m), 7.21(1H,t,J=7.9), 6.84–6.91(2H,m), 6.71–6.77(1H,m), 6.61(2H,s,fumaric acid), 4.48(2H,s), 3.74(3H,s), 3.40(2H,d,J=7.3), 3.07–3.15(2H,m), 2.90–2.97(2H,m), 2.56–2.63(2H,m), 2.02–2.09(2H,m), 1.6–1.8(1H,m), 1.5–1.6(2H,m), 1.1–1.3 (2H,m)

Example 112

2-[[1-[2-(2-Fluorophenylthio)ethyl]piperidin-4-yl]methyl]isoindolin-1-one fumarate (Compound 716 in Table 1)

By using 2-fluorobenzenethiol, 2-[[1-[2-(2-fluorophenylthio)ethyl]piperidin-4-yl]methyl]isoindolin-1-one was obtained as crude product by similar procedures to those of Example 107a. By using the resulting product, the title compound was obtained as colorless solid by similar procedures to those of Example 36c (yield: 46%).

Melting point: 187–189° C. $^1$H-NMR(DMSO-$d_6$): 7.67 (1H,d,J=7.2), 7.55–7.60(2H,m), 7.41–7.52(2H,m), 7.14–7.28(3H,m), 6.61(2H,s,fumaric acid), 4.47(2H,s), 3.39 (2H,d,J=7.2), 3.05–3.13(2H,m), 2.86–2.92(2H,m), 2.54–2.63(2H,m), 1.9–2.1(2H,m), 1.6–1.8(1H,m), 1.5–1.6 (2H,m), 1.1–1.3(2H,m)

Example 113

2-[[1-[2-(3-Fluorophenylthio)ethyl]piperidin-4-yl] methyl]isoindolin-1-one fumarate (Compound 721 in Table 1)

By using 3-fluorobenzenethiol, 2-[[1-[2-(3-fluorophenylthio)ethyl]piperidin-4-yl]methyl]isoindolin-1-one was obtained as crude product by similar procedures to those of Example 107a. By using the resulting product, the title compound was obtained as colorless solid by similar procedures to those of Example 36c (yield: 48%).

Melting point: 194–198° C. $^1$H-NMR(DMSO-$d_6$): 7.67 (1H,d,J=7.4), 7.55–7.61(2H,m), 7.45–7.45–7.52(1H,m), 7.28–7.36(1H,m), 7.11–7.22(2H,m), 6.94–7.02(1H,m), 6.60 (2H,s,fumaric acid), 4.48(2H,s), 3.40(2H,d,J=7.2), 3.12–3.19(2H,m), 2.90–2.96(2H,m), 2.56–2.64(2H,m), 1.97–2.08(2H,m), 1.6–1.8(1H,m), 1.5–1.6(2H,m), 1.1–1.3 (2H,m)

Example 114

2-[[1-(2-Phenoxyethyl)piperidin-4-yl]methyl]isoindolin-1-one fumarate (Compound 611 in Table 1)

a) 1-(4-Methylbenzene)sulfonyloxy-2-phenoxyethane

2-Phenoxyethanol (500 mg, 3.62 mmol) was dissolved in dichloromethane (7 ml), and the solution was added with p-toluenesulfonyl chloride (690 mg, 3.62 mmol) and triethylamine (0.51 ml, 3.62 mmol) and stirred at room temperature for 15 hours. The reaction mixture was diluted with dichloromethane and washed with water, and dried over magnesium sulfate. Insoluble solids were removed by filtration and the filtrate was evaporated under reduced pressure to obtain the title compound (1.08 g, yield: quantitative).

$^1$H-NMR(CDCl$_3$): 7.83(2H,d,J=1.8 Hz), 7.34(2H,d,J=8.4 Hz), 7.28–7.23(2H,m), 6.98–6.93(1H,m), 6.78(2H,d,J=7.8 Hz), 4.37(2H,t,J=4.8 Hz), 4.14(2H,t,J=5.0 Hz), 2.44(3H,s).

b) 2-[[1-(2-Phenoxyethyl)piperidin-4-yl]methyl] isoindolin-1-one

The compound obtained in Example 114a (547 mg, 1.87 mmol) was dissolved in dimethylformamide (3 ml), and the solution was added with the compound obtained in Example 1d (500 mg, 1.87 mmol) and potassium carbonate (517 mg, 3.74 mmol) and then heated at 60° C. for 7 hours with stirring. The reaction mixture was stand for cooling, and then added with water (10 ml) and extracted with ethyl acetate. The extract was washed with water and saturated brine, and dried over sodium sulfate. Insoluble solids were removed by filtration and the filtrate was evaporated under reduced pressure. The resulting solid was suspended and washed in diethyl ether-hexane, and collected by filtration to obtain the title compound as crude product (171 mg). The product was used in the next reaction without purification.

c) 2-[[1-(2-Phenoxyethyl)piperidin-4-yl]methyl] isoindolin-1-one fumarate

By using the compound obtained in Example 114b (170 mg), the title compound was obtained as colorless solid by similar procedures to those of Example 36c (170 mg, yield: 19%, 2 steps).

Melting point: 178–181° C. $^1$H-NMR(DMSO-$d_6$): 7.67 (1H,d,J=7.5 Hz), 7.59(2H,d,J=4.2 Hz), 7.51–7.47(1H,m), 6.95–6.90(3H,m), 6.59(2H,s), 4.48(2H,s), 4.11(2H,brt,J=5.7 Hz), 3.42(2H,brd,J=10.2 Hz), 2.85(2H,brt,J=5.4 hz), 2.23 (2H,brdd,J=11.3,11.3 Hz), 1.80–1.75(1H,m), 1.61(2H,brd, J=12.9 Hz), 1.28(2H,brdd,J=23.0,10.2 Hz).

Example 115

2-[[1-[2-(4-Chlorophenoxy)ethyl]piperidin-4-yl] methyl]isoindolin-1-one fumarate (Compound 626 in Table 1)

a) 1-Bromo-2-(4-chlorophenoxy)ethane

4-Chlorophenol (500 mg, 3.89 mg), 2-bromoethanol (0.28 ml, 3.89 mmol), triphenylphosphine (1.02 g, 3.89 mmol) were dissolved in tetrahydrofuran (8 ml). The solution was added dropwise with diisopropylazodicarboxylate (0.84 ml, 3.89 mmol) and stirred at room temperature for 3 hours. The solvent of the reaction mixture was evaporated, and then solids were precipitated by using diethyl ether-hexane and removed by filtration. The filtrate was evaporated under reduced pressure to obtain the title compound as crude product (1.18 g). The crude product was used for the next reaction without purification.

b) 2-[[1-[2-(4-Chlorophenoxy)ethyl]piperidin-4-yl] methyl]isoindolin-1-one

The compound obtained in Example 115a (500 mg) was dissolved in dimethylformamide (2 ml). The solution was added with the compound obtained in Example 1d (440 mg, 1.65 mmol), potassium carbonate (456 mg, 3.30 mmol), and sodium iodide (247 mg, 1.65 mmol), and the mixture was heated at 60° C. for 17 hours with stirring. The reaction mixture was stand for cooling, and then diluted with ethyl acetate. The mixture was washed with water and saturated brine, and dried over sodium sulfate. Insoluble solids were removed by filtration and the filtrate was evaporated under reduced pressure. The resulting crude product was purified by silica gel column chromatography (methanol-dichloromethane) to obtain the title compound as pale brown solid (273 mg, 18%, 2 steps).

$^1$H-NMR(CDCl$_3$): 7.85(1H,d,J=7.4 Hz), 7.56–7.42(3H, m), 7.23–7.19(2H,m), 6.84–6.80(2H,m), 4.40(2H,s), 4.05 (2H,t,J=5.8 Hz), 3.51(2H,d,J=7.3 Hz), 2.98(2H,brd,J=11.8 Hz), 2.77(2H,t,J=5.9 Hz), 2.10(2H,ddd,J=2.3,11.6,11.6 Hz), 1.84–1.68(3H,m), 1.45–1.40(2H,m)

c) 2-[[1-[2-(4-Chlorophenoxy)ethyl]piperidin-4-yl] methyl]isoindolin-1-one fumarate By using the compound obtained in Example 115b (270 mg, 0.70 mmol), the title compound was obtained as colorless solid by similar procedures to those of Example 36c (272 mg, yield: 78%).

Melting point: 189–192° C. $^1$H-NMR(DMSO-d$_6$): 7.67 (1H,d,J=7.4 Hz), 7.59(2H,d,J=1.4 Hz), 7.58–7.46(1H,m), 7.31(1H,dd,J=7.5,2.1 Hz), 6.97(2H,dd,J=6.7,2.1 Hz), 6.59 (2H,s), 4.48(2H,s), 4.10(2H,t,J=5.7 Hz), 3.41(2H,d,J=7.3 Hz), 3.00(2H,brd,J=11.7 Hz), 2.80(2H,t,J=5.8 Hz), 2.17(2H, dd,J=10.7,10.7 Hz), 1.79(1H,m), 1.60(2H,brd,J=12.4 Hz), 1.33–1.21(2H,m).

Example 116

2-[[1-[2-(2-Methoxyphenoxy)ethyl]piperidin-4-yl] methyl]isoindolin-1-one fumarate (Compound 631 in Table 1)

a) 1-Bromo-2-(2-methoxyphenoxy)ethane

By using 2-methoxyphenol (186 mg, 1.5 mmol), the title compound was obtained as crude product by similar procedures to those of Example 115a (551 mg). The resulting crude product was used in the next reaction without purification.

b) 2-[[1-[2-(2-Methoxyphenoxy)ethyl]piperidin-4-yl]methyl]isoindolin-1-one

By using the compound obtained in Example 116a (551 mg), the title compound was obtained as brown oil by similar procedures to those of Example 115b (119 mg, yield: 21%, 2 steps).
$^1$H-NMR(CDCl$_3$): 7.85(1H,d,J=7.5 Hz), 7.56–7.42(3H, m), 6.92–6.87(4H,m), 4.41(2H,s), 4.14(2H,t,J=6.2 Hz), 3.85 (3H,s), 3.51(2H,d,J=7.2 Hz), 3.02(2H,brd,J=11.7 Hz), 2.83 (2H,t,J=6.2 Hz), 2.15–2.07(2H,m), 1.87–1.69(3H,m), 1.51–1.37(2H,m).

c) 2-[[1-[2-(2-Methoxyphenoxy)ethyl]piperidin-4-yl]methyl]isoindolin-1-one fumarate By using the compound obtained in Example 116b (119 mg, 0.32 mmol), the title compound was obtained as colorless solid by similar procedures to those of Example 36c (108 mg, yield: 69%).
Melting point: 188–191° C. $^1$H-NMR(DMSO-d$_6$): 7.67 (1H,d,J=7.5 Hz), 7.59–7.50(3H,m), 7.00–6.84(4H,m), 6.59 (2H,s), 4.48(2H,s), 4.09(2H,t,J=5.7 Hz), 3.74(3H,s), 3.41 (2H,d,J=7.2 Hz), 3.05(2H,brd,J=11.1 Hz), 2.83(2H,brs), 2.22(2H,brdd,J=11.0,11.0 Hz), 1.78–1.77(1H,m), 1.62(2H, brd,J=12.0 Hz), 1.28(2H,brdd,J=21.8,11.4 Hz).

Example 117

2-[[1-[2-(2-Fluorophenoxy)ethyl]piperidin-4-yl]methyl]isoindolin-1-one fumarate (Compound 616 in Table 1)

a) 1-Bromo-2-(2-fluorophenoxy)ethane

By using 2-fluorophenol (168 mg, 1.5 mmol), the title compound was obtained as crude product by carrying out a reaction similar to that of Example 115a (418 mg). The resulting crude product was used in the next reaction without purification.

b) 2-[[1-[2-(2-Fluorophenoxy)ethyl]piperidin-4-yl] methyl]isoindolin-1-one

By using the compound obtained in Example 117a (418 mg), the title compound was obtained as brown oil by carrying out reactions similar to those of Example 115b (240 mg, yield: 43%, 2 steps).
$^1$H-NMR(CDCl$_3$): 7.85(1H,d,J=7.2 Hz), 7.53–7.42(3H, m), 7.07–6.96(4H,m), 4.41(2H,s), 4.16(2H,t,J=6.0 Hz), 3.51 (2H,d,J=7.2 Hz), 3.01(2H,brd,J=11.7 Hz), 2.82(2H,t,J=6.0 Hz), 2.13(2H,ddd,J=23.3,11.6,11.6 Hz), 1.84–1.68(3H,m), 1.49–1.40(2H,m).

c) 2-[[1-[2-(2-Fluorophenoxy)ethyl]piperidin-4-yl] methyl]isoindolin-1-one fumarate By using the compound obtained in Example 117b (240 mg), the title compound was obtained as colorless solid by carrying out a reaction similar to that of Example 36c (108 mg, yield: 78%).
Melting point: 168–171° C.
$^1$H-NMR(DMSO-d$_6$): 7.67(1H,d,J=7.5 Hz), 7.58(2H,brs), 7.50–7.47(1H,m), 7.22–7.11(3H,m), 6.94–6.92(1H,m), 6.60 (2H,s), 4.48(2H,s), 4.17(2H,t,J=5.6 Hz), 3.40(2H,d,J=7.2 Hz), 3.00(2H,brd,J=11.1 Hz), 2.81(2H,brdd,J=5.6,5.6 Hz), 2.17(2H,brdd,J=10.7,10.7 Hz), 1.76–1.73(1H,m), 1.62(2H, brd,J=12.0 Hz), 1.25(2H,brdd,J=22.4,10.6 Hz).

Example 118

2-[[1-[2-(3-Fluorophenoxy)ethyl]piperidin-4-yl]methyl]isoindolin-1-one fumarate (Compound 621 in Table 1)

a) 1-Bromo-2-(3-fluorophenoxy)ethane

By using 3-fluorophenol (500 mg, 4.46 mmol), the title compound was obtained as crude product by carrying out a reaction similar to that of Example 115a (1.26 g). The resulting crude product was used in the next reaction without purification.

b) 2-[[1-[2-(3-Fluorophenoxy)ethyl]piperidin-4-yl] methyl]isoindolin-1-one

By using the compound obtained in Example 118a (1.26 g), the title compound was obtained as brown oil by carrying out reactions similar to those of Example 115b ('823 mg, yield: 50%, 2 steps).
$^1$H-NMR(CDCl$_3$): 7.85(1H,d,J=7.2 Hz), 7.53–7.42(3H, m), 7.21–7.16(1H,m), 6.69–6.59(3H,m), 4.41(2H,s), 4.07 (2H,t,J=5.9 Hz), 3.51(2H,d,J=7.2 Hz), 2.99(2H,brd,J=12.0 Hz), 2.78(2H,t,J=6.0 Hz), 2.11(2H,ddd,J=2.5,11.6,11.6 Hz), 1.82–1.68(3H,m), 1.49–1.40(2H,m).

c) 2-[[1-[2-(3-Fluorophenoxy)ethyl]piperidin-4-yl] methyl]isoindolin-1-one fumarate By using the compound obtained in Example 118b (823 mg), the title compound was obtained as colorless solid by carrying out a reaction similar to that of Example 36c (720 mg, yield: 67%).
Melting point: 193–194° C. $^1$H-NMR(DMSO-d$_6$): 7.67 (1H,d,J=7.4 Hz), 7.60–7.58(2H,m), 7.51–7.48(1H,m), 7.34–7.31(1H,m), 6.84–6.75(3H,m), 6.59(2H,s), 4.48(2H,s), 4.12(2H,t,J=5.7 Hz), 3.41(2H,d,J=7.3 Hz), 3.02(2H,brd, J=11.7 Hz), 2.81(2H,brdd,J=5.7,5.7 Hz), 2.19(2H,brdd, J=10.5,10.5 Hz), 1.79–1.74(1H,m), 1.61(2H,brd,J=12.0 Hz), 1.32–1.20(2H,m).

Example 119

2-[[1-[2-(4-Methylphenoxy)ethyl]piperidin-4-yl]methyl]isoindolin-1-one fumarate (Compound 656 in Table 1)

a) 1-Bromo-2-(4-methylphenoxy)ethane

By using 4-methylphenol (162 mg, 1.5 mmol), the title compound was obtained by as crude product by carrying out a reaction similar to that of Example 115a (458 mg). The crude product was used in the next reaction without purification.

b) 2-[[1-[2-(4-Methylphenoxy)ethyl]piperidin-4-yl]methyl]isoindolin-1-one

By using the compound obtained in Example 119a (458 mg), the title compound was obtained as brown oil by carrying out reactions similar to those of Example 115b (210 mg, yield: 38%, 2 steps).
$^1$H-NMR(CDCl$_3$): 7.84(1H,d,J=6.9 Hz), 7.55–7.42(3H, m), 7.06(2H,d,J=8.4 Hz), 6.81–6.77(2H,m), 4.40(2H,s), 4.06(2H,t,J=6.0 Hz), 3.50(2H,d,J=7.2 Hz), 3.00(2H,brd, J=11.7 Hz), 2.77(2H,t,J=6.0 Hz), 2.27(3H,s), 2.10(2H,ddd, J=2.3,11.6,11.6 Hz), 1.84–1.70(3H,m), 1.49–1.40(2H,m).

c) 2-[[1-[2-(4-Methylphenoxy)ethyl]piperidin-4-yl]methyl]isoindolin-1-one fumarate By using the compound obtained in Example 119b (210 mg), the title compound was obtained as colorless solid by carrying out a reaction similar to that of Example 36c (220 mg, yield: 79%).
Melting point: 183–185° C. $^1$H-NMR(DMSO-d$_6$): 7.67 (1H,d,J=7.6 Hz), 7.62–7.58(2H,m), 7.52–7.45(1H,m), 7.07 (2H,d,J=8.3 Hz), 6.82(2H,d,J=8.4 Hz), 6.59(2H,s), 4.48(2H, s), 4.05(2H,t,J=5.7 Hz), 3.41(2H,d,J=7.2 Hz), 3.00(2H,brd, J=11.6 Hz), 2.78(2H,t,J=5.7 Hz), 2.22–2.09(5H,m), 1.79–1.73(1H,m), 1.61(2H,brd,J=13.3 Hz), 1.26(2H,brdd, J=21.4,11.4 Hz).

Example 120

2-[[1-[2-(3-Methoxyphenoxy)ethyl]piperidin-4-yl]methyl]isoindolin-1-one fumarate (Compound 636 in Table 1)

a) 1-Bromo-2-(3-methoxyphenoxy)ethane

By using 4-methoxyphenol (186 mg, 1.5 mmol), the title compound was obtained as crude product by carrying out a reaction similar to that of Example 115a (953 mg). The resulting crude product was used in the next reaction without purification.

b) 2-[[1-[2-(3-Methoxyphenoxy)ethyl]piperidin-4-yl]methyl]isoindolin-1-one

By using the compound obtained in Example 120a (953 mg), the title compound was obtained as brown oil by carrying out reactions similar to those of Example 115b (192 mg, yield: 34%, 2 steps).
$^1$H-NMR(CDCl$_3$): 7.85(1H,d,J=7.2 Hz), 7.55–7.42(3H, m), 7.16(1H,dd,J=8.0,8.0 Hz), 6.51–6.46(3H,m), 4.41(2H, s), 4.08(2H,t,J=6.0 Hz), 3.78(3H,s), 3.51(2H,d,J=7.2 Hz), 3.00(2H,brd,J=11.7 Hz), 2.79(2H,t,J=6.0 Hz), 2.16–2.08(2H,m), 1.83–1.68(3H,m), 1.50–1.41(2H,m).

c) 2-[[1-[2-(3-Methoxyphenoxy)ethyl]piperidin-4-yl]methyl]isoindolin-1-one fumarate By using the compound obtained in Example 120b (190 mg), the title compound was obtained as colorless solid by carrying out a reaction similar to that of Example 36c (200 mg, yield: 81%).
Melting point: 173–174° C. $^1$H-NMR(DMSO-d$_6$): 7.67 (1H,d,J=7.5 Hz), 7.62–7.58(2H,m), 7.52–7.45(1H,m), 7.17 (1H,dd,J=8.3,8.0 Hz), 6.59(2H,s), 6.53–6.49(3H,m), 4.48 (2H,s), 4.09(2H,t,J=5.4 Hz), 3.72(3H,s), 3.41(2H,d,J=7.2 Hz), 3.03(2H,brd,J=11.2 Hz), 2.82(2H,brs), 2.21(2H,brdd, J=11.4,11.4 Hz), 1.78–1.77(1H,m), 1.62(2H,brd,J=12.5 Hz), 1.28(2H,brdd,J=22.0,11.0 Hz).

Example 121

2-[[1-[2-(3-Methylphenoxy)ethyl]piperidin-4-yl]methyl]isoindolin-1-one fumarate (Compound 651 in Table 1)

a) 1-Bromo2-(3-methylphenoxy)ethane

By using 3-methylphenol (162 mg, 1.5 mmol), the title compound was obtained as crude product by carrying out a similar reaction to that of Example 115a (410 mg). The resulting crude product was used in the next reaction without purification.

b) 2-[[1-[2-(3-Methylphenoxy)ethyl]piperidin-4-yl]methyl]isoindolin-1-one

By using the compound obtained in Example 121a (410 mg), the title compound was obtained as brown oil by carrying out reactions similar to those of Example 115b 213 mg (yield: 39%, 2 steps).
$^1$H-NMR(CDCl$_3$): 7.85(1H,d,J=7.5 Hz), 7.55–7.42(3H, m), 7.14(1H,dd,J=7.7,7.7 Hz), 6.76–6.69(3H,m), 4.40(2H, s), 4.08(2H,t,J=5.9 Hz), 3.51(2H,d,J=6.9 Hz), 3.00(2H,brd, J=11.7 Hz), 2.79(2H,t,J=5.9 Hz), 2.31(3H,s), 2.12(2H,brdd, J=10.5, 10.5 Hz), 1.82–1.69(3H,m), 1.49–1.26(2H,m).

c) 2-[1-[2-(3-Methylphenoxy)ethyl]piperidin-4-yl]methyl]isoindolin-1-one fumarate By using the compound obtained in Example 121b (210 mg), the title compound was obtained as colorless solid by carrying out a reaction similar to that of Example 36c (252 mg, yield: 91%).
Melting point: 202–203° C. $^1$H-NMR(DMSO-d$_6$): 7.67 (1H,d,J=7.4 Hz), 7.59–7.58(2H,m), 7.50–7.45(1H,m), 7.15 (1H,dd,J=7.8,7.8 Hz), 6.75–6.71(3H,m), 6.59(2H,s), 4.48 (2H,s), 4.09(2H,t,J=5.5 Hz), 3.41(2H,d,J=7.3 Hz), 3.04(2H, brd,J=11.3 Hz), 2.83(2H,t,J=5.0 Hz), 2.26–2.19(5H,m), 1.78 (1H,brs), 1.62(2H,brd,J=12.7 Hz), 1.28(2H,brdd,J=21.9, 10.7 Hz).

Example 122

2-[[1-[2-(4-Methoxyphenoxy)ethyl]piperidin-4-yl]methyl]isoindolin-1-one fumarate (Compound 641 in Table 1)

a) 1-Bromo-2-(4-methoxyphenoxy)ethane

By using 4-methoxyphenol (186 mg, 1.5 mmol), the title compound was obtained as crude product by carrying out a reaction similar to that of Example 115a (347 mg). The resulting crude product was used in the next reaction without purification.

b) 2-[[1-[2-(4-Methoxyphenoxy)ethyl]piperidin-4-yl]methyl]isoindolin-1-one

By using the compound obtained in Example 122a (347 mg), the title compound was obtained as brown oil by carrying out reactions similar to those of Example 115b (274 mg, yield: 48%, 2 steps).

$^1$H-NMR(CDCl$_3$): 7.85(1H,d,J=7.2 Hz), 7.56–7.42(3H,m), 6.82–6.78(4H,m), 4.41(2H,s), 4.05(2H,t,J=5.9 Hz), 3.76(3H,s), 3.51(2H,d,J=7.2 Hz), 3.00(2H,brd,J=12.0 Hz), 2.77(2H,t,J=6.0 Hz), 2.11(2H,ddd,J=2.3,11.6,11.6 Hz), 1.82–1.68(3H,m), 1.51–1.41(2H,m).

c) 2-[[1-[2-(4-Methoxyphenoxy)ethyl]piperidin-4-yl]methyl]isoindolin-1-one fumarate By using the compound obtained in Example 122b (270 mg), the title compound was obtained as colorless solid by carrying out a reaction similar to that of Example 36c (232 mg, yield: 82%).

Melting point: 165–168° C. $^1$H-NMR(DMSO-d$_6$): 7.67 (1H,d,J=7.3 Hz), 7.59–7.58(2H,m), 7.52–7.45(1H,m), 6.89–6.82(4H,m), 6.59(2H,s), 4.48(2H,s), 4.04(2H,t,J=5.7 Hz), 3.41(2H,d,J=7.3 Hz), 3.03(2H,brd,J=11.6 Hz), 2.80(2H,t,J=5.7 Hz), 2.21(2H,brdd,J=10.7,10.7 Hz), 1.80–1.79(1H,m), 1.61(2H,brd,J=11.6 Hz), 1.33–1.18(2H,m).

Example 123

2-[[1-[2-(2-Methylphenoxy)ethyl]piperidin-4-yl]methyl]isoindolin-1-one fumarate (Compound 646 in Table 1)

a) 1-Bromo-2-(2-methylphenoxy)ethane

By using 2-methylphenol (162 mg, 1.5 mmol), the title compound was obtained as crude product by carrying out a reaction similar to that of Example 115a (334 mg). The resulting crud product was used in the next reaction without purification.

b) 2-[[1-[2-(2-Methylphenoxy)ethyl]piperidin-4-yl]methyl]isoindolin-1-one

By using the compound obtained in Example 123a (334 mg), the title compound was obtained as brown oil by carrying out a reaction similar to that of Example 115b (485 mg). The resulting crude product was used in the next reaction without purification.

c) 2-[[1-[2-(2-Methylphenoxy)ethyl]piperidin-4-yl]methyl]isoindolin-1-one fumarate By using the compound obtained in Example 123b (485 mg), the title compound was obtained as colorless solid by carrying out reactions similar to those of Example 36c (89 mg, yield: 14%, 3 steps).

Melting point: 214–218° C. $^1$H-NMR(DMSO-d$_6$): 7.67 (1H,d,J=7.2 Hz), 7.59–7.58(2H,m), 7.52–7.45(1H,m), 7.16–7.11(2H,m), 6.92(1H,d,J=8.1 Hz), 6.82(1H,dd,J=7.5, 7.5 Hz)), 6.59(2H,s), 4.48(2H,s), 4.10(2H,t,J=5.6 Hz), 3.41(2H,d,J=7.2 Hz), 3.03(2H,brd,J=12.0 Hz), 2.85(2H,brs), 2.23(2H,brdd,J=11.0,11.0 Hz), 2.13(s,3H), 1.77(1H,brs), 1.61(2H,brd,J=12.3 Hz), 1.32–1.24 (2H,m).

Example 124

2-[[1-[2-(4-Trifluoromethylphenoxy)ethyl]piperidin-4-yl]methyl]-isoindolin-1-one fumarate (Compound 661 in Table 1)

a) 1-Bromo-2-(4-trifluoromethylphenoxy)ethane

By using 4-trifluoromethylphenol (243 mg, 1.5 mmol), the title compound was obtained as crud product by carrying out a reaction similar to that of Example 115a (519 mg). The resulting crude product was used in the next reaction without purification.

b) 2-[[1-[2-(4-Trifluoromethylphenoxy)ethyl]piperidin-4-yl]methyl]isoindolin-1-one By using the compound obtained in Example 124a (519 mg), the title compound was obtained by carrying out reactions similar to those of Example 115b (150 mg, yield: 19%, 2 steps).

$^1$H-NMR(CDCl$_3$): 7.85(1H,d,J=7.2 Hz), 7.56–7.42(5H,m), 6.95(2H,d,J=8.7 Hz), 4.41(2H,s), 4.13(2H,t,J=5.9 Hz), 3.51(2H,d,J=6.9 Hz), 3.00(2H,brd,J=11.4 Hz), 2.81(2H,t,J=5.9 Hz), 2.17–2.09(2H,m), 1.85–1.63(3H,m), 1.50–1.38 (2H,m).

c) 2-[[1-[2-(4-Trifluoromethylphenoxy)ethyl]piperidin-4-yl]methyl]isoindolin-1-one fumarate By using the compound obtained in Example 124b (150 mg), the title compound was obtained as colorless solid by carrying out a reaction similar to that of Example 36c (171 mg, yield: 89%).

Melting point: 198–199° C. $^1$H-NMR(DMSO-d$_6$): 7.68–7.56(5H,m), 7.52–7.45(1H,m), 7.12(2H,d,J=8.6 Hz), 6.60(2H,s), 4.48(2H,s), 4.18(2H,t,J=5.7 Hz), 3.41(2H,d, J=7.2 Hz), 2.98(2H,brd,J=11.6 Hz), 2.79(2H,t,J=5.7 Hz), 2.13(2H,brdd,J=11.7,11.7 Hz), 1.79–1.72(1H,m), 1.60(2H, brd,J=12.3 Hz), 1.38–1.18(2H,m).

Example 125

2-[[1-[2-(4-Trifluoromethoxyphenoxy)ethyl]piperidin-4-yl]methyl]isoindolin-1-one fumarate (Compound 666 in Table 1)

a) 1-Bromo-2-(4-trifluoromethoxyphenoxy)ethane

By using 4-trifluoromethoxyphenol (267 mg, 1.5 mmol), the title compound was obtained as crude product by carrying out a reaction similar to that of Example 115a (598 mg). The resulting crude product was used in the next reaction without purification.

b) 2-[[1-[2-(4-Trifluoromethylphenoxy)ethyl]piperidin-4-yl]methyl]isoindolin-1-one By using the compound obtained in Example 125a (598 mg), the title compound was obtained as crude product by carrying out a reaction similar to that of Example 115b (589 mg). The resulting crude product was used in the next reaction without purification.

c) 2-[[1-[2-(4-Trifluoromethylphenoxy)ethyl]piperidin-4-yl]methyl]isoindolin-1-one fumarate By using the compound obtained in Example 125b (589 mg), the title compound was obtained as colorless solid by carrying out reactions similar to those of Example 36c (304 mg, yield: 55%, 3 steps).

Melting point: 181–183° C. $^1$H-NMR(DMSO-$d_6$): 7.67 (1H,d,J=7.3 Hz), 7.59–7.58(2H,m), 7.50–7.45(1H,m), 7.28 (2H,d,J=8.9 Hz), 7.06–7.00(2H,m), 6.60(2H,s), 4.48(2H,s), 4.11(2H,t,J=5.7 Hz), 3.41(2H,d,J=7.2 Hz), 2.98(2H,brd, J=11.7 Hz), 2.78(2H,t,J=5.7 Hz), 2.18–2.09(2H,m), 1.80–1.72(1H,m), 1.60(2H,m), 1.30–1.19(2H,m).

Example 126

2-[[1-[2-(1,3-Benzodioxol-5-yloxy)ethyl]piperidin-4-yl]methyl]isoindolin-1-one fumarate (Compound 671 in Table 1)

By using 3,4-methylenedioxyphenol, the title compound was obtained as colorless solid by similar procedures to those of Example 115a and Example 36c (yield: 52%).

Melting point: 220–232° C. $^1$H-NMR(DMSO-$d_6$): 7.67 (1H,d,J=7.5), 7.55–7.60(2H,m), 7.45–7.52(1H,m), 6.79(1H, d,J=8.4), 6.62(1H,d,J=2.4), 6.59(2H,s,fumaric acid), 6.36 (1H,dd,J=2.4,8.4), 5.94(2H,s), 4.48(2H,s), 3.98–4.04(2H,m), 3.41(2H,d,J=7.2), 2.94–3.01(2H,m), 2.71–2.77(2H,m), 2.08–2.19(2H,m), 1.6–1.8(1H,m), 1.5–1.6(2H,m), 1.1–1.3(2H,m)

Example 127

2-[[1-[2-(2,3-Dihydro-1H-inden-5-yloxy)ethyl]piperidin-4-yl]methyl]isoindolin-1-one fumarate (Compound 676 in Table 1)

By using 5-indanol, the title compound was obtained as colorless solid by similar procedures to those of Example 115a and Example 36c (yield: 22%).

Melting point: 181–185° C. $^1$H-NMR(DMSO-$d_6$): 7.67 (1H,d,J=7.2), 7.55–7.60(2H,m), 7.45–7.52(1H,m), 7.08(1H, d,J=8.4), 6.80(1H,d,J=2.1), 6.67(1H,dd,J=2.1,8.4), 6.59(2H, s,fumaric acid), 4.49(2H,s), 4.02–4.08(2H,m), 3.41(2H,d, J=7.2), 2.96–3.03(2H,m), 2.72–2.84(6H,m), 2.12–2.22(2H, m), 1.93–2.04(2H,m), 1.6–1.8(1H,m), 1.5–1.6(2H,m), 1.1–1.3(2H,m)

Example 128

2-[[1-[2-(5,6,7,8-Tetrahydronaphthalen-2-yloxy) ethyl]piperidin-4-yl]methyl]isoindolin-1-one fumarate (Compound 681 in Table 1)

By using 5,6,7,8-tetrahydro-2-naphthol, the title compound was obtained as colorless solid by similar procedures to those of Example 115a and Example 36c (yield: 19%).

Melting point: 186–190° C. $^1$H-NMR(DMSO-$d_6$): 7.67 (1H,d,J=7.2), 7.55–7.60(2H,m), 7.45–7.52(1H,m), 6.92(1H, d,J=8.1), 6.60–6.67(2H,m), 6.59(2H,s,fumaric acid), 4.48 (2H,s), 3.99–4.06(2H,m), 3.41(2H,d,J=7.2), 2.95–3.02(2H, m), 2.72–2.79(2H,m), 2.60–2.69(4H,m), 2.10–2.20(2H,m), 1.55–1.80(7H,m), 1.1–1.3(2H,m)

Example 129

2-[[1-[2-(5,6,7,8-Tetrahydronaphthalen-1-yloxy) ethyl]piperidin-4-yl]methyl]isoindolin-1-one fumarate (Compound 686 in Table 1)

By using 5,6,7,8-tetrahydro-1-naphthol, the title compound was obtained as colorless solid by similar procedures to those of Example 115a and Example 36c (yield: 13%).

Melting point: 196–203° C. $^1$H-NMR(DMSO-$d_6$): 7.67 (1H,d,J=7.5), 7.55–7.60(2H,m), 7.45–7.52(1H,m), 6.97–7.05(1H,m), 6.70(1H,d,J=8.1), 6.64(1H,d,J=7.5), 6.59 (2H,s,fumaric acid), 4.48(2H,s), 4.03–4.09(2H,m), 3.41(2H, d,J=7.2), 2.98–3.05(2H,m), 2.80–2.85(2H,m), 2.62–2.70(2H,m), 2.50–2.55(2H,m), 2.1–2.3(2H,m), 1.5–1.8(7H,m), 1.1–1.3(2H,m)

Example 130

2-[[1-[2-[Methyl(4-fluorophenyl)amino]ethyl]piperidin-4-yl]methyl]isoindolin-1-one hydrochloride (Compound 295 in Table 1)

a) tert-Butyl N-(4-fluorophenyl)carbamate

A solution of 4-fluoroaniline (2.00 g, 18.0 mmol) in dichloromethane (15 mL) was added with (Boc)$_2$O (3.93 g, 18.0 mmol) and a catalytic amount of triethylamine, and then the mixture was stirred at room temperature for 8 hours. The reaction mixture was diluted with ethyl acetate and washed with water, twice with 0.5N aqueous HCl solution, saturated NaHCO$_3$ solution, and then with brine, and dried over Na$_2$SO$_4$.

The drying agent was removed by filtration and the filtrate was concentrated. The resulting solid was suspended and washed in hexane to obtain the title compound (yield: 80%).

$^1$H-NMR (CDCl$_3$): δ 7.31 (m, 2H), 6.98 (m, 2H), 6.42 (br s, 1H), 1.51 (s, 9H).

b) 2-[Methyl(4-fluorophenyl)amino]ethyl methanesulfonate

To a stirred suspension of 60% NaH (273 mg, 6.82 mmol)/1.5 mL, was added dropwise the compound obtained in Example 130a (1.20 g, 5.68 mmol)/3 mL NMP solution under nitrogen at 0° C. After stirring for 10 minutes, the reaction mixture ws added dropwise with bromoethylacetate (0.995 g, 5.96 mmol) and then warmed to room temperature. After stirring for 1 hour, the reaction mixture was diluted with ethyl acetate and washed our times with water and then with brine, and dried over Na$_2$SO$_4$.

The drying agent was removed by filtration and the filtrate ws concentrated, the resulting compound (0.600 g, 2.02 mmol)/8 mL THF solution was added dropwise with LiAlH₄ (230 mg, 6.06 mmol)/5 mL THF and heated under reflux for 4 hours. The reaction mixture was diluted with ether (10 mL) and added with water (0.25 mL), 15% aqueous solution of NaOH (0.25 mL), and water (0.75 mL), and then filtered. The filtrate was concentrated, and the resulting oil was purified by silica gel chromatography (ethyl acetate/hexane).

The resulting compound (0.401 g, 2.37 mmol) was dissolved in dichloromethane (2 mL) and the solution was added with triethylamine (0.46 mL, 3.32 mmol) and cooled to 0° C. The mixture was added dropwise with methanesulfonyl chloride (0.220 mL, 2.84 mmol) and stirred for 1.5 hours. The reaction mixture was diluted with ether and washed three times with water and then with brine, and dried over $Na_2SO_4$. The drying agent was removed by filtration and the filtrate was concentrated to obtain the title compound.

$^1$H-NMR (CDCl$_3$): δ 6.95 (m, 2H), 6.68 (m, 2H), 4.36 (t, J=5.8 Hz, 2H), 3.64 (t, J=5.8 Hz, 2H), 2.69 (s, 3H), 2.94 (s, 3H).

c) 2-[[1-[2-[Methyl(4-fluorophenyl)amino]ethyl] piperidin-4-yl]methyl]isoindolin-1-one hydrochloride By using the compound obtained in Example 130b, a product was obtained by similar procedures to those of Example 26b, which was further subjected to procedures similar to those of Example 1f without purification to obtain the title compound (yield: 60%).

Melting point: 223–231° C. $^1$H-NMR (DMSO-d$_6$): δ 10.59 (br s, 1H), 7.69 (d, J=7.5 Hz, 1H), 7.61 (m, 2H), 7.50 (m, 1H), 7.03 (t, J=9 Hz, 2H), 6.83 (m, 2H), 4.51 (s, 2H), 3.73 (m, 2H), 2.87–3.54 (m, 11H), 1.99 (m, 1H), 1.80 (m, 2H), 1.59 (m, 2H).

Example 131

2-[[1-[2-[Benzyl(4-fluorophenyl)amino]ethyl]piperidin-4-yl]methyl]isoindolin-1-one fumarate (Compound 301 in Table 1)

a) Benzyl(4-fluorophenyl)amine

A solution of 4-fluoroaniline (1.50 g, 13.5 mmol) and triethylamine (2.26 mL, 16.2 mmol) in dichloromethane (7 mL) was cooled to 0° C., and the solution was added dropwise with benzyl bromide (1.61 mL, 13.5 mmol). After stirring at room temperature for 1 hour, the reaction mixture was diluted with ethyl acetate and washed three times with water and then with brine, and dried over $Na_2SO_4$. The drying agent was removed by filtration and the filtrate was concentrated, the residue was purified by silica gel chromatography (ethyl acetate/hexane) to obtain the title compound (yield: 46%).

$^1$H-NMR (CDCl$_3$): δ 7.26–7.36 (m, 5H), 6.88 (m, 2H), 6.56 (m, 2H), 4.29 (s, 2H).

b) 2-[Benzyl(4-fluorophenyl)amino]ethyl methanesulfonate

By using the compound obtained in Example 131a, the title compound was obtained by similar procedures to those of Example 130b (93%).

$^1$H-NMR (CDCl$_3$): δ 7.19–7.34 (m, 5H), 6.91 (m, 2H), 6.69 (m, 2H), 4.55 (s, 2H), 4.34 (m, 2H), 3.74 (m, 2H), 2.91 (s, 3H).

c) 2-[[1-[2-[Benzyl(4-fluorophenyl)amino]ethyl] piperidin-4-yl]methyl]isoindolin-1-one By using the compound obtained in Example 131b, the title compound was obtained by similar procedures to those of Example 26b (yield: 79%).

$^1$H-NMR (CDCl$_3$): δ 7.86 (d, J=7.2 Hz, 1H), 7.41–7.58 (m, 3H), 7.19–7.32 (m, 5H), 6.87 (m, 2H), 6.60 (m, 2H), 4.50 (s, 2H), 4.39 (s, 2H), 3.48–3.53 (m, 4H), 2.90 (m, 2H), 2.55 (m, 2H), 2.00 (dt, J=11.7, 2.1 Hz, 2H), 1.78 (m, 1H), 1.67 (m, 2H), 1.38 (m, 2H).

d) 2-[[1-[2-[Benzyl(4-fluorophenyl)amino]ethyl] piperidin-4-yl]methyl]isoindolin-1-one fumarate By using the compound obtained in Example 131c, the title compound was obtained by similar procedures to those of Example 40f (yield: 33%).

Melting point: 174–185° C. $^1$H-NMR (DMSO-d$_6$): δ 7.67 (d, J=7.5 Hz, 1H), 7.59 (m, 2H), 7.48 (m, 1H), 7.25 (m, 2H), 7.20–7.21 (m, 3H), 6.94 (t, J=8.8 Hz, 2H), 6.64 (m, 2H), 5.59 (s, 2H), 4.53 (s, 2H), 4.47 (s, 2H), 3.55 (t, J=7.0 Hz, 2H), 3.40 (d, J=7.3 Hz, 2H), 2.98 (d, J=11.4 Hz, 2H) 2.62 (t, J=7.0 Hz, 2H), 2.14 (t, J=11.2 Hz, 2H), 1.77 (m, 1H), 1.59 (br d, J=12 Hz, 2H), 1.27 (m, 2H).

Example 132

2-[[1-[2-[(4-Fluorophenyl)amino]ethyl]piperidin-4-yl]methyl]isoindolin-1-one hydrochloride (Compound 275 in Table 1)

a) 2-[[1-[2-[(4-Fluorophenyl)amino]ethyl]piperidin-4-yl]methyl]isoindolin-1-one

By using the compound obtained in Example 131c, the title compound was obtained by similar procedures to those of Example 104a (yield: 96%).

$^1$H-NMR (CDCl$_3$): δ 7.85 (d, J=7.1 Hz, 1H), 7.42–7.53 (m, 3H), 6.88 (m, 2H), 6.55 (m, 2H), 4.40 (s, 2H), 3.52 (d, J=7.2 Hz, 2H), 3.09 (t, J=6.0 Hz, 2H), 2.89 (br d, J=11.5 Hz, 2H), 2.59 (t, J=6.0 Hz, 2H), 1.98 (dt, J=11.5, 2.2 Hz, 2H), 1.79 (m, 1H), 1.68 (br d, J=12 Hz, 2H), 1.39 (m, 2H).

b) 2-[[1-[2-[(4-Fluorophenyl)amino]ethyl]piperidin-4-yl]methyl]isoindolin-1-one hydrochloride By using the compound obtained in Example 132a, the title compound was obtained by similar procedures to those of Example 1f.

Melting point: 221–230° C. $^1$H-NMR (DMSO-d$_6$): δ 7.69 (d, J=7.4 Hz, 1H), 7.61 (m, 2H), 7.50 (m, 1H), 6.99 (m, 2H), 6.72 (m, 2H), 4.51 (s, 2H), 2.80–3.97 (m, 10H), 1.99 (m, 1H), 1.80 (m, 2H), 1.62 (m, 2H).

Example 133

2-[[1-[2-[(4-Methoxyphenyl)amino]ethyl]piperidin-4-yl]methyl]isoindolin-1-one fumarate (Compound 307 in Table 1)

a) 2-[[1-(2-Hydroxyethyl)piperidin-4-yl]methyl]isoindolin-1-one

The compound obtained in Example 1d (1.50 g, 5.62 mmol) and 2-bromoethanol (0.703 g, 5.62 mmol) was dissolved in acetonitrile (10 mL), and the solution was added with NaI (0.842 g, 5.62 mmol) and potassium carbonate (2.34 g, 16.9 mmol) and heated at 80° C. After 3 hours, the solvent was evaporated, and the residue was added with saturated aqueous NaHCO$_3$ solution and extracted four times with dichloromethane. The extract was dried over Na$_2$SO$_4$, and the drying agent was removed by filtration and the filtrate was concentrated. The resulting solid was suspended and washed in ether to obtain the title compound (yield: 76%).

$^1$H-NMR (CDCl$_3$): δ 7.85 (d, J=7.5 Hz, 1H), 7.44–7.56 (m, 3H), 4.41 (s, 2H), 3.59 (t, J=5.4 Hz, 2H), 3.51 (d, J=7.5 Hz, 2H), 2.91 (br d, J=12 Hz, 2H), 2.51 (t, J=5.4 Hz, 2H), 2.06 (dt, J=11.7, 2.4 Hz, 2H), 1.83 (m, 1H), 1.70 (br d, J=12 Hz, 2H), 1.39 (m, 2H).

b) 2-[[1-(2-Methanesulfonyloxyethyl)piperidin-4-yl]methyl]isoindolin-1-one hydrochloride A solution of the compound obtained in Example 133a (1.00 g, 4.20 mmol) and triethylamine (0.88 mL, 6.31 mmol) in dichloromethane (5 mL) was cooled to 0° C., and added dropwise with methanesulfonyl chloride (0.488 mL, 6.31 mmol). The mixture was warmed to room temperature and stirred for 1 hour, then the reaction mixture was diluted with ethyl acetate and washed with saturated NaHCO$_3$ solution, twice with water, and then with brine, and dried over Na$_2$SO$_4$. The drying agent was removed by filtration and the filtrate was treated with 1.30 mL of 4N HCl-AcOEt solution. The crystals precipitated were collected by filtration to obtain the title compound (49%).

$^1$H-NMR (DMSO-d$_6$): δ 10.61 (br s, 1H), 7.69 (d, J=7.5 Hz, 1H), 7.61 (m, 2H), 7.49 (m, 1H), 4.51 (s, 2H), 4.04 (t, J=6.9 Hz, 2H), 2.88–3.62 (m, 11H), 1.99 (m, 1H), 1.80 (m, 2H), 1.59 (m, 2H).

c) 2-[[1-[2-[(4-Methoxyphenyl)amino]ethyl]piperidin-4-yl]methyl]isoindolin-1-one A solution of the compound obtained in Example 133b (200 mg, 0.514 mmol) and para-methoxyaniline (63 mg, 0.51 mmol) in acetonitrile (2 mL) was added with sodium iodide (77 mg, 0.51 mmol) and potassium carbonate (178 mg, 1.29 mmol) and heated at 70° C. After 2 hours, the solvent was evaporated, and then the residue was added with brine and 1N aqueous solution of NaOH, and extracted three times with dichloromethane and dried over Na$_2$SO$_4$. The drying agent was removed by filtration and the filtrate was concentrated, the residue was purified by silica gel chromatography (dichloromethane/methanol) to obtain the title compound (yield: 47%).

$^1$H-NMR (CDCl$_3$): δ 7.85 (d, J=7.2 Hz, 1H), 7.42–7.53 (m, 3H), 6.79 (d, J=9.0 Hz, 2H), 6.60 (d, J=9.0 Hz, 2H), 4.40 (s, 2H), 3.75 (s, 3H), 3.51 (d, J=7.2 Hz, 2H), 3.10 (t, J=6.0 Hz, 2H), 2.90 (br d, J=11.7 Hz, 2H), 2.59 (t, J=6.0 Hz, 2H), 1.98 (dt, J=11.7, 2.1 Hz, 2H), 1.81 (m, 1H), 1.68 (br d, J=12 Hz, 2H), 1.40 (m, 2H).

d) 2-[[1-[2-[(4-Methoxyphenyl)amino]ethyl]piperidin-4-yl]methyl]isoindolin-1-one fumarate By using the compound obtained in Example 133c, the title compound was obtained by similar procedures to those of Example 40f (yield: 84%).

Melting point: 202° C. $^1$H-NMR (DMSO-d$_6$): δ 7.67 (d, J=7.5 Hz, 1H), 7.59 (m, 2H), 7.49 (m, 1H), 6.71 (d, J=9 Hz, 2H), 6.58 (s, 2H), 6.54 (d, J=9 Hz, 2H), 4.48 (s, 2H), 3.63 (s, 3H), 3.42 (d, J=7.2 Hz, 2H), 3.12 (t, J=6.6 Hz, 2H), 3.03 (d, J=12 Hz, 2H), 2.66 (t, J=6.6 Hz, 2H), 2.21 (t, J=12 Hz, 2H), 1.81 (m, 1H), 1.63 (br d, J=12 Hz, 2H), 1.31 (m, 2H).

Example 134

2-[[1-[2-[(3-methoxyphenyl)amino]ethyl]piperidin-4-yl]methyl]isoindolin-1-one fumarate (Compound 313 in Table1)

a) 2-[[1-[2-[(3-Methoxyphenyl)amino]ethyl]piperidin-4-yl]methyl]isoindolin-1-one By using meta-methoxyaniline, the title compound was obtained by similar procedures to those of Example 133c (yield: 31%).

$^1$H-NMR (CDCl$_1$): δ 7.85 (d, J=7.5 Hz, 1H), 7.42–7.53 (m, 3H), 7.08 (t, J=8.1 Hz, 1H), 6.26 (m, 2H), 6.18 (m, 1H), 4.40 (s, 2H), 3.78 (s, 3H), 3.52 (d, J=7.2 Hz, 2H), 3.14 (t, J=6.0 Hz, 2H), 2.91 (br d, J=11.7 Hz, 2H), 2.60 (t, J=6.0 Hz, 2H), 1.99 (br t, J=12 Hz, 2H), 1.82 (m, 1H), 1.68 (m, 2H), 1.40 (m, 2H).

b) 2-[[1-[2-[(3-Methoxyphenyl)amino]ethyl]piperidin-4-yl]methyl]isoindolin-1-one fumarate By using the compound obtained in Example 134a, the title compound was obtained by similar procedures to those of Example 40f (yield: 88%).

Melting point: 178–182° C. $^1$H-NMR (DMSO-d$_6$): δ 7.67 (d, J=7.5 Hz, 1H), 7.60 (m, 2H), 7.50 (m, 1H), 6.96 (t, J=8.4 Hz, 1H), 6.58 (s, 2H), 6.11–6.19 (m, 3H), 4.48 (s, 2H), 3.66 (s, 3H), 3.42 (d, J=7.2 Hz, 2H), 3.16 (t, J=6.6 Hz, 2H), 3.02 (br d, J=11.7 Hz, 2H), 2.65 (t, J=6.6 Hz 2H), 2.20 (br t, J=12 Hz, 2H), 1.82 (m, 1H), 1.63 (br d, J=12 Hz, 2H), 1.31 (m, 2H).

Example 135

2-[[1-[2-[(2-Methoxyphenyl)amino]ethyl]piperidin-4-yl]methyl]isoindolin-1-one fumarate (Compound 319 in Table 1)

a) 2-[[1-[2-[(2-Methoxyphenyl)amino]ethyl]piperidin-4-yl]methyl]isoindolin-1-one By using ortho-methoxyaniline, the title compound was obtained by similar procedures to those of Example 133c (yield: 36%).

$^1$H-NMR (CDCl$_3$): δ 7.85 (d, J=7.5 Hz, 1H), 7.45–7.53 (m, 3H), 6.86 (m, 1H), 6.77 (m, 1H), 6.58–6.67 (m, 2H), 4.40 (s, 2H), 3.86 (s, 3H), 3.52 (d, J=7.5 Hz, 2H), 3.19 (t, J=6.0 Hz, 2H), 2.93 (br d, J=11.4 Hz, 2H), 2.64 (t, J=6.0 Hz, 2H), 1.99 (m, 2H), 1.80 (m, 1H), 1.68 (m, 2H), 1.41 (m, 2H).

b) 2-[[1-[2-[(2-Methoxyphenyl)amino]ethyl]piperidin-4-yl]methyl]isoindolin-1-one fumarate By using the compound obtained in Example 135a, the title compound was obtained by similar procedures to those of Example 40f (yield: 89%).
Melting point: 183–191° C. $^1$H-NMR (DMSO-$d_6$): δ 7.67 (d, J=7.5 Hz, 1H), 7.59 (m, 2H), 7.48 (m, 1H), 6.75–6.81 (m, 2H), 6.58 (s, 2H), 6.56 (m, 2H), 4.49 (s, 2H), 3.77 (s, 3H), 3.43 (d, J=7.3 Hz, 2H), 3.18 (t, J=6.3 Hz, 2H), 3.00 (br d, J=11 Hz, 2H), 2.69 (t, J=6.3 Hz, 2H), 2.17 (m, 2H), 1.81 (m, 1H), 1.63 (m, 2H), 1.28 (m, 2H).

Example 136

2-[[1-[2-(4-Fluorophenyl)allyl]piperidin-4-yl]methyl]isoindolin-1-one hydrochloride (Compound 358 in Table 1)

Methyltriphenylphosphonium bromide (801 mg, 2.24 mmol) was suspended in tetrahydrofuran (4 ml) and added with potassium t-butoxide (257 mg, 2.29 mmol) at room temperature. The mixture was added with a solution of the compound obtained in Example 1e (819 mg, 2.24 mmol) dissolved in tetrahydrofuran (4 ml), and then the mixture was stirred at the same temperature for 1 hours. The reaction mixture was diluted with ethyl acetate and washed with saturated aqueous sidium bicarbonate solution, water, and then with saturated brine, and dried over sodium sulfate. Insoluble solids were removed by filtration and the filtrate was concentrated under reduced pressure to obtain 2-[[1-[2-(4-fluorophenyl)allyl]piperidin-4-yl]methyl]isoindolin-1-one as crude product. By using the resulting product, the title compound was obtained as colorless solid by similar procedures to those of Example 1f (yield: 34%).
Melting point: 173–181° C. $^1$H-NMR(DMSO-$d_6$): 9.6–10.0(1H,brs,HCl), 7.59–7.70(5H,m), 7.45–7.51(1H,m), 7.22–7.30(2H,m), 5.79(1H,s), 5.72(1H,s), 4.48(2H,s), 4.37–4.40(0.4H,m), 4.20–4.23(1.6H,m), 3.1–3.6(4H,m), 2.7–2.9(2H,m), 1.4–2.2(5H,m)

Example 137

2-[[1-[2-(4-Fluorophenyl)-2-oxoethyl]piperidin-4-yl]methyl]-3,4-dihydroisoquinolin-1(2H)-one hydrochloride Compound 761 in Table 1)

a) tert-Butyl 4-(4-methylbenzenesulfonyloxymethyl)piperidine-1-carboxylate tert-Butyl 4-hydroxymethylpiperidine-1-carboxylate (prepared by referring to Japanese Patent Unexamined Publication No. 11-217377, 12.12 g, 56.30 mmol) was dissolved in dichloromethane (26 ml), and the solution was added with p-toluenesulfonyl chloride (10.73 g, 56.30 mmol) and triethylamine (8.63 mmol, 61.9 mmol) at room temperature, and then stirred at the same temperature for 5 hours. The reaction mixture was diluted with dichloromethane (100 ml) and washed with water and saturated brine, and dried over sodium sulfate. Insoluble solids were removed by filtration and the filtrate was evaporated under reduced pressure. The residue was recrystallized from hexane (100 ml) to obtain the title compound as colorless solid (14.13 g, yield: 85%).
$^1$H-NMR(CDCl$_3$): 7.78(2H,d,J=8.1 Hz), 7.35(2H,d,J=8.4 Hz), 4.09(2H,brs), 3.85(2H,d,J=6.9 Hz), 2.65(2H,brdd, J=12.5,12.5 Hz), 2.46(3H,s), 1.87–1.79(1H,m), 1.65–1.62 (2H,m), 1.44(9H,s), 1.17–1.03(2H,m).

b) tert-Butyl 4-[3,4-dihydroisoquinolin-2(1H)-ylmethyl]piperidine-1-carboxylate

The compound obtained in Example 137a (1.0 g, 2.71 mmol), potassium carbonate (375 mg, 2.71 mmol), and 3,4-dihydroisoquinoline (399 mg, 2.71 mmol) were dissolved in dimethylformamide (9 ml) and the mixture was heated at 80° C. for 13 hours with stirring. The reaction mixture was stand for cooing, and then diluted with ethyl acetate and washed with water, and then dried over sodium sulfate. Insoluble solids were removed by filtration and the filtrate was evaporated under reduced pressure. The resulting crude product was purified by silica gel column chromatography (methanol-dichloromethane) to obtain the title compound as colorless oil (948 mg, yield: quantitative).
$^1$H-NMR(CDCl$_3$): 7.20–7.07(3H,m), 7.02–7.00(1H,m), 4.11(2H,brs), 3.60(2H,s), 2.91–2.87(2H,m), 2.76–2.68(4H, m), 2.35(2H,d,J=6.6 Hz), 1.80–1.68(3H,m),1.46(9H,s), 1.18–1.09(2H,m)

c) tert-Butyl 4-[[1-oxo-3,4-dihydroisoquinolin-2(1H)-yl]methyl]piperidinecarboxylate The compound obtained in Example 137b (488 mg, 1.48 mmol) was dissolved in dichloromethane (15 ml), and the solution was added with potassium permanganate (702 mg, 4.44 mmol) and triethylbenzylammonium chloride (337 mg, 1.48 mmol) and heated under reflux for 5.5 hours. The reaction mixture was stand for cooling, and then added with saturated aqueous solution of sodium hydrosulfite (15 ml) and stirred for 20 minutes. The reaction mixture was extracted with dichloromethane, and washed with water and dried over sodium sulfate. Insoluble solids were removed by filtration and the filtrate was evaporated under reduced pressure, and the residue ws purified by silica gel column chromatography (methanol-dichloromethane) to obtain the title compound as colorless oil (281 mg, yield: 55%).
$^1$H-NMR(CDCl$_3$): 8.07(1H,dd,J=7.5,1.2 Hz), 7.45–7.32 (2H,m), 7.19–7.17(1H,m), 4.10(2H,brs), 3.57(2H,dd,J=6.6, 6.6 Hz), 3.00(2H,dd,J=6.6,6.6 Hz), 3.02(2H,brs), 2.69(2H, brdd,J=12.1,12.1 Hz), 1.96–1.90(1H,m), 1.72–1.62(2H,m), 1.46(9H,s), 1.31–1.18(2H,m)

d) 2-(Piperidin-4-ylmethyl)-3,4-dihydroisoquinolin-1-(2H)-one hydrochloride

By using the crude product obtained in Example 137c (281 mg), the title compound was obtained as colorless solid by similar procedures to those of Example 1d (232 mg, yield: quantitative).

e) 2-[[1-[2-(4-Fluorophenyl)-2-oxoethyl]piperidin-4-yl]methyl]-3,4-dihydroisoquinolin-1-(2H)-one By using the compound obtained in Example 137d (230 mg, 0.82 mmol), the title compound was obtained as brown oil by similar procedures to those of Example 1e (110 mg, yield: 35%).
$^1$H-NMR(CDCl$_3$): 8.10–8.05(3H,m), 7.43–7.33(2H,m), 7.19–7.09(3H,m), 3.73(2H,s), 3.57(2H,dd,J=6.8,6.8 Hz), 3.45(2H,d,J7.2 Hz), 3.01–2.95(4H,m), 2.15(2H,ddd,J=1.1, 11.5,11.5 Hz), 1.83–1.44(5H,m).

f) 2-[[1-[2-(4-Fluorophenyl)-2-oxoethyl]piperidin-4-yl]methyl]-3,4-dihydroisoquinolin-1(2H)-one hydrochloride By using the compound obtained in Example 137e (110 mg, 0.29 mmol), the title compound was obtained as pale brown solid by similar procedures to those of Example 1f (80 mg, yield: 66%).

Melting point: 151–156° C. $^1$H-NMR(DMSO-d$_6$): 10.02 (1H,brs), 8.19–8.06(2H,m), 7.87(1H,d,J=7.8 Hz), 7.51–7.45 (3H,m), 7.38–7.29(2H,m), 5.11–5.04(2H,m), 3.60–3.53(4H, m), 3.44–3.37(2H,m), 3.07–2.98(4H,m), 1.99–1.07(5H,m).

Example 138

2-[[1-[(E)-2-(4-Fluorophenyl)-2-methoxyiminoethyl]piperidin-4-yl]methyl]isoindolin-1-one fumarate (E-isomer of Compound 741 in Table 1)

a) 2-[[1-[(E )-2-(4-Fluorophenyl)-2-methoxyiminoethyl]piperidin-4-yl]methyl]-isoindolin-1-one and 2-[[1-[(Z)-2-(4-fluorophenyl)-2-methoxyiminoethyl]piperidin-4-yl]methyl]isoindolin-1-one By using the compound obtained in Example 1e and methoxylamine hydrochloride, the title compounds were obtained by similar procedures to those of Example 18a.

2-[[1-[(E)-2-(4-Fluorophenyl)-2-methoxyiminoethyl]piperidin-4-yl]methyl]isoindolin-1-one(yield: 30%)

$^1$H-NMR (CDCl$_3$): δ 7.84 (d, J=7.5 Hz, 1H), 7.78 (m, 2H), 7.41–7.52 (m, 3H), 7.01 (t, J=9 Hz, 2H), 4.37 (s, 2H), 3.94 (s, 3H), 3.57 (s, 2H), 3.46 (d, J=7.4 Hz, 2H), 2.82 (br d, J=11.6 Hz, 2H), 2.04 (t, J=10 Hz, 2H), 1.74 (m, 1H), 1.59 (m, 2H), 1.30 (m,2H).

2-[[1-[(Z)-2-(4-Fluorophenyl)-2-methoxyiminoethyl]piperidin-4-yl]methyl]isoindolin-1-one(yield: 6%)

$^1$H-NMR (CDCl$_3$): δ 7.84 (d, J=7.5 Hz, 1H), 7.59 (m, 2H), 7.42–7.53 (m, 3H), 7.05 (t, J=8.9 Hz, 2H), 4.38 (s, 2H), 3.86 (s, 3H), 3.48 (d, J=7.3 Hz, 2H), 3.30 (s, 2H), 2.91 (br d, J=11.6 Hz, 2H), 2.01 (br t, J=11 Hz, 2H), 1.76 (m, 1H), 1.62 (m, 2H), 1.33 (m, 2H).

b) 2-[[1-[(E)-2-(4-Fluorophenyl)-2-methoxyiminoethyl]piperidin-4-yl]methyl]-isoindolin-1-one fumarate By using the compound obtained in Example 138a, the title compound was obtained by similar procedures to those of Example 40f (yield: 66%).

Melting point: 176° C. $^1$H-NMR (DMSO-d$_6$): δ 7.79 (m, 2H), 7.65 (d, J=7.5 Hz, 1H), 7.58 (m, 2H), 7.49 (m, 1H), 7.21 (m, 2H), 6.63 (s, 2H), 4.45 (s, 2H), 3.88 (s, 3H), 3.59 (s, 2H), 3.35 (d, J=7.3 Hz, 2H), 2.76 (br d, J=11.5 Hz, 2H), 1.99 (br t, J=10 Hz, 2H), 1.69 (m, 1H), 1.51 (br d, J=11.4 Hz, 2H), 1.08 (m, 2H).

Example 139

2-[[1-[(Z)-2-(4-Fluorophenyl)-2-methoxyiminoethyl]piperidin-4-yl]methyl]isoindolin-1-one fumarate (Z-isomer of Compound 741 in Table 1)

By using the compound obtained in Example 138a, the title compound was obtained by similar procedures to those of Example 40f (yield: 91%).

Melting point: 164° C. $^1$H-NMR (DMSO-d$_6$): δ 7.65 (d, J=7.5 Hz, 1H), 7.55–7.62 (m, 4H), 7.47 (m, 1H), 7.23 (t, J=8.9 Hz, 2H), 6.61 (s, 2H), 4.49 (s, 2H), 3.75 (s, 3H), 3.35 (d, J=7.4 Hz, 2H), 3.30 (s, 2H), 2.80 (br d, J=11.5 Hz, 2H), 1.93 (br t, J=11 Hz, 2H), 1.68 (m, 1H), 1.52 (br d,J=11.8 Hz, 2H), 1.07 (m, 2H).

Example 140

2-[[1-[(E)-2-(4-fluorophenyl)-2-methoxycarbonylhydrazonoethyl]piperidin-4-yl]methyl]isoindolin-1-one ¼.fumarate (E-isomer of Compound 746 in Table 1)

a) 2-[[1-[(E)-2-(4-Fluorophenyl)-2-methoxycarbonylhydrazonoethyl]piperidin-4-yl]methyl]isoindolin-1-one By using the compound obtained in Example 1e and methyl hydrazinocarboxylate, the title compound was obtained by similar procedures to those of Example 18a (yield: 46%)

$^1$H-NMR (CDCl$_3$): δ 11.95 (s, 1H), 7.85 (d, J=6.9 Hz, 1H), 7.68 (m, 2H), 7.43–7.55 (m, 3H), 7.03 (t, J=9 Hz, 2H), 4.41 (s, 2H), 3.85 (s, 3H), 3.64 (s, 2H), 3.54 (d, J=7.2 Hz, 2H), 2.95 (br d, J=11 Hz, 2H), 2.08 (br t, J=11 Hz, 2H), 1.87 (m, 1H), 1.76 (br d, J=12 Hz, 2H), 1.44 (m, 2H).

2-[[1-[(Z)-2-(4-fluorophenyl)-2-methoxycarbonylhydrazonoethyl]piperidin-4-yl]methyl]isoindolin-1-one (yield: 15%)

$^1$H-NMR (CDCl$_3$): δ 7.84 (d, J=7.2 Hz, 1H), 7.45–7.53 (m, 3H), 7.28 (m, 2H), 7.18 (t, J=9 Hz, 2H), 4.38 (s, 2H), 3.78 (br s, 3H), 3.47 (d, J=7.5 Hz, 2H), 3.36 (s, 2H), 2.85 (br d, J=11 Hz, 2H), 2.06 (br t, J=10 Hz, 2H), 1.72 (m, 1H), 1.61 (m, 2H), 1.28 (m, 2H).

b) 2-[[1-[(E)-2-(4-Fluorophenyl)-2-methoxycarbonylhydrazonoethyl]piperidin-4-yl]methyl]isoindolin-1-one ¼.fumarate By using the compound obtained in Example 140a, the title compound was obtained by similar procedures to those of Example 40f (yield: 76%).

Melting point: 154° C. $^1$H-NMR (DMSO-d$_6$): δ 12.08 (br s, 1H), 7.75 (m, 2H), 7.67 (d, J=7.5 Hz, 1H), 7.59 (m, 2H), 7.50 (m, 1H), 7.22 (t, J=9 Hz, 2H), 6.63 (s, 0.5H), 4.48 (s, 2H), 3.73 (s, 2H), 3.71 (s, 3H), 3.42 (d, J=7.2 Hz, 2H), 2.82 (br d, J=12 Hz, 2H), 2.08 (br t, J=11 Hz, 2H), 1.77 (m, 1H), 1.64 (br d, J=12 Hz, 2H), 1.18 (m, 2H).

Example 141

2-[[1-[(Z)-2-(4-fluorophenyl)-2-methoxycarbonylhydrazonoethyl]-piperidin-4-yl]methyl]isoindolin-1-one fumarate (Z-isomer of Compound 746 in Table 1)

By using the compound obtained in Example 140a, the title compound was obtained by similar procedures to those of Example 40 (yield: 73%).

Melting point: 153° C. $^1$H-NMR (DMSO-d$_6$): δ 9.39 (s, 1H), 7.65 (d, J=7.5 Hz, 1H), 7.58 (m, 2H), 7.48 (m, 1H), 7.38 (m, 2H), 7.27 (t, J=9 Hz, 2H), 6.62 (s, 2H), 4.45 (s, 2H), 3.60 (s, 3H), 3.35 (d, J=7.5 Hz, 2H), 3.32 (s, 2H), 2.80 (br d, J=11 Hz, 2H), 1.98 (m, 2H), 1.70 (m, 1H), 1.52 (m, 2H), 1.07 (m, 2H).

Example 142

2-[[1-[(E)-2-(4-Fluorophenyl)-2-acetylhydrazonoethyl]piperidin-4-yl]methyl]isoindolin-1-one fumarate (E-isomer of Compound 751 in Table 1)

a) 2-[[1-[(E)-2-(4-Fluorophenyl)-2-acetylhydrazonoethyl]piperidin-4-yl]methyl]isoindolin-1-one By using the compound obtained in Example 1e and acetic hydrazide, the title compound was obtained by similar procedures to those of Example 18a (yield: 64%).

$^1$H-NMR (CDCl$_3$): δ 11.98 (s, 1H), 7.84 (d, J=7.2 Hz, 1H), 7.67 (m, 2H), 7.24–7.54 (m, 3H), 7.06 (t, J=8.7 Hz, 2H), 4.41 (s, 2H), 3.63 (s, 2H), 3.51 (d, J=7.5 Hz, 2H), 2.91 (br d, J=11.4 Hz, 2H), 2.32 (s, 3H), 2.09 (br t, J=10 Hz, 2H), 1.83 (m, 1H), 1.76 (br d, J=12 Hz, 2H), 1.47 (m, 2H).

b) 2-[[1-[(E)-2-(4-Fluorophenyl)-2-acetylhydrazonoethyl]piperidin-4-yl]methyl]isoindolin-1-one fumarate By using the compound obtained in Example 142a, the title compound was obtained by similar procedures to those of Example 40f (yield: 75%).

Melting point: 168–170° C. $^1$H-NMR (DMSO-d$_6$): δ 12.06 (s, 1H), 7.80 (m, 2H), 7.67 (d, J=7.5 Hz, 1H), 7.59 (m, 2H), 7.48 (m, 1H), 7.23 (t, J=9 Hz, 2H), 4.48 (s, 2H), 3.75 (s, 2H), 3.42 (d, J=7.2 Hz, 2H), 2.83 (br d, J=11 Hz, 2H), 2.20 (s, 3H), 2.08 (br t, J=11 Hz, 2H), 1.76 (m, 1H), 1.64 (br d, J=12 Hz, 2H), 1.19 (m, 2H).

Example 143

2-[[1-[(Z)-2-(4-Fluorophenyl)-2-acetylhydrazonoethyl]piperidin-4-yl]methyl]isoindolin-1-one fumarate (Z-isomer of Compound 751 in Table 1)

a) N'-[2-Chloro-1-(4-fluorophenyl)ethylidene]acetohydrazido

2-Chloro-4'-fluoroacetophenone (1.00 g, 5.79 mmol) and acetic hydrazido (0.472 g, 6.37 mmol) was dissolved in ethanol (10 mL), and the mixture was stirred at room temperature for 8 hours. The reaction mixture was concentrated, and then the residual solid was suspended and washed in hexane. The resulting solid was purified by silica gel column chromatography (dichloromethane/ethyl acetate) to obtain the title compound (yield: 94%).

$^1$H-NMR (CDCl$_3$): δ 9.19 (br s, 1H), 7.75 (m, 2H), 7.12 (m, 2H), 4.44 (s, 2H), 2.41 (s, 3H).

b) 2-[[1-[(Z)-2-(4-Fluorophenyl)-2-acetylhydrazonoethyl]piperidin4-yl]methyl]isoindolin-1-one By using the compound obtained in Example 143a, the title compound was obtained by similar procedures to those of Example 1f and then purification using silica gel chromatography (dichloromethane/methanol) (yield: 53%).

$^1$H-NMR (CDCl$_3$): δ 8.29 (s, 1H), 7.85 (d, J=7.2 Hz, 1H), 7.42–7.54 (m, 3H), 7.24 (m, 2H), 7.16 (t, J=8.7 Hz, 2H), 4.39 (s, 2H), 3.49 (d, J=7.2 Hz, 2H), 3.30 (s, 2H), 2.90 (br d, J=11.7 Hz, 2H), 2.30 (s, 3H), 2.06 (m, 2H), 1.78 (m, 1H), 1.65 (m, 2H), 1.34 (m, 2H).

c) 2-[[1-[(Z)-2-(4-Fluorophenyl)-2-acetylhydrazonoethyl]piperidin-4-yl]methyl]-isoindolin-1-one fumarate By using the compound obtained in Example 143b, the title compound was obtained by similar procedures to those of Example 40f (yield: 63%).

Melting point: 15° C. $^1$H-NMR (DMSO-d$_6$): δ 9.34–9.92 (m, 1H), 7.66 (d, J=7.2 Hz, 1H), 7.58 (m, 2H), 7.40–7.57 (m, 3H), 7.31 (t, J=9.0 Hz, 2H), 6.62 (s, 2H), 4.45 (s, 2H), 3.35–3.40 (m, 4H), 2.83 (m, 2H), 1.82–2.15 (m, 5H), 1.71 (m, 1H), 1.53 (m, 2H), 1.08 (m, 2H).

Example 144

(E,Z)-2-[[1-[2-(4-Fluorophenyl)-2-(benzyloxy)iminoethyl]piperidin-4-yl]methyl]isoindolin-1-one fumarate (Compound 756 in Table 1)

The compound obtained in Example 1e (581 mg, 1.59 mmol) and benzyloxyamine hydrochloride (568 mg, 3.56 mmol) were dissolved in a mixed solvent of pyridine (12 ml) and ethanol (12 ml), and the mixure was stirred at room temperature for 3 days. The reaction mixture was diluted with ethyl acetate and washed with saturated aqueous sodium bicarbonate solution and then with saturated brine, and dried over sodium sulfate. Insoluble solids were removed by filtration and the filtrate was concentrated under reduced pressure to obtain (E,Z) 2-[[1-[2-(4-fluorophenyl)-2-(benzyloxy)iminoethyl]piperidin-4-yl]methyl]isoindolin-1-one as crude product. By using the resulting product, the title compound was obtained as colorless solid by similar procedures to those of Example 36c (255 mg, yield: 27%).

Melting point: 151–155° C. $^1$H-NMR(DMSO-d$_6$): 7.18–7.78(13H,m), 6.63(2H,s,fumaric acid), 5.17(0.8H,s), 5.07(1.2H,s), 4.45(2H,s), 3.63(0.8H,s), 3.2–3.4(3.2H,m), 2.70–2.80(2H,m), 1.86–2.03(2H,m), 1.6–1.8(1H,m), 1.4–1.5(2H,m), 0.9–1.1(2H,m)

Example 145

2-[[1[(E)-3-Phenylpro-2-penyl]piperidin-4-yl]methyl]isoindolin-1-one hydrochloride (E-isomer of Compound 364 in Table 1)

a) 2-[[1[(E)-3-phenylpro-2-penyl]piperidin-4-yl]methyl]isoindolin-1-one

The compound obtained in Example 1e (500 mg, 1.87 mmol) and 3-bromo-1-phenyl-1-propene (369 mg, 1.87 mmol) were dissolved in dimethylformamide (6 ml), and the solution was added with potassium carbonate (516 mg, 3.74 mmol) and stirred at room temperature for 20 hours. The reaction mixture was added with water (20 ml) and the solid precipitated was collected by filtration to obtain the title compound as colorless solid (402 mg, yield: 62%).

$^1$H-NMR(CDCl$_3$): 7.85(1H,d,J=7.0 Hz), 7.83–7.22(8H, m), 6.50(1H,d,J=16.0 Hz), 6.28(1H,dt,J=15.8,6.7 Hz), 4.41 (2H,s), 3.51(2H,d,J=7.1 Hz), 3.14(2H,d,J=6.7 Hz), 2.98(2H, brd,J=11.0 Hz), 1.97(2H,dd,J=11.4 Hz), 1.86–1.69(3H,m), 1.42(2H,ddd,J=24.5,12.5,2.9 Hz).

b) 2-[[1[(E)-3-Phenylpro-2-penyl]piperidin-4-yl]methyl]isoindolin-1-one hydrochloride By using the compound obtained in Example 145a, the title compound was obtained as colorless solid by similar procedures to those of Example 1f (197 mg, yield: 45%).

Melting point: 212–215° C. $^1$H-NMR(DMSO-d$_6$): 10.8 (1H,m), 7.68(1H,d,J=4.8 Hz), 7.61(2H,d,J=3.9 Hz), 7.53–7.46(3H,m), 7.41–7.30(3H,m), 6.81(1H,d,J=15.9 Hz), 6.43(1H,dt,J=15.9,7.6 Hz), 4.51(2H,s), 3.84(2H,s), 3.44(2H, d,J=6.9 Hz), 3.35(2H,s), 2.90–2.87(2H,m), 1.99(1H,brs), 1.81(2H,brd,J=13.5 Hz), 1.57(2H,brdd,J=15.2,11.6 Hz).

Example 146

2-[[1[(Z)-3-Phenylpro-2-penyl]piperidin-4-yl]methyl]isoindolin-1-one hydrochloride (Z-isomer of Compound 364 in Table 1)

a) (Z)-3-Phenylpro-2-pen-1-ol

3-Phenylpro-2-pyn-1-ol (500 mg, 3.78 mmol) was dissolved in ethanol (3 ml), and then Lindlar catalyst (25 mg) was suspended in the solution. The mixture was stirred for 6 hours under hydrogen flow. The reaction mixture was filtered, and the filtrate was concentrated and then the residue was purified by silica gel column chromatography (dichloromethane) to obtain the title compound as yellow oil (500 mg, quantitative).
$^1$H-NMR(CDCl$_3$): 7.41–7.19(5H,m), 6.58(1H,d,J=11.7 Hz), 5.88(1H,dt,J=11.7,6.2 Hz) 4.44(2H,dd,J=6.3,1.5 Hz).

b) (Z)-3-Chloro-1-phenylpro-1-pene

The compound obtained in Example 146a (300 mg, 2.24 mmol) was dissolved in dichloromethane (7 ml), and the solution was added with p-toluenesulfonyl chloride (427 mg, 2.24 mmol) and triethylamine (0.31 ml, 2.24 mmol) with ice cooling. Then the mixture was warmed to room temperature and stirred for 16 hours. The reaction mixture was added with water (10 ml) and extracted with dichloromethane. The extract was washed with water and saturated brine, and then dried over sodium sulfate. Insoluble solids were removed by filtration and the filtrate was evaporated under reduced pressure. The resulting residue was purified by silica gel column chromatography (hexane) to obtain the title compound as colorless oil (113 mg, yield: 33%).
$^1$H-NMR(CDCl$_3$): 7.41–7.26(5H,m), 6.66(1H,d,J=11.4 Hz), 5.90(1H,dt,J=11.4,8.2 Hz) 4.27(2H,d,J=6.9 Hz).

c) 2-[[1[(Z)-3-Phenylpro-2-penyl]piperidin-4-yl]methyl]isoindolin-1-one

By using the compound obtained in Example 146b (110 mg, 0.721 mmol) and the compound obtained in Example 1d (183 mg, 0.685 mmol), the title compound was obtained as colorless solid by similar procedures to those of Example 145a (236 mg, yield: quantitative).
$^1$H-NMR(CDCl$_3$): 7.84(1H,d,J=7.5 Hz), 7.54–7.21(8H, m), 6.55(1H,d,J=11.9 Hz), 5.79(1H,dt,J=11.2,6.1 Hz), 4.40 (2H,s), 3.50(2H,d,J=7.0 Hz), 3.26(2H,dd,J=6.1,1.2 Hz), 2.96(2H,brd,J=8.3 Hz) 1.98–1.87(2H,m), 1.79–1.67(3H,m), 1.48–1.40(2H,m).

d) 2-[[1[(Z)-3-Phenylpro-2-penyl]piperidin-4-yl]methyl]isoindolin-1-one hydrochloride By using the compound obtained in Example 146c (230 mg, 0.664 mmol), the title compound was obtained as colorless solid by similar procedures to those of Example 1f (148 mg, yield: 58%).
Melting point: 206–215° C. (dec.) $^1$H-NMR(DMSO-d$_6$): 10.96(1H,brs), 7.68(1H,d,J=7.2 Hz), 7.60(2H,d,J=3.9 Hz), 6.83(1H,d,J=12.0 Hz), 6.00(1H,dt,J=11.7,6.2 Hz), 4.49(2H, s), 4.11–3.99(2H,m), 3.62–3.41(2H,m), 2.85(2H,brdd, J=21.8,10.1 Hz), 1.99–1.91(1H,m), 1.78(2H,brd,J=12.3 Hz), 1.62(2H,brd,J=23.7,12.3 Hz).

Example 147

2-[[1-(3-Phenylpro-2-pynyl)piperidin-4-yl]methyl]isoindolin-1-one hydrochloride (Compound 370 in Table 1)

a) 3-Chloro-1-phenylpro-1-pyne

By using 3-phenylpro-2-pyn-1-ol (300 mg, 2.27 mmol), the title compound was obtained as colorless oil by carrying out a reaction similar to that of Example146b (99 mg, yield: 29%).
$^1$H-NMR(CDCl$_3$): 7.47–7.44(2H,m), 7.45–7.32(3H,m), 4.38(2H,s).

b) 2-[[1-(3-Phenylpro-2-pynyl)piperidin-4-yl]methyl]isoindolin-1-one

By using the compound obtained in Example 147a (99 mg, 0.657 mmol) and the compound obtained in Example 1d (158 mg, 0.591 mmol),the title compound was obtained as colorless solid by similar procedures to those of Example145a (163 mg, yield: 80%).
$^1$H-NMR(CDCl$_3$): 7.85(1H,d,J=7.5 Hz), 7.56–7.41(5H, m), 7.31–7.26(3H,m), 4.42(2H,s), 3.53–3.51(4H,m), 2.98 (2H,brd,J=12.6 Hz), 2.27(2H,ddd,J=2.2,11.6,11.6 Hz), 1.85–1.73(3H,m), 1.53–1.43(2H,m).

c) 2-[[1-(3-Phenylpro-2-pynyl)piperidin-4-yl]methyl]isoindolin-1-one hydrochloride By using the compound obtained in Example 147b (160 mg, 0.465 mmol), the title compound was obtained as colorless solid by similar procedures to those of Example 1f (138 mg, yield: 78%).
Melting point: 205–211° C. $^1$H-NMR(DMSO-d$_6$): 11.16 (1H,brs), 7.70–7.43(9H,m), 4.52(2H,s), 4.31(2H,s), 3.57–3.36(4H,m), 3.02(2H,brs), 2.03–1.59(5H,m).

Example 148

2-[[1-[2-(1-Oxo-1,3-dihydro-2H-isoindol-2-yl)ethyl]piperidin-4-yl]methyl]isoindolin-1-one hydrochloride (Compound 576 in Table 1)

a) 2-(Hydroxyethyl)isoindolin-1-one methanesulfonate

By using the compound obtained in Example 1b and 2-aminoethanol, 2-(hydroxyethyl)isoindolin-1-one was obtained as crude product by similar procedures to those of Example 1c. By using the resulting product, the title compound was obtained as colorless solid by similar procedures to those of Example 26a (yield: 30%).

b) 2-[[1-[2-(1-Oxo-1,3-dihydro-2H-isoindol-2-yl)ethyl]piperidin-4-yl]methyl]isoindolin-1-one By using the compound obtained in Example 148b, the title compound was obtained as pale yellow oil by similar procedures to those of Example 26b (yield: 72%).

$^1$H-NMR(CDCl$_3$): 7.84(2H,d,J=7.2), 7.41–7.56(6H,m), 4.51(2H,s), 4.39(2H,s), 3.72(2H,t,J=6.3), 3.50(2H,d,J=7.2), 2.92–3.00(2H,m), 2.62(2H,t,J=6.3), 1.95–2.06(2H,m), 1.5–1.9(3H,m), 1.2–1.4(2H,m)

c) 2-[[1-[2-(1-Oxo-1,3-dihydro-2H-isoindol-2-yl)ethyl]piperidin-4-yl]methyl]isoindolin-1-one hydrochloride By using the compound obtained in Example 148b, the title compound was obtained as colorless solid by similar procedures to those of Example 1f (yield: 51%).

Melting point: 212–218° C. $^1$H-NMR(DMSO-d$_6$): 9.6–10.0(1H,broad,HCl), 7.56–7.73(6H,m), 7.45–7.54(2H,m), 4.55(2H,s), 4.50(2H,s), 3.93(2H,t,J=6.0), 3.58–3.68(2H,m), 3.3–3.5(4H,m), 2.84–2.98(2H,m), 1.9–2.1(1H,m), 1.7–1.9(2H,m), 1.3–1.7(2H,m)

Example 149

2-[[1-[3-(1-Oxo-1,3-dihydro-2H-isoindol-2-yl)propyl]piperidin-4-yl]methyl]isoindolin-1-one hydrochloride (Compound 581 in Table 1)

a) 3-(Hydroxypropyl)isoindolin-1-one methanesulfonate

By using the compound obtained in Example 1b and 3-aminopropanol, 3-(hydroxypropyl)isoindolin-1-one was obtained as crude product by similar procedures to those of Example 1c. By using the resulting product, the title compound was obtained as colorless solid by similar procedures to those of Example 26a (yield: 38%).

b) 2-[[1-[3-(1-Oxo-1,3-dihydro-2H-isoindol-2-yl)propyl]piperidin-4-yl]methyl]isoindolin-1-one By using the compound obtained in Example 149b, the title compound was obtained as yellow solid by similar procedures to those of Example 26b (yield: 54%).

$^1$H-NMR(CDCl$_3$): 7.84(1H,d,J=6.0), 7.83(1H,d,J=6.3), 7.41–7.56(6H,m), 4.39(4H,s), 3.65(2H,t,J=7.1), 3.48(2H,d,J=7.2), 2.87–3.95(2H,m), 2.39(2H,t,J=7.4), 1.5–1.9(7H,m), 1.2–1.4(2H,m)

c) 2-[[1-[2-(1-Oxo-1,3-dihydro-2H-isoindol-2-yl)ethyl]piperidin-4-yl]methyl]isoindolin-1-one hydrochloride By using the compound obtained in Example 149b, the title compound was obtained as colorless solid by similar procedures to those of Example 1f (yield: 58%).

Melting point: 236–246° C. $^1$H-NMR(DMSO-d$_6$): 9.8–10.0(1H,broad,HCl), 7.68(2H,d,J=7.3), 7.56–7.65(4H,m), 7.45–7.53(2H,m), 4.52(2H,s), 4.50(2H,s), 3.60(2H,t,J=6.6), 3.0–3.5(4H,m), 2.9–3.0(2H,m), 2.6–2.8(2H,m), 1.8–2.2(3H,m), 1.6–1.8(2H,m), 1.3–1.6(2H,m)

Example 150

2-[[1-[4-(1-Oxo-1,3-dihydro-2H-isoindol-2-yl)butyl]piperidin-4-yl]methyl]isoindolin-1-one hydrochloride (Compound 586 in Table 1)

a) 4-(Hydroxybutyl)isoindolin-1-one methanesulfonate

By using the compound obtained in Example 1b and 4-aminobutanol, 4-(hydroxybutyl)isoindolin-1-one was obtained as crude product by similar procedures to those of Example 1c. By using the resulting product, the title compound was obtained as colorless oil by similar procedures to those of Example 26a (yield: 43%).

b) 2-[[1-[4-(1-Oxo-1,3-dihydro-2H-isoindol-2-yl)butyl]piperidin-4-yl]methyl]isoindolin-1-one By using the compound obtained in Example 150b, the title compound was obtained as yellow solid by similar procedures to those of Example 26b (yield: 87%).

$^1$H-NMR(CDCl$_3$): 7.84(1H,d,J=6.6), 7.83(1H,d,J=6.9), 7.42–7.56(6H,m), 4.39(2H,s), 4.37(2H,s), 3.63(2H,t,J=7.1), 3.49(2H,d,J=7.2), 2.84–2.92(2H,m), 2.34(2H,t,J=7.5), 1.4–1.9(9H,m), 1.2–1.4(2H,m)

c) 2-[[1-[4-(1-Oxo-1,3-dihydro-2H-isoindol-2-yl)butyl]piperidin-4-yl]methyl]isoindolin-1-one hydrochloride By using the compound obtained in Example 150b, the title compound was obtained as colorless solid by similar procedures to those of Example 1f (yield: 87%).

Melting point: 207–216° C. $^1$H-NMR(DMSO-d$_6$): 10.1–10.4(1H,broad,HCl), 7.68(2H,d,J=7.5), 7.56–7.65(4H,m), 7.46–7.53(2H,m), 4.50(4H,s), 3.50–3.62(2H,m), 3.0–3.5(4H,m), 2.9–3.0(2H,m), 2.6–2.8(2H,m), 1.4–2.2(9H,m)

Example 151

2-[[1-[3-[2-Oxo-3,4-dihydroquinolin-1(2H)-yl]propyl]piperidin-4-yl]methyl]isoindolin-1-one fumarate (Compound 601 in Table 1)

a) 1-(3-Hydroxypropyl)-3,4-dihydroquinolin-2(1H)-one 3,4-Dihydro-2(1H)-quinolinone (1.20 g, 8.15 mmol) was dissolved in dimethylformamide (10 ml), and the solution was added with 60% sodium hydride (376 mg, 9.40 mmol) at room temperature and stirred at the same temperature for 30 minutes. The mixture was added with 2-(3-bromopropoxy)tetrahydro-2H-pyran (1.94 g, 8.70 mmol) and heated at 70° C. for 1 hour. The reaction mixture was cooled to room temperature and diluted with water, and then extracted with a mixed solvent of ethyl acetate-hexane. The extract was washed with saturated brine and dried over magnesium sulfate. Insoluble solids were removed by filtration and the filtrate was concentrated under reduced pressure. The resulting oil was dissolved in methanol (90 ml) and the solution was added with a catalytic amount of p-toluenesulfonic acid and stirred at room temperature for 19 hours. The reaction solvent was evaporated under reduced pressure, and the residue was diluted with ethyl acetate. The mixture was washed with saturated aqueous sodium bicarbonate solution and then with saturated brine, and dried over magnesium sulfate. Insoluble solids were removed by filtration and the filtrate was concentrated under reduced pressure. The resulting oil was purified by silica gel column chromatography (ethyl acetate-hexane) to obtain the title compound as colorless oil (1.47 g, yield: 88%).

$^1$H-NMR(CDCl$_3$): 7.15–7.29(2H,m), 7.00–7.11(2H,m), 4.12(2H,t,J=6.2), 3.56(2H,t,J'5.6), 3.38(1H,brs,OH), 2.89–2.96(2H,m), 2.67–2.74(2H,m), 1.83–1.94(2H,m)

b) 2-[[1-[3-[2-Oxo-3,4-dihydroquinolin-1(2H)-yl]propyl]piperidin-4-yl]methyl]isoindolin-1-one By using the compound obtained in Example 151a, 1-(3-hydroxypropyl)-3,4-dihydroquinolin-2(1H)-one methanesulfonate was obtained as crude product by similar procedures to those of Example 26a. By using the resulting product, the title compound was obtained as yellow oil by similar procedures to those of Example 26b (yield: 59%).

$^1$H-NMR(CDCl$_3$): 7.85(1H,d,J=7.4), 7.41–7.54(3H,m), 7.20–7.26(1H,m), 7.15(1H,d,J=7.2), 7.08(1H,d,J=8.0), 6.99(1H,t,J=7.6), 4.40(2H,s), 3.96(2H,t,J=7.5), 3.51(2H,d,J=7.2), 2.84–2.96(4H,m), 2.59–2.67(2H,m), 2.34–2.43(2H,m), 1.6–2.1(7H,m), 1.3–1.5(2H,m)

c) 2-[[1-[3-[2-Oxo-3,4-dihydroquinolin-1(2H)-yl]propyl]piperidin-4-yl]methyl]isoindolin-1-one fumarate By using the compound obtained in Example 151b, the title compound was obtained as colorless solid by similar procedures to those of Example 36c (yield: 55%).

Melting point:, 185–193° C. $^1$H-NMR(DMSO-d$_6$): 7.67(1H,d,J=7.5), 7.56–7.61(2H,m), 7.45–7.52(1H,m), 7.14–7.27(3H,m), 6.99(1H,t,J=7.2), 6.56(2H,s,fumaric acid), 4.48(2H,s), 3.89(2H,t,J=7.2), 3.41(2H,d,J=7.2), 2.94–3.02(2H,m), 2.84(2H,t,J=7.6), 2.4–2.6(4H,m), 2.0–2.2(2H,m), 1.5–1.9(5H,m), 1.1–1.3(2H,m)

Example 152

2-[[1-[3-[2-Oxoquinolin-1(2H)-yl]propyl]piperidin-4-yl]methyl]isoindolin-1-one fumarate (Compound 606 in Table 1)

a) 1-(3-Hydroxypropyl)quinolin-2(1H)-one

By using 2-hydroxyquinoline, the title compound was obtained as colorless solid by similar procedures to those of Example 151a (yield: 41%).

$^1$H-NMR(CDCl$_3$): 7.76(1H,d,J=9.5), 7.57–7.64(2H,m), 7.46(1H,d,J=8.9), 7.25–7.32(1H,m), 6.75(1H,d,J=9.5), 4.51(2H,t,J=6.0), 3.6–4.4(1H,broad,OH), 3.51(2H,t,J=5.5), 1.97–2.07(2H,m)

b) 2-[[1-[3-[2-Oxoquinoline-1(2H)-yl]propyl]piperidin-4-yl]methyl]isoindolin-1-one By using the compound obtained in Example 152a, 1-(3-hydroxypropyl)quinolin-2(1H)-one methanesulfonate was obtained as crude product by similar procedures to those of Example 26a. By using the resulting product, the title compound was obtained as yellow oil by similar procedures to those of Example 26b (yield: 88%).

$^1$H-NMR(CDCl$_3$): 7.85(1H,d,J=7.2),7.66(1H,d,J=9.5), 7.42–7.58(6H,m), 7.15–7.27(2H,m), 6.68(1H,d,J=9.5), 4.40(2H,s), 4.34(2H,t,J=7.4), 3.52(2H,d,J=7.2), 2.90–2.98(2H,m), 2.46(2H,t,J=6.9), 2.0–2.2(2H,m), 1.6–2.0(7H,m), 1.3–1.5(2H,m)

c) 2-[1-[3-[2-Oxoquinoline-1(2H)-yl]propyl]piperidin-4-yl]methyl]isoindolin-1-one fumarate By using the compound obtained in Example 152b, the title compound was obtained as colorless solid by similar procedures tot hose of Example 36c (yield: 82%).

Melting point: 208–215° C. $^1$H-NMR(DMSO-d$_6$): 7.90(1H,d,J=9.5), 7.57–7.74(6H,m), 7.45–7.52(1H,m), 7.22–7.31(1H,m), 6.60(1H,d,J=9.5), 6.57(2H,s,fumaric acid), 4.48(2H,s), 4.25(2H,t,J=7.2), 3.42(2H,d,J=7.1), 2.95–3.03(2H,m), 2.57(2H,t,J=6.9), 2.06–2.18(2H,m), 1.7–1.9(3H,m), 1.5–1.6(2H,m), 1.2–1.4(2H,m)

Example 153

2-[[1-[2-(2-Oxo-3-phenylimidazolidin-1-yl)ethyl]piperidin-4-yl]methyl]isoindolin-1-one hydrochloride (Compound 596 in Table 1)

a) 1-(2-Hydroxyethyl)-3-phenylimidazolidin-2-one

By using 1-phenylimidazolidin-2-one obtained by the method described in literature (J. Org. Chem., 1951, 16, 1829) and t-butyldimethylsilyl 2-bromoethyl ether obtained by the method of Example 92a, 1-[2-(t-butyldimethylsilyloxy)ethyl]-3-phenylimidazolidin-2-one was obtained as crude product by similar procedures to those of Example 151a. By using the resulting product, the title compound was obtained as colorless solid by similar procedures to those of Example 92b (yield: 75%).

$^1$H-NMR(CDCl$_3$): 7.53(2H,d,J=8.0), 7.34(2H,t,J=8.4), 7.05(1H,t,J=7.4), 3.82–3.89(4H,m), 3.59(2H,t,J=7.3), 3.45(2H,t,J=5.1), 3.01(1H,brs,OH)

b) 2-[[1-[2-(2-Oxo-3-phenylimidazolidin-1-yl)ethyl]piperidin-4-yl]methyl]isoindolin-1-one By using the compound obtained in Example 153a, 1-(2-hydroxyethyl)-3-phenylimidazolidin-2-one methanesulfonate was obtained as crude product by similar procedures to those of Example 26a. By using the resulting product, the title compound was obtained as colorless oil by similar procedures to those of Example 26b (yield: 65%).

$^1$H-NMR(CDCl$_3$): 7.85(1H,d,J=7.5), 7.41–7.57(5H,m), 7.32(2H,t,J=7.5), 7.02(1H,t,J=7.5), 4.40(2H,s), 3.77–3.84(2H,m), 3.53–3.60(2H,m), 3.50(2H,d,J=7.2), 3.42(2H,t,J=6.3), 2.93–3.02(2H,m), 2.55(2H,t,J=6.6), 1.95–2.07(2H,m), 1.5–1.8(3H,m), 1.2–1.4(2H,m)

c) 2-[[1-[2-(2-Oxo-3-phenylimidazolidin-1-yl)ethyl]piperidin-4-yl]methyl]isoindolin-1-one hydrochloride By using the compound obtained in Example 153b, the title compound was obtained as colorless solid by similar procedures to those of Example 1f (yield: 93%).

Melting point: 207–219° C. $^1$H-NMR(DMSO-d$_6$): 9.6–10.0(1H,broad,HCl), 7.68(1H,d,J=7.5), 7.45–7.62(5H,m), 7.33(2H,t,J=7.8), 7.01(1H,t,J=7.4), 4.51(2H,s), 3.80–3.88(2H,m), 3.50–3.62(6H,m), 3.43(2H,d,J=7.5), 3.27(2H,t,J=5.9), 2.80–3.0(2H,m), 1.9–2.1(1H,m), 1.6–1.8(2H,m), 1.4–1.6(2H,m)

Example 154

5-Fluoro-2-[[1-[2-(4-fluorophenyl)-2-oxoethyl]piperidin-4-yl]methyl]isoindolin-1-one hydrochloride (Compound 9 in Table 1)

a) 4-Fluoro-2-methylbenzoic acid ethyl ester

Magnesium (0.644 g, 26.5 mmol) was added wit THF (4 mL) and a small amount of iodine. After the mixture was stirred, the mixture was added dropwise with a solution of 1-bromo-4-fluoro-2-methylbenzene (5.00 g, 26.5 mmol) in THF (50 mL). The mixture was stirred at room temperature for 30 minutes, and then cooled at −78° C. and added dropwise with a solution of ethyl chloroformate (3.80 mL, 39.8mmol) in THF (40 mL). The mixture was warmed slowly up to room temperature and stirring was continued at room temperature for 2 hours. The reaction mixture was diluted with ether and washed with water, saturated aqueous sodium bicarbonate solution, and then with saturated brine, and dried over sodium sulfate. The drying agent was removed by filtration and the filtrate was concentrated, and the resulting oily substance was purified by silica gel column chromatography (hexane/ether) to obtain the title compound (3.65 g, yield: 76%).

$^1$H-NMR (CDCl$_3$): δ 1.39 (t, J=7.0 Hz, 3H), 2.61 (s, 3H), 4.35 (q, J=7.0 Hz, 2H), 6.89–6.95 (m, 2H), 7.95 (m, 1H).

b) tert-Butyl 4-(5-fluoro-1-oxoisoindolin-2-ylmethyl)piperidine-1-carboxylate

By using the compound obtained in Example 154a, the title compound was obtained by similar procedures to those of Examples 1b and 1c (yield: 57%).

$^1$H-NMR (CDCl$_3$): δ 1.25 (m, 2H), 1.45 (s, 9H), 1.64 (m, 2H), 1.93 (m, 1H), 2.69 (m, 2H), 3.47 (m, 2H), 4.11 (m, 2H), 4.39 (s, 2H), 7.12–7.20 (m, 2H), 7.82 (dd, J=5.0, 8.3 Hz, 1H).

c) 5-Fluoro-2-(piperidin-4-ylmethyl)isoindolin-1-one hydrochloride

By using the compound obtained in Example 154b, the title compound was obtained by similar procedures to those of Example 1d (yield: 91%).

$^1$H-NMR (DMSO-d$_6$): δ 1.36 (m, 2H), 1.73 (m, 2H), 2.00 (m, 1H), 2.80 (m, 2H), 3.24 (m, 2H), 3.42 (d, J=7.5 Hz, 2H), 4.49 (s, 2H), 7.32 (m, 1H), 7.49 (d, J=8.6 Hz, 1H), 7.71 (dd, J=5.1, 8.4 Hz, 1H), 8.49 (br s, 1H), 8.78 (br s, 1H).

d) 5-Fluoro-2-[[1-[2-(4-fluorophenyl)-2-oxoethyl]piperidin-4-yl]methyl]isoindolin-1-one By using the compound obtained in Example 154c, the title compound was obtained by similar procedures to those of Example 1e (yield: 85%).

$^1$H-NMR (CDCl$_3$): δ 1.47 (m, 2H), 1.68 (m, 2H), 1.81 (m, 1H), 2.15 (m, 2H), 2.96 (m, 2H), 3.49 (d, J=7.2 Hz, 2H), 3.72 (s, 2H), 4.38 (s, 2H), 7.08–7.18 (m, 4H), 7.91 (dd, J=5.0, 8.3 Hz, 1H), 8.07 (m, 2H).

e) 5-Fluoro-2-[[1-[2-(4-fluorophenyl)-2-oxoethyl]piperidin-4-yl]methyl]isoindolin-1-one hydrochloride By using the compound obtained in Example 154d, the title compound was obtained by similar procedures to those of Example 1f (yield: 90%).

Melting point: 209–216° C. $^1$H-NMR (DMSO-d$_6$): δ 1.58–1.86 (m, 4H), 2.03 (m, 1H), 3.04 (m, 2H), 3.45 (d, J=8.6 Hz, 2H), 3.54 (m, 2H), 4.53 (s, 2H ), 5.04–5.10 (m, 2H), 7.33 (m, 1H), 7.45–7.53 (m, 3H), 7.73 (dd, J=5.2, 8.3 Hz, 1H), 8.06–8.15 (m, 2H), 9.96 (br s, 1H).

Example 155

6-Methyloxy-2-[[1-[2-(4-fluorophenyl)-2-oxoethyl]piperidin-4-yl]methyl]isoindolin-1-one hydrochloride (Compound 18 in Table 1)

a) 3-Hydroxy-2-methylbenzoic acid methyl ester

By using 3-hydroxy-2-methylbenzoic acid, the title compound was obtained by similar procedures to those of Example 3a (yield: 97%).

$^1$H-NMR (CDCl$_3$): δ 2.46 (s, 3H), 3.89 (s, 3H), 6.94 (d, J=8.3 Hz, 1H), 7.11 (t, J=8.3 Hz, 1H), 7.42 (d, J=8.3 Hz, 1H).

b) 3-(tert-Butyl-dimethyl-silanyloxy)-2-methylbenzoic acid methyl ester

The compound obtained in Example155a (4.99 g, 30.0 mmol) was dissolved in DMF (26 mL), and then the solution was added with tert-butyldimethylchlorosilane (5.43 g, 36.0 mmol) and imidazole (5.11 g, 75.0 mmol) and stirred at room temperature. The reaction mixture was added with saturated aqueous sodium bicarbonate solution and extracted four times with hexane, and then the combined organic layer was dried over sodium sulfate. The drying agent was removed by filtration and the filtrate was concentrated, the resulting oily substance was purified by silica gel column chromatography (hexane/ethyl acetate) to obtain the title compound (8.24 g, yield: 93%).

$^1$H-NMR (CDCl$_3$): δ 0.21 (s, 6H), 1.02 (s, 9H), 2.41 (s, 3H), 3.88 (s, 3H), 6.93 (d, J=8.4 Hz, 1H), 7.09 (t, J=8.4 Hz, 1H), 7.42 (d, J=8.4 Hz, 1H).

c) tert-Butyl-4-[6-(tert-butyl-dimethyl-silanyloxy)-1-oxoisoindolin-2-ylmethyl]piperidine-1-carboxylate By using the compound obtained in Example155b, the title compound was obtained by similar procedures to those of Example 1b and 1c (yield: 71%).

$^1$H-NMR (CDCl$_3$): δ 0.25 (s, 6H), 1.02 (s, 9H), 1.26 (m, 2H), 1.45 (s, 9H), 1.66 (m, 2H), 1.95 (m, 1H), 2.70 (m, 2H), 3.49 (m, 2H), 4.10 (m, 2H), 4.30 (s, 2H), 6.93 (d, J=7.7 Hz, 1H), 7.33 (t, J=7.7 Hz, 1H), 7.45 (d, J=7.7 Hz, 1H).

d) tert-Butyl-4-(6-hydroxy-1-oxoisoindolin-2-ylmethyl)piperidine-1-carboxylate

The compound obtained in Example 155c (9.20 g, 20.0 mmol) and acetic acid (9.44 mL) was dissolved in THF (100 mL), and the solution was cooled to 0° C. and added dropwise with 1M solution of tetrabutylammoniumfluoride in THF (20.0 mL, 20.0 mmol). After 30 minutes, the reaction mixture was diluted with ethyl acetate and washed three times with 0.5N aqueous solution of hydrochloric acid and then with saturated brine, and dried over sodium sulfate. The drying agent was removed by filtration and the filtrate was concentrated, the resulting oily substance was crystallized from dichloromethane/ether/hexane to obtain the title compound (5.70 g, yield: 82%).

$^1$H-NMR (CDCl$_3$): δ 1.23 (m, 2H), 1.46 (s, 9H), 1.65 (m, 2H), 1.95 (m, 1H), 2.69 (m, 2H), 3.50 (m, 2H), 4.12 (m, 2H), 4.41 (s, 2H), 7.03 (d, J=7.5 Hz, 1H), 7.29 (t, J=7.5 Hz, 1H), 7.39 (d, J=7.5 Hz, 1H).

e) 6-Methyloxy-2-(piperidin-4-ylmethyl)isoindolin-1-one hydrochloride

A solution of the compound obtained in Example 155d (0.600 g, 1.74 mmol) in acetonitrile (6 mL) was added with iodomethane (0.216 mL, 3.46 mmol) and potassium carbonate (478 mg, 3.46 mmol), and heated at 60° C. After 2.5 hours, the mixture was cooled to room temperature, and diluted with ethyl acetate and washed twice with saturated aqueous sodium bicarbonate solution and saturated brine, and then dried over sodium sulfate. The drying agent was removed by filtration and the filtrate was concentrated, the resulting crude product was subjected to similar procedures to those of Example 1d without purification to obtain the title compound (yield: 94%).

$^1$H-NMR (DMSO-$d_6$): δ 1.36 (m, 2H), 1.71 (m, 2H), 2.04 (m, 1H), 2.79 (m, 2H), 3.24 (m, 2H), 3.42 (d, J=7.4 Hz, 2H), 3.89 (s, 3H), 4.41 (s, 2H), 7.21 (d, J=8.1 Hz, 1H), 7.26 (d, J=7.4 Hz, 1H), 7.47 (dd, J=7.4, 8.1 Hz, 1H), 8.55 (br s, 1H), 8.84 (br s, 1H).

f) 6-Methyloxy-2-[[1-[2-(4-fluorophenyl)-2-oxoethyl]piperidin-4-yl]methyl]isoindolin-1-one hydrochloride By using the compound obtained in Example 155e, the title compound was obtained by similar procedures to those of Examples 1e and 1f (yield: 67%).

Melting point: 213–229° C. $^1$H-NMR (DMSO-$d_6$): d157–1.84 (m, 4H), 2.05 (m, 1H), 3.02 (m, 2H), 3.45 (d, J=6.9 Hz, 2H), 3.53 (m, 2H), 3.89 (s, 3H), 4.45 (s, 2H), 5.03–5.09 (m, 2H), 7.22 (d, J=8.1 Hz, 1H), 7.27 (d, J=7.4 Hz, 1H), 7.45–7.50 (m, 3H), 8.05–8.15 (m, 2H), 9.95 (br s, 1H).

Example 156

6-Ethyloxy2-[[1-[2-(4-fluorophenyl)-2-oxoethyl]piperidin-4-yl]methyl]isoindolin-1-one hydrochloride a) 6-Ethyloxy2-(piperidin-4-ylmethyl)isoindolin-1-one hydrochloride

By using the compound obtained in Example 155d, the title compound was obtained by similar procedures to those of Example 155e (yield: 97%).

$^1$H-NMR (DMSO-$d_6$): δ 1.36 (m, 2H), 1.37 (t, J=6.9 Hz, 3H), 1.71 (m, 2H), 2.05 (m, 1H), 2.79 (m, 2H), 3.23 (m, 2H), 3.42 (d, J=7.1 Hz, 2H), 4.16 (q, J=6.9 Hz, 2H), 4.41 (s, 2H), 7.19 (d, J=8.1 Hz, 1H), 7.25 (d, J=7.4 Hz, 1H), 7.45 (dd, J=7.4, 8.1 Hz, 1H), 8.74 (br s, 1H), 9.02 (br s, 1H).

b) 6-Ethyloxy-2-[[1-[2-(4-fluorophenyl)-2-oxoethyl]piperidin-4-yl]methyl]isoindolin-1-one hydrochloride By using the compound obtained in Example 156a, the title compound was obtained by similar procedures to those of Examples 1e and 1f (yield: 43%).

Melting point: 200–209° C. $^1$H-NMR (DMSO-$d_6$): δ 1.37 (t, J=6.9 Hz, 3H), 1.57–1.84 (m, 4H), 2.08 (m, 1H), 3.01 (m, 2H), 3.45 (d, J=6.8 Hz, 2H), 3.53 (m, 2H), 4.17 (q, J=6.9 Hz, 2H), 4.44 (s, 2H), 5.03–5.09 (m, 2H), 7.20 (d, J=8.0 Hz, 1H), 7.26 (d, J=7.4 Hz, 1H), 7.42–7.50 (m, 3H), 8.06–8.16 (m, 2H), 9.93 (br s, 1H).

Example 157

6-Isopropyloxy-2-[[1-[2-(4-fluorophenyl)-2-oxoethyl]piperidin-4-yl]methyl]isoindolin-1-one hydrochloride a) Isopropyloxy-2-(piperidin-4-ylmethyl)isoindolin-1-one hydrochloride

By using the compound obtained in Example 155d, the title compound was obtained by similar procedures to those of Example 155e (yield: 99%).

$^1$H-NMR (DMSO-$d_6$): δ 1.30 (d, J=5.5 Hz, 6H), 1.34 (m, 2H), 1.71 (m, 2H), 2.04 (m, 1H), 2.79 (m, 2H), 3.23 (m, 2H), 3.41 (d, J=6.6 Hz, 2H), 4.37 (s, 2H), 4.74 (m, 1H), 7.21–7.23 (m, 2H), 7.43 (m, 1H), 8.60 (br s, 1H), 8.88 (br s, 1H).

b) 6-Isopropyloxy2-[[1-[2-(4-fluorophenyl)-2-oxoethyl]piperidin-4-yl]methyl]isoindolin-1-one fumarate By using the compound obtained in Example 157a, the title compound was obtained by similar procedures to those of Examples 1e and 36c (yield: 53%).

Melting point: 132° C. $^1$H-NMR (DMSO-$d_6$): δ 1.21 (m, 2H), 1.30 (d, J=6.0 Hz, 6H), 1.55 (m, 2H), 1.76 (m, 1H), 2.13 (m, 2H), 2.87 (m, 2H), 3.38 (d, J=7.2 Hz, 2H), 3.81 (s, 2H), 4.35 (s, 2H), 4.74 (m, 1H), 6.61 (s, 2H), 7.19–7.23 (m, 2H), 7.35 (t, J=8.7 Hz, 2H), 7.42 (t, J=7.8 Hz, 1H), 8.09 (dd, J=5.7, 8.7 Hz, 2H).

Example 158

5-[[1-[2-(4-Fluorophenyl)-2-oxoethyl]piperidin-4-yl]methyl]-4,5-dihydro-6H-furo[2,3-c]pyrrol-6-one fumarate (Compound 817 in Table 2)

a) Methyl 3-bromomethylfuran-2-carboxylate

By using methyl 3-methylfurancarboxylate (2.00 g, 14.27 mmol), the title compound as crude product was obtained as yellow oil by carrying out a reaction similar to that of Example 1c (3.51 g). The crude product was used in the next reaction without purification.

b) Methyl 3-[[1-(tert-butoxycarbonyl)piperidin-4-yl]methylaminomethyl]-2-furancarboxylate By using the compound obtained in Example 158a (3.51 g), the title compound was obtained as yellow oil by carrying out reactions similar to those of Example 1c (1.80 g, yield: 36%, 2 steps).

$^1$H-NMR(CDCl$_3$): 7.48(1H,d,J=1.5 Hz), 6.55(1H,d,J=1.8 Hz), 4.09(2H,brd,J=11.7 Hz), 3.94–3.91(5H,m), 2.69((2H, brt,J=12.5 Hz), 2.51(2H,d,J=6.6Hz), 1.73–1.58(3H,m), 1.45 (9H,s), 1.18–1.06(2H,m).

c) 3-[[1-(tert-Butoxycarbonyl)piperidin-4-yl]methylaminomethyl]-2-furancarboxylic acid By using the compound obtained in Example 158b (1.80 g), the title compound was obtained as yellow semisolid by carrying out a reaction similar to that of Example 22d (1.35 g, yield: 78%).

$^1$H-NMR(CDCl$_3$): 10.36(2H,brs), 7.48(1H,d,J=1.5 Hz), 6.58(1H,d,J=1.2 Hz), 4.23(2H, brs), 4.09(2H,brd,J=7.4 Hz), 2.97–2.70(4H,m), 2.08(1H,brs), 1.85(2H, brd,J=12.0 Hz), 1.42(9H,s), 1.25–1.11(2H,m).

d) tert-Butyl-4-[(4,5-dihydro-6H-furo[2,3-c]pyrrol-6-one)-2-ylmethyl]piperidine-1-carboxylate The compound obtained in Example 158c (658 mg, 1.94 mmol), 2,2'-dipyridyldisulfide (513 mg, 2.33 mmol), and triphenylphosphine (611 mg, 2.33 mmol) were dissolved in acetonitrile (6 ml), and the mixture was heated under reflux for 4 hours. The reaction mixture was stand for cooling, and the solvent was evaporated. The residue was added with water and extracted with ethyl acetate. The organic layer was washed with saturated aqueous sodium bicarbonate solution, water, and then with saturated brine, and dried over anhydrous sodium sulfate. Insoluble solids were removed by filtration and the solvent was evaporated under reduced pressure. The resulting crude product was applied to silica gel chromatography (ethyl acetate/hexane=1/1) to obtain the title compound as yellow oil (694 mg, a mixture with the reagent).

e) 5-(Piperidin-4-ylmethyl)-4,5-dihydro-6H-furo[2,3-c]pyrrol-6-one hydrochloride By using the compound obtained in Example 158d (658 mg), the title compound was obtained as colorless solid by carrying out reactions similar to those of Example 1d (161 mg, yield: 12%, 3 steps).
$^1$H-NMR(DMSO-$d_6$): 8.92(1H,brs), 8.65(1H,brs), 7.99 (1H,s), 6.77(1H,s), 4.30(2H,s), 3.33(1H,d,J=7.4 Hz), 3.24 (1H,brd,J=12.7 Hz), 2.79(2H,brdd,J=23.2,12.0 Hz), 1.99–1.91(1H,m), 1.72(2H,d,J=13.2 Hz), 1.42–1.29(2H,m).

f) 5-[[1-[2-(4-Fluorophenyl)-2-oxoethyl]piperidin-4-yl]methyl]-4,5-dihydro-6H-furo[2,3-c]pyrrol-6-one By using the compound obtained in Example 158e (80 mg, 0.312 mmol), the title compound was obtained as colorless solid by carrying out a reaction similar to that of Example 1e (90 mg, yield: 81%).
$^1$H-NMR(CDCl$_3$): 8.10–8.05(2H,m), 7.61(1H,d,J=1.7 Hz), 7.12(2H,t,J=8.7 Hz), 6.50(1H,d,J=1.6 Hz), 4.18(2H,s), 3.41(2H,d,J=7.2 Hz), 2.96(2H,brd,J=11.4 Hz), 2.18–2.10 (2H,m), 1.78–1.62(3H,m), 1.50–1.41(2H),m).

g) 4-Fluoro-2-[1-[2-(4-fluorophenyl)ethyl]piperidin-4-ylmethyl]isoindolin-1-one fumarate By using the compound obtained in Example 158f (90 mg, 0.253 mmol), the title compound was obtained as colorless solid by carrying out a reaction similar to that of Example 36c (109 mg, yield: 91%).
Melting point: 230–232° C. $^1$H-NMR((DMSO-$d_6$): 8.11–8.07(2H,m), 7.97(1H,d,J=1.7 Hz), 7.38–7.32(2H,m), 6.75(1H,d,J=1.6 Hz), 6.61(2H,s), 4.27(2H,s), 3.84(2H,s), 3.29(2H,d,J=7.2 Hz), 2.88(2H,brd,J=11.4 Hz), 2.14(2H,t, J=10.8 Hz), 1.70–1.67(1H,m), 1.56(2H,d,J=12.3 Hz), 1.26–1.16(2H,m).

Example 159

5-Methoxy-2-[1-[2-(4-fluorophenyl)ethyl]piperidin-4-ylmethyl]isoindolin-1-one fumarate (Compound 204 in Table 1)

By using the compound obtained in Example 8c, the title compound was obtained by similar procedures to those of Examples 26b and 36c.

Melting point: 178–180° C. $^1$H-NMR (DMSO-$d_6$): δ 1.26 (m, 2H), 1.63 (m, 2H), 1.79 (m, 1H), 2.25 (m, 2H), 2.72 (m, 2H), 2.78 (m, 2H), 3.08 (m, 2H), 3.38 (d, J=7.1 Hz, 2H), 3.83 (s, 3H), 4.42 (s, 2H), 6.57 (s, 2H), 7.00–7.14 (m, 4H), 7.27(m, 2H), 7.57 (d, J=8.4 Hz, 1H).

Example 160

5-Bromo-2-[1-[2-(4-fluorophenyl)ethyl]piperidin-4-ylmethyl]isoindolin-1-one fumarate (Compound 198 in Table 1)

By using the compound obtained in Example 3d, the title compound was obtained by similar procedures to those of Examples 26b and 36c.

Melting point: 203–219° C. $^1$H-NMR (DMSO-$d_6$): δ 1.26 (m, 2H), 1.62 (m, 2H), 1.79 (m, 1H), 2.20 (m, 2H), 2.69 (m, 2H), 2.77 (m, 2H), 3.05 (m, 2H), 3.40 (d, J=7.0 Hz, 2H), 4.49 (s, 2H), 6.58 (s, 2H), 7.10 (t, J=8.6 Hz, 2H), 7.24–7.29 (m, 2H), 7.59 (m, 2H), 7.86 (s, 1H).

Example 161

5-Chloro-2-[1-[2-(4-fluorophenyl)ethyl]piperidin-4-ylmethyl]isoindolin-1-one fumarate (Compound 203 in Table 1)

a) 5-Chloro-2-[1-[2-(4-fluorophenyl)ethyl]piperidin-4-ylmethyl]isoindolin-1-one

By using the compound obtained in Example 9c (250 mg, 0.83 mmol) and the compound obtained in Example 26a (181 mg, 0.83 mmol), the title compound as crude product was obtained as pale brown solid by carrying out a reaction similar to that of Example 26b (245 mg). The resulting crude product was used in the next reaction without purification.

b) 5-Chloro-2-[1-[2-(4-fluorophenyl)ethyl]piperidin-4-ylmethyl]isoindolin-1-one fumarate By using the compound obtained in Example 161a (240 mg), the title compound was obtained as colorless solid by carrying out reactions similar to those of Example 36c (299 mg, yield: 72%, 2 steps).

Melting point: 220–229° C. $^1$H-NMR(DMSO-$d_6$): 7.69 (2H,t,J=7.7 Hz), 7.54(1H,dd,J=7.9,1.4 Hz), 7.27(2H,dd, J=8.4,5.7 Hz), 7.10(2H,t,J=8.9 Hz), 6.57(2H,s), 4.49(2H,s), 3.41(2H,d,J=7.2 Hz), 3.10(2H,brd,J=11.6 Hz), 2.82–2.70 (4H,m), 2.26(2H,brt,J=11.0 Hz), 1.83–1.77(1H,m), 1.64 (2H,brd,J=11.7 Hz), 1.32–1.24(2H,m).

Example 162

5-Cyano-2-[1-[2-(4-fluorophenyl)ethyl]piperidin-4-ylmethyl]isoindolin-1-one fumarate (Compound 205 in Table 1)

a) 5-Cyano-2-[1-[2-(4-fluorophenyl)ethyl]piperidin-4-ylmethyl]isoindolin-1-one

By using the compound obtained in Example 10c (300 mg, 1.03 mmol) and the compound obtained in Example 26a (225 mg, 1.03 mmol), the title compound as crud product was obtained as pale brown solid by carrying out a reaction similar to that of Example 26b (224 mg). The resulting crude product was used in the next reaction without purification.

b) 5-Cyano-2-[1-[2-(4-fluorophenyl)ethyl]piperidin-4-ylmethyl]isoindolin-1-one fumarate By using the compound obtained in Example 162a (224 mg), the title compound was obtained as colorless solid by carrying out reactions similar to those of Example 36c (258 mg, yield: 50%, 2 steps).
Melting point: 201–208° C. $^1$H-NMR(DMSO-d$_6$): 8.13 (1H,s), 7.96(1H,d,J=7.9 Hz), 7.85(1H,d,J=7.7 Hz), 7.27(2H, dd,J=8.4,5.7 Hz), 6.57(2H,s), 4.57(2H,s), 3.45(2H,d,J=7.3 Hz), 3.08(2H,brd,J=11.5 Hz), 2.82–2.68(4H,m), 2.23(2H, brt,J=11.1 Hz), 1.29(2H,brdd,J=21.7,11.4 Hz).

Example 163

5-Fluoro-2-[[1-[2-(4-fluorophenyl)ethyl]piperidin-4-yl]methyl]isoindolin-1-one fumarate By using the compound obtained in Example 154c, the title compound was obtained by similar procedures to those of Examples 26b and 36c (yield: 72%).
Melting point: 197–204° C. $^1$H-NMR (DMSO-d$_6$): δ 1.26 (m, 2H), 1.62 (m, 2H), 1.76 (m, 1H), 2.16 (m, 2H), 2.66 (m, 2H), 2.78 (m, 2H), 3.03 (m, 2H), 3.40 (d, J=7.2 Hz, 2H), 4.48 (s, 2H), 6.58 (s, 2H), 7.10 (t, J=9.0 Hz, 2H), 7.24–7.35 (m, 3H), 7.46 (dd, J=2.0, 8.9 Hz, 1H), 7.71 (dd, J=5.1, 8.4 Hz, 1H).

Example 164

4-Fluoro-2-[1-[2-(4-fluorophenyl)ethyl]piperidin-4-ylmethyl]isoindolin-1-one fumarate (Compound 202 in Table 1)

a) 4-Fluoro-2-[1-[2-(4-fluorophenyl)ethyl]piperidin-4-ylmethyl]isoindolin-1-one

By using the compound obtained in Example 6d (500 mg, 1.76 mmol) and the compound obtained in Example 26a (384 mg, 1.76 mmol), the title compound as crude product was obtained as colorless oil by carrying out a reaction similar to that of Example 26b (478 mg). The resulting crude product was used in the next reaction without purification.

b) 4-Fluoro-2-[1-[2-(4-fluorophenyl)ethyl]piperidin-4-ylmethyl]isoindolin-1-one fumarate By using the compound obtained in Example 164a (478 mg), the title compound was obtained as colorless solid by carrying out a reactions similar to those of Example 36c (560 mg, yield: 89%, 2 steps).
Melting point: 230–232° C. $^1$H-NMR(DMSO-d$_6$): 7.57–7.53(2H,m), 7.47–7.42(1H,m), 7.26(2H,dd,J=8.6,5.7 Hz), 7.12–7.06(2H,m), 6.58(2H,s), 4.58(2H,s), 3.42(2H,d, J=7.3 Hz), 3.02(2H,brd,J=brd,J=11.9 Hz), 2.79–2.74(2H, m), 2.66–2.61(2H,m), 2.14(2H,brt,J=11.6 Hz), 1.81(1H,brs), 1.63(2H,brd,J=13.1 Hz), 1.27–1.20(2H,m).

Example 165

2-[1-[2-(2-Methoxyphenyl)ethyl]piperidin-4-ylmethyl]-5-methoxyisoindolin-1-one hydrochloride (Compound 154 in Table 1)

a) 2-[1-[2-(2-Methoxyphenyl)ethyl]piperidin-4-ylmethyl]-5-methoxyisoindolin-1-one The compound obtained in Example 9c (297 mg, 1 mmol) and 1-methoxy-2-(2-methanesulfonyloxy)ethylbenzene (230 mg, 1 mmol) were reacted in N,N-dimethylformamide in the presence of sodium carbonate (233 mg) and sodium iodide (165 mg) at 80° C. for 8 hours. The reaction mixture was added with water and extracted with ethyl acetate, and the extract was washed with water and the solvent was evaporated under reduced pressure. The resulting oil was purified by silica gel column chromatography (methylene chloride-methanol) to obtain the title compound.
$^1$H-NMR(CDCl$_3$): δ 7.75 (d, J=8.4Hz, 1H), 7.15 (m, 2H), 6.99–6.81 (m, 3H), 4.35 (s, 2H), 3.86 (s, 3H), 3.80 (s, 3H), 3.47 (d, J=7.1 Hz, 2H), 3.03 (brd, J=11.5 Hz, 2H), 2.85–2.79 (m, 2H), 2.58–2.52 (m, 2H), 2.04 (t, J=10.0 Hz), 1.80 (m, 1H), 1.74–1.68 (m, 2H), 1.50–1.39 (m, 2H)

b) 2-[1-[2-(2-Methoxyphenyl)ethyl]piperidin-4-ylmethyl]-5-methoxyisoindolin-1-one hydrochloride By using the compound obtained in Example 165a, the title compound was obtained by similar procedures to those of Example 1f (yield: 46%).
Melting point: 204–207° C. $^1$H-NMR(DMSO-d$_6$): δ 10.12 (brs, 1H), 7.58 (d, J=8.4 Hz), 7.28–7.17 (m, 3H), 7.05–6.89 (m, 3H), 4.45 (s, 2H), 3.84 (s, 3H), 3.80 (s, 3H), 3.57–3.53 (m, 2H), 3.41 (d, J=7.2 Hz), 3.20–3.12 (m, 2H), 3.02–2.88 (m, 4H), 1.98 (m, 1H), 1.83–1.78 (m, 2H), 1.51 (m, 2H)

Example 166

5-Chloro-2-[1-[2-(2-methoxyphenyl)ethyl]piperidin-4-ylmethyl]isoindolin-1-one ³⁄₂.fumarate (Compound 153 in Table 1)

a) 5-Chloro-2-[1-[2-(2-methoxyphenyl)ethyl]piperidin-4-ylmethyl]isoindolin-1-one By using the compound obtained in Example 8e (250 mg, 0.83 mmol) and the compound obtained in Example 26a (191 mg, 0.83 mmol), the title compound as crude product was obtained as pale brown solid by carrying out a reaction similar to that of Example 26b (270 mg). The resulting crude product was used in the next reaction without purification.

b) 5-Chloro-2-[1-[2-(2-methoxyphenyl)ethyl]piperidin-4-ylmethyl]isoindolin-1-one 1.5.fumarate By using the compound obtained in Example 166a (270 mg), the title compound was obtained as colorless solid by carrying out reactions similar to those of Example 36c (269 mg, yield: 60%, 2 steps).
Melting point: 165–185° C. $^1$H-NMR(DMSO-d$_6$): 7.69 (2H,t,J=7.5 Hz), 7.54(1H,dd,J=8.1,1.5 Hz), 7.23–7.14(2H, m), 6.96(1H,d,J=7.8 Hz), 6.87(1H,d,J=7.5 Hz), 6.57(3H,s), 4.50(2H,s), 3.78(2H,s), 3.42(2H,d,J=7.2 Hz), 3.20(2H,brd, J=12.0 Hz), 2.81(2H,brs), 2.43(2H,brt,J=11.1 Hz), 1.86(1H, brs), 1.69(2H,brd,J=11.4 Hz), 1.36(2H,brdd,J=22.5,10.8 Hz).

Example 167

2-[1-[2-(2-Methoxyphenyl)ethyl]piperidin-4-ylmethyl]-5-bromoisoindolin-1-one hydrochloride (Compound 148 in Table 1)

a) 2-[1-[2-(2-Methoxyphenyl)ethyl]piperidin-4-ylmethyl]-5-bromoisoindolin-1-one

By using the compound obtained in Example 3d, the title compound was obtained by similar procedures to those of Example 165a (yield: 43%)

¹H-NMR(CDCl₃): δ 7.70 (d, J=8.4Hz), 7.59 (m, 2H), 7.17–7.11 (m, 2H), 6.89–6.81 (m, 2H), 4.38 (s, 2H), 3.80 (s, 3H), 3.49 (d, J=7.1 Hz, 2H), 3.02 (brd, J=11.7 Hz, 2H), 2.85–2.79 (m, 2H), 2.58–2.52 (m, 2H), 2.04 (t, J=11.6 Hz), 1.82 (m, 1H), 1.73–1.68 (m, 2H), 1.47–1.41 (m, 2H)

b) 2-[1-[2-(2-Methoxyphenyl)ethyl]piperidin-4-ylmethyl]-5-bromoisoindolin-1-one hydrochloride By using the compound obtained in Example 167a, the title compound was obtained by similar procedures to those of Example 1f (yield: 81%).

Melting point: 240–245° C.

Example 168

5-Cyano-2-[1-[2-(2-methoxyphenyl)ethyl]piperidin-4-ylmethyl]isoindolin-1-one fumarate (Compound 155 in Table 1)

a) 5-Cyano-2-[1-[2-(2-methoxyphenyl)ethyl]piperidin-4-ylmethyl]isoindolin-1-one

By using the compound of Example 10c (300 mg, 1.03 mmol) and the compound obtained in Example 26a (237 mg, 1.03 mmol), the title compound as crude product was obtained as pale brown solid by carrying out a reaction similar to that of Example 26b (174 mg). The resulting crude product was used in the next reaction without purification.

b) 5-Cyano-2-[1-[2-(2-methoxyphenyl)ethyl]piperidin-4-ylmethyl]isoindolin-1-one fumarate By using the compound obtained in Example 168a (174 mg), the title compound was obtained as colorless solid by carrying out reactions similar to those of Example 36c (202 mg, yield: 39%, 2 steps).

Melting point: 201–208° C.

¹H-NMR(DMSO-d₆): 8.14(1H,s), 7.96(1H,d,J=8.1 Hz), 7.85(1H,d,J=7.5 Hz), 7.22–7.14(2H,m), 6.95(1H,d,J=8.1 Hz), 6.86(1H,t,J=7.5 Hz), 6.57(2H,s), 4.57(2H,s), 3.77(3H,s), 3.45(2H,d,J=7.2Hz), 3.09(2H,brd,J=10.8 Hz), 2.80–2.75 (2H,m), 2.66(2H,brd,J=8.7 Hz), 2.24(2H,brt,J=11.0 Hz), 1.82(1H,brs), 1.65(2H,bed,J=12.0H), 1.29(2H,brdd, J=21.8, 11.6 Hz).

Example 169

5-Fluoro-2-[[1-[2-(2-methyloxyphenyl)ethyl]piperidin-4-yl]methyl]isoindolin-1-one fumarate By using the compound obtained in Example 154c, the title compound was obtained by similar procedures to those of Examples 26b and 36c (yield: 69%).

Melting point: 210–216° C. ¹H-NMR (DMSO-d₆): δ 1.30 (m, 2H), 1.65 (m, 2H), 1.76 (m, 1H), 2.27 (m, 2H), 2.68 (m, 2H), 2.77 (m, 2H), 3.10 (m, 2H), 3.41 (d, J=7.2 Hz, 2H), 3.77 (s, 3H), 4.49 (s, 2H), 6.56 (s, 2H), 6.87 (t, J=7.4 Hz, 1H), 6.95 (d, J=8.1 Hz), 7.14–7.22 (m, 2H), 7.32 (m, 1H), 7.47 (dd, J=2.1, 8.7 Hz, 1H), 7.71 (dd, J=5.3, 8.3 Hz, 1H).

Example 170

5-Cyano-2-[1-[2-(2-methoxyphenyl)ethyl]piperidin-4-ylmethyl]isoindolin-1-one fumarate (Compound 152 in Table 1)

a) 5-Cyano-2-[1-[2-(2-methoxyphenyl)ethyl]piperidin-4-ylmethyl]isoindolin-1-one

By using the compound obtained in Example 10c (300 mg, 1.05 mmol) and the compound obtained in Example 26a (242 mg, 1.05 mmol), the title compound as crude product was obtained as pale brown solid by carrying out a reaction similar to that of Example 26b (308 mg). The crude product was used in the next reaction without purification.

b) 5-Cyano-2-[1-[2-(2-methoxyphenyl)ethyl]piperidin-4-ylmethyl]isoindolin-1-one fumarate By using the compound obtained in Example 170a (308 mg), the title compound was obtained as colorless solid by carrying out reactions similar to those of Example 36c (346 mg, yield: 86%, 2 steps).

Melting point: 242–247° C. ¹H-NMR(DMSO-d₆): 7.57–7.54(2H,m),7.47–7.42(1H,m), 7.22–7.14(1H,m), 6.95 (1H,d,J=7.6 Hz), 6.89–6.87(1H,m), 6.56(2H,s), 4.58(2H,s), 3.78(3H,s), 3.43(2H,d,J=7.3 Hz), 3.13(2H,brd,J=11.8 Hz), 2.82–2.68(4H,m), 2.32(2H,brt,J=11.0 Hz), 1.86(1H,brs), 1.67(2H,brd,J=11.1 Hz), 1.38–1.27(2H,m).

Example 171

(R,S)-2-[1-[2-(4-Fluorophenyl)-2-hydroxyethyl] piperidin-4-ylmethyl]-4-fluoroisoindolin-1-one hydrochloride (Compound 83 in Table 1)

a) (R,S)-2-[1-[2-(4-Fluorophenyl)-2-hydroxyethyl] piperidin-4-ylmethyl]-4-fluoroisoindolin-1-one By using the compound obtained in Example 6, the title compound was obtained by similar procedures to those of Example 16a (yield: 85%).

¹H-NMR(CDCl₃): δ 7.66 (d, J=7.8 Hz, 1H), 7.46 (m, 1H), 7.35–7.30 (m, 2H), 7.22 (t, J=8.1 Hz, 1H), 7.04–6.99 (m, 2H), 4.71–4.66 (m, 1H), 4.46 (s, 2H), 3.53 (d, J=7.2 Hz, 2H), 3.15 (brd, J=11.7 Hz, 1H), 2.82 (brd, J=10.2 Hz, 1H), 2.51–2.31 (m, 3H), 2.04 (m, 1H), 1.85 (m, 1H), 1.80–1.65 (m, 2H), 1.49–1.22 (m, 2H)

b) (R,S)-2-[1-[2-(4-Fluorophenyl)-2-hydroxyethyl] piperidin-4-ylmethyl]-4-fluoroisoindolin-1-one hydrochloride By using the compound obtained in Example 171a, the title compound was obtained by similar procedures to those of Example 1f (yield: 78%).

Melting point: 221–224° C. ¹H-NMR(DMSO-d₆): δ 9.63 (brs, 1H), 7.56–7.42 (m, 5H), 7.20 (t, J=8.7 Hz, 2H), 6.24 (brs, 1H), 5.11 (brs, 1H), 4.59 (s, 2H), 3.55–2.90 (m, 8H), 2.00 (m, 1H), 1.86–1.56 (m, 4H)

Example 172

(R,S)-2-[1-[2-(4-Fluorophenyl)-2-hydroxyethyl]piperidin-4-ylmethyl]-5-chloroisoindolin-1-one hydrochloride (Compound 84 in Table 1)

a) (R,S)-2-[1-[2-(4-Fluorophenyl)-2-hydroxyethyl]piperidin-4-ylmethyl]-5-chloroisoindolin-1-one By using the compound obtained in Example 8, the title compound was obtained by similar procedures to those of Example 16a (yield: 82%)

$^1$H-NMR(CDCl$_3$): δ 7.78 (d, J=8.7 Hz, 1H), 7.44 (m, 2H), 7.35–7.30 (m, 2H), 7.02 (m, 2H), 4.69 (m, 1H), 4.44 (s, 2H), 4.09 (brs, 1H), 3.51 (d, J=7.2 Hz, 2H), 3.15 (brd, J=11.4 Hz, 1H), 2.81 (brd, J=11.1 Hz, 1H), 2.49–2.30 (m, 3H), 2.02 (m, 1H), 1.80–1.20 (m, 4H)

b) (R,S)-2-[1-[2-(4-Fluorophenyl)-2-hydroxyethyl]piperidin-4-ylmethyl]-5-chloroisoindolin-1-one hydrochloride By using the compound obtained in Example 172a, the title compound was obtained by similar procedures to those of Example 1f (yield: 90%).

Melting point: 254–256° C. $^1$H-NMR(DMSO-d$_6$): δ 9.59 (brs, 1H), 7.74–7.67 (m, 2H), 7.56–7.43 (m, 3H), 7.25–7.20 (m, 2H), 6.27 (brs, 1H), 5.13 (brs, 1H), 4.52 (s, 2H), 3.64–2.95 (m, 8H), 1.99–1.57 (m, 5H

Example 173

(R,S)-2-[1-[2-(4-fluorophenyl)-2-hydroxyethyl]piperidin-4-ylmethyl]-5-fluoroisoindolin-1-one hydrochloride a) (R,S)-2-[1-[2-(4-Fluorophenyl)-2-hydroxyethyl]piperidin-4-ylmethyl]-5-fluoroisoindolin-1-one By using the compound obtained in Example 154, the title compound was obtained by similar procedures to those of Example 16a (yield: 61%).

$^1$H-NMR(CDCl$_3$): δ 7.83 (m, 1H), 7.35–7.25 (m, 2H), 7.17–7.12 (m, 2H), 7.05–6.99 (m, 2H), 4.67 (m, 1H), 4.44 (s, 2H), 4.08 (brs, 1H), 3.51 (d, J=7.2 Hz, 2H), 3.15 (brd, J=11.1 Hz, 1H), 2.82 (brs, J=11.1 Hz, 1H), 2.49–2.28 (m, 3H), 2.02 (m, 1H), 1.80 (m, 1H), 1.77–1.25 (m, 4H)

b) (R,S)-2-[1-[2-(4-Fluorophenyl)-2-hydroxyethyl]piperidin-4-ylmethyl]-5-fluoroisoindolin-1-one hydrochloride By using the compound obtained in Example 173a, the title compound was obtained by similar procedures to those of Example 1f (yield: 70%).

Melting point: 243–245° C. $^1$H-NMR(DMSO-d$_6$): δ 9.66 (brs, 1H), 7.71 (m, 1H), 7.43 (m, 3H), 7.34–7.17 (m, 3H), 6.24 (d, J=3.9 Hz, 1H), 5.11 (brs, 1H), 4.49 (s, 2H), 3.66–2.91 (m, 8H), 1.97–1.52 (m, 5H).

Example 174

(R,S)-2-[1-[2-(4-Fluorophenyl)-2-hydroxyethyl]piperidin-4-ylmethyl]-5-cyanoisoindolin-1-one hydrochloride (Compound 87 in Table 1)

a) (R,S)-2-[1-[2-(4-Fluorophenyl)-2-hydroxyethyl]piperidin-4-ylmethyl]-5-cyanoisoindolin-1-one By using the compound obtained in Example 10, the title compound was obtained by similar procedures to those of Example 16a (yield: 37%).

$^1$-NMR(CDCl$_3$): δ 7.95 (d, J=7.8 Hz, 1H), 7.76 (m, 2H), 7.32 (m, 2H), 7.01 (m, 2H), 4.69 (m, 1H), 4.47 (s, 2H), 3.55 (d, J=7.2 Hz, 2H), 3.14 (brd, J=10.5 Hz, 1H), 2.81 (brd, J=10.5 Hz, 1H), 2.79–2.29 (m, 3H), 2.03 (m, 1H), 1.95–1.35 (m, 5H)

b) (R,S)-2-[1-[2-(4-Fluorophenyl)-2-hydroxyethyl]piperidin-4-ylmethyl]-5-cyanoisoindolin-1-one hydrochloride By using the compound obtained in Example 174a, the title compound was obtained by similar procedures to those of Example 1f (yield: 74%).

Melting point: 255–262° C. $^1$H-NMR(DMSO-d$_6$): δ 9.66 (brs, 1H), 8.16 (s, 1H), 7.96 (d, J=7.5 Hz, 1H), 7.86 (d, J=7.8 Hz, 1H), 7.45 (m, 2H), 7.22 (m, 2H), 6.27 (brs, 1H), 5.13 (brs, 1H), 4.59 (s, 2H), 3.60–2.92 (m, 8H), 1.98–1.54 (m, 5H)

Example 175

(R,S)-5-[1-[2-(Fluorophenyl)-2-hydroxyethyl]piperidin-4-ylmethyl]-4,5-dihydro-6H-thieno[2,3-c]pyrrol-6-one fumarate (Compound 780 in Table 2)

a) (R,S)-5-[1-[2-(Fluorophenyl)-2-hydroxyethyl]piperidin-4-ylmethyl]-4,5-dihydro-6H-thieno[2,3-c]pyrrol-6-one By using the compound obtained in Example 22, the title compound was obtained by similar procedures to those of Example 16a (yield: 87%).

$^1$H-NMR(CDCl$_3$): δ 7.63 (d, J=4.8 Hz,1H), 7.32 (m, 3H), 7.01 (m, 3H), 4.67 (m, 1H), 4.34 (s, 2H), 4.11 (brs, 1H), 3.47 (d, J=6.9 Hz, 2H), 3.15 (brd, J=11.1 Hz, 1H), 2.82 (brd, J=10.8 Hz, 1H), 2.50–2.30 (m, 3H), 2.03 (m, 1H), 1.81–1.71 (m, 3H), 1.47–1.37 (m, 1H)

b) (R,S)-5-[1-[2-(Fluorophenyl)-2-hydroxyethyl]piperidin-4-ylmethyl]-4,5-dihydro-6H-thieno[2,3-c]pyrrol-6-one fumarate The compound obtained in Example 176a (70 mg) was dissolved in ethanol (1 ml) and ethyl acetate (3 ml), and the solution was added with fumaric acid (26 mg). The crystals precipitated which appeared after complete dissolution were collected by filtration to obtain the title compound (yield: 87%).

Melting point: 174–176° C. $^1$H-NMR(DMSO-d$_6$): δ 7.95 (d, J=5.1 Hz, 1H), 7.41–7.35 (m, 2H), 7.23–7.11 (m, 3H), 6.57 (s, 2H), 4.76 (brs, 1H), 4.42 (s, 2H), 3.33–2.15 (m, 8H), 1.72–1.57 (m, 3H), 1.25–1.15 (m, 2H)

Example 176

2-[1-[2-(4-Fluorophenyloxy)ethyl]piperidin-4-ylmethyl]-5-methoxyisoindolin-1-one hydrochloride (Compound 214 in Table 1)

a) 2-[1-[2-(4-Fluorophenyloxy)ethyl]piperidin-4-ylmethyl]-5-methoxyisoindolin-1-one By using the compound obtained in Example 9c and 1-fluoro-4-(2-bromoethoxy)benzene, the title compound was obtained by similar procedures to those of Example 165a (yield: 78%).

$^1$H-NMR(CDCl$_3$): δ 7.75 (d, J=8.4 Hz), 7.00–6.91 (m, 4H), 6.85–6.80 (m, 2H), 4.34 (s, 2H), 4.04 (t, J=6.0 Hz, 2H), 3.87 (s, 3H), 3.47 (d, J=7.2 Hz, 2H), 2.98 (brd, J=11.7 Hz, 2H), 2.76 (t, J=6.0 Hz, 2H), 2.09 (t, J=9.3 Hz, 2H), 1.77 (m, 1H), 1.72 (m, 2H), 1.48–1.39 (m, 2H)

b) 2-[1-[2-(4-Fluorophenyloxy)ethyl]piperidin-4-ylmethyl]-5-methoxyisoindolin-1-one hydrochloride By using the compound obtained in Example 176a, the title compound was obtained by similar procedures to those of Example 1f (yield: 47%).

Melting point: 216–219° C. $^1$H-NMR(DMSO-d$_6$): δ 10.44 (brs, 1H), 7.58 (d, J=8.4 Hz), 7.19–7.13 (m, 3H), 7.06–6.99 (m, 3H), 4.44 (s, 2H), 4.37 (t, J=4.5 Hz, 2H), 3.84 (s, 3H), 3.59–3.45 (m, 2H), 3.45–3.30 (m, 4H), 3.05–2.94 (m, 2H), 1.97 (m, 1H), 1.81–1.76 (m, 2H), 1.64–1.52 (m, 2H)

Example 177

2-[1-[2-(4-Fluorophenyloxy)ethyl]piperidin-4-ylmethyl]-5-bromoisoindolin-1-one hydrochloride (Compound 208 in Table 1)

a) 2-[1-[2-(4-Fluorophenyloxy)ethyl]piperidin-4-ylmethyl]-5-bromoisoindolin-1-one The compound obtained in Example 3d and 1-fluoro-4-(2-bromoethoxy)benzene, the title compound was obtained by similar procedures to those of Example 165a (yield: 66%).

$^1$H-NMR(CDCl$_3$): δ 7.71 (d, J=8.4 Hz, 1H), 7.62–7.59 (m, 2H), 6.99–6.93 (m, 2H), 6.85–6.80 (m, 2H), 4.38 (s, 2H), 4.04 (t, J=6.0 Hz, 2H), 3.48 (d, J=4.9 Hz, 2H), 2.99 (brd, J=11.7 Hz), 2.77 (t, J=6.0 Hz), 2.10 (t, J=11.7 Hz, 2H), 1.80 (m, 1H), 1.78–1.70 (m, 2H), 1.48–1.39 (m, 2H)

b) 2-[1-[2-(4-Fluorophenyloxy)ethyl]piperidin-4-ylmethyl]-5-bromoisoindolin-1-one hydrochloride By using the compound obtained in Example 177a, the title compound was obtained by similar procedures to those of Example 1f (yield: 86%).

Melting point: 222–225° C.

Example 178

5-Chloro-2-[1-[2-(4-fluorophenoxy)ethyl]piperidin-4-ylmethyl]isoindolin-1-one fumarate (Compound 213 in Table 1)

a) 5-Chloro-2-[1-[2-(4-fluorophenoxy)ethyl]piperidin-4-ylmethyl]isoindolin-1-one By using the compound obtained in Example 8e (250 mg, 0.83 mmol) and the compound obtained in Example 32a (182 mg, 0.83 mmol), the title compound as crude product was obtained as pale brown solid by similar procedures to those of Example 26b (321 mg). The resulting crude product was used in the next reaction without purification.

b) 5-Chloro-2-[1-[2-(4-fluorophenoxy)ethyl]piperidin-4-ylmethyl]isoindolin-1-one fumarate By using the compound obtained in Example 178a (321 mg), the title compound was obtained as colorless solid by carrying out reactions similar to those of Example 36c (320 mg, yield: 74%, 2 steps).

Melting point: 172–176° C. $^1$H-NMR(DMSO-d$_6$): 7.68 (2H,t,J=7.6 Hz), 7.55(1H,d,J=2.7 Hz), 7.11(2H,t,J=8.8 Hz), 6.93–6.79(2H,m), 6.59(2H,s), 4.49(2H,s), 4.08(2H,t,J=5.6 Hz), 3.40(2H,d,J=7.2 Hz), 3.01(2H,brd,J=11.5 Hz), 2.80 (2H,t,J=5.6 Hz), 2.21–2.14(2H,m), 1.76–1.72(1H,m), 1.60 (2H,brd,J=12.1 Hz), 1.26(2H,brdd,J=21.4,11.3 Hz).

Example 179

5-Cyano-2-[1-[2-(4-fluorophenoxy)ethyl]piperidin-4-ylmethyl]isoindolin-1-one fumarate (Compound 215 in Table 1)

a) 5-Cyano-2-[1-[2-(4-fluorophenoxy)ethyl]piperidin-4-ylmethyl]isoindolin-1-one

BY using the compound obtained in Example 8e (300 mg, 1.03 mmol) and the compound obtained in Example 10c (226 mg, 1.03 mmol), the title compound as crude product was obtained as pale brown solid by carrying out a reaction similar to that of Example 26b (314 mg). The resulting crude product was used in the next reaction without purification.

b) 5-Cyano-2-[1-[2-(4-fluorophenoxy)ethyl]piperidin-4-ylmethyl]isoindolin-1-one fumarate By using the compound obtained in Example 179a (314 mg), the title compound was obtained as colorless solid by carrying out reactions similar to those of Example 36c (331 mg, yield: 63%, 2 steps).

Melting point: 194–198° C. $^1$H-NMR(DMSO-d$_6$): 8.13 (1H,s), 7.95(1H,d,J=7.9 Hz), 7.84(1H,d,J=7.7 Hz), 7.14–7.07(2H,t,J=5.6 Hz), 6.99(2H,m), 6.59(2H,s), 4.57(2H,s), 4.11(2H,t,J=5.6 Hz), 3.44(2H,d,J=7.2 Hz), 3.06 (2H,brd,J=11.6 Hz), 2.87(2H,t,J=5.5 Hz), 2.27(2H,brt, J=11.0 Hz), 1.83–1.77(1H,m), 1.63(2H,brd,J=11.7 Hz), 1.36–1.23(2H,m).

Example 180

5-Fluoro-2-[[1-[2-(4-fluorophenyloxy)ethyl]piperidin-4-yl]methyl]isoindolin-1-one fumarate By using the compound obtained in Example154c, the title compound was obtained by similar procedures to those of Examples 26b and 36c (yield: 88%).

Melting point: 174–176° C. $^1$H-NMR (DMSO-$d_6$): d1.25 (m, 2H), 1.60 (m, 2H), 1.76 (m, 1H), 2.17 (m, 2H), 2.79 (t,J=5.6 Hz, 2H), 3.50 (m, 2H), 3.39 (d, J=7.2 Hz, 2H), 4.07 (t, J=5.6 Hz, 2H), 4.47 (s, 2H), 6.60 (s, 2H), 6.95 (m, 2H), 7.10 (t, J=8.9 Hz, 2H), 7.31 (m, 1H), 7.46 (dd, J=1.9, 8.7 Hz, 1H), 7.70 (dd, J=5.2, 8.3 Hz, 1H).

Example 181

4-Fluoro-2-[1-[2-(4-fluorophenoxy)ethyl]piperidin-4-ylmethyl]isoindolin-1-one fumarate (Compound 212 in Table 1)

a) 4-Fluoro-2-[1-[2-(4-fluorophenoxy)ethyl]piperidin-4-ylmethyl]isoindolin-1-one By using the compound in Example 6d (300 mg, 1.05 mmol) and the compound obtained in Example 32a (230 mg, 1.05 mmol), the title compound as crude product was obtained as pale brown solid by carrying out a reaction similar to that of Example 26b (356 mg). The resulting crude product was used in the next reaction without purification.

b) 4-Fluoro-2-[1-[2-(4-fluorophenoxy)ethyl]piperidin-4-ylmethyl]isoindolin-1-one fumarate By using the compound obtained in Example181a (356 mg), the title compound was obtained as colorless solid by carrying out reactions similar to those of Example36c (412 mg, yield: 89%, 2 steps).

Melting point: 196–198° C. $^1$H-NMR(DMSO-$d_6$): 7.56–7.53(2H,m), 7.46(1H,m), 7.13–7.07(2H,m), 6.97–6.92 (2H,m), 6.60(2H,s), 4.57(2H,s), 4.07(2H, t,J=5.7 Hz), 3.41 (2H,d,J=7.4 Hz), 2.99(2H,brd, J=11.7 Hz), 2.78(2H,t,J=5.7 Hz), 2.16(2H,brt,J=10.9 Hz), 1.80–1.75(1H,m), 1.61(2H, brd,J=11.6 Hz), 1.32–1.23(2H,m).

Example 182

2-[[1-[2-(4-Fluorophenyl)-2-oxoethyl]piperidin-4-yl]methyl]isoindolin-1-one hydrochloride dihydrate 2-[[1-[2-(4-Fluorophenyl)-2-oxoethyl]piperidin-4-yl]methyl]isoindolin-1-one hydrochloride (the compound of Example 1, 39.4 mmol) was added to water (30 mL) and acetone (210 mL), and mixture was heated at 60° C. for dissolution. The mixture was added dropwise with ethyl acetate (100 mL) and stand for cooling to room temperature. The crystals precipitated were collected by filtration and the resulting crystals were washed with ethyl acetate and dried under reduced pressure to obtain the title compound (yield: 79%).

Anal. (Calcd.) C, 60.20; H, 6.43; N, 6.38; Cl, 8.08. (Found)C, 60.02; H, 6.24; N, 5.97; Cl, 7.74. Analysis of water content (Karl Fisher method) (Calcd.) 8.2%. (Found) 8.3%.

Test Example

Sigma Binding Site-Binding Inhibition Test

A sigma 2-selective receptor binding inhibition test was performed by using [$^3$H]-di-o-tolylguanidine (DTG, final concentration: 1 nM, 37 Ci/mmol, New England Nuclear, Dupont de Nemours) as a radioactive ligand. A crude P2 membrane fraction was prepared from livers of male rats (Sprague-Dawley rats) according to a method described in the literature (X. He, et al., J. Med. Chem., 36, pp. 566–571, 1993). In the presence of 500 nM pentazocine and a control compound at various concentrations (haloperidol, $10^{-10}$ to $10^{-6}$ M) or a test ligand at various concentrations ($10^{-10}$ to $10^{-5}$ M) together with a radioactive ligand, the P2 fraction (0.4 ml) was incubated in 50 mM Tris-HCl (pH 7.4, final volume: 0.5 ml) at 25° C. for 2 hours. The reaction mixture was rapidly filtered on a Brandel cell harvester using Whatman GF/B filter paper, which was immersed beforehand in 0.5% polyethyleneimine for 1 hour, to stop the reaction. The filter paper was washed 4 times with the ice cooled incubation buffer. The non-specific results were evaluated by using 1 μM haloperidol, and the scintillation analysis and the curve analysis were performed as described above. The Kd value for [$^3$H]-DTG was 6.9 nM. Results are shown in Tables 3 and 4 below.

TABLE 3

| Test Compound | Sigma 2 Ki(nM) |
| --- | --- |
| Example 1 | 13 |
| Example 2 | 2.8 |
| Example 3 | 7 |
| Example 4 | 7.6 |
| Example 6 | 8.7 |
| Example 7 | 16 |
| Example 8 | 3.1 |
| Example 9 | 4.9 |
| Example 13 | 6.6 |
| Example 17 | 24 |
| Example 22 | 22 |
| Example 24 | 13 |
| Example 26 | 10 |
| Example 30 | 22 |
| Example 31 | 22 |
| Example 32 | 2.8 |
| Example 36 | 50 |
| Example 50 | 14 |
| Example 84 | 3.4 |
| Example 137 | 7.8 |
| Example 154 | 16 |
| Example 159 | 25 |
| Example 160 | 10 |

TABLE 4

| Test Compound | Inhibitory rate against sigma 2 (%, 10 nM) |
| --- | --- |
| Example 48 | 59 |
| Example 50 | 52 |
| Example 51 | 74 |
| Example 53 | 57 |
| Example 72 | 55 |
| Example 76 | 84 |
| Example 77 | 80 |
| Example 78 | 86 |
| Example 84 | 58 |
| Example 85 | 59 |
| Example 94 | 83 |
| Example 95 | 69 |

TABLE 4-continued

| Test Compound | Inhibitory rate against sigma 2 (%, 10 nM) |
| --- | --- |
| Example 96 | 66 |
| Example 97 | 59 |
| Example 109 | 68 |
| Example 110 | 68 |
| Example 111 | 51 |
| Example 112 | 60 |
| Example 113 | 64 |
| Example 114 | 51 |
| Example 117 | 52 |
| Example 118 | 50 |
| Example 158 | 57 |
| Example 167 | 62 |
| Example 170 | 52 |
| Example 177 | 55 |
| Example 178 | 50 |
| Example 181 | 70 |

Formulation Examples

The pharmaceutical compositions of present invention can be manufactured by utilizing methods and pharmaceutical additives conventionally used in the field of the art. Typical formulation examples are shown below. However, the pharmaceutical compositions of the present invention are not limited to these examples.

| 1) Tablet | |
| --- | --- |
| Compound of Example 2 | 0.1 to 50 mg |
| Calcium phosphate | 20 mg |
| Lactose | 30 mg |
| Talc | 10 mg |
| Magnesium stearate | 5 mg |
| Potato starch | ad 200 mg |

2) Suspension

Water is added to the compound of Example 2 (1 to 5 mg), carboxymethyl-cellulose sodium (50 mg), sodium benzoate (1 mg), and sorbitol (500 mg) to produce an aqueous suspension for oral administration in a total volume of 1 ml.

3) Injection

The compound of Example 2 is mixed in an amount of 1.5% by weight as an active ingredient with a mixture of propylene glycol (10% by volume) and distilled water for injection by stirring, and the resulting solution is sterilized by filtration through a membrane filter to produce a composition for injection.

| 4) Ointment | |
| --- | --- |
| Compound of Example 2 | 1 to 1,000 mg |
| Stearyl alcohol | 3 g |
| Lanolin | 5 g |
| White Vaseline | 15 g |
| Water | ad 100 g |

INDUSTRIAL APPLICABILITY

The compounds of the present invention have high affinity for the sigma binding site. In addition, the compounds of the present invention have excellent pharmacokinetic profiles such as high oral absorbability and a low rate of metabolism, and moreover, they are highly safe, and exhibit high efficacy in pharmacological study using model animals. Therefore, the compounds of the present invention are useful as sigma ligands for therapeutic and/or preventive treatment of various kinds of diseases and symptoms in which the sigma ligands involve.

What is claimed is:

1. A compound represented by the following formula (I) or a salt thereof, or a hydrate or a solvate thereof:

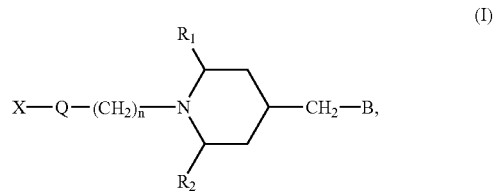

(I)

wherein:
X represents an alkyl group, a cycloalkyl-substituted alkyl group, an aryl-substituted alkyl group, an aryl-substituted alkenyl group, an aryl-substitutes alkynyl group, a monocyclic or polycyclic cycloalkyl group which may be substituted with an alkyl group, an aryl group, a heterocyclic group, or a substituted or unsubstituted amino group;
Q represents a group represented by —CO—, —O—, —S—, —CH(OR$_7$)—, —C(=CH$_2$)— or —C(=NR$_8$)— wherein R$_7$ represents a hydrogen atom, an alkyl group, a hydroxyalkyl group, or an acyl group, and R$_8$ represents a hydroxyl group, an alkoxyl group, an aralkyloxy group, an acyloxy group, an acylamino group, or an alkoxycarbonyl amino group;
n represents an integer of from 0 to 5;
R$_1$ and R$_2$ each independently represent a hydrogen atom or an alkyl group;
B represents the following groups:

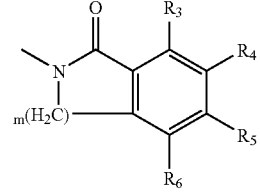

wherein R$_3$, R$_4$, R$_5$ and R$_6$ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group;
m represents 1 or 2.

2. The compound or a salt thereof, or a hydrate or a solvate thereof according to claim 1, wherein X represents an alkyl group, an aryl-substituted alkyl group, an aryl-substituted alkenyl group, an aryl-substituted alkynyl group, an aryl group, a monocyclic cycloalkyl group, a monoclyclic heterocyclic group, a 8- to 10-membered bicyclic heteroaryl group containing 1 or 2 heteroatoms, or an amino group substituted with an alkyl group or an aryl group; Q represents a group represented by —CO—, —O—, —S—, —CH (OR$_7$)— or —C(=NR$_8$) wherein R$_7$ represents a hydrogen atom, an alkyl group, or an acyl group, and R$_8$ represents a hydroxyl group, an alkoxyl group, or an acylamino group; n represents an integer of from 0 to 4; each of R$_1$ and R$_2$ represents a hydrogen atom; R$_3$, R$_4$, R$_5$, and R$_6$ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group; m represents 1 or 2.

3. The compound or a salt thereof, or a hydrate or a solvate thereof according to claim 2, wherein X represents a substituted or unsubstituted phenyl group wherein the substituent is one or more substituents selected from the group consisting of a halogen atom, an alkyl group, a halogenated alkyl group, an alkoxyl group, a halogenated alkoxyl group, and a cyano group), a 5- or 6-membered monocyclic heterocyclic group, or a 8- to 10-membered bicyclic heteroaryl group containing one or two heteroatoms.

4. The compound or a salt thereof, or a hydrate or a solvate thereof according to claim 2, wherein B is represented by the following formula:

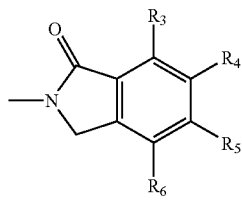

wherein three of R$_3$, R$_4$, R$_5$, and R$_6$ are hydrogen atoms and the remaining one represents a substituent selected from the group consisting of a hydrogen atom, a halogen atom, a nitro group, an alkyl group, a hydroxyl group, an alkoxyl group, and a cyano group.

5. The compound or a salt thereof, or a hydrate or a solvate thereof according to claim 1, wherein X represents a substituted or unsubstituted phenyl group wherein said substituent is one or more substituents selected from the group consisting of a halogen atom and an alkoxyl group, Q represents —CO—, —O—, or —CH(OH)13 , n represents an integer of from 1 to 3, each of R$_1$ and R$_2$ is a hydrogen atom, three of R$_3$, R$_4$, R$_5$, and R$_6$ are hydrogen atoms and the remaining one represents a hydrogen atom, a halogen atom, or an alkoxyl group, m represents 1 or 2.

6. The compound or a salt thereof, or a hydrate or a solvate thereof according to claim 5, wherein X represents p-fluorophenyl group, n represents 1, three of R$_3$, R$_4$, R$_5$, and R$_6$ are hydrogen atoms and the remaining one represents a hydrogen atom, a halogen atom, or a methoxy group, and m represents 1.

7. The compound or a salt thereof, or a hydrate or a solvate thereof according to claim 6, wherein Q represents —CO—.

8. The compound or a salt thereof, or a hydrate or a solvate thereof according to claim 6, wherein Q represents —O—.

9. The compound or a salt thereof, or a hydrate or a solvate thereof according to claim 6, wherein Q represents —CH(OH)—.

10. 2-((1-(2-(4-Fluorophenyl)-2-oxoethyl)piperidin-4-yl) methyl)isoindolin-1-one or a salt thereof, or a hydrate or a solvate thereof.

11. 4-Fluoro-2-((1-(2-(4-fluorophenyl)-2-oxoethyl)piperidin-4-yl)methyl)-isoindolin-1-one or a salt thereof, or a hydrate or a solvate thereof.

12. 5-Chloro-2-((1-(2-(4-fluorophenyl)-2-oxoethyl)piperidin-4-yl)methyl)-isoindolin-1-one or a salt thereof, or a hydrate or a solvate thereof.

13. 5-Fluoro-2-[[1-[2-(4-fluorophenyl)-2-oxoethyl]piperidin-4-yl]methyl]-isoindolin-1-one or a salt thereof, or a hydrate or a solvate thereof.

14. The compound or a salt thereof, or a hydrate or a solvate thereof according to claim 1, which functions as a sigma ligand.

15. A pharmaceutical composition which comprises an effective amount of a compound represented by the following formula (I) or a pharmaceutically acceptable salt thereof, or a hydrate or a solvate thereof:

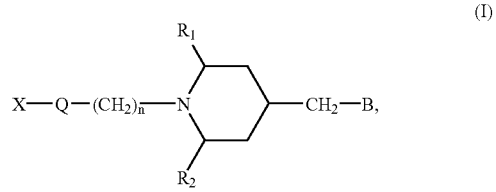

wherein:

X represents an alkyl group, a cycloalkyl-substituted alkyl group, an aryl-substituted alkyl group, an aryl-substituted alkenyl group, an aryl-substituted alkynyl group, a monocyclic or polycyclic cycloalkyl group which may be substituted with an alkyl group, an aryl group, a heterocyclic group, or a substituted or unsubstituted amino group;

Q represents a group represented by —CO—, —O—, —S—, —CH(OR$_7$)—, —C(=CH$_2$)— or —C(=NR$_8$) — wherein R$_7$ represents a hydrogen atom, an alkyl group, a hydroxyalkyl group, or an acyl group, and R$_8$ represents a hydroxyl group, an alkoxyl group, an aralkyloxy group, an acyloxy group, an acylamino group, or an alkoxycarbonyl amino group;

n represents an integer of from 0 to 5;

R$_1$ and R$_2$ each independently represent a hydrogen atom or an alkyl group;

B represents the following group:

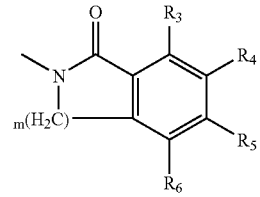

wherein R$_8$, R$_4$, R$_5$ and R$_4$ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group;

in represents 1 or 2, as an active ingredient and a pharmaceutically acceptable carrier.

* * * * *